United States Patent
Basarab et al.

(10) Patent No.: US 7,285,558 B2
(45) Date of Patent: Oct. 23, 2007

(54) **PYRAZOLO[3,4-D]PYRIMIDINES INHIBITING *H. PYLORI* INFECTIONS**

(75) Inventors: Gregory Basarab, Waltham, MA (US); Joseph Eyermann, Waltham, MA (US); Madhusudhan Gowravaram, Waltham, MA (US); Oluyinka Green, Waltham, MA (US); Lawrence MacPherson, Waltham, MA (US); Marshall Morningstar, Waltham, MA (US); Thanh Nguyen, San Diego, CA (US)

(73) Assignee: AstraZeneca AB, Södertälje (SE)

( * ) Notice: Subject to any disclaimer, the term of this patent is extended or adjusted under 35 U.S.C. 154(b) by 286 days.

(21) Appl. No.: 10/481,178

(22) PCT Filed: Jun. 28, 2002

(86) PCT No.: PCT/SE02/01303

§ 371 (c)(1),
(2), (4) Date: Jun. 14, 2004

(87) PCT Pub. No.: WO03/002567

PCT Pub. Date: Jan. 9, 2003

(65) Prior Publication Data

US 2004/0254183 A1    Dec. 16, 2004

(30) Foreign Application Priority Data

Jun. 28, 2001    (SE)    .................................... 0102315

(51) Int. Cl.
*C07D 271/02*    (2006.01)
*C07D 473/00*    (2006.01)
*A61K 31/519*    (2006.01)

(52) U.S. Cl. ............................... 514/262.1; 514/263.1; 544/262; 544/264; 544/265; 548/100; 548/125

(58) Field of Classification Search ............. 514/262.1, 514/263.1; 544/262, 264, 265; 548/100, 548/125
See application file for complete search history.

(56) References Cited

FOREIGN PATENT DOCUMENTS

WO    WO 9006116 A2    6/1990

OTHER PUBLICATIONS

Fumio et al., "Synthesis of Pyrazolo[3,4-d]pyrimidines by Intramolecular cycloaddition of azahexatrienes", J.C.S. Perkin I, (1977), 7, pp. 765-767.*
Fumio Yoneda et al., "Synthesis of pyrazolo(3,4-d)pyrimidines by intramolecular cycloaddition of azahexatrienes" STN International, file CAPLUS, CAPLUS accession No. 1977:468272, Document No. 87:68272; & J. Chem. Soc., Perkin Trans.1 (1977), (7), 765-7.
Gunther Schimpl et al.; "Allopurinol Reduces Bacterial Translocation, Intestinal Mucosal Lipid Peroxidation, and Neutrophil-Derived Myeloperoxidase Activity in Chronic Portal Hypertensive and Common Bile Duct-Ligated Growing Rats", Pediatric Research, vol. 40, No. 3, 1996, p. 422-428.
George L. Mendz et al., "Purine Metabolism and the Microaerophily of Helicobacter Pylori", Arch Microbiol, vol. 168, 1997, p. 448-456.
Vikram S. Patel et al., "Allopurinol absorption from differenct sites of the rat gastrointestinal tract", STN International, file CAPLUS, CAPLUS accession No. 1986:179711, Document No. 104:179711; & J. Pharm. Sci. (1986, 75(3), 275-7.

* cited by examiner

*Primary Examiner*—James O. Wilson
*Assistant Examiner*—Paul V. Ward

(57) ABSTRACT

Compounds having the general formula

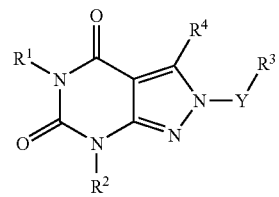

and pharmaceutical compositions containing them, and their use in the treatment or prophylaxis of *H. pylori* infection.

16 Claims, No Drawings

PYRAZOLO[3,4-D]PYRIMIDINES INHIBITING H. PYLORI INFECTIONS

RELATED APPLICATIONS

This application is the National Stage of International Application No. PCT/SE02/01303, filed Jun. 28, 2002, which claims the benefit under 35 U.S.C. § 119(a-d) of Application No. 0102315-9 filed in Sweden on Jun. 28, 2001.

BACKGROUND

*Helicobactor pylori* (*H. pylori*) is a highly motile, S-shaped, microaerophilic bacterium that colonizes in the gut. *H. pylori* infection is widespread with seroprevalence in the developed world between 30-60% (Everhart, 2000). Infection with the bacterium is usually contracted during childhood and patients remain infected for life unless treated. *H. pylori* infection has been shown to result in the development of gastritis, peptic ulcer, and mucosa-associated lymphoid tissue (MALT) lymphoma and has been linked to gastric adenocarcinoma (Go, 2000). Eradication of *H. pylori* infection is currently achieved using combination therapy of antimicrobial and antisecretory agents (Malfertheiner, 2000). However, compliance to these therapies is compromised due to adverse side effects and cumbersome dosing regimens. In addition, increasing prevalence of *H. pylori* strains resistant to existing antimicrobial therapies threatens to limit the use of these treatments (Qureshi, 2000; Graham, 2000). Given these considerations, an ideal therapy for *H. pylori* infection would be a novel (no existing resistance mechanisms), monotherapy antimicrobial that is selective for *H. pylori* eradication. The selectivity attribute is expected to aid in minimizing side effects due to gut sterilization.

*H. pylori*, like all Gram positive and Gram negative bacteria, utilize a cell wall comprised of crosslinked peptidoglycan units to maintain shape and resist high osmotic pressure potentials. Bacterial cell wall biosynthesis is a validated target for antibimicrobial activity; cephalosphorins, penicillins and glycopeptides are antimicrobial agents, which block cell wall biosynthesis (Walsh, 2000). Cell wall biosynthesis requires the enzyme MurI, a glutamate racemase, and therefore this enzyme is essential for bacterial viability (Doublet, 1993).

The present invention describes compounds, which specifically inhibit *H. pylori* MurI, compositions of such compounds and methods of use. The compounds disclosed herein represent a valuable contribution to the development of selective therapies directed to diseases resulting from *H. pylori* infection.

REFERENCES

1. Doublet, P., et al., *The murI gene of Escherichia coli is an essential gene that encodes a glutamate racemase activity*. Journal of Bacteriology, 1993, 175(10): p. 2970-9.
2. Everhart J. E., *Recent developments in the epidemiology of Helicobacter pylori*. Gastroenterology Clinics of North America, 2000, 29(3): p. 559-578.
3. Go, M. F. and D. T. Smoot, *Helicobacter pylori, gastric MALT lymphoma, and adenocarcinoma of the stomach*. Seminars in Gastrointestinal Disease, 2000, 11(3): p. 134-141.
4. Graham, D. Y., *Therapy of Helicobacter pylori: Current status and issues*. Gastroenterology, 2000,118(2 SUPPL): p. S2-S8.
5. Malfertheiner, P., A. Leodolter, and U. Peitz, *Cure of Helicobacter pylori-associated ulcer disease through eradication*. Bailiere's Best Practice and Research in Clinical Gastroenterology, 2000, 14(1): p. 119-132.
6. Qureshi, W. A. and D. Y. Graham, *Antibiotic-resistant H. pylori infection and its treatment*. Current Pharmaceutical Design, 2000, 6(15): p. 1537-1544.
7. Walsh, C., *Molecular mechanisms that confer antibacterial resistance*. Nature, 2000, 406: p. 775-781.

SUMMARY OF THE INVENTION

The present invention relates to compounds having the general formula

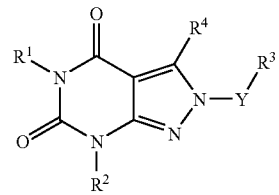

and pharmaceutical compositions containing them, and their use in the treatment or prophylaxis of *H. pylori* infection. Also included herein are pharmaceutically acceptable salts of said compounds.

More specifically, compounds of the present invention have the formula:

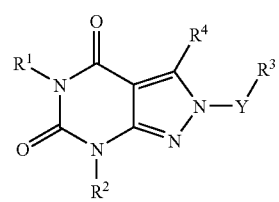

(I)

$R^1$ is H, —OH, optionally substituted alkyl optionally substituted alkenyl, optionally substituted alkynyl, optionally substituted cycloalkyl, optionally substituted cycloalkenyl, optionally substituted cycloalkynyl, optionally substituted aryl, optionally substituted alkoxy, amino, or optionally substituted heterocycle.

$R^2$ is H, optionally substituted alkyl, optionally substituted alkenyl, optionally substituted alkynyl, optionally substituted cycloalkyl, optionally substituted cycloalkenyl, optionally substituted cycloalkynyl, optionally substituted aryl, optionally substituted alkoxy, amino, or optionally substituted heterocycle;

$R^3$ is a monocyclic or bicyclic, saturated or unsaturated, ring system, which may contain from 5 to 12, preferably 5 to 10, ring atoms, 0, 1, 2 or 3 of which are heteroatoms independently selected from N, O, or S, the ring being substituted by 0, 1, 2 or 3 substituents selected from =O, halogen, —$OR^a$, $C_{1-6}$alkyl, $C_{1-6}$haloalkyl, —CN, nitro, —S(=O)$_n R^c$, —O(CH$_2$)$_m$Het, —O(CH$_2$)$_m$C(=O)Het, —O(CH$_2$)$_m$C(=O)NR$^a$R$^a$, —O(CH$_2$)$_m$C(=O)OR$^a$, —O(CH$_2$)$_m$NR$^a$R$^a$, —O(CH$_2$)$_m$OR$^a$, —S(CH$_2$)$_m$Het, —S(CH$_2$)$_m$C(=O)Het, —S(CH$_2$)$_m$C(=O)NR$^a$R$^a$, —S(CH$_2$)$_m$C(=O)OR$^a$, —S(CH$_2$)$_m$NR$^a$R$^a$, —S(CH$_2$)$_m$OR$^a$, —NHR$^a$, —NR$^a{}_2$, —NHC(=O)R$^a$, N=NR$^a$, aminocarbonyl, phenyl or benzyl; or $R^3$ is represented by, -Het, -Het-Het, $R^5,R^5$-Het, -Het-$R^5$, -Het-O—$R^5$, -phenyl-$R^5$ or -phenyl-OR$^5$.

$R^4$ is $C_{1-6}$alkyl, —NC$_{1-6}$alkyl, or —N(C$_{1-6}$alkyl)$_2$ wherein the $C_{1-6}$alkyl, —NC$_{1-6}$alkyl, —N(C$_{1-6}$alkyl)$_2$ are substituted by 0, 1 or 2 substituents selected from $R^a$, OR$^a$, halogen or phenyl provided however that $R^4$ is not —(CH$_2$)$_z$CH$_3$, —(CH$_2$)$_z$CH$_2$OH, —(CH$_2$)$_z$CO$_2$H, or —(CH$_2$)$_z$CO$_2$C$_{1-6}$alkyl wherein z is 1, 2, 3, 4, 5, or 6.

$R^4$ may also be represented by —(CH$_2$)$_n$phenyl-Het, —(CH$_2$)$_n$R$^d$, -Het, -Het-Het, $R^5$, —R$^5$-Het, -Het-R$^5$, -Het-O—R$^5$, -phenyl-R$^5$ or -phenyl-OR$^5$ or a monocyclic or bicyclic, saturated or unsaturated, ring system, or a vicinal-fused derivative thereof, which may contain from 5 to 12, preferably 5 to 10, ring atoms, 0, 1, 2, 3 or 4 of which are heteroatoms independently selected from N, O, or S, the ring system being substituted by 0, 1, 2 or 3 substituents selected from B(OH)$_2$, vicinal —OCH$_2$CH$_2$O—, vicinal —OC$_{1-2}$haloalkylO—, vicinal —OCH$_2$O—, vicinal —CH$_2$OCH$_2$O—, =O, halogen, —R$^b$OR$^a$, —SR$^a$, —OR$^a$, $C_{1-6}$alkyl, $C_{1-6}$haloalkyl, —CN, —S(=O)$_n$R$^c$, —O(CH$_2$)$_m$Het, —O(CH$_2$)$_m$C(=O)Het, —O(CH$_2$)$_m$C(=O)NR$^a$R$^a$, —O(CH$_2$)$_m$C(=O)OR$^a$, —O(CH$_2$)$_m$NR$^a$R$^a$, —O(CH$_2$)$_m$OR$^a$, —S(CH$_2$)$_m$Het, —S(CH$_2$)$_m$C(=O)Het, —S(CH$_2$)$_m$C(=O)NR$^a$R$^a$, —S(CH$_2$)$_m$C(=O)OR$^a$, —S(CH$_2$)$_m$NR$^a$R$^a$, —S(CH$_2$)$_m$OR$^a$, —NHR$^a$, —NR$^a_2$, —NHC(=O)R$^a$, N=NR$^a$, NO$_2$, —C(=O)NR$^a$R$^a$, —C(=O)NR$^a$OR$^a$, —C(=O)NR$^a$R$^b$NR$^a$R$^a$, —C(=O)NR$^a$R$^b$OR$^a$, —C(=O)NR$^a$R$^b$S(=O)$_n$R$^a$, —C(=O)NR$^a$R$^b$Het, —C(=O)OR$^a$, —OC(=O)R$^a$, —C(=O)OR$^b$NR$^a$R$^a$, —C(=O)R$^a$, —C(=O)R$^b$NR$^a$R$^a$, —C(=NOR$^a$)R$^a$, —C(=NCN)R$^a$, —S(=O)$_2$NR$^a$R$^a$, —NR$^a$S(=O)$_2$R$^a$, —S(=O)$_2$NR$^a$R$^b$C(=O)NR$^a$R$^a$, —S(=O)$_2$NR$^a$R$^b$C(=O)OR$^a$, aminocarbonyl, phenyl or benzyl.

$R^5$ is independently at each instance, phenyl substituted by 0, 1, 2, or 3 groups selected from halogen, $C_{1-6}$haloalkyl, —OC$_{1-6}$haloalkyl, $C_{1-6}$alkyl, —CN, nitro, —OH, —OR$^c$, —S(=O)$_n$R$^c$, —O(CH$_2$)$_m$Het, —O(CH$_2$)$_m$C(=O)Het, —O(CH$_2$)$_m$C(=O)NR$^a$R$^a$, —O(CH$_2$)$_m$C(=O)OR$^a$, —O(CH$_2$)$_m$NR$^a$R$^a$, —O(CH$_2$)$_m$OR$^a$, —S(CH$_2$)$_m$Het, —S(CH$_2$)$_m$C(=O)Het, —S(CH$_2$)$_m$C(=O)NR$^a$R$^a$, —S(CH$_2$)$_m$C(=O)OR$^a$, —S(CH$_2$)$_m$NR$^a$R$^a$, —S(CH$_2$)$_m$OR$^a$, —R$^b$OR$^a$, —SR$^a$, —C(=O)NR$^a$R$^a$, —C(=O)NR$^a$OR$^a$, —C(=O)NR$^a$R$^b$NR$^a$R$^a$, —C(=O)NR$^a$R$^b$OR$^a$, —C(=O)NR$^a$R$^b$S(=O)$_n$R$^a$, —C(=O)NR$^a$R$^b$Het, —C(=O)OR$^a$, —OC(=O)R$^a$, —C(=O)OR$^b$NR$^a$R$^a$, —C(=O)R$^a$, —C(=O)R$^b$NR$^a$R$^a$, —C(=NOR$^a$)R$^a$, —C(=NCN)R$^a$, —S(=O)$_2$NR$^a$R$^a$, —NR$^a$S(=O)$_2$R$^a$, —S(=O)$_2$NR$^a$R$^b$C(=O)NR$^a$R$^a$, or —S(=O)$_2$NR$^a$R$^b$C(=O)OR$^a$.

$R^a$ is, independently at each instance, H, $C_{1-6}$alkyl, —C(=O)C$_{1-4}$alkyl, $C_{1-4}$haloalkyl, —(CH$^2$)$_q$—, phenyl, benzyl, or 5 or 6-membered ring, saturated or unsaturated heterocycle containing 1 2, 3, or 4 heteroatoms independently selected from N, O or S and wherein q is 0, 1, 2, 3, 4, 5 or 6.

$R^b$ is, independently at each instance $C_{1-6}$alkyl, —C(=O)C$_{1-4}$alkyl, $C_{1-4}$haloalkyl, —(CH$^2$)$_q$—, phenyl, benzyl, or 5 or 6-membered ring, saturated or unsaturated heterocycle containing 1, 2, 3, or 4 heteroatoms independently selected from N, O or S and wherein q is 0, 1, 2, 3, 4, 5 or 6.

$R^c$ is $C_{1-6}$alkyl, $C_{1-4}$haloalkyl phenyl or benzyl.

$R^d$ is phenyl substituted by 0, 1 2 or 3 groups selected from —CN, halogen, nitro, $C_{1-6}$alkyl, $C_{1-4}$haloalkyl, —OH, —OR$^c$, —NR$^a$R$^b$, —S(=O)$_n$R$^c$, —C(=O)Ra, —S(=O)NR$^a$R$^b$, —C(=O)NR$^a$R$^a$, —C(=O)OR$^a$, —NR$^a$C(=O)R$^a$, —OC(=O)R$^a$, B(OH)$_2$, vicinal —OCH$_2$CH$_2$O—, vicinal —OC$_{1-2}$haloalkylO—, vicinal —OCH$_2$O—, vicinal —CH$_2$OCH$_2$O—, phenyl, benzyl or a 5- or 6-membered ring, saturated or unsaturated heterocycle containing 1, 2, 3 or 4 heteroatoms independently selected from N, O, or S.

Y is CH$_2$, CHCH$_3$, S(=O) or S(=O)$_2$.

m is 1, 2 or 3.

n is 0, 1 or 2.

Het, unless otherwise defined, is a 5- or 6-membered ring, saturated or unsaturated heterocycle containing 1, 2, 3 or 4 heteroatoms independently selected from N, O, or S, and substituted by 0, 1 2 or 3 substituents selected from halogen, —(CH$_2$)$_n$R$^d$ $C_{1-4}$alkyl, —S(=O)$_n$R$^c$—C(=O) R$^a$, or (=C)$_2$ NR$^a$R$^a$ vicinal —OCH$_2$CH$_2$O—, vicinal —OC$_{1-2}$haloalkylO—, vicinal —OCH$_2$O—, or vicinal —CH$_2$OCH$_2$O—, =O, halogen, cyano, —R$^b$OR$^a$, —R$^b$-SR$^a$, —SR$^a$, —OR$^a$, $C_{1-6}$alkyl, $C_{1-6}$haloalkyl, —CN, nitro, —OH, —NHR$^a$, —NR$^a_2$, —NHC(=O)R$^a$, N=NR$^a$, —C(=O)NR$^a$R$^a$, —C(=O)NR$^a$OR$^a$, —C(=O)NR$^a$R$^b$NR$^a$R$^a$, —C(=O)NR$^a$R$^b$OR$^a$, —C(=O)NR$^a$R$^b$S(=O)$_n$R$^a$, —C(=O)NR$^a$R$^b$Het, —C(=O)OR$^a$, —OC(=O)R$^a$, —C(=O)OR$^b$NR$^a$R$^a$, —C(=O)R$^b$NR$^a$R$^a$, —C(=NOR$^a$) R$^a$, —C(=NCN)R$^a$, —NR$^a$S(=O)$_2$R$^a$, —S(=O)$_2$NR$^a$R$^b$C(=O)NR$^a$R$^a$, —S(=O)$_2$NR$^a$R$^b$C(=O)OR$^a$.

DETAILED DESCRIPTION

In a further aspect of the invention, $R^1$ may also be represented by $C_{1-6}$alkyl, wherein it is optionally substituted by 1 or 2 substituents selected from halogen, —OR$^a$, —NR$^a$R$^a$, —C(=O)OR$^a$, —C(=O)NR$^a$R$^a$, —OC(=O)C$_{1-4}$alkyl or —NR$^a$C(=O)C$_{1-4}$alkyl. In an additional embodiment, $R^1$ is Het-C$_{1-3}$alkyl-, R$^d$-(CH$_2$)$_n$— or —C$_{1-6}$alkyl that is substituted by 1 or 2 substituents selected from halogen, —OR$^a$, —NR$^a$R$^a$, —C(=O)OR$^a$, —C(=O)NR$^a$R$^a$, —OC(=O)C$_{1-4}$alkyl or —NR$^a$C(=O)C$_{1-4}$alkyl.

When $R^1$ is represented by an optionally substituted alkyl it is preferably methyl or ethyl wherein the preferred substituent is an optionally substituted 5 or 6-membered heterocyclic ring. The heterocyclic rings may include for example thiophene, furan, pyrrole, triazole, diazole, imidazole, oxazole, thiazole, oxodiazole, isothiazole, isoxazole, thiadiazole, pyridine, pyrimidine, pyrrolidine and pyrazine. The heterocyclic rings can be linked to the remainder of the molecule via any suitable carbon atom, or, when present, a nitrogen atom. The preferred heterocyclic rings include, but are not limited to, imidazole (preferably attached to a carbon atom on the ring), piperidine (preferably attached to the nitrogen atom on the ring), methylpiperidine (preferably attached to a carbon atom on the ring), morpholine (preferably attached at the nitrogen).

In an additional embodiment, $R^2$ is —C$_{1-3}$alkyl-C(=O)R$^a$; —C$_{1-3}$alkyl-C(=O)OR$^a$; —C$_{1-3}$alkyl-C(=O)NR$^a$R$^a$; —C$_{1-3}$alkyl-S(=O)$_n$R$^c$; Het-C$_{1-3}$alkyl-; R$^5$—C$_{1-3}$alkyl-; or $C_{1-12}$alkyl substituted with 0, 1, 2 or 3 substituents selected from —OH, halogen, —CN, —OR$^a$, —NR$^a$R$^a$ and —SR$^c$.

In a further embodiment, $R^2$ is Het-C$_{1-3}$alkyl-; R$^5$—C$_{1-3}$alkyl-; $C_{1-6}$alkyl substituted with 0, 1 or 2 substituents selected from —OH, halogen, —CN, —OR$^a$, —NR$^a$R$^a$ and SR$^c$. In another aspect of the invention, $R^2$ is —CH$_2$ CH$_2$ CH$_3$, —CH$_2$-cyclopropyl, —CH$_2$ CH(CH$_3$)$_2$, —CH$_2$ CH$_2$ CH$_2$F, CH$_2$-cyclobutyl, —CH$_2$C(CH$_3$)$_3$, —CH$_2$CH$_2$ CH(CH$_3$)$_2$, —CH$_2$ CF$_3$, —CH$_2$-phenyl (preferably ortho substituted with —CH$_3$,) —CH$_2$-phenyl (preferably para substituted with —OH), CH$_2$-isoxazolyl (preferably dimethyl), —CH$_2$—S-phenyl, —CH$_2$-phenylcarboxyl, or —CH$_2$SCF$_3$ In another aspect of the invention, R³ is preferably represented by (* indicates the point of attachment to the Y group) formulas (i) or (ii):

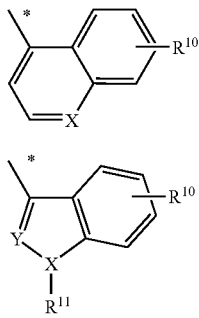

R¹¹ is optionally substituted alkyl and optionally substituted —S(=O)NRᵃRᵃ and S(=O)n, n=1 or 2. X and Y are independently C, N, S or O provided that when R⁴ is represented by Formula (i), X is not S or O and when R⁴ is represented by Formula (ii) X and Y are not simultaneously C, S, or O, or X and Y are not S and O respectively or vice versa R¹⁰ is, at any position on the bicyclic ring, H, optionally substituted C₁₋₆alkyl, halogen, —CN, nitro, —CF₃, or —S(=O)₂CH₃.

In an additional embodiment, R³ is napth-1-yl, quinolin-4-yl, indol-3-yl, indazol-3-yl, or benzothien-3-yl, any of which is substituted by 0, 1, 2 or 3 substituents selected from —ORᵃ, halogen and C₁₋₄alkyl, —C₁₋₄haloalkyl.

In another aspect of the invention R⁴ is —(CH₂)ₙphenyl, wherein the phenyl is substituted by 0, 1, 2 or 3 groups selected from —CN, nitro, C₁₋₆alkyl, halogen, C₁₋₄haloalkyl, —OH, —ORᶜ, —NRᵃRᵃ, —S(=O)ₙRᶜ, —C(=O)NRᵃRᵃ, —C(=O)ORᵃ, —NRᵃC(=O)Rᵃ, —OC(O)Rᵃ, B(OH)₂, vicinal —OCH₂CH₂O—, vicinal —OC₁₋₂haloalkylO—, vicinal —OCH₂O—, vicinal —CH₂OCH₂O—, phenyl or benzyl.

Additionally, R⁴ is a saturated or unsaturated 5- or 6-membered heterocyclic ring, or a vicinal-fused benzo derivative thereof, containing 1, 2, 3 or 4 heteroatoms independently selected from N, O, or S, wherein the not more than one of the heteroatoms is S or O, and the ring is substituted by 0, 1 or 2 groups selected from —CN, nitro, C₁₋₆alkyl, C₁₋₄haloalkyl, —OH, —ORᶜ, —NRᵃRᵃ, —S(=O)ₙRᶜ, —S(=O)₂NRᵃ₂, —C(=O)NRᵃRᵃ, —C(=O)ORᵃ, —NRᵃC(=O)Rᵃ, —OC(=O)Rᵃ, B(OH)₂, vicinal —OCH₂CH₂O—, vicinal —OC₁₋₂haloalkylO—, vicinal —OCH₂O—, vicinal —CH₂OCH₂O—, phenyl and benzyl.

When R⁴ is represented by a heterocyclic ring system having a vicinal fused derivative as defined above, it may be a vicinal fused benzo derivative thereof In another aspect of the invention, R⁴ is represented by formulas a, b, c, d, e, f, g, h, i, j, k, l, m or n as follows (* indicates the point of attachment to the ring system):

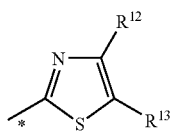

(a)

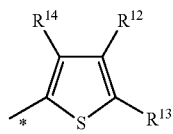

(b)

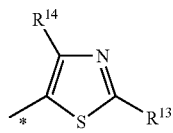

(c)

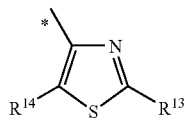

(d)

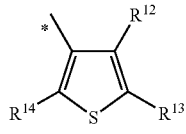

(e)

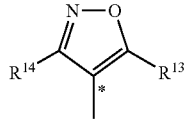

(f)

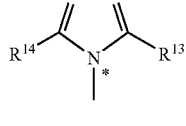

(g)

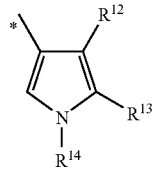

(h)

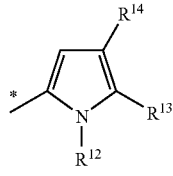

(i)

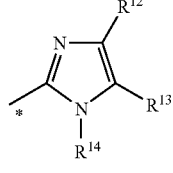

(j)

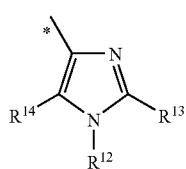

(k)

-continued

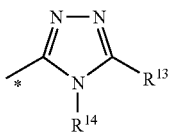
(l)

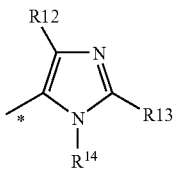
(m)

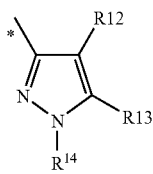
(n)

In another aspect of the invention, $R^4$ may additionally be represented by formulas o-r as follows (* indicates the point of attachment to the ring system):

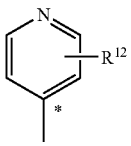
(o)

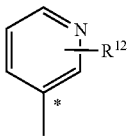
(p)

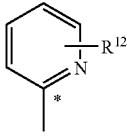
(r)

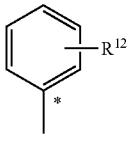
(r)

wherein $R^{12}$, $R^{13}$ and $R^{14}$ are each independently represented by H, $C_{1-6}$alkyl, —CN, —$NR^aR^a$, -nitro, —C(=O)$R^a$, —C(=O)$NR^a$, —C(=O)$NR^aR^a$, —C(=O)$NR^aS(=O)_2$ $R^a$, —C(=O)$NR^a$-Het, —C(=O)$NR^aN$, —C(=O)$NR^aNR^a$, —C(=O)$NR^aR^bNR^a_2$, —C(=O)$NR^aR^bNR^aR^a$, C(=O)$NR^aR^bOR^a$, —C(=O)$NR^aR^bS(=O)_2R^a$, —C(=O) $NR^aR^bHet-C(=O)NR^aO$, —C(=O)$NR^aOR^a$, —C(=O) $NOR^a$, 13 C(=O) $R^bNR^a$, —C(=O)$R^aN_2R^a$, —C(=O) $R^bNR^aR^a$, —C(NOR$^a$) $R^a$, —C(=NCN)$R^a$, —C(=O)$OR^a$, —C(=O)$OR^bNR^a$, —C(=O)$OR^bNR^aR^a$, —C(=O) $R^a$, —C(=O)$OR^bNR^aR^a$. —OC(=O)$R^a$, —C(=O) $R^a$—$SR^a$, =S, —NC(=O)$R^a$, —NC(=O)$OR^a$, —NS(=O)$_2$ $R^aR^b$, —$NR^bS(=O)_2$_$R^a$, C(=NO)$R^a$ —C(=NOR$^a$)$R^a$, —S(=O)$_2$ $R^a$, —S(=O)$_2N$ $R^a$, —S(=O)$_2NR^aR^a$, —S(=O)$^2NR^b$ C(=O)$NR^aR^a$, —S(=O)$_2NR^aR^bC$(=O) $OR^a$, —S(=O)$_2NR^aC$(=O)O,— and —C(=NCN) $R^a$.

In an additional embodiment for formulas b-e, b, j, l, m, and n, when $R^{12}$, $R^{13}$ or $R^{14}$ is a 5-, or 6-membered saturated or unsaturated ring, it is preferably a piperizine, pyridine, tetrazole, imidazole, or morpholine ring.

In formulas a-n, when $R^{14}$ is represented $C_{1-6}$alkyl, it is preferably represented by methyl, ethyl, propyl, butyl, isopropyl, and isobutyl, most preferably methyl.

Informula b, $R^{12}$ and $R^{13}$ are preferably represented by H and $R^{14}$ is preferably represented by $C_{1-6}$alkyl, preferably, methyl, ethyl, propyl, butyl, isopropyl, isobutyl, or t-butyl.

When $R^{12}$ or $R^{13}$ is represented by —C(=O)$R^a$, —C(=O)O $R^a$, —C(O) $R^a$, —S $R^a$, S(=O) $R^a$, —C(=O)N $R^a$, —C(=O)NO $R^a$, —NC(=O) $R^a$, $R^a$ is preferably $C_{1-6}$alkyl, most preferably, methyl, ethyl, butyl, isopropyl, cyclopropyl, or isobutyl.

When the expression "optionally substituted" is used above, it is meant that the substituent referred to is optionally substituted and the substituent is preferably selected from halogen, nitro, cyano, hydroxy, trifluoromethyl, amino, carboxy, carboxamido, amidino, carbamoyl, mercapto, sulfamoyl, $C_{1-4}$ alkyl, $C_{2-4}$ alkenyl, $C_{2-4}$ alkynyl, $C_{1-4}$ alkoxy, $C_{1b-4}$ alkanoyl, $C_{1-4}$ alkanoyloxy, N-($C_{1-4}$ alkyl), N($C_{1-4}$ alkyl)$_2$, $C_{1-4}$ alkanoylamino, ($C_{1-4}$ alkanoyl)$_2$amino, N-($C_{1-4}$ alkyl)carbamoyl, N,N-($C_{1-4}$ alkyl)$_2$carbamoyl, ($C_{1-4}$)S, ($C_{1-4}$ alkyl)S(O), ($C_{1-4}$alkyl)S(O)$_2$, ($C_{1-4}$) alkoxycarbonyl, N-($C_{1-4}$ alkyl)sulfamoyl, N,N-$C_{1-4}$ alkyl)sulfamoyl, $C_{1-4}$ alkylsolfonylamino, phenyl, and heterocyclic.

The term "hydrocarbyl" refers to any structure comprising only carbon and hydrogen atoms up to 14 carbon atoms.

The term "alkyl" used alone or as a suffix or prefix, refers to straight or branched chain hydrocarbyl radicals comprising 1 to about 12 carbon atoms.

The term "alkenyl" refers to straight or branched chain hydrocarbyl radicals having at least one carbon-carbon double bond and comprising at least 2 up to about 12 carbon atoms.

The term "alkynyl" refers to straight or branched chain hydrocarbyl radicals having at least one carbon-carbon triple bond and comprising at least 2 up to about 12 carbon atoms.

The term "cycloalkyl" refers to ring-containing hydrocarbyl radicals comprising at least 3 up to about 12 carbon atoms.

The term "cycloalkenyl" refers to ring-containing hydrocarbyl radicals having at least one carbon-carbon double bond and comprising at least 3 up to about 12 carbon atoms.

The term "cycloalkynyl" refers to ring-containing hydrocarbyl radicals having at least one carbon-carbon triple bond and comprising about 7 up to about 12 carbon atoms.

The term "aromatic" refers to hydrocarbyl radicals having one or more polyunsaturated carbon rings having aromatic character, (e.g., 4n+2 delocalized electrons) and comprising 6 up to about 14 carbon atoms.

The term "aryl" refers to aromatic radicals including both monocyclic aromatic radicals comprising 6 carbon atoms and polycyclic aromatic radicals comprising up to about 14 carbon atoms.

The term "alkylene" refers to divalent alkyl moieties, wherein said moiety serves to link two structures together.

The term "heterocycle", "heterocyclic" or "heterocyclyl" refers to ring-containing monovalent and divalent radicals having one or more heteroatoms, independently selected from N, O and S, as part of the ring structure and comprising at least 3 and up to about 20 atoms in the rings preferably 5 and 6 membered rings. Heterocyclic moieties may be saturated or unsaturated, containing one or more double bonds, and heterocyclic moieties may contain more than one ring.

The term "heteroaryl" refers to heterocyclic monovalent and divalent radicals having aromatic character.

Heterocyclic, heterocycle or heterocyclyl compounds include for example monocyclic moieties such as: aziridine, oxirane, thiirane, azetidine, oxetane, thietane, pyrrolidine, pyrroline, imidazolidine, pyrazolidine, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide. In addition heterocyclic moieties include heteroaryl rings such as: pyridine, pyrazine, pyrimidine, pyridazine, thiene, furanl, pyrrole, imidazole, thiazole, oxazole, pyrazole, isothiazole, isoxazole, 1,2,3-triazole, tetrazole1, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4 oxadiazole. Additionally, heterocyclic moieties encompass polycyclic moieties such as: indazole, indole, indoline, quinoline, tetrahydroquinoline, isoquinoline, tetrahydroisoquinoline, 1,4-benzodioxan, coumarin, dihydrocoumarin, benzofuran, 2,3-dihydrobenzofuran, 1,2-benzisoxazole, benzothiophene, benzoxazole, benzthiazole, benzinidazole, benztriazole, thioxanthine, carbazole, carboline, acridine, pyrolizidine, and quinolizidine.

In addition to the polycyclic heterocycles described above, heterocyclic or heterocycle compounds include polycyclic heterocyclic moieties wherein the ring fusion between two or more rings comprises more than one bond common to both rings and more than two atoms common to both rings. Examples of such bridged heterocycles include quinuclidine, diazabicyclo[2.2.1]heptane and 7-oxabicyclo[2.2.1]heptane.

The term "halo" or "halogen" refers to fluorine, chlorine, bromine and iodine radicals.

The term "alkoxy" refers to radicals of the general formula —O—R, wherein R is selected from a hydrocarbyl radical. Examples of alkoxy moieties include methoxy, ethoxy, propoxy, isopropoxy, butoxy, t-butoxy, isobutoxy, cyclopropylmethoxy, allyloxy, and propargyloxy.

The term amine or amino refers to radicals of the general formula —NRR', wherein R and R' are independently selected from hydrogen or a hydrocarbyl radical.

Processes for making compounds of formula 1 are provided as further embodiments of the invention. Also provided are novel intermediates represented by formulas, Ia, Ib, Ic, Id, Ie, and If.

In an aspect of the invention, intermediate compounds of formula Ib may be formed by reacting a compound of formula Ia with a dicarboxylic acid, acetic anhydride and acetic acid mixing with heat for about 3 hours and then cooled:

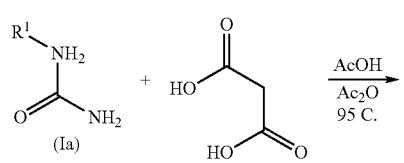
(Ia)

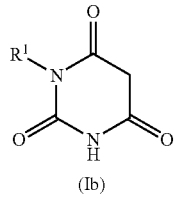
(Ib)

Unless otherwise specified or defined, $R^1$, $R^2$, $R^3$, $R^4$ are as defined above. Intermediate Ic may be formed by for example reacting a compound of Ib with for example a chlorinating compound such asphosphorous oxychloride, sometimes with small amounts of water and refluxed for about an hour and then cooled:

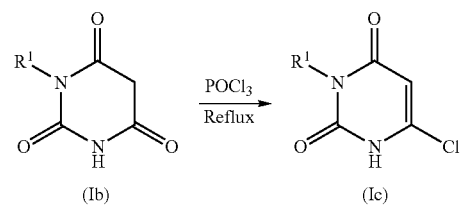

Intermediate Id may be formed by reacting a compound of formula Ic with $R^2$—X in a solvent such as DMF and a base such as $K_2CO_3$, with heat as set forth below:

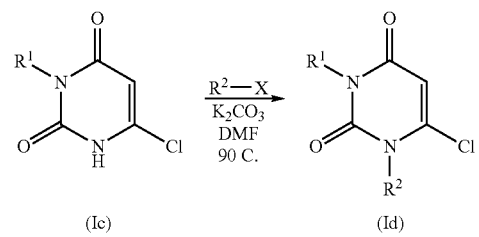

Intermediate Id also can be synthesized by using an alternate approach as shown below.

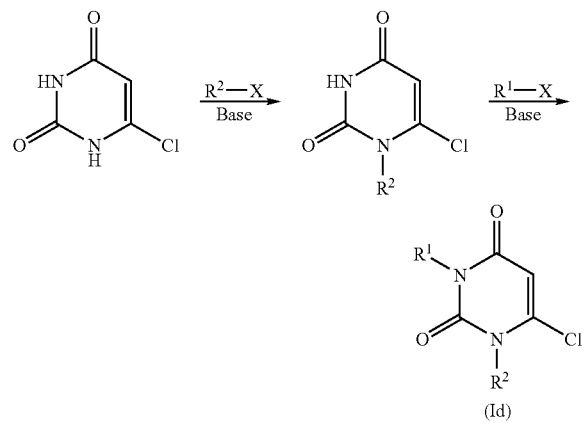

wherein X is a leaving group such as a halogen, mesylate, or tosylate.

An intermediate compound of formula Ie may be formed by reacting a compound of Formula Id with NH$_2$NH$_2$H$_2$O in a solvent such as ethanol and refluxed as follows:

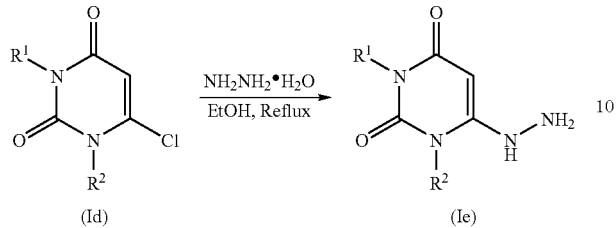

(Id)  (Ie)

Intermediate compound of Formula If may be formed by reacting a compound of formula Ie with R$^3$—CHO in a solvent such as Methanol as follows:

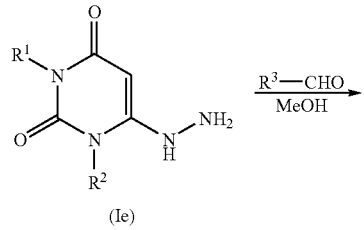

(Ie)

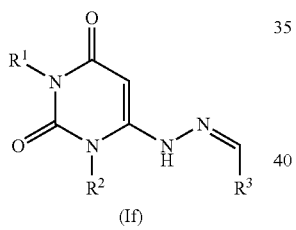

(If)

In another aspect of the invention, compounds of formula I may by formed by reaction of compounds of formula If with R$^4$—CHO in a polar protic or aprotic solvent such as DMF, DMSO, ethanol or acetic acid. The conversion of 1f to a compound of the present invention, represented by formula II, may be accelerated by addition of an amine catalyst such as piperidine or triethylamine, or a salt catalyst such as piperidinium acetate or sodium acetate. Reaction temperatures may range between 60° C. and 180° C.

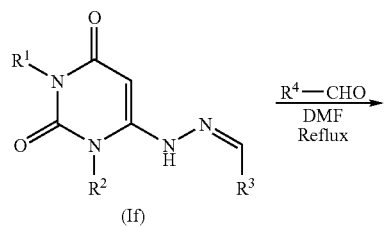

(If)

-continued

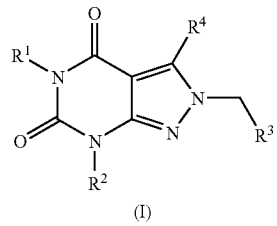

(I)

Another aspect of the invention involves the manufacture of a medicament for the treatment or prophylaxis of *H. pylori* infection comprising a compound included in any of the above embodiments.

Another aspect of the invention involves the use of a compound included in any of the above embodiments for the treatment or prophylaxis of *H. pylori* infection.

Another aspect of the invention involves a pharmaceutical composition for the treatment or prophylaxis of *H. pylori* infection, comprising: a therapeutically-effective amount of a compound included in any of the above embodiments; and a pharmaceutically-acceptable diluent or carrier.

Particular compounds of this invention are provided as the Examples herein below. C$_{Y-Z}$alkyl, unless otherwise specified, means an alkyl chain containing a minimum Y total carbon atoms and a maximum Z total carbon atoms. These alkyl chains may be branched or unbranched, cyclic, acyclic or a combination of cyclic and acyclic. For example, the following substituents would be included in the general description "C$_{4-7}$alkyl":

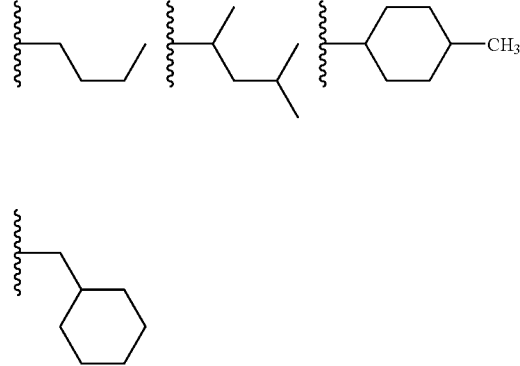

C$_{Y-Z}$haloalkyl, unless otherwise specified, means an alkyl group, as described above, wherein any number of the hydrogen atoms usually present on the alkyl are replaced with halogen atoms.

Pharmaceutically-acceptable salts may be prepared from the corresponding acid in conventional manner. Non-pharmaceutically-acceptable salts may be useful as intermediates and as such are another aspect of the present invention.

The term "oxo" means, a double bonded oxygen (═O).

Some of the compounds of the present invention are capable of forming salts with various inorganic and organic acids and bases and such salts are also within the scope of this invention. Examples of such acid addition salts include acetate, adipate, ascorbate, benzoate, benzenesulfonate, bisulfate, butyrate, camphorate, camphorsulfonate, citrate, cyclohexyl sulfamate, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, 2-naphthalenesulfonate, nitrate, oxalate, pamoate, persulfate, phenylacetate, phosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Base salts include ammonium salts, alkali metal salts such as sodium, lithium and potassium salts, alkaline earth metal salts such as aluminum, calcium and magnesium salts, salts with organic bases such as dicyclohexylamine salts, N-methyl-D-glucamine, and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates like dimethyl, diethyl, dibutyl; diamyl sulfates; long chain halides such as decyl, lauryl, myristyl and stearyl halides; aralkyl halides like benzyl bromide and others. Non-toxic physiologically-acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

In order to use a compound of the formula (I) or a pharmaceutically acceptable salt thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition, which comprises a compound of the formula (I) or a pharmaceutically acceptable salt and pharmaceutically acceptable carrier.

The pharmaceutical compositions of this invention may be administered in a standard manner for the disease condition that it is desired to treat, for example by oral, topical, parenteral, buccal, nasal, vaginal or rectal administration or by inhalation or insufflation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

In addition to the compounds of the present invention, the pharmaceutical composition of this invention may also contain, or be co-administered (simultaneously or sequentially) with, one or more pharmacological agents of value in treating one or more disease conditions referred to herein.

The pharmaceutical compositions of this invention will normally be administered to humans so that, for example, a daily dose of 0.01 to 25 mg/kg body weight (and preferably of 0.1 to 5 mg/kg body weight) is received. This daily dose may be given in divided doses as necessary, the precise amount of the compound received and the route of administration depending on the weight, age and sex of the patient being treated and on the particular disease condition being treated according to principles known in the art Typically unit dosage forms will contain about 1 mg to 500 mg of a compound of this invention. For example a tablet or capsule for oral administration may conveniently contain up to 250 mg (and typically 5 to 100 mg) of a compound of the formula (I) or a pharmaceutically acceptable salt thereof. In another example, for administration by inhalation, a compound of the formula (I) or a pharmaceutically acceptable salt thereof may be administered in a daily dosage range of 5 to 100 mg, in a single dose or divided into two to four daily doses. In a further example, for administration by intravenous or intramuscular injection or infusion, a sterile solution or suspension containing up to 10% w/w (and typically 5% w/w) of a compound of the formula (I) or a pharmaceutically acceptable salt thereof may be used.

The compounds of the formula (I) and their pharmaceutically acceptable salts may be made by processes as described and exemplified herein and by processes similar thereto and by processes known in the chemical art. If not commercially available, starting materials for these processes may be made by procedures, which are selected from the chemical art using techniques which are similar or analogous to the synthesis of known compounds.

Some individual compounds within the scope of this invention may contain double bonds. Representations of double bonds in this invention are meant to include both the E and the Z isomer of the double bond. Additionally, some species within the scope of this invention may contain one or more asymmetric centers. This invention includes the use of any of the optically pure stereoisomers as well as any combination of stereoisomers.

The following biological test methods, data and Examples serve to illustrate and further describe the invention.

The utility of a compound of the invention or a pharmaceutically acceptable salt thereof (hereinafter, collectively referred to as a "compound") may be demonstrated by standard tests and clinical studies, including those disclosed in the publications described below.

Glutamate Racemase Activity Assay:

Glutamate racemase (MurI) activity was assayed by measuring the conversion of glutamate from D to L enantiomer. This reaction was coupled to the reduction of $NAD^+$ to NADH by L-glutamate dehydrogenase (LGDH). LGDH from bovine liver was obtained as a lyophilized powder (Sigma #G-7882) and dissolved in 10 mM Tris (Sigma #T-6791), pH 7.5, buffer containing 0.1 mM EDTA (Fisher #BP118-500) and 50% glycerol (Sigma #G-9012). The assay mixture consisted of 100 mM Tris-HCl, pH 8.0, 10 mM β-NAD (Sigma #N-7004), 5 mM DTT (Sigma #D-5545), 0.03% PEG (mw 8000, Sigma #P-5413), 0.03 mg/mL BSA (Pierce #23210), 15 U/mL LGDH, D-glutamate (Fluka #49460), and purified MurI. The following MurI concentrations were used: 1000 nM *H. pylori* MurI, 0.7 nM *E. faecalis* MurI, or 0.4 nM *E. coli* MurI. In the case of *E. coli* MurI 14 µM UDP-MurNAc-Ala was also added. The final concentration of D-glutamate added for *H. pylori* MurI was 40 µM, and the other orthologs used 1 mM D-glutamate. The assay was performed in 96-well black microtiter plates (Greiner #XN2-9511) with a final assay volume of 100 µL. Compounds were prepared (x) Mass spectra (MS) were run using an automated system with atmospheric pressure electrospray ionization (ESI). Generally, only spectra where parent masses are observed are reported. The lowest mass major ion is reported for molecules where isotope splitting results in multiple mass spectral peaks (for example when chlorine is present).

Terms and abbreviations: solvent mixture compositions are given as volume percentages or volume ratios. In cases where the NMR spectra are complex, only diagnostic signals are reported. atm=atmospheric pressure, Boc=t-butoxycarbonyl, Cbz=benzyloxycarbonyl, DCM=methylene chloride, DIPEA=diisopropylethylamine, DMF=N,N-dimethylformamide, DMSO=dimethyl sulfoxide, Et$_2$O=diethyl ether, EtOAc=ethyl acetate, equiv.=equivalent(s), h=hour(s), PLC=high performance liquid chromatography, mm=minutes, NMR=nuclear magnetic resonance, psi=pounds per square inch, TFA=trifluoroacetic acid, THP=tetrahydrofuran.

EXAMPLE 1

N-{4-[7-isobutyl-5-methyl-2-(1-naphthylmethyl)-4,6-dioxo-4,5,6,7-tetrahydro-2H-pyrazolo[3,4-d]pyrimidin-3-yl]phenyl}acetamide

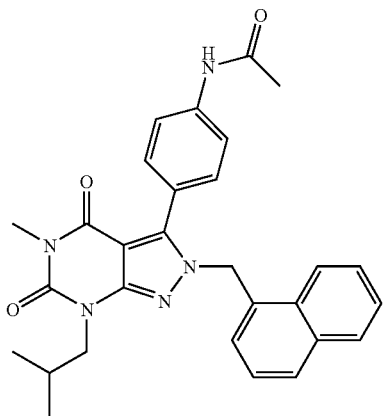

(a) 1-Methylpyrimidine-2,4,6(1H,3H,5H)-trione

Acetic anhydride (34 ml) was added to a solution of malonic acid (20 g) and methylurea (12.5 g) in acetic acid (46 ml). The mixture was heated to 95° C. for 3 hours then cooled to room temperature. The resulting solution was concentrated under reduced pressure and the residue as 20 mM stock solutions in dimethyl sulphoxide (DMSO, Sigma #D-5879) and serial dilutions were prepared from these solutions using DMSO, 2 µL of which were added to the wells. Activity at room temperature was measured by monitoring the increase in fluorescence using a TECAN Ultra platereader with 340 nm excitation and 465 nm emission filters. The compounds provided have measured IC50 of less then 400 µM The expression use in the below examples "was made following the procedure describe above" refers generally the to process steps above and other examples where necessary.

EXAMPLES

The invention will now be illustrated by the following non-limiting examples, in which, unless stated otherwise:
(i) temperatures are given in degrees Celsius (° C.); unless otherwise stated, operations were carried out at room or ambient temperature, that is, at a temperature in the range of 18-25° C.;
(ii) organic solutions were dried over anhydrous magnesium sulfate or sodium sulfate; evaporation of solvent was carried out using a rotary evaporator under reduced pressure (600-4000 Pascals; 4.5-30 mm Hg) with a bath temperature of up to 60° C.;
(iii) chromatography means flash chromatography on silica gel; thin layer chromatography (TLC) was carried out on silica gel plates;
(iv) in general, the course of reactions was followed by TLC or analytical HPLC and reaction times are given for illustration only;
(v) melting points are uncorrected and (dec) indicates decomposition;
(vi) final products had satisfactory proton nuclear magnetic resonance (NMR) spectra;
(vii) when given, NMR data is in the form of delta values for major diagnostic protons, given in parts per million (ppm) relative to tetramethylsilane (TMS) as an internal standard, determined at 500 MHz using deuterated chloroform (CDCl$_3$) or DMSO-d$_6$/CD$_3$OD as solvent; conventional abbreviations for signal shape are used; for AB spectra the directly observed shifts are reported; coupling constants (J) are given in Hz; Ar designates an aromatic proton when such an assignment is made;
(viii) reduced pressures are given as absolute pressures in pascals (Pa); elevated pressures are given as gauge pressures in bars;
(ix) solvent ratios are given in volume:volume (v/v) terms; and was taken into ethanol (50 ml) and stirred vigorously. The precipitated solid was filtered and washed with ether. The solid was recrystallized in warm water to give the sub-title compound (6.6 g) as a solid. Mass: 140.91 (M–H).

(b) 6-Chloro-3-methylpyrimidine-2,4[1H,3H]-dione

1-Methylpyrimidine-2,4,6(1H,3H,5H)-trione (3 g) was suspended in phosphorus oxychloride (70 ml). Water (0.6 ml) was added and the mixture was heated at reflux for 1 hour. The reaction was allowed to cool and was then concentrated under reduced pressure. The residue was poured onto a mixture of ice and water (60 ml). The precipitated solid was collected, washed with water and dried to give the sub-title compound (2.2 g). Mass: 158.87 (M–H).

(c) 6Chloro-1-isobutyl-3-methylpyrimidine-2,4(1H,3H)-dione

3-Iodo-2-methylpropane (4.6 g) and potassium carbonate (8.62 g) were added to a solution of 6-Chloro-3-methylpyrimidine-2,4[1H,3H]-dione (2.0 g) in dimethylformamide (10 ml). The mixture was heated at 90° C. for 18 hours then cooled to room temperature. The solution was diluted with 5% aqueous HCl solution until solution becomes acidic and extracted twice with diethyl ether. The combined organic extracts were dried over anhydrous sodium sulfate, filtered and evaporated under reduced pressure. The residue was purified by column chromatography over silica eluting with hexanes: ethyl acetate (1:1) to give the subtitle compound (1.5 g).

Mass: 216.88 (M+H).

(d) 6-Hydrazino-1-isobutyl-3-methylpyrimidine-2,4(1H,3H)-dione

Hydrazine hydrate (6.5 ml) was added to a solution of 6-Chloro-1-isobutyl-3-methylpyrmidine-2,4(1H,3H)-dione (10 g) in ethanol (40 ml). The mixture was heated at reflux for 5 hours, cooled to room temperature and then evaporated under reduced pressure. The residue was crystallized from ethanol to give the subtitle compound (6.7 g). Mass: 213.00 (M+H).

(e) 1-naphthaldehyde(3-isobutyl-1-methyl-2,6-dioxo-1,2,3,6-tetrahydropyrimidin-4-yl)hydrazone 6-Hydrazino-1-isobutyl-3-methylpyrimidine-2,4(1H,3H)-dione (1 g) was dissolved in warm methanol (40 ml) and treated with 1-naphthaldehyde (0.78 g). After 2 hours, the precipitated solid was filtered and dried to give the subtitle compound (1.5 g). Mass: 350.96 (M+H).

(f) N-{4-[7-isobutyl-5-methyl-2-(1-naphthylmethyl)-4,6-dioxo-4,5,6,7-tetrahydro-2H-pyrazolo[3,4d]pyrimidin-3-yl]phenyl}acetamide N-(4-formylphenyl)acetamide (0.041 g) was added to a solution of 1-naphthaldehyde (3-isobutyl-1-methyl-2,6-dioxo-1,2,3,6-tetrahydropyrimidin-4-yl)hydrazone (0.07 g) in dimethylformamide (1.5 ml). The solution was heated at 165° C. for 5 hours. Reaction cooled to room temperature and purified on preparative HPLC to give the title compound (0.051 g). Mass: 495.79 (M+H)

Example 2

7-isobutyl-5-methyl-3-(3-methylthien-2-yl)-2-(1-naphthylmethyl)-2H-pyrazolo[3,4-d]pyrimidine-4,6 (5H,7H)-dione

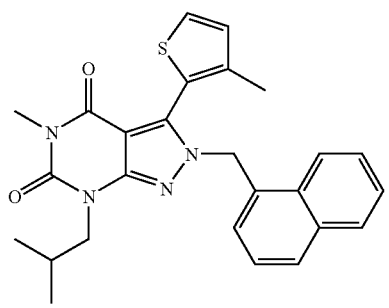

3-methyl-2-thiophenecarbaldehyde (0.063 g) and triethylamine (0.1 ml) was added to a solution of 1-naphthaldehyde (3-isobutyl-1-methyl-2,6-dioxo-1,2,3,6-tetrahydropyrimidin-4-yl)hydrazone (0.0875 g) in dimethylformamide (1.5 ml). The solution was heated at 90° C. for 24 hours. Reaction cooled to room temperature and purified on preparative HPLC to give the title compound (0.072 g). Mass: 458.87 (M+H).

Example 3

5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carbonitrile

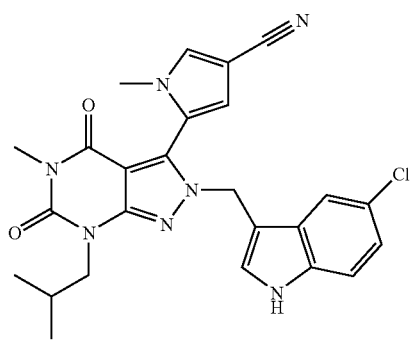

(a) 5-chloro-1H-indole-3-carbaldehyde (3-isobutyl-1-methyl-2,6-dioxo-1,2,3,6-tetrahydropyrimidin-4-yl)hydrazone 6-Hydrazino-1-isobutyl-3-methylpyrimidine-2,4(1H,3B)-dione was reacted with 5-chloro-1H-indole-3-carbaldehyde as described in example 1 to give the subtitle compound.

(b) 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carbonitrile 5-formyl-1-methyl-1H-pyrrole-3-carbonitrile (0.032 g) and piperidine (0.05 ml) was added to a solution of 5-chloro-1H-indole-3-carbaldehyde (3-isobutyl-1-methyl-2,6-dioxo-1,2,3,6-tetrahydropyrimidin-4-yl)hydrazone (0.075 g) in dimethylformamide (1.5 ml). The solution was heated at 50° C. for 5 hours. Reaction cooled to room temperature and purified on preparative HPLC to give the title compound (0.058 g). Mass: 490.16 (M+H).

Example 4

5-methyl-7-(2-methylbenzyl)-2-(1-naphthylmethyl)-3-pyridin-4-yl-2H-pyrazolo[3,4-d]pyrimidine-4,6 (5H,7B)-dione)

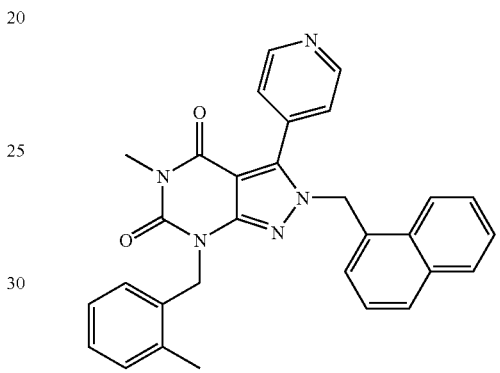

(a) 6-hydrazino-3-methyl-2,4(1H,3H)-pyrimidinedione

Hydrazine hydrate (12.7 ml) was added to a suspension 6-chloro-3-methyl-2,4(1H,3H)-pyrimidinedione (10 g) in ethanol (190 ml). The mixture was heated at 75° C. for 40 hours, cooled to room temperature. The yellow solid precipitated was filtered and dried give the subtitle compound (8.5 g). Mass: 156.76 (M+H).

(b) 1-naphthaldehyde (1-methyl-2,6-dioxo-1,2,3,6-tetrahydropyrimidin-4-yl)hydrazone 6-hydrazino-3-methyl-2,4(1H,3B)-pyrimidinedione (11.5 g) was dissolved in warm methanol (690 ml) and treated with 1-naphthaldehyde (11.88 g). After 2 hours, the precipitated light yellow solid was filtered and dried to give the subtitle compound (15 g). Mass: 294.90 (M+H).

(c) 5-methyl-2-(1-naphthylmethyl)-3-pyridin-4-yl-2H-pyrazolo[3,4-d]pyrimidine-4,6(5H,7H)-dione Isonicotinaldehyde (0.87 g) was added to a solution of 1-naphthaldehyde (1-methyl-2,6-dioxo-1,2,3,6-tetrahydropyrimidin-4-yl)hydrazone (2.0 g) in dimethylformamide (66 ml) and isopropanol (16 ml). Piperidine (0.66 ml) was added followed by glacial acetic acid (0.08 ml). The solution was heated at 120° C. for 16 hours. Reaction cooled to room temperature, solids precipitated was filtered, and dried to give the subtitle compound (1.63 g). Mass: 383.93 (M+H).

(d) 5-methyl-7-(2-methylbenzyl)-2-(1-naphthylmethyl)-3-pyridin-4-yl-2H-pyrazolo[3,4-d]pyrimidine-4,6(5H,7H)-dione 1-(chloromethyl)-2-methylbenzene (0.045 ml) and potassium carbonate (0.6 g) were added to a solution of 5-methyl-2-(1-naphthylmethyl)-3-pyridin-4-yl-2H-pyrazolo[3,4-d]

pyrimidine-4,6(5H,7H)-dione (2 ml). The mixture was heated at 80° C. for 18 hours then cooled to room temperature. Solids removed by filtration and the crude product was purified on preparative HPLC to give the title compound (0.057 g). Mass: 487.87 (M+H).

Example 5

3-[7-[(3,5-dimethylisoxazol-4-yl)methyl]-5-methyl-2-(1-naphthylmethyl)-4,6-dioxo-4,5,6,7-tetrahydro-2H-pyrazolo[3,4-d]pyrimidin-3-yl]benzoic acid

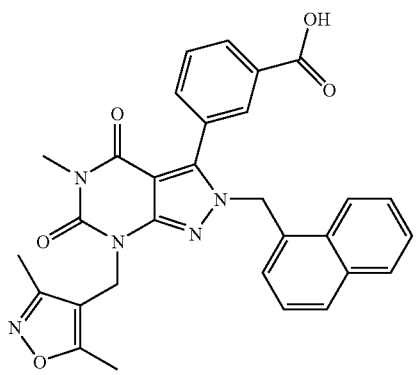

(a) Resin bound 3-formylbenzoic acid

Diisopropylcarbodiimide (0.378 ml) followed by 4-dimetylaminopyridine (0.02 g) was added to a suspension of Wang resin (0.5 g; 1.2 mmol/g) in dimethylformamide (4 ml), and the mixture was shaken at room temperature for 4 hours. The resin was filtered and washed (3 times) DMF, CH2Cl2, MeOH, CH2Cl2, and dried in vacuum to give the subtitle compound.

(b) Resin bound 3-[5-methyl-2-(1-naphthylmethyl)-4,6-dioxo-4,5,6,7-tetrahydro-2H-pyrazolo[3,4-d]pyrimidin-3-yl] benzoic acid 1-naphthaldehyde (1-methyl-2,6-dioxo-1,2,3,6-tetrahydropyrimidin-4-yl)hydrazone (2.12 g) and triethylamine (0.8 ml) was added to a suspension of Resin bound 3-formylbenzoic acid in dimethylformamide (15 ml), and the mixture was shaken at 90° C. for 16 hours. The resin was filtered and washed (3 times) DMF, CH2Cl2, MeOH, CH2Cl2, and dried in vacuum to give the subtitle compound.

(c) Resin bound 3-[7-[(3,5-dimethylisoxazol-4-yl)methyl]-5-methyl-2-(1-naphthylmethyl)-4,6-dioxo-4,5,6,7-tetrahydro-2H-pyrazolo[3,4-d]pyrimidin-3-yl]benzoic acid 4-(chloromethyl)-3,5-dimethylisoxazole (0.145 g) was added to a suspension of Resin bound 3-[5-methyl-2-(1-naphthylmethyl)-4,6-dioxo-4,5,6,7-tetrahydro-2H-pyrazolo[3,4-d]pyrimidin-3-yl]benzoic acid (0.120 g) and potassium carbonate (0.397 g) in dimethylformamide (1 ml). Reaction mixture was shaken at 85° C. for 20 hours. The resin was filtered and washed (3 times) DMF, H2O, DMF, CH2Cl2, MeOH, CH2Cl2, and dried in vacuum to give the subtitle compound.

(d) 3-[7-[(3,5-dimethylisoxazol-4-yl)methyl]-5-methyl-2-(1-naphthylmethyl)-4,6-dioxo-4,5,6,7-tetrahydro-2H-pyrazolo[3,4-d]pyrimidin-3-yl]benzoic acid Resin bound 3-[7-[(3,5-dimethyl-4-isoxazolyl)methyl]-5-methyl-2-(1-naphthylmethyl)-4,& dioxo-4,5,6,7-tetrahydro-2H-pyrazolo[3,4-d]pyrimidin-3-yl]benzoic acid (0. 12 g) was treated with 15% TFA in dichloromethane (1 ml) for 2 hours. The resin was filtered and washed (2 times) with dichloromethane. Combined filtrates were concentrated, and crude product was purified on preparative HPLC to give the title compound (0.013 g). Mass: 535.86 (M+H).

Example 6

7-Isobutyl-5-(2-morpholin-4-ylethyl)-2-(1-naphthylmethyl)-3-pyridin-4-yl-2H-pyrazolo[3,4-d]pyrimidine-4,6(5H,7H)-dione

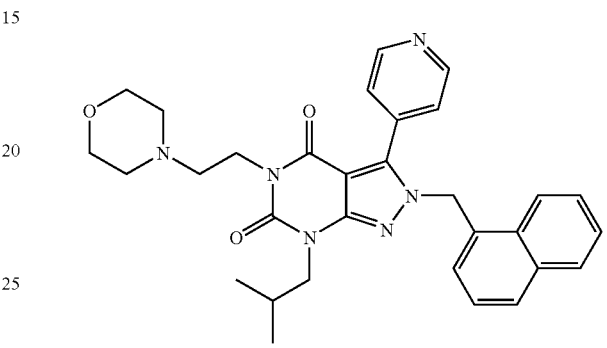

(a) 6-hydrazino-1-isobutylpyrimidine-2,4(1H,3H)-dione

Hydrazine hydrate (5.9 ml) was added to a solution of 6-chloro-1-isobutylpyrimidine-2,4(1H,3H)-dione synthesized according to procedure described in *Heterocycles*, 1990, 31(9), 1641-1646, (5.9 g) in ethanol (100 ml). The mixture was heated at reflux for 16 hours, cooled to room temperature and then evaporated under reduced pressure. The residue was crystallized from ethanol to give the subtitle compound (5.8 g).

(b) 1-naphthaldehyde (3-isobutyl-2,6-dioxo-1,2,3,6-tetrahydropyrimidin-4-yl)hydrazone 6-hydrazino-1-isobutylpyrimidine-2,4(1H,3H)-dione (1.8 g) was dissolved in warm methanol (90 ml) and treated with 1-naphthaldehyde (1.5 g). After 24 hours, the precipitated solid was filtered and dried to give the subtitle compound (3.03 g).

(c) 7-isobutyl-2-(1-naphthylmethyl)-3-pyridin-4-yl-2H-pyrazolo[3,4-d]pyrimidine-4,6(5H,7H)-dione 1-naphthaldehyde (3-isobutyl-2,6-dioxo-1,2,3,6-tetrahydropyrimidin-4-yl)hydrazone (3.4 g) was dissolved in a solution of dimethylformamide (99 ml) and isopropanol (24 ml). isonicotinaldehyde (1.3 g) was added followed by piperidine (0.99 ml) and acetic acid (0.12 ml) The mixture was stirred at room temperature for 18 hours. Solvents were removed under reduced pressure. Crude residue was crystallized in methanol/water to give the title compound (3.28 g). Mass: 425.95 (M+H).

(d) 7-Isobutyl-5-(2-morpholin-4-ylethyl)-2-(1-naphthylmethyl)-3-pyridin-4-yl-2H-pyrazolo[3,4-d]pyrimidine-4,6 (5H,7H)-dione 4-(2-chloroethyl)morpholine hydrochloride (0.0435 g) followed by DBU (0.094 g) were added to a solution of 7-isobutyl-2-(1-naphthylmethyl)-3-pyridin-4-yl-2H-pyrazolo[3,4-d]pyrimidine-4,6(5H,7H)-dione (0.0668 g) in dimethylformamide (1 ml). The mixture was heated at 80° C. for 18 hours then cooled to room temperature. The crude reaction was purified on preparative HPLC to give the title compound (0.077 g). Mass: 538.90 (M+H).

Example 7 methyl 5-{7-isobutyl-5-methyl-2-[(5-methyl-1H-indol-3-yl)methyl]-4,6-dioxo-4,5,6,7-tetrahydro-2H-pyrazolo[3,4-d]pyrimidin-3-yl}-1-methyl-1H-pyrrole-3-carboxylate

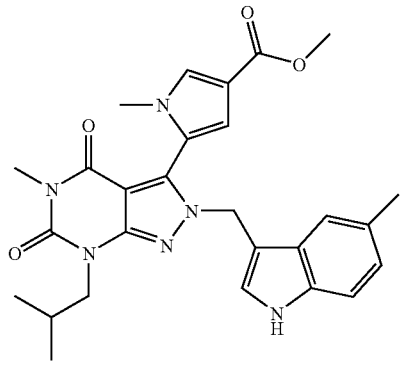

This compound was made following the procedure described above, starting with 6-hydrazino-1-isobutyl-3-methylpyrimidine-2,4(1H,3H)-dione, and condensing first with 5-methyl-1H-indole-3-carbaldehyde, followed by methyl 5-formyl-1-methyl-1H-pyrrole-3-carboxylate. Mass: 503.20 (M+H).

Example 8

5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid

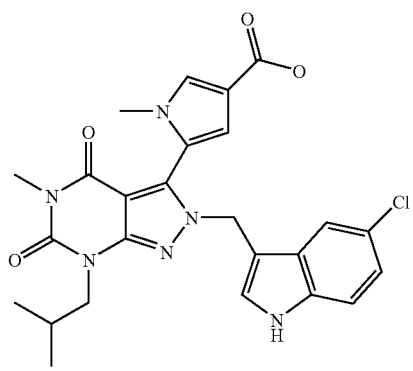

This compound was made following the procedure described above, starting with 6-hydrazino-1-isobutyl-3-methylpyrimidine-2,4(1H,3H)-dione, and condensing first with 5-chloro-1H-indole-3-carbaldehyde, followed by 5-formyl-1-methyl-1H-pyrrole-3-carboxylic acid. Mass: 509.18 (M+H).

Example 9

5-{2-[(5-chloro-1H-indol-3-yl)methyl]-7-isobutyl-5-methyl-4,6-dioxo-4,5,6,7-tertrahydro-2H-pyrazolo[3,4-d]pyrimidin-3-yl}-N-[2-(dimethylamino)ethyl]-1-methyl-1H-pyrrole-3-carboxamide

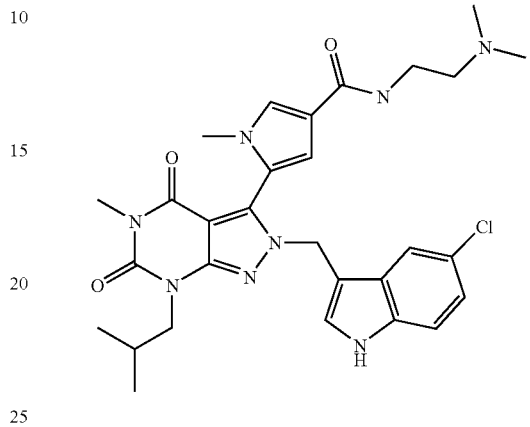

Diethyl cyanophosphonate (0.0466 g) followed by triehylamine (0.160 ml) were added to a solution of 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid (0.072 g) and N,N-dimethylethane-1,2-diamine (0.049 g) in dimethylformamide (2 ml) at 0° C. The mixture was stirred at ice-cold temperature for 1 hour then at room temperature for 3 hours. The crude reaction was purified on preparative HPLC to give the title compound (0.048 g). Mass: 579.25 (M+H).

Example 10

5-[2-[(6-chloro-4-quinolinyl)methyl]-7-(cyclopropylmethyl)-4,5,6,7-tetrahydro-5-methyl-4,6-dioxo-2H-pyrazolo[3,4-d]pyrimidin-3-yl]-1-methyl-1H-pyrrole-3-carbonitrile

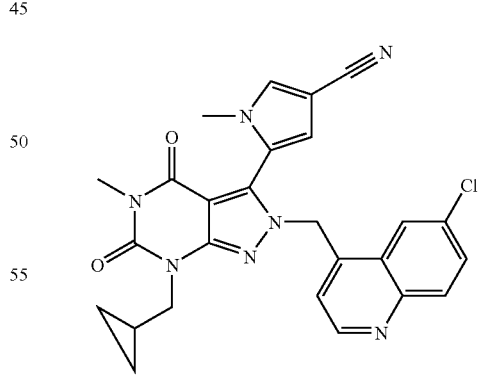

This compound was made following the procedure described above, startng with 1-(cyclopropylmethyl)-6-hydrazino-3-methylpyrimidine-2,4(1H,3H)-dione synthesized according to the procedure used in example 1 for the corresponding isobutyl substituted compound, and condensing first with 6-chloroquinoline-4-carbaldehyde, followed by 5-formyl-1-methyl-1H-pyrrole-3-carbonitrile. Mass: 500.11 (M+H).

Example 11

2-[(6-chloroquinolin-4-yl)methyl]-7-(cyclopropylmethyl)-5-methyl-3-[-1-methyl-4-(1H-tetrazol-5-yl)-1H-pyrrol-2-yl]-2H-pyrazolo[3,4-d]-pyrimidine-4,6(5H,7H)-dione

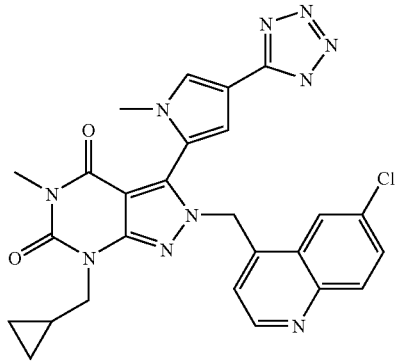

Sodium azide (0.054 g) and ammonium chloride (0.044 g) were added to a solution of 5-[2-[(6-chloro-4-quinolinyl)methyl]-7-(cyclopropylmethyl)-4,5,6,7-tetrahydro-5-methyl-4,6-dioxo-2H-pyrazolo[3,4-d]pyrimidin-3-yl]-1-methyl-1H-pyrrole-3-carbonitrile (0.083 g) in dimethylformamide (5 ml) at 0° C. The mixture was heated at 120° C. for 31 hour. The crude reaction was purified on preparative HPLC to give the title compound (0.058 g). Mass: 543.08 (M+H).

Example 12 methyl 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylate

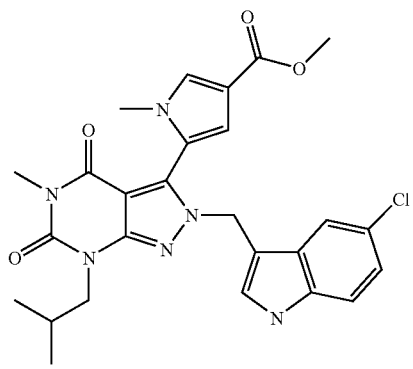

This compound was made following the procedure described above, starting with 6-hydrazino-1-isobutyl-3-methylpyrimidine-2,4(1H,3H)-dione, and condensing first with 5-chloro-1H-indole-3-carbaldehyde, followed by methyl 5-formyl-1-methyl-1H-pyrrole-3-carboxylate. Mass: 523.15 (M+H).

Example 13 methyl 5-{2-[(5-bromo-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylate

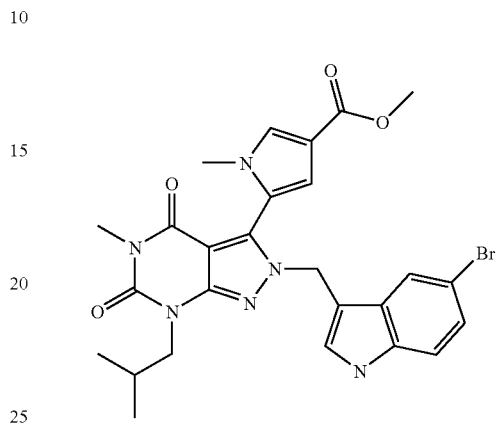

This compound was made following the procedure described above, starting with 6-hydrazino-1-isobutyl-3-methylpyrimidine-2,4(1H,3H)-dione, and condensing first with 5-bromo-1H-indole-3-carbaldehyde, followed by methyl 5-formyl-1-methyl-1H-pyrrole-3-carboxylate.

Example 14 methyl 5-[2-[(5-chloro-1H-indol-3-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-pyrrole-3-carboxylate

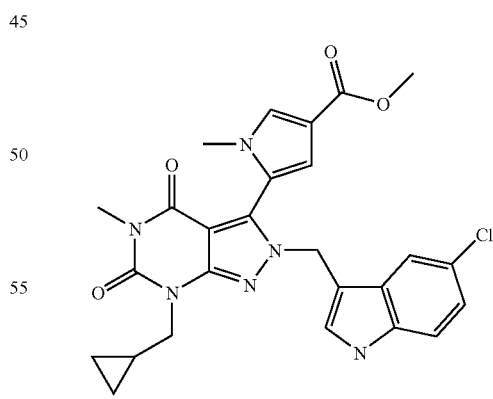

This compound was made following the procedure described above, starting with 1-(cyclopropylmethyl)-6-hydrazino-3-methylpyrimidine-2,4(1H,3H)-dione, and condensing first with 5-chloro-1H-indole-3-carbaldehyde, followed by methyl 5-formyl-1-methyl-1H-pyrrole-3-carboxylate. Mass: 520.97 (M+H).

Example 15 methyl 5-[2-(1-benzothien-3-ylmethyl)-7-isobutyl-5-methyl-4,6-dioxo-4,5,6,7-tetrahydro-2H-pyrazolo[3,4-d]pyrimidin-3-yl]-1-methyl-1H-pyrrole-3-carboxylate

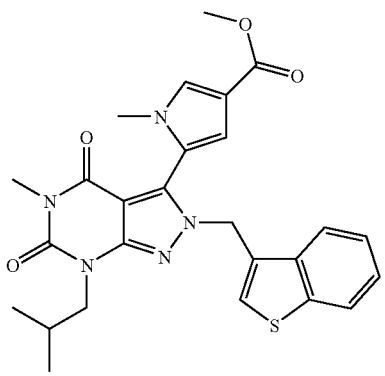

This compound was made following the procedure described above, starting with 6-hydrazino-1-isobutyl-3-methylpyrimidine-2,4(1H,3H)-dione, and condensing first with 1-benzothiophene-3-carbaldehyde, followed by methyl 5-formyl-1-methyl-1H-pyrrole-3-carboxylate. Mass: 506.31 (M+H).

Example 16 methyl 5-[7-isobutyl-5-methyl-2-(1-naphthylmethyl)-4,6-dioxo-4,5,6,7-tetrahydro-2H-pyrazolo[3,4-d]pyrimidin-3-yl]-1-methyl-1H-pyrrole-3-carboxylate

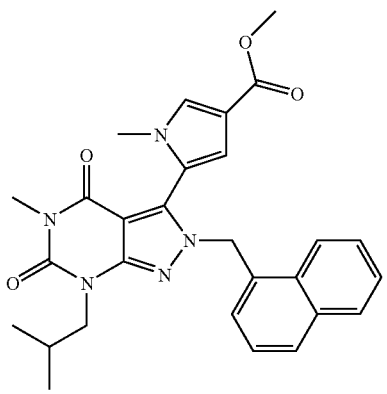

This compound was made following the procedure described above, starting with 6-hydrazino-1-isobutyl-3-methylpyrimidine-2,4(1H,3H)-dione, and condensing first with 1-naphthaldehyde, followed by methyl 5-formyl-1-methyl-1H-pyrrole-3-carboxylate. Mass: 500.38 (M+H).

Example 17 methyl 5-{2-[(5-chloro-2-methyl-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylate

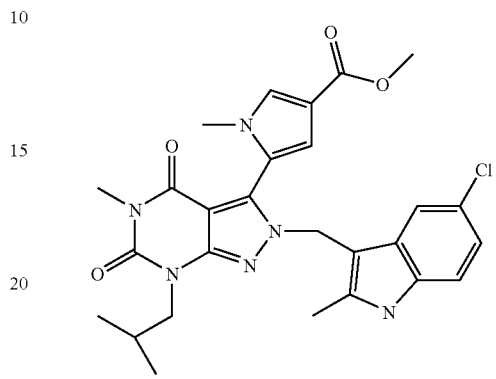

This compound was made following the procedure described above, starting with 6-hydrazino-1-isobutyl-3-methylpyrimidine-2,4(1H,3H)-dione, and condensing first with 5-chloro-2-methyl-1H-indole-3-carbaldehyde, followed by methyl 5-formyl-1-methyl-1H-pyrrole-3-carboxylate. Mass: 537.01 (M+H).

Example 18 methyl 5-{2-[(6-chloroquinolin-4-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylate

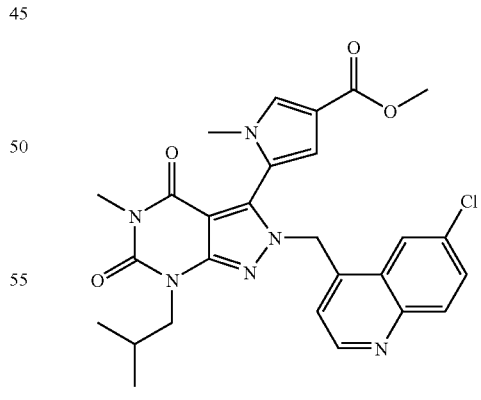

This compound was made following the procedure described above, starting with 6-hydrazino-1-isobutyl-3-methylpyrimidine-2,4(1H,3H)-dione, and condensing first with 6-chloroquinoline-4-carbaldehyde, followed by methyl 5-formyl-1-methyl-1H-pyrrole-3-carboxylate. Mass: 535.05 (M+H).

Example 19 methyl 5-{2-[(5-fluoro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylate

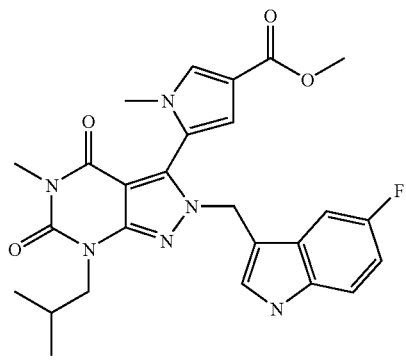

This compound was made following the procedure described above, starting with 6-hydrazino-1-isobutyl-3-methylpyrimidine-2,4(1H,3H)-dione, and condensing first with 5-fluoro-1H-indole-3-carbaldehyde, followed by methyl 5-formyl-1-methyl-1H-pyrrole-3-carboxylate. Mass: 507.05 (M+H).

Example 20 methyl 5-{2-[(5-cyano-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylate

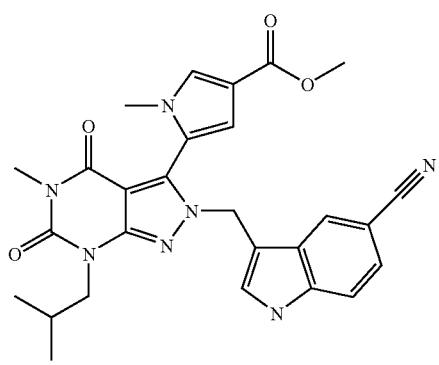

This compound was made following the procedure described above, starting with 6-hydrazino-1-isobutyl-3-methylpyrimidine-2,4(1H,3H)-dione, and condensing first with 3-formyl-1H-indole-5-carbonitrile, followed by methyl 5-formyl-1-methyl-1H-pyrrole-3-carboxylate. Mass: 514.05 (M+H).

Example 21 methyl 5-{7-(cyclopropylmethyl)-2-[(5-ethyl-1H-indol-3-yl)methyl]-5-methyl-4,6-dioxo-4,5,6,7-tetrahydro-2H-pyrazolo[3,4-d]pyrimidin-3-yl}-1-methyl-1H-pyrrole-3-carboxylate

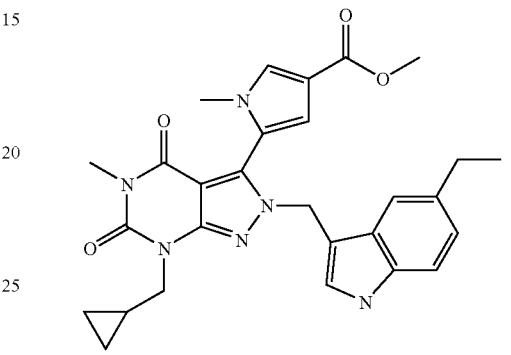

This compound was made following the procedure described above, starting with 1-(cyclopropylmethyl)-6-hydrazino-3-methylpyrimidine-2,4(1H,3H)-dione, and condensing first with 5-ethyl-1H-indole-3-carbaldehyde, followed by methyl 5-formyl-1-methyl-1H-pyrrole-3-carboxylate. Mass: 515.25 (M+H).

Example 22

5-{7-(cyclopropylmethyl)-5-methyl-2-[(5-methyl-1H-indol-3-yl)methyl]4,6-dioxo-4,5,6,7-tetrahydro-2H-pyrazolo[3,4-d]pyrimidin-3-yl}-1-methyl-1H-pyrrole-3-carboxylic acid

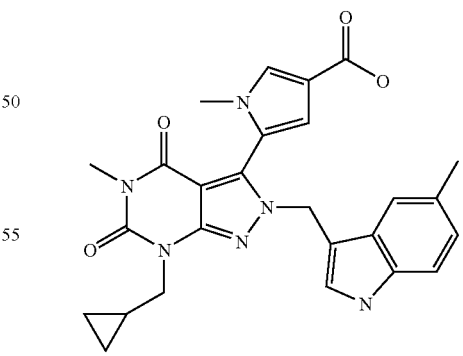

This compound was made following the procedure described above, staring with 1-(cyclopropylmethyl)-6-hydrazino-3-methylpyrimidine-2,4(1H,3H)-dione, and condensing first with 5-methyl-1H-indole-3-carbaldehyde, followed by 5-formyl-1-methyl-1H-pyrrole-3-carboxylic acid. Mass: 487.23 (M+H).

Example 23

5-{2-[(5-bromo-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid

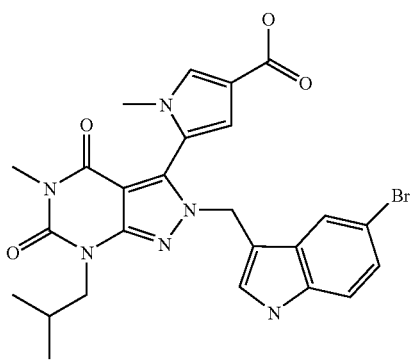

This compound was made following the procedure described above, starting with 6-hydrazino-1-isobutyl-3-methylpyrimidine-2,4(1H,3H)-dione, and condensing first with 5-bromo-1H-indole-3-carbaldehyde, followed by 5-formyl-1-methyl-1H-pyrrole-3-carboxylic acid.

Example 24

5-[2-[(5-chloro-1H-indazol-3-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-pyrrole-3-carboxylic acid

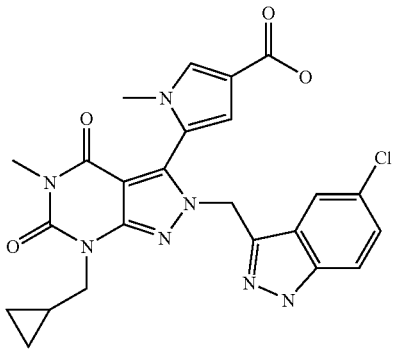

This compound was made following the procedure described above, starting with 1-(cyclopropylmethyl)-6-hydrazino-3-methylpyrimidine-2,4(1H,3H)-dione, and condensing first with 5-chloro-1H-indazole-3-carbaldehyde, followed by 5-formyl-1-methyl-1H-pyrrole-3-carboxylic acid. Mass: 508.13 (M+H).

Example 25

5-{7-isobutyl-5-methyl-2-[(5-methyl-1H-indol-3-yl)methyl]-4,6-dioxo-4,5,6,7-tetrahydro-2H-pyrazolo[3,4-d]pyrimidin-3-yl}-1-methyl-1H-pyrrole-3-carboxylic acid

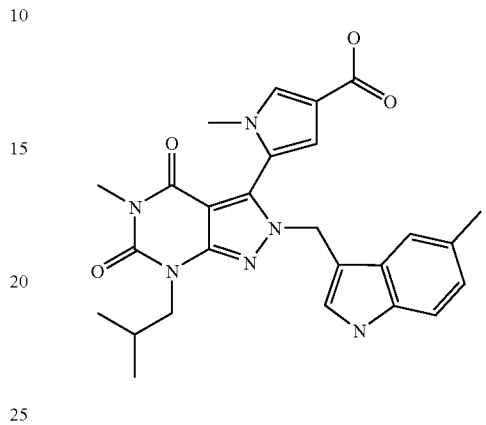

This compound was made following the procedure described above, starting with 6-hydrazino-1-isobutyl-3-methylpyrimidine-2,4(1H,3H)-dione, and condensing first with 5-methyl-1H-indole-3-carbaldehyde, followed by 5-formyl-1-methyl-1H-pyrrole-3-carboxylic acid. Mass: 489.16 (M+H).

Example 26

5-{2-[(6-chloroquinolin-4-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid

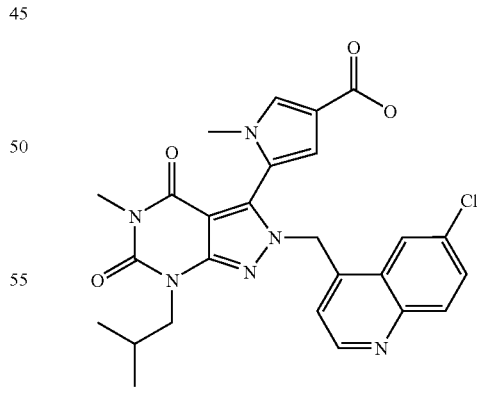

This compound was made following the procedure described above, starting with 6-hydrazino-1-isobutyl-3-methylpyrimidine-2,4(1H,3H)-dione, and condensing first with 6-chloroquinoline-4-carbaldehyde, followed by 5-formyl-1-methyl-1H-pyrrole-3-carboxylic acid. Mass: 521.09 (M+H).

Example 27

5-[2-(1-benzothien-3-ylmethyl)-7-isobutyl-5-methyl-4,6-dioxo-4,5,6,7-tetrahydro-2H-pyrazolo[3,4-d]pyrimidin-3-yl]-1-methyl-1H-pyrrole-3-carboxylic acid

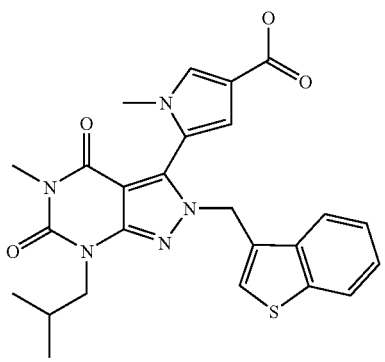

This compound was made following the procedure described above, starting with 6-hydrazino-1-isobutyl-3-methylpyrimidine-2,4(1H,3H)-dione, and condensing first with 1-benzothiophene-3-carbaldehyde, followed by 5-formyl-1-methyl-1H-pyrrole-3-carboxylic acid. Mass: 492.09 (M+H).

Example 28

5-{2-[(5-chloro-1H-indazol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid

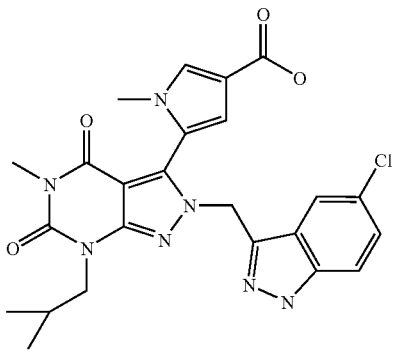

This compound was made following the procedure described above, starting with 6-hydrazino-1-isobutyl-3-methylpyrimidine-2,4(1H,3H)-dione, and condensing first with 5-chloro-1H-indazole-3-carbaldehyde, followed by 5-formyl-1-methyl-1H-pyrrole-3-carboxylic acid. Mass: 510.13 (M+H).

Example 29

5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-N,1-dimethyl-1H-pyrrole-3-carboxamide

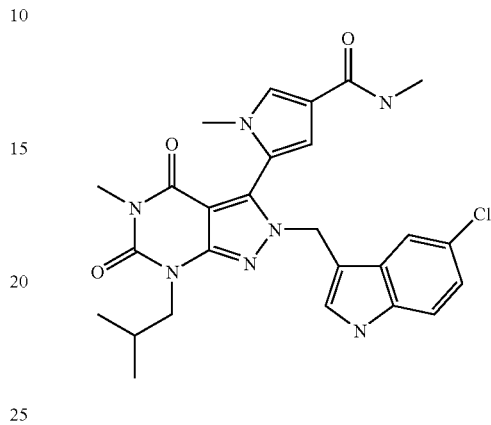

This compound was synthesized by the reaction of 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and methylamine using diethyl cyanophosphonate as a coupling reagent. Mass: 522.19 (M+H).

Example 30

N-cyclopropyl-5-{7-(cyclopropylmethyl)-5-methyl-2[(5-methyl-1H-indol-3-yl)methyl]-4,6-dioxo-4,5,6,7-tetrahydro-2H-pyrazolo[3,4-d]pyrimidin-3-yl}-1-methyl-1H-pyrrole-3-carboxamide

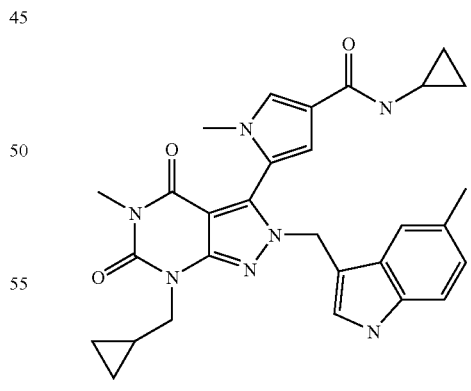

This compound was synthesized by the reaction of 5-{7-(cyclopropylmethyl)-5-methyl-2-[(5-methyl-1H-indol-3-yl)methyl]-4,6-dioxo-4,5,6,7-tertrahydro-2H-pyrazolo-[3,4-d]pyrimidin-3-yl}-1-methyl-1H-pyrrole-3-carboxylic acid and cyclopropylamine using diethyl cyanophosphonate as a coupling reagent. Mass: 526.22 (M+H).

Example 31

5-{7-(cyclopropylmethyl)-5-methyl-2[(5-methyl-1H-indol-3-yl)methyl]-4,6-dioxo-4,5,6,7-tetrahydro-2H-pyrazolo[3,4-d]pyrimidin-3-yl}-N-methoxy-1-methyl-1H-pyrrole-3-carboxamide

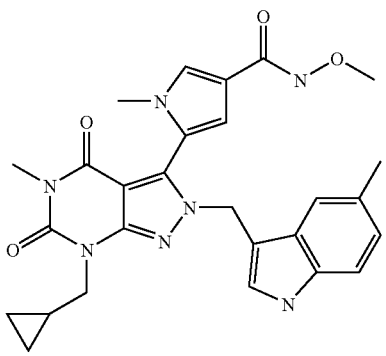

This compound was synthesized by the reaction of 5-{7-(cyclopropylmethyl)-5-methyl-2-[(5-methyl-1H-indol-3-yl)methyl]-4,5,6,7-tetrahydro-2H-pyrazolo[3,4-d]pyrimidin-3-yl}-1-methyl-1H-pyrrole-3-carboxylic acid and methoxylamine hydrochloride using diethyl cyanophosphonate as a coupling reagent. Mass: 516.21 (M+H).

Example 32

5-[2-[(5-chloro-1H-indol-3-yl)methyl]-7-(cyclopropylmethyl)-5-methyl-4,6-dioxo-4,5,6,7-tetrahydro-2H-pyrazolo[3,4-d]pyrimidin-3-yl]-N,1-dimethyl-1H-pyrrole-3-carboxamide

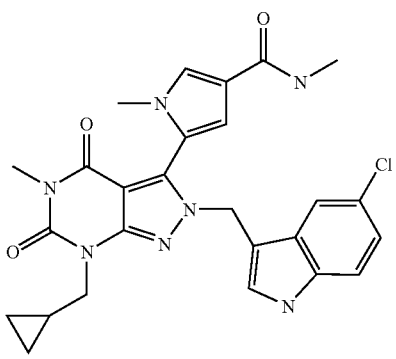

This compound was synthesized by the reaction of 5-[2-[(5-chloro-1H-indol-3-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-pyrrole-3-carboxylic acid and methlamine using diethyl cyanophosphonate as a coupling reagent. Mass: 520.15 (M+H).

Example 33

5-[2-[(5-chloro-1H-indol-3-yl)methyl]-7-(cyclopropylmethyl)-5-methyl-4,6-dioxo-4,5,6,7-tetrahydro-2H-pyrazolo[3,4-d]pyrimidin-3-yl]-N-methoxy-1-methyl-1H-pyrrole-3-carboxamide

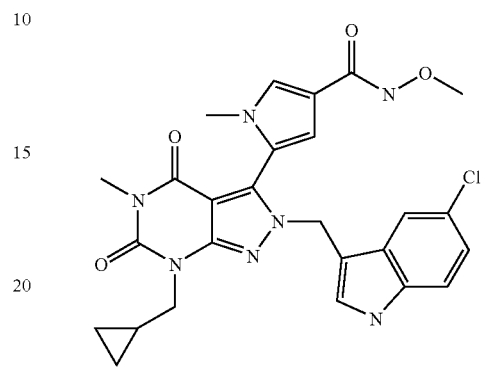

This compound was synthesized by the reaction of 5-[2-[(5-chloro-1H-indol-3-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-pyrrole-3-carboxylic acid and methoxylamine hydrochloride using diethyl cyanophosphonate as a coupling reagent Mass: 536.18 (M+H).

Example 34

5{-7-(cyclopropylmethyl)-5-methyl-2[-(5-methyl-1H-indol-3-yl)methyl]4,6-dioxo-4,5,6,7-tetrahydro-2H-pyrazolo[3,4-d]pyrimidin-3-yl}-N,1-dimethyl-1H-pyrrole-3-carboxamide

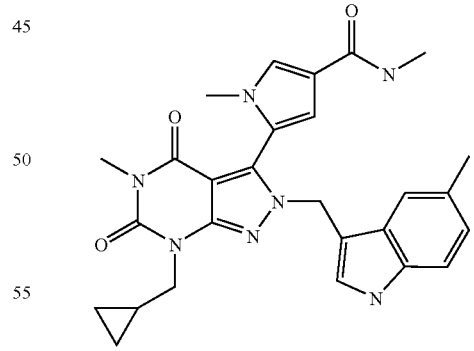

This compound was synthesized by the reaction of 5-{7-(cyclopropylmethyl)-5-methyl-2-[(5-methyl-1H-indol-3-yl)methyl]4,6-dioxo-4,5,6,7-tetrahydro-2H-pyrazolo[3,4-d]pyrimidin-3-yl}-1-methyl-1H-pyrrole-3-carboxylic acid and methylamine using diethyl cyanophosphonate as a coupling reagent Mass: 500.25 (M+H).

Example 35

5-[2-[(5-chloro-1H-indol-3-yl)methyl]-7-(cyclopropylmethyl)-5-methyl-4,6-dioxo-4,5,6,7-tetrahydro-2H-pyrazolo[3,4-d]pyrimidin-3-yl]-N-[2-(dimethylamino)ethyl]-1-methyl-1H-pyrrole-3-carboxamide

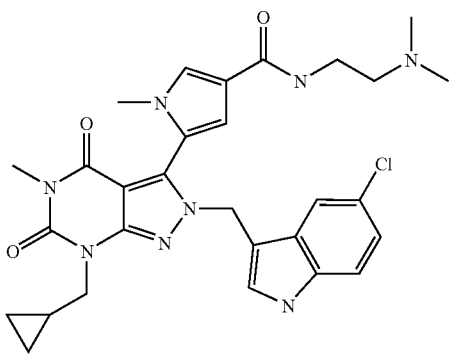

This compound was synthesized by the reaction of 5-[2-[(5chloro-1H-indol-3-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-pyrrole-3-carboxylic acid and N,N-dimethylethane-1,2-diamine using diethyl cyanophosphonate as a coupling reagent Mass: 577.31 (M+H).

Example 36

5-[2-[(5-chloro-1H-indol-3-yl)methyl]-7-(cyclopropylmethyl)-5-methyl-4,6-dioxo-4,5,6,7-tetrahydro-2H-pyrazolo[3,4-d]pyrimidin-3-yl]-N-cyclopropyl-1-methyl-1H-pyrrole-3-carboxamide

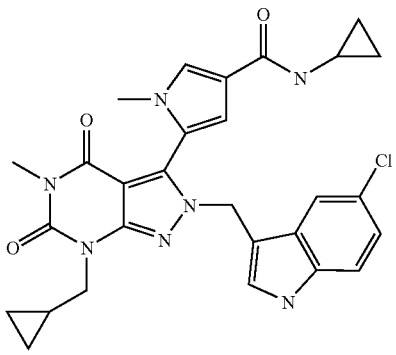

This compound was synthesized by the reaction of 5-[2-[(5-chloro-1H-indol-3-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-pyrrole-3-carboxylic acid and cyclpropylamine using diethyl cyanophosphonate as a coupling reagent. Mass: 546.19 (M+H).

Example 37

5-[2-[(6-chloroquinolin-4-yl)methyl]-7-(cyclopropylmethyl)-5-methyl-4,6-dioxo-4,5,6,7-tetrahydro-2H-pyrazolo[3,4-d]pyrimidin-3-yl]-N-methoxy-1-methyl-1H-pyrrole-3-carboxamide

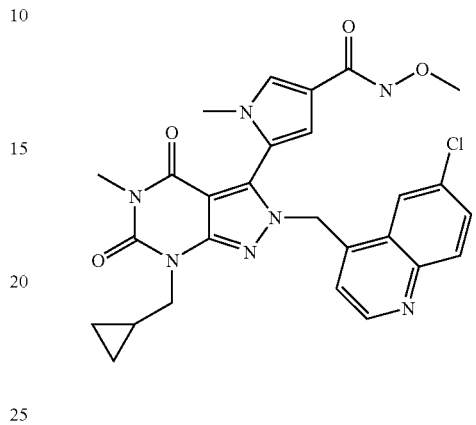

This compound was synthesized by the reaction 5-[2-[(6-chloroquinolin-4-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-pyrrole-3-carboxylic acid and methoxylamine hydrochloride using diethyl cyanophosphonate as a coupling reagent. Mass: 548.13 (M+H).

Example 38

5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-N-[3-(4-methylpiperazin-1-yl)propyl]-1H-pyrrole-3-carboxamide

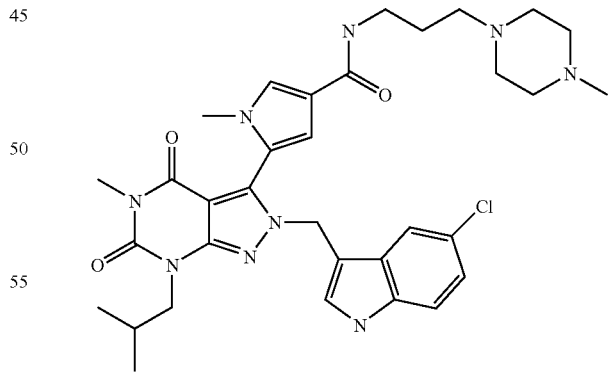

This compound was synthesized by the reaction of 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl -1H-pyrrole-3-carboxylic acid and 3-(4-methylpiperazin-1-yl)propylamine using diethyl cyanophosphonate as a coupling reagent Mass: 648.20 (M+H).

Example 39

N-(2-aminoethyl)-5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxamide

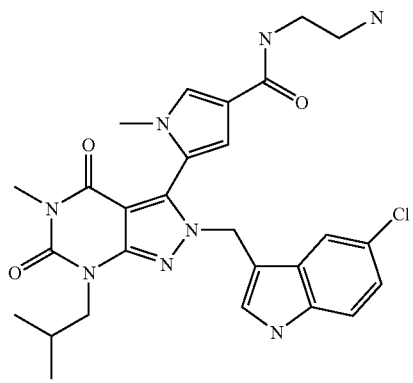

This compound was synthesized by the reaction of 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and ethane-1,2-diamine using diethyl cyanophosphonate as a coupling reagent. Mass: 551.15 (M+H).

Example 40

5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-N-isopropyl-1-methyl-1H-pyrrole-3-carboxamide

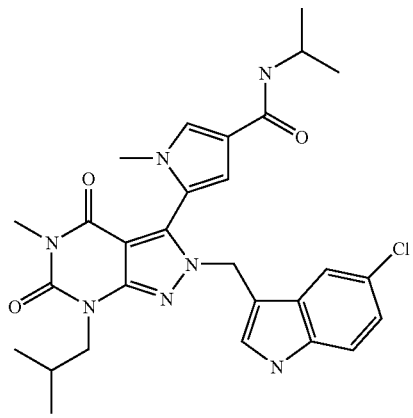

This compound was synthesized by the reaction of 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and isopropylamine using diethyl cyanophosphonate as a coupling reagent. Mass: 550.14 (M+H).

Example 41

5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-N-[3-(1H-imidazol-1-yl)propyl]-1-methyl-1H-pyrrole-3-carboxamide

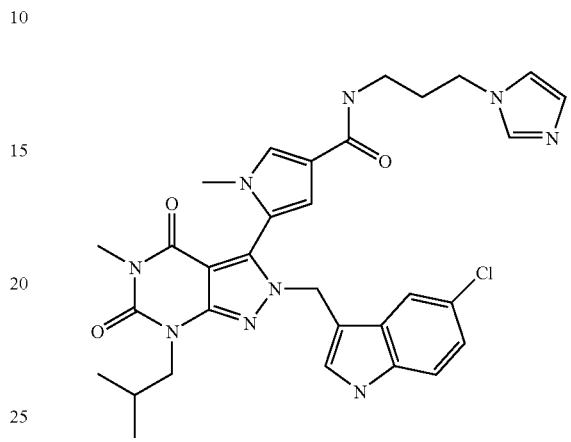

This compound was synthesized by the reaction of 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and 3-(1H-imidazol-1-yl)propylamine using diethyl cyanophosphonate as a coupling reagent Mass: 616.15 (M+H).

Example 42

5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-N-(2-hydroxyethyl)-1-methyl-1H-pyrrole-3-carboxamide

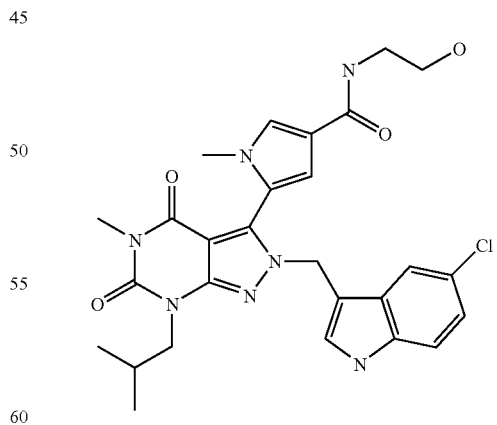

This compound was synthesized by the reaction of 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and 2-aminoethanol using diethyl cyanophosphonate as a coupling reagent. Mass: 552.16 (M+H).

Example 43

5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-N-(2-morpholin-4-ylethyl)-1H-pyrrole-3-carboxamide

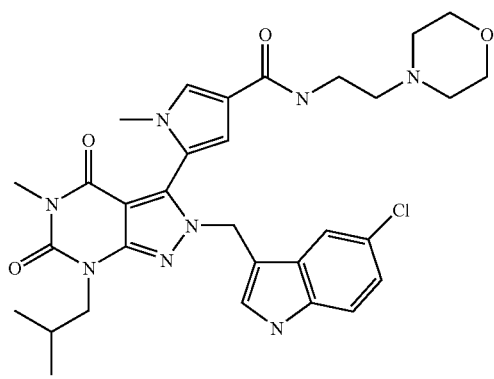

This compound was synthesized by the reaction of 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and 2-morpholin-4-ylethanamine using diethyl cyanophosphonate as a coupling reagent. Mass: 621.20 (M+H).

Example 44

5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-N-[2-(methylsulfonyl)ethyl]-1H-pyrrole-3-carboxamide

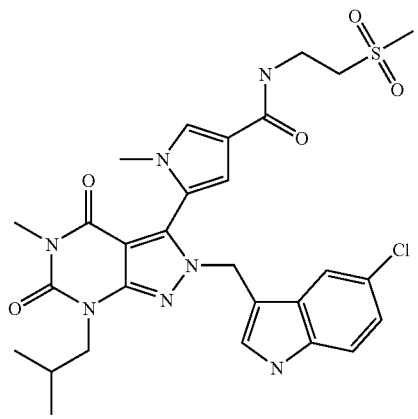

This compound was synthesized by the reaction of 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and 2-(methylsulfonyl)ethylamine using diethyl cyanophosphonate as a coupling reagent. Mass: 614.00 (M+H).

Example 45

5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-N-methoxy-1-methyl-1H-pyrrole-3-carboxamide

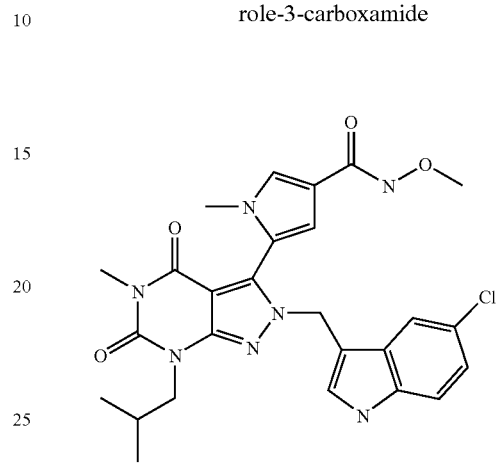

This compound was synthesized by the reaction of 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and methoxylamine hydrochloride using diethyl cyanophosphonate as a coupling reagent. Mass: 537.98 (M+H).

Example 46

5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-N-(2-methoxyethyl)-1-methyl-1H-pyrrole-3-carboxamide

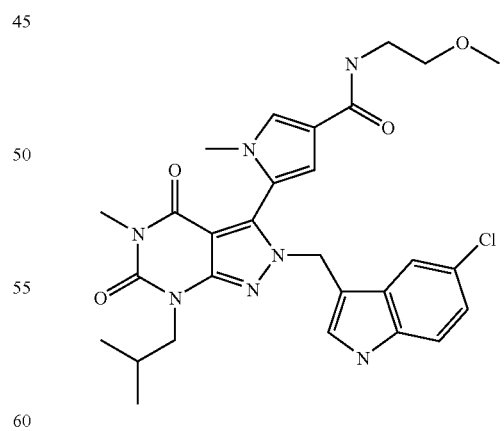

This compound was synthesized by the reaction of 5-{2-[(5-chloro-1H-indol-3-yl)methyl]-7-isobutyl-1-methyl-4,6-dioxo-4,5,6,7-tetrahydro-2H-pyrazolo[3,4-d]pyrimidin-3-yl}-1-methyl-1H-pyrrole-3-carboxylic acid and 2-methoxyethylamine using diethyl cyanophosphonate as a coupling reagent. Mass: 566.10 (M+H).

Example 47

5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-N-(pyridin-4-ylmethyl)-1H-pyrrole-3-carboxamide

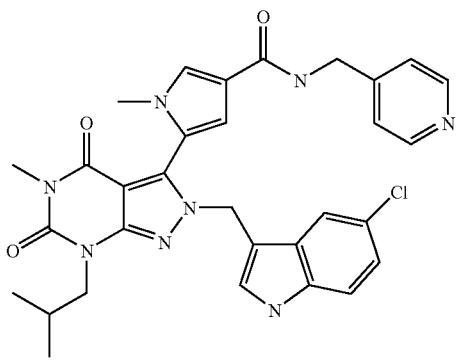

This compound was synthesized by the reaction of 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and pyridin-4-yl-methylamine using diethyl cyanophosphonate as a coupling reagent. Mass: 599.15 (M+H).

Example 48

5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-N-[2-(isopropylamino)ethyl]-1-methyl-1H-pyrrole-3-carboxamide

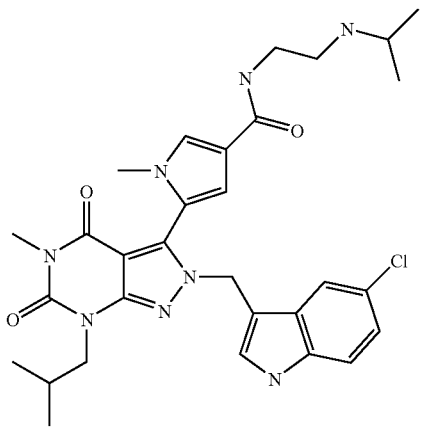

This compound was synthesized by the reaction of 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and N-isopropylethane-1,2-diamine using diethyl cyanophosphonate as a coupling reagent. Mass: 593.16 (M+H).

Example 49

5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxamide

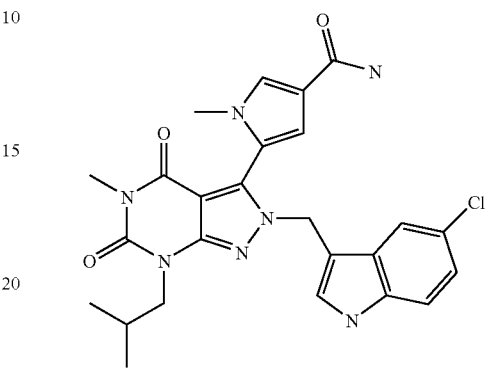

This compound was synthesized by the reaction of 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and ammonia using diethyl cyanophosphonate as a coupling reagent Mass: 508.10 (M+H).

Example 50

5-[2-[(6-chloroquinolin-4-yl)methyl]-7-(cyclopropylmethyl)-5-methyl-4,6-dioxo-4,5,6,7-tetrahydro-2H-pyrazolo[3,4-d]pyrimidin-3-yl]-N-cyclopropyl-1-methyl-1H-pyrrole-3-carboxamide

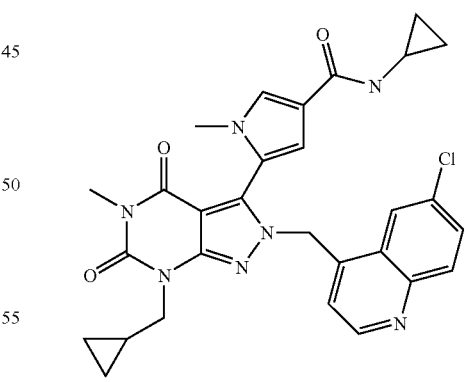

This compound was synthesized by the reaction of 5-[2-[(6-chloroquinolin-4-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-pyrrole-3-carboxylic acid and cyclopropylamine using diethyl cyanophosphonate as a coupling reagent. Mass: 558.15 (M+H).

Example 51

5-[2-[(6-chloroquinolin-4-yl)methyl]-7-(cyclopropylmethyl)-methyl-4,6-dioxo-4,5,6,7-tetrahydro-2H-pyrazolo[3,4-d]pyrimidin-3-yl]-N-[2-(dimethylamino)ethyl]-1-methyl-1H-pyrrole-3-carboxamide

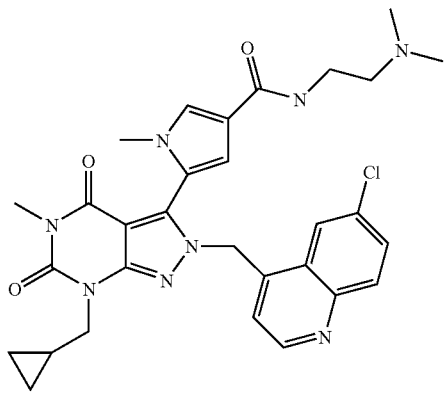

This compound was synthesized by the reaction of 5-[2-[(6-chloroquinolin-4-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-pyrrole-3-carboxylic acid and N,N-dimethylethane-1,2-diamine using diethyl cyanophosphonate as a coupling reagent. Mass: 589.35 (M+H).

Example 52

5-[2-[(6-chloroquinolin-4-yl)methyl]-7-(cyclopropylmethyl)-5-methyl-4,6-dioxo-4,5,6,7-tetrahydro-2H-pyrazolo[3,4-d]pyrimidin-3-yl]-N,1-dimethyl-1H-pyrrole-3-carboxamide

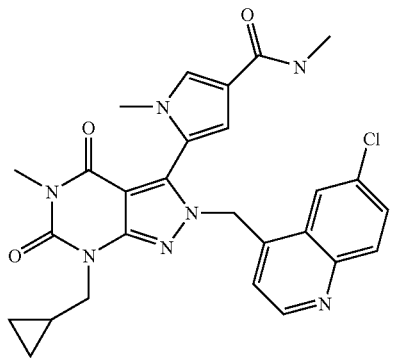

This compound was synthesized by the reaction of 5-[2-[(6-chloroquinolin-4-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-pyrrole-3-carboxylic acid and ammonia using diethyl cyanophosphonate as a coupling reagent. Mass: 532.17 (M+H).

Example 53

N-cyclopropyl-5-{7-isobutyl-5-methyl-2-[(5-methyl-1H-indol-3-yl)methyl]4,6-dioxo-4,5,6,7-tetrahydro-2H-pyrazolo[3,4-d]pyrimidin-3-yl}-1-methyl-1H-pyrrole-3-carboxamide

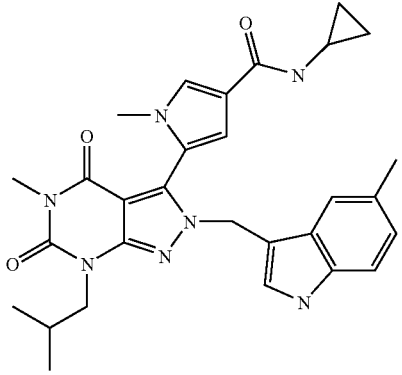

This compound was synthesized by the reaction of 5-{7-isobutyl-5-methyl-2-[(5-methyl-1H-indol-3-yl)methyl]-4,6-dioxo-4,5,6,7-tetrahydro-2H-pyrazolo[3,4-d]pyrimidin-3-yl}-1-methyl-1H-pyrrole-3-carboxylic acid and cyclopropylamine using diethyl cyanophosphonate as a coupling reagent Mass: 528.30 (M+H).

Example 54

5-{7-isobutyl-5-methyl-2-[(5-methyl-1H-indol-3-yl)methyl]-4,6-dioxo-4,5,6,7-tetrahydro-2H-pyrazolo[3,4-d]pyrimidin-3-yl}-N-methoxy-1-methyl-1H-pyrrole-3-carboxamide

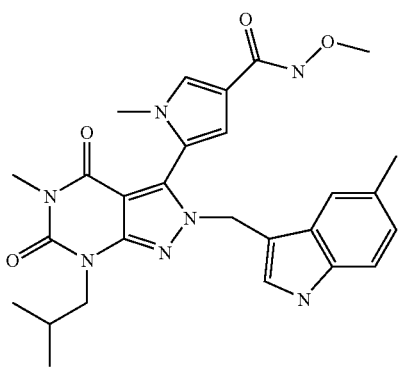

This compound was synthesized by the reaction of 5-{7-isobutyl-5-methyl-2-[(5-methyl-1H-indol-3-yl)methyl]4,6-dioxo-4,5,6,7-tetrahydro-2H-pyrazolo[3,4-d]pyrimidin-3-yl}-1-methyl-1H-pyrrole-3-carboxylic acid and methoxylamine hydrochloride using diethyl cyanophosphonate as a coupling reagent. Mass: 518.28 (M+H).

Example 55

5-{7-isobutyl-5-methyl-2-[(5-methyl-1H-indol-3-yl)methyl]4,6-dioxo-4,5,6,7-tetrahydro-2H-pyrazolo[3,4-d]pyrimidin-3-yl}-N,1-dimethyl-1H-pyrrole-3-carboxamide

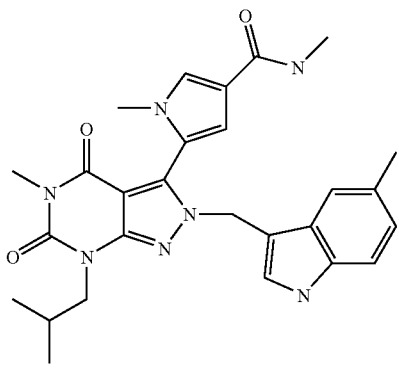

This compound was synthesized by the reaction of 5-{7-isobutyl-5-methyl-2-[(5-methyl-1H-indol-3-yl)methyl]4,6-dioxo-4,5,6,7-tetrahydro-2H-pyrazolo[3,4-d]pyrimidin-3-yl}-1-methyl-1H-pyrrole-3-carboxylic acid and ammonia using diethyl cyanophosphonate as a coupling reagent. Mass: 502.25 (M+H).

Example 56

5-[2-[(5-chloro-1H-indazol-3-yl)methyl]-7-(cyclopropylmethyl)-5-methyl-4,6-dioxo-4,5,6,7-tetrahydro-2H-pyrazolo[3,4-d]pyrimidin-3-yl]-N,1-dimethyl-1H-pyrrole-3-carboxamide

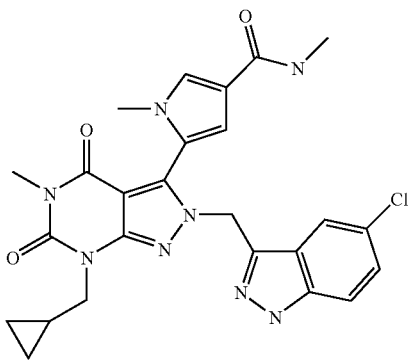

This compound was synthesized by the reaction of 5-[2-[(5-chloro-1H-indazol-3-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-pyrrole-3-carboxylic acid and ammonia using diethyl cyanophosphonate as a coupling reagent. Mass: 521.15 (M+H).

Example 57

5-[2-[(5-chloro-1H-indazol-3-yl)methyl]-7-(cyclopropylmethyl)-5-methyl-4,6-dioxo-4,5,6,7-tetrahydro-2H-pyrazolo[3,4-d]pyrimidin-3-yl]-N-cyclopropyl-1-methyl-1H-pyrrole-3-carboxamide

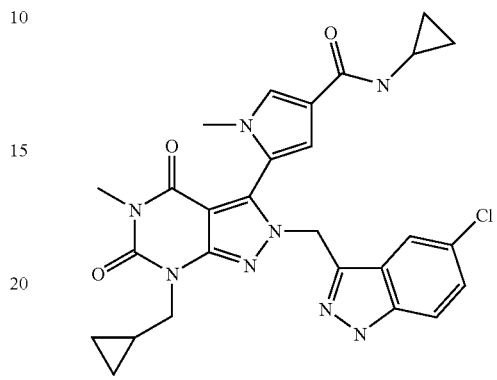

This compound was synthesized by the reaction of 5-[2-[(5-chloro-1H-indazol-3-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-pyrrole-3-carboxylic acid and cyclopropylamine using diethyl cyanophosphonate as a coupling reagent Mass: 547.19 (M+H).

Example 58

5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-N-1H-1,2,4-triazol-3-yl-1H-pyrrole-3-carboxamide

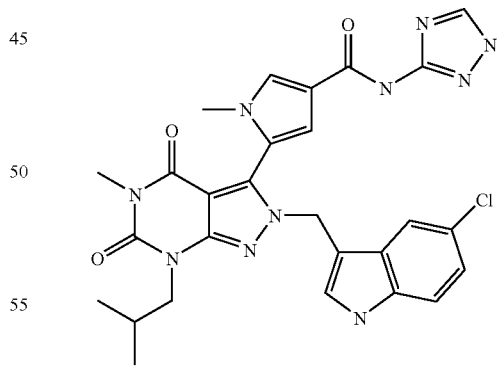

This compound was synthesized by the reaction of 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and 1H-1,2,4-triazol-3-amine using diethyl cyanophosphonate as a coupling reagent. Mass: 575.13 (M+H).

Example 59

5-{2-[(6-chloroquinolin-4-yl)methyl]-7-isobutyl-5-methyl-4,6-dioxo-4,5,6,7-tetrahydro-2H-pyrazolo[3,4-d]pyrimidin-3-yl}-N-cyclopropyl-1-methyl-1H-pyrrole-3-carboxamide

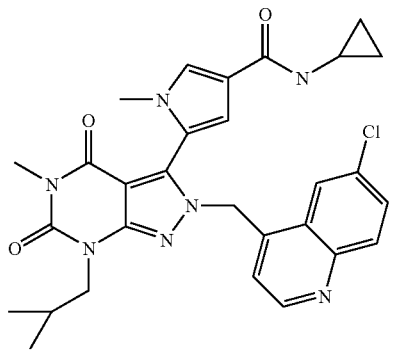

This compound was synthesized by the reaction of 5-{2-[(6-chloroquinolin-4-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and cyclopropylamine using diethyl cyanophosphonate as a coupling reagent. Mass: 560.22 (M+H).

Example 60

5-{2-[(6-chloroquinolin-4-yl)methyl]-7-isobutyl-5-methyl-4,6-dioxo-4,5,6,7-tetrahydro-2H-pyrazolo[3,4-d]pyrimidin-3-yl}-N-methoxy-1-methyl-1H-pyrrole-3-carboxamide

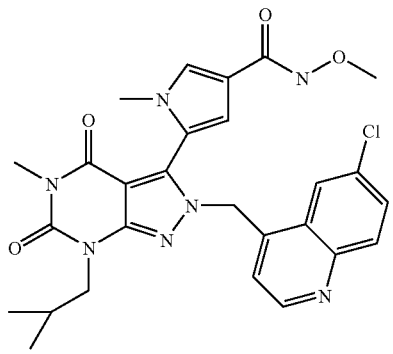

This compound was synthesized by the reaction of 5-{2-[(6-chloroquinolin-4-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and methoxylamine hydrochloride using diethyl cyanophosphonate as a coupling reagent Mass: 550.13 (M+H).

Example 61

5-{2-[(6-chloroquinolin-4-yl)methyl]-7-isobutyl-5-methyl-4,6-dioxo-4,5,6,7-tetrahydro-2H-pyrazolo[3,4-d]pyrimidin-3-yl}-N,1-dimethyl-1H-pyrrole-3-carboxamide

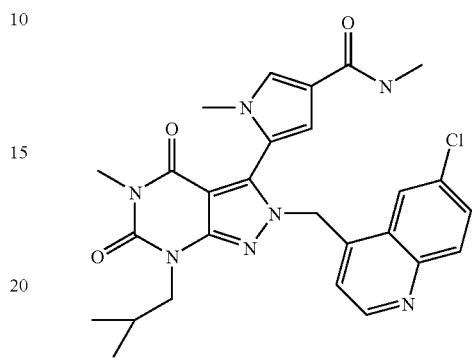

This compound was synthesized by the reaction of 5-{2-[(6-chloroquinolin-4-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and ammonia using diethyl cyanophosphonate as a coupling reagent. Mass: 534.17 (M+H).

Example 62

5-[2-(1-benzothien-3-ylmethyl)-7-isobutyl-5-methyl-4,6-dioxo-4,5,6,7-tetrahydro-2H-pyrazolo[3,4-d]pyrimidin-3-yl]-N-[2-(dimethylamino)ethyl]-1-methyl-1H-pyrrole-3-carboxamide

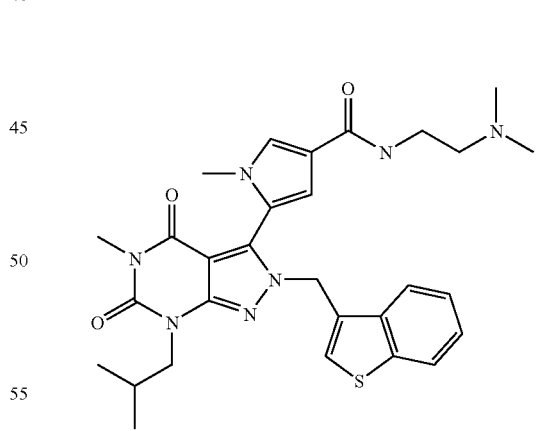

This compound was synthesized by the reaction of 5-[2-(1-benzothien-3-ylmethyl)-7-isobutyl-5-methyl-4,6-dioxo-4,5,6,7-tetrahydro-2H-pyrazolo[3,4-d]pyrimidin-3-yl]-1-methyl-1H-pyrrole-3-carboxylic acid and N,N-dimethylethane-1,2-diamine using diethyl cyanophosphonate as a coupling reagent. Mass: 562.18 (M+H).

Example 63

5-[2-(1-benzothien-3-ylmethyl)-7-isobutyl-5-methyl-4,6-dioxo-4,5,6,7-tetrahydro-2H-pyrazolo[3,4-d]pyrimidin-3-yl]-N,1-dimethyl-1H-pyrrole-3-carboxamide

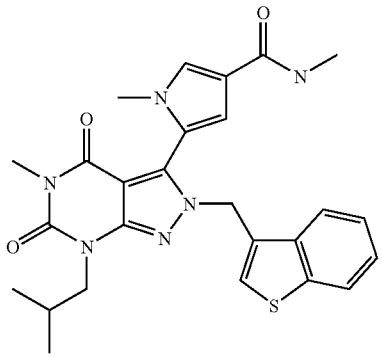

This compound was synthesized by the reaction of 5-[2-(1-benzothien-3-ylmethyl)-7-isobutyl-5-methyl-4,6-dioxo-4,5,6,7-tetrahydro-2H-pyrazolo[3,4-d]pyrimidin-3-yl]-1-methyl-1H-pyrrole-3-carboxylic acid and ammonia using diethyl cyanophospnonate as a coupling reagent Mass: 505.13 (M+H).

Example 64

N-[2-(dimethylamino)ethyl]-5-{7-isobutyl-5-methyl-2-[(5-methyl-1H-indol-3-yl)methyl]-4,6-dioxo-4,5,6,7-tetrahydro-2H-pyrazolo[3,4-d]pyrimidin-3-yl}-1-methyl-1H-pyrrole-3-carboxamide

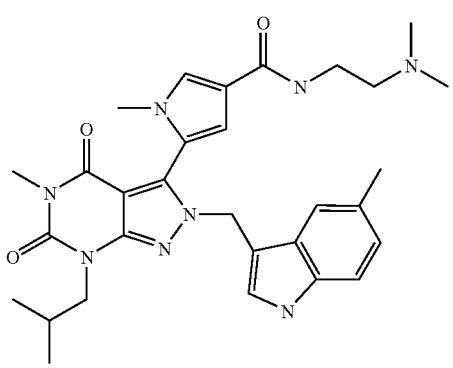

This compound was synthesized by the reaction of 5-{7-isobutyl-5-methyl-2-[(5-methyl-1H-indol-3-yl)methyl]4,6-dioxo-4,5,6,7-tetrahydro-2H-pyrazolo[3,4-d]pyrimidin-3-yl]-1-methyl-1H-pyrrole-3-carboxylic acid and N,N-dimethylethane-1,2-diamine using diethyl cyanophosphonate as a coupling reagent Mass: 559.35 (M+H).

Example 65

2-(dimethylamino)ethyl 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylate

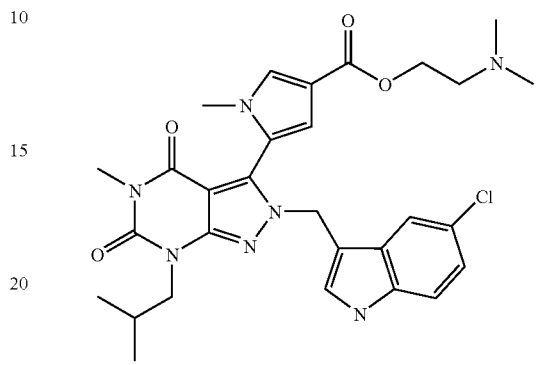

This compound was synthesized by the reaction of 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and 2-(dimethylamino)ethnol using PyBOP as a coupling reagent Mass: 580.08 (M+H).

Example 66

5-{2-[(6-chloroquinolin-4-yl)methyl]-7-isobutyl-5-methyl-4,6-dioxo-4,5,6,7-tetrahydro-2H-pyrazolo[3,4-d]pyrimidin-3-yl}-N-[2-(dimethylamino)ethyl]-1-methyl-1H-pyrrole-3-carboxamide

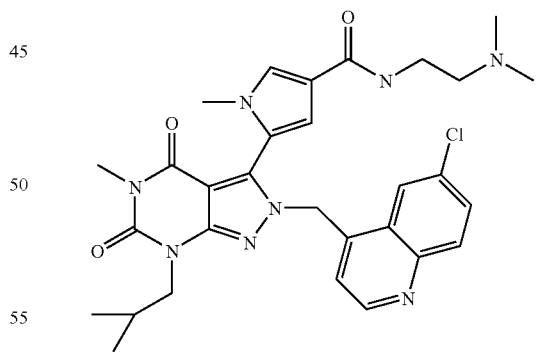

This compound was synthesized by the reaction of 5-{2-[(6-chloroquinolin-4-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and N,N-dimethylethane-1,2-diamine using diethyl cyanophosphonate as a coupling reagent. Mass: 591.27 (M+H).

Example 67

2-[(5-chloro-1H-indol-3-yl)methyl]-7-isobutyl-5-methyl-3-[1-methyl-4-(piperazin-1-ylcarbonyl)-1H-pyrrol-2-yl]-2H-pyrazolo[3,4-d]pyrimidine-4,6(5H,7H)-dione

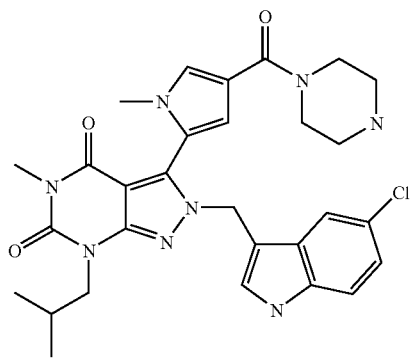

This compound was synthesized by the reaction of 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and piperazine using diethyl cyanophosphonate as a coupling reagent Mass: 577.17 (M+H).

Example 68

5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-N,N,1-trimethyl-1H-pyrrole-3-carboxamide

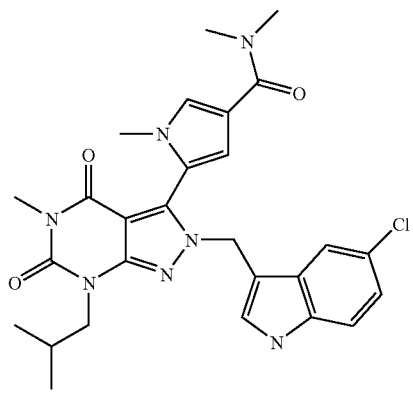

This compound was synthesized by the reaction of 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carboxylic acid and dimethylamine using diethyl cyanophosphonate as a coupling reagent. Mass: 536.03 (M+H).

Example 69

5-[2-[(5-chloro-1H-indol-3-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-pyrrole-3-carbonitrile

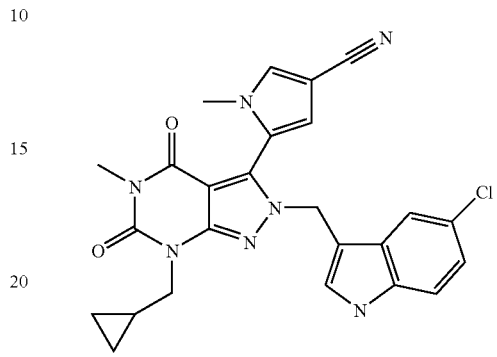

This compound was made following the procedure described above, starting with 1-(cyclopropylmethyl)-6-hydrazino-3-methylpyrimidine-2,4(1H,3H)-dione, and condensing first with 5-chloro-1H-indole-3-carbaldehyde, followed by 5-formyl-1-methyl-1H-pyrrole-3-carbonitrile. Mass: 488.16 (M+H).

Example 70

5-{7-(cyclopropylmethyl)-5-methyl-2-[(5-methyl-1H-indol-3-yl)methyl]-4,6-dioxo-4,5,6,7-tetrahydro-2H-pyrazolo[3,4-d]pyrimidin-3-yl}-1-methyl-1H-pyrrole-3-carbonitrile

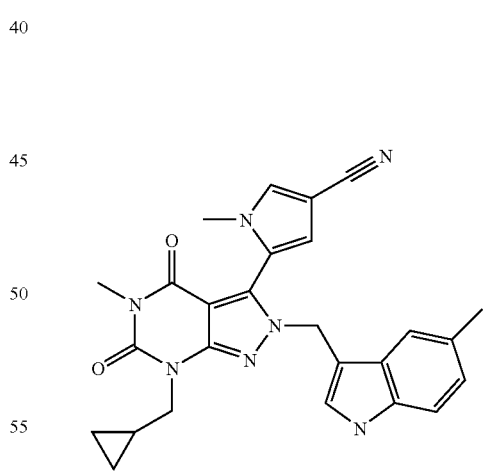

This compound was made following the procedure described above, starting with 1-(cyclopropylmethyl)-6-hydrazino-3-methylpyrimidine-2,4(1H,3H)-dione, and condensing first with 5-methyl-1H-indole-3-carbaldehyde, followed by 5-formyl-1-methyl-1H-pyrrole-3-carbonitrile. Mass: 468.26 (M+H).

Example 71

5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-carbonitrile

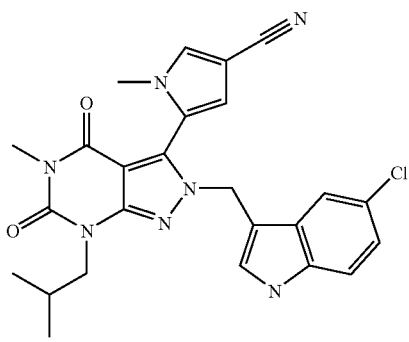

This compound was made following the procedure described above, startng with 6-hydrazino-1-isobutyl-3-methylpyrimidine-2,4(1H,3H)-dione, and condensing first with 5-chloro1-1H-indole-3-carbaldehyde, followed by 5-formyl-1-methyl-1H-pyrrole-3-carbonitrile. Mass: 490.16 (M+H).

Example 72

5-{7-isobutyl-5-methyl-2-[(5-methyl-1H-indol-3-yl)methyl]-4,6-dioxo-4,5,6,7-tetrahydro-2H-pyrazolo[3,4-d]pyrimidin-3-yl}-1-methyl-1H-pyrrole-3-carbonitrile

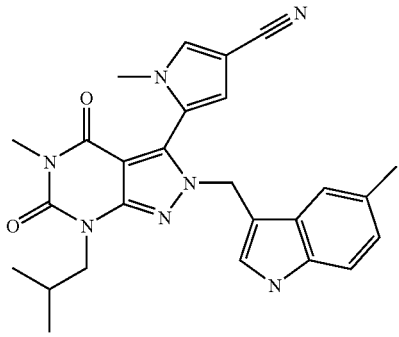

This compound was made following the procedure described above, starting with 6-hydrazino-1-isobutyl-3-methylpyrimidine-2,4(1H,3H)-dione, and condensing first with 5-methyl-1H-indole-3-carbaldehyde, followed by 5-formyl-1-methyl-1H-pyrrole-3-carbonitrile. Mass: 470.26 (M+H).

Example 73

3-(4-acetyl-1-methyl-1H-pyrrol-2-yl)-2-[(5-chloro-1H-indol-3-yl)methyl]-7-(cyclopropylmethyl)-5-methyl-2H-pyrazolo[3,4-d]pyrimidine-4,6(5H,7H)-dione

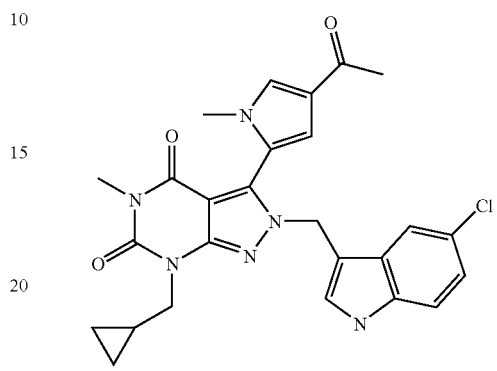

This compound was made following the procedure described above, starting with 1-(cyclopropylmethyl)-6-hydrazino-3-methylpyrimidine-2,4(1H,3H)-dione, and condensing first with 5-chloro-1H-indole-3-carbaldehyde, followed by 4-acetyl-1-methyl-1H-pyrrole-2-carbaldehyde. Mass: 505.12 (M+H).

Example 74

3-(4-acetyl-1-methyl-1H-pyrrol-2-yl)-2-[(6-chloro-quinolin-4-yl)methyl]-7-(cyclopropylmethyl)-5-methyl-2H-pyrazolo[3,4-d]pyrimidine-4,6(5H,7H)-dione

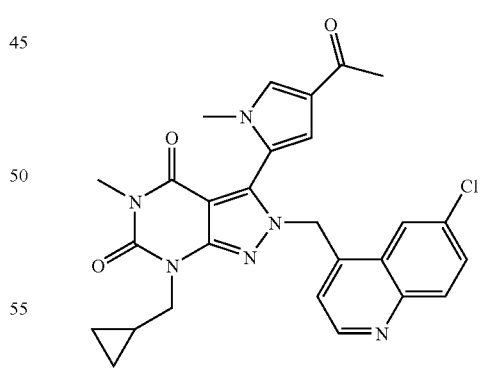

This compound was made following the procedure described above, starting with 1-(cyclopropylmethyl)-6-hydrazino-3-methylpyrimidine-2,4(1H,3H)-dione, and condensing first with 6-chloroquinoline-4-carbaldehyde, followed by 4-acetyl-1-methyl-1H-pyrrole-2-carbaldehyde. Mass: 517.14 (M+H).

Example 75

2-[(5-chloro-1H-indol-3-yl)methyl]-7-(cyclopropylmethyl)-5-methyl-3[1-methyl-4-(trifluoroacetyl)-1H-pyrrol-2-yl]-2H-pyrazolo[3,4-d]pyrimidine-4,6(5H,7H)-dione

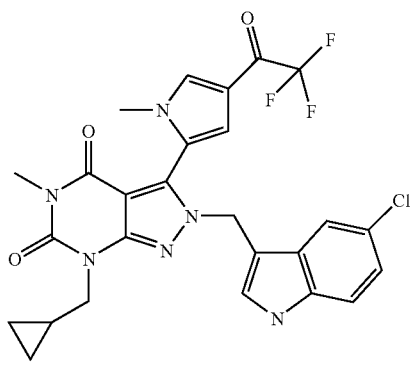

This compound was made following the procedure described above, starting with 1-(cyclopropylmethyl)-6-hydrazino-3-methylpyrimidine-2,4(1H,3H)-dione, and condensing first with 5-chloro-1H-indole-3-carbaldehyde, followed by 1-methyl-4-(trifluoroacetyl)-1H-pyrrole-2-carbaldehyde. Mass: 559.15 (M+H).

Example 76

5-methyl-2-(1-naphthylmethyl)-7-neopentyl-3-pyridin-4-yl-2H-pyrazolo[3,4-d]pyrimidine-4,6(5H,7H)-dione

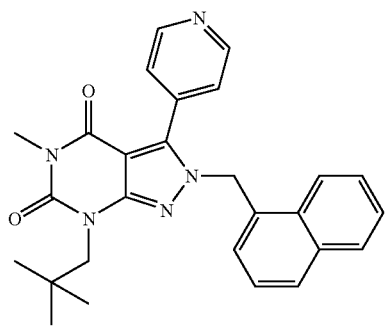

This compound was synthesized by the reaction of 5-methyl-2-(1-naphthylmethyl)-3-pyridin-4-yl-2H-pyrazolo[3,4-d]pyrimidine-4,6(5H,7H)-dione and 1-bromo-2-methylpropane using DBU as abase in DMF at 100° C. Mass: 454.36 (M+H).

Example 77

5-[2-[(5-chloro-1H-indazol-3-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-pyrrole-3-carbonitrile

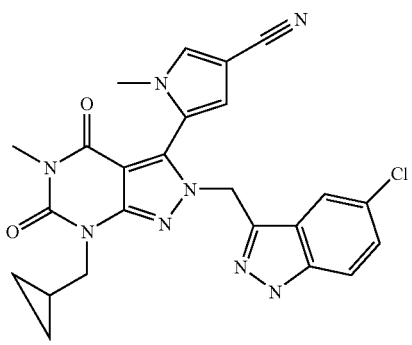

This compound was made following the procedure described above, starting with 1-(cyclopropylmethyl)-6-hydrazino-3-methylpyrimidine-2,4(1H,3H)-dione, and condensing first with 5-chloro-1H-indazole-3-carbaldehyde, followed by 5-formyl-1-methyl-1H-pyrrole-3-carbonitrile. Mass: 489.10 (M+H).

Example 78

2-[(5-chloro-1H-indol-3-yl)methyl]-7-isobutyl-5-methyl-3-(1-methyl-1-imidazol-2-yl)-2H-pyrazolo[3,4-d]pyrimidine-4,6(5H,7H)-dione

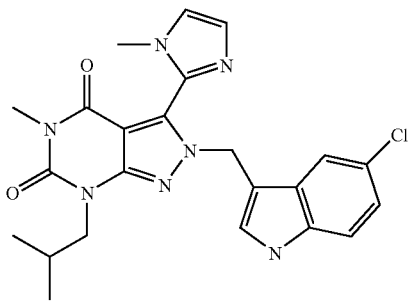

This compound was made following the procedure described above, starting with 6-hydrazino-1-isobutyl-3-methylpyrimidine-2,4(1H,3H)-dione, and condensing first with 5-chloro-1H-indole-3-carbaldehyde, followed by 1-methyl-1H-imidazole-2-carbaldehyde. Mass: 466.17 (M+H).

Example 79

7-isobutyl-5-methyl-3-(1-methyl-1H-imidazol-2-yl)-2-[(5-nitro-1H-indol-3-yl)methyl]-2H-pyrazolo[3,4-d]pyrimidine-4,6(5H,7H)-dione

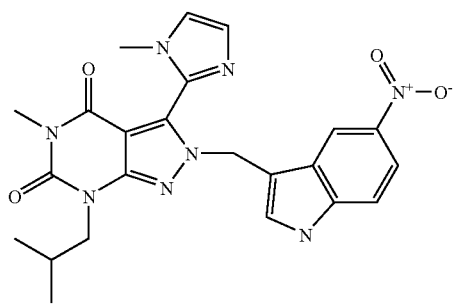

This compound was made following the procedure described above, starting with 6-hydrazino-1-isobutyl-3-methylpyrimidine-2,4(1H,3H)-dione, and condensing first with 5-nitro-1H-indole-3-carbaldehyde, followed by 1-methyl-1H-imidazole-2-carbaldehyde. Mass: 477.19 (M+H).

Example 80

2-[(5-chloro-2-methyl-1H-indol-3-yl)methyl]-7-isobutyl-5-methyl-3-(1-methyl-1H-imidazol-2-yl)-2H-pyrazolo[3,4-d]pyrimidine-4,6(5H,7H)-dione

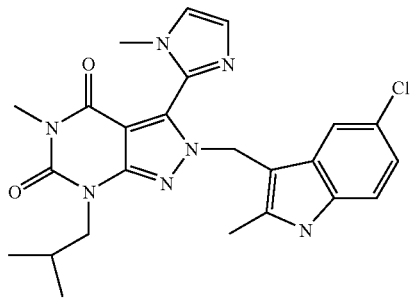

This compound was made following the procedure described above, starting with 6-hydrazino-1-isobutyl-3-methylpyrimidine-2,4(1H,3H)-dione, and condensing first with 5-chloro-2-methyl-1H-indole-3-carbaldehyde, followed by 1-methyl-1H-imidazole-2-carbaldehyde. Mass: 480.10 (M+H).

Example 81

7-isobutyl-5-methyl-3-(1-methyl-1H-imidazol-2-yl)-2-[(5-methyl-1H-indol-3-yl)methyl]-2H-pyrazolo[3,4-d]pyrimidine-4,6(5H,7H)-dione

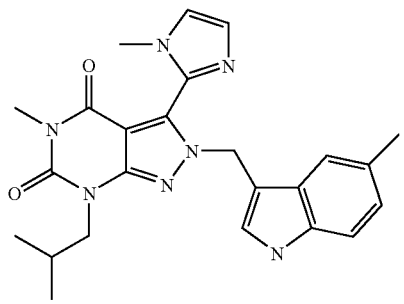

This compound was made following the procedure described above, starting with 6-hydrazino-1-isobutyl-3-methylpyrimidine-2,4(1H,3H)-dione, and condensing first with 5-methyl-1H-indole-3-carbaldehyde, followed by 1-methyl-1H-imidazole-2-carbaldehyde. Mass: 446.26 (M+H).

Example 82

7-isobutyl-5-methyl-3-(1-methyl-1H-pyrrol-2-yl)-2-(1-naphthylmethyl)-2H-pyrazolo[3,4-d]pyrimidine-4,6(5H,7H)-dione

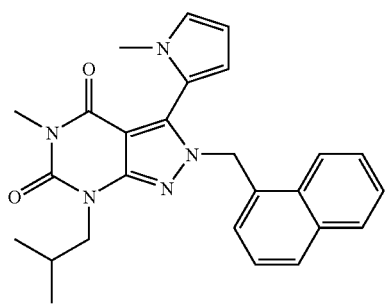

This compound was made following the procedure described above, starting with 6-hydrazino-1-isobutyl-3-methylpyrimidine-2,4(1H,3H)-dione, and condensing first with 1-naphthaldehyde, followed by 1-methyl-1H-pyrrole-2-carbaldehyde. Mass: 442.35 (M+H).

Example 83

7-isobutyl-5-methyl-3-(3-methylthien-2-yl)-2-(1-naphthylmethyl)-2H-pyrazolo[3,4-d]pyrimidine-4,6(5H,7H)-dione

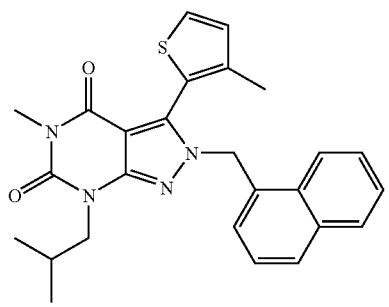

This compound was made following the procedure described above, starting with 6-hydrazino-1-isobutyl-3-methylpyrimidine-2,4(1H,3H)-dione, and condensing first with 1-naphthaldehyde, followed by 3-methylthiophene-2-carbaldehyde. Mass: 458.87 (M+H).

Example 84

5-{7-isobutyl-5-methyl-2-[(2-methyl-1H-indol-3-yl)methyl]4,6-dioxo-4,5,6,7-tetrahydro-2H-pyrazolo[3,4-d]pyrimidin-3-yl}-methyl-1H-pyrrole-3-carbonitrile

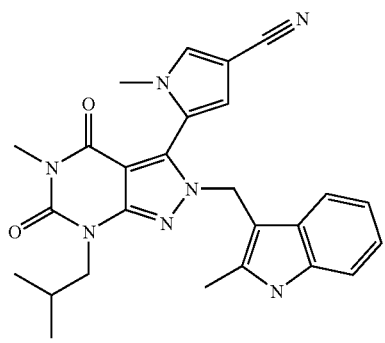

This compound was made following the procedure described above, starting with 6-hydrazino-1-isobutyl-3-methylpyrimidine-2,4(1H,3H)-dione, and condensing first with 2-methyl-1H-indole-3-carbaldehyde, followed by 5-formyl-1-methyl-1H-pyrrole-3-carbonitrile. Mass: 470.20 (M+H).

Example 85

7-isobutyl-5-methyl-2-(1-naphthylmethyl)-3-pyridin-4-yl-2H-pyrazolo[3,4-d]pyrimidine-4,6(5H,7H)-dione

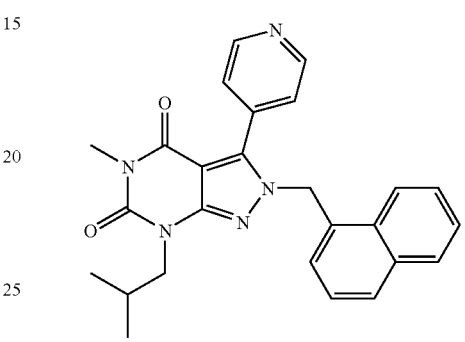

This compound was made following the procedure described above, starting with 6-hydrazino-1-isobutyl-3-methylpyrimidine-2,4(1H,3H)-dione, and condensing first with 1-naphthaldehyde, followed by isonicotinaldehyde. Mass: 439.79 (M+H).

Example 86

2-(1-benzothien-3-ylmethyl)-7-isobutyl-5-methyl-3-(3-methylthien-2-yl)-2H-pyrazolo[3,4-d]pyrimidine-4,6(5H,7H)-dione

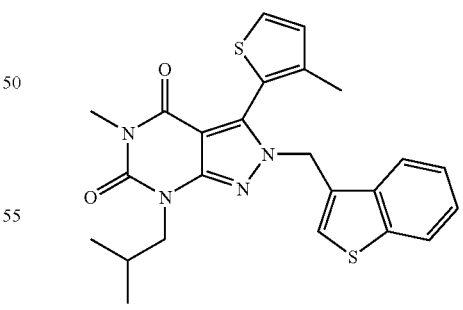

This compound was made following the procedure described above, starting with 6-hydrazino-1-isobutyl-3-methylpyrimidine-2,4(1H,3H)-dione, and condensing first with 1-benzothiophene-3-carbaldehyde, followed by 3-methylthiophene-2-carbaldehyde. Mass: 464.85 (M+H).

Example 87

3-{[7-isobutyl-5-methyl-3-(1-methyl-1H-imidazol-2-yl)-4,6-dioxo-4,5,6,7-tetrahydro-2H-pyrazolo[3,4-d]pyrimidin-2-yl]methyl}-1H-indole-5-carbonitrile

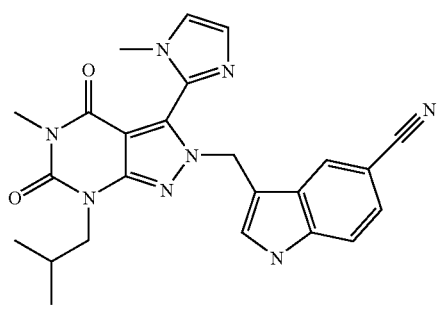

This compound was made following the procedure described above, starting with 6-hydrazino-1-isobutyl-3-methylpyrimidine-2,4(1H,3H)-dione, and condensing first with 3-formyl-1H-indole-5-carbonitrile, followed by 1-methyl-1H-imidazole-2-carbaldehyde. Mass: 457.14 (M+H).

Example 88

7-isobutyl-2-[(5-methoxy-1-indol-3-yl)methyl]-5-methyl-3-(1-methyl-1-imidazol-2-yl)-2H-pyrazolo[3,4-d]pyrimidine-4,6(5H,7H)-dione

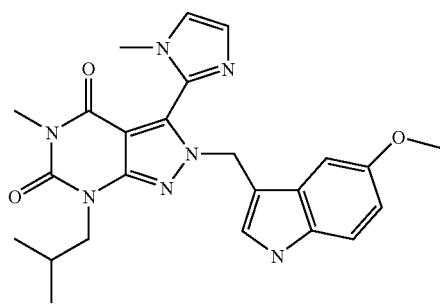

This compound was made following the procedure described above, starting with 6-hydrazino-1-isobutyl-3-methylpyrimidine-2,4(1H,3H)-dione, and condensing first with 5-methoxy 1H-indole-3-carbaldehyde, followed by 1-methyl-1H-imidazole-2-carbaldehyde. Mass: 462.21 (M+H).

Example 89

7-isobutyl-5-methyl-3-(1-methyl-1H-imidazol-2-yl)-2-[(4-methyl-1H-indol-3-yl) methyl]-2H-pyrazolo[3,4-d]pyrimidine-4,6(5H,7H)-dione

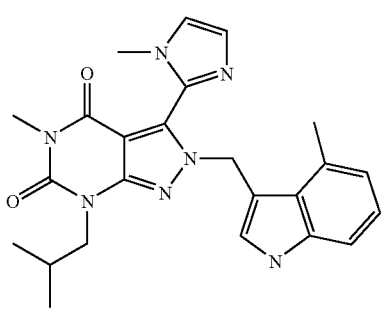

This compound was made following the procedure described above, starting with 6-hydrazino-1-isobutyl-3-methylpyrimidine-2,4(1H,3H)-dione, and condensing first with 4-methyl-1H-indole-3-carbaldehyde, followed by 1-methyl-1H-imidazole-2-carbaldehyde. Mass: 446.45 (M+H).

Example 90

7-isobutyl-5-methyl-2-(1-naphthylmethyl)-3-thien-2-yl-2H-pyrazolo[3,4-d]pyrimidine-4,6(5H,7H)-dione

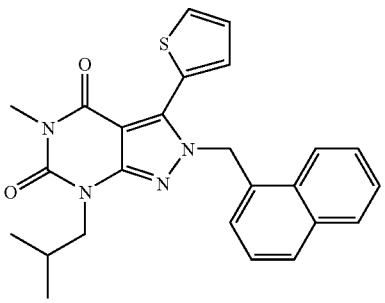

This compound was made following the procedure described above, starting with 6-hydrazino-1-isobutyl-3-methylpyrimidine-2,4(1H,3H)-dione, and condensing first with 1-naphthaldehyde, followed by thiophene-2-carbaldehyde. Mass: 444.88 (M+H).

Example 91

2-[(5-bromo-1H-indol-3-yl)methyl]-7-isobutyl-5-methyl-3-(1-methyl-1H-imidazol-2-yl)-2H-pyrazolo[3,4-d]pyrimidine-4,6(5H,7H)-dione

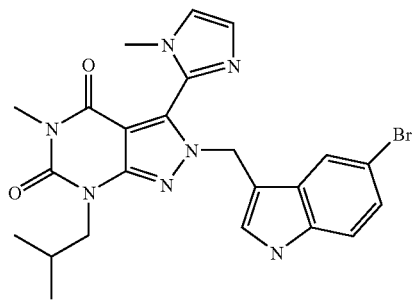

This compound was made following the procedure described above, starting with 6-hydrazino-1-isobutyl-3-methylpyrimidine-2,4(1H,3H)-dione, and condensing first with 5-bromo-1H-indole-3-carbaldehyde, followed by 1-methyl-1H-imidazole-2-carbaldehyde.

Example 92

2-(1-benzothien-3-ylmethyl)-7-isobutyl-5-methyl-3-pyridin-4-yl-2H-pyrazolo[3,4-d]pyrimidine-4,6(5H,7H)-dione

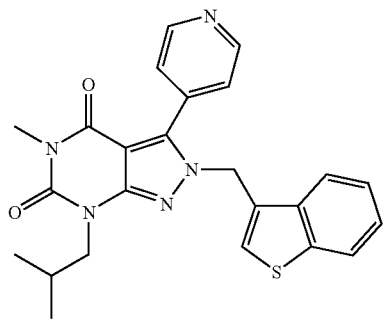

This compound was made following the procedure described above, starting with 6-hydrazino-1-isobutyl-3-methylpyrimidine-2,4(1H,3H)-dione, and condensing first with 1-benzothiophene-3-carbaldehyde, followed by isonicotinaldenyde. Mass: 445.92 (M+H).

Example 93

2-[(5-chloro-1H-indol-3-yl)methyl]-7-isobutyl-3-(1-methyl-1H-imidazol-2-yl)-2H-pyrazolo[3,4-d]pyrimidine-4,6(5H,7H)-dione

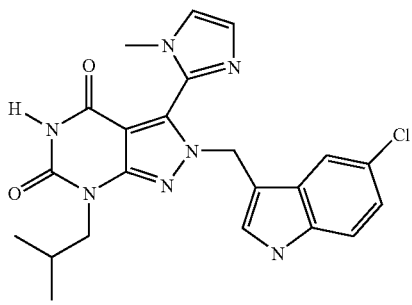

This compound was made following the procedure described above, starting with 6-hydrazino-1-isobutylpyrimidine-2,4(1H,3H)-dione, and condensing first with 5-chloro-1H-indole-3-carbaldehyde, followed by 1-methyl-1H-imidazole-2-carbaldehyde. Mass: 452.18 (M+H).

Example 94

2-[(5-choro-1H-indol-3-yl)methyl]-7-isobutyl-3-(1-methyl-1H-imidazol-2-yl)-5-(2-morpholin-4-yl-ethyl)-2H-pyrazolo[3,4-d]pyrimidine-4,6(5H,7H)-dione

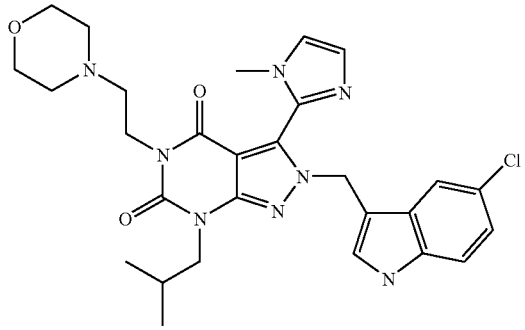

This compound was synthesized by the reaction of 2-[(5-chloro-1H-indol-3-yl)methyl]-7-isobutyl-3-(1-methyl-1H-imidazol-2-yl)-2H-pyrazolo[3,4-d]pyrimidine-4,6(5H,7H)-dione and 4-(2-chloroethyl)morpholine using potassium carbonate as a base. Mass: 565.17 (M+H).

Example 95

2-[(5-chloro-1H-indol-3-yl)methyl]-5-(2-hydroxyethyl)-7-isobutyl-3-(1-methyl-1H-imidazol-2-yl)-2H-pyrazolo[3,4-d]pyrimidine-4,6(5H,7H)-dione

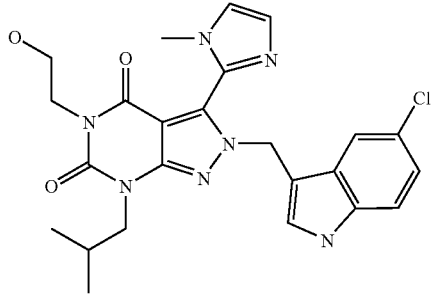

This compound was synthesized by the reaction of 2-[(5-chloro-1H-indol-3-yl)methyl]-7-isobutyl-3-(1-methyl-1H-imidazol-2-yl)-2H-pyrazolo[3,4-d]pyrimidine-4,6(5H,7H)-dione and 2-bromoethanol using potassium carbonate as a base. Mass: 496.17 (M+H).

Example 96

7-isobutyl-2-(1-naphthylmethyl)-3-pyridin-4-yl-5-(pyridin-3-ylmethyl)-2H-pyrazolo[3,4-d]pyrimidine-4,6(5H,7H)-dione

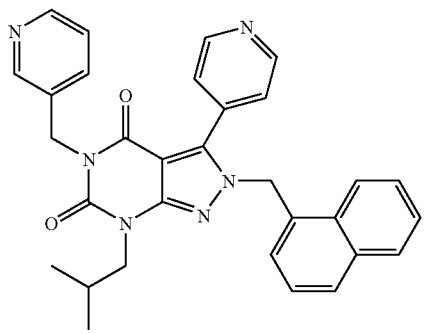

This compound was synthesized by the reaction of 7-isobutyl-2-(1-naphthylmethyl)-3-pyridin-4-yl-2H-pyrazolo[3,4-d]pyrimidine-4,6(5H,7H)-dione and 3-(chloromethyl)pyridine hydrochloride using DBU as a base. Mass: 516.86 (M+H).

Example 97

7-isobutyl-2-(1-naphthylmethyl)-3-pyridin-4-yl-5-(pyridin-4-ylmethyl)-2H-pyrazolo[3,4-d]pyrimidine-4,6(5H,7H)-dione

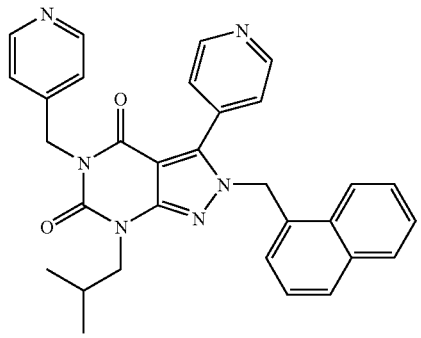

This compound was synthesized by the reaction of 7-isobutyl-2-(1-naphthylmethyl)-3-pyridin-4-yl-2H-pyrazolo[3,4-d]pyrimidine-4,6(5H,7H)-dione and 4-(chloromethyl)pyridine hydrochloride using DBU as a base. Mass: 516.88 (M+H).

Example 98

2-[(5-chloro-1H-indol-3-yl)methyl]-5-methyl-7-(3-methylbutyl)-3-(1-methyl-1H-imidazol-2-yl)-2H-pyrazolo[3,4-d]pyrimidine-4,6(5H,7H)-dione

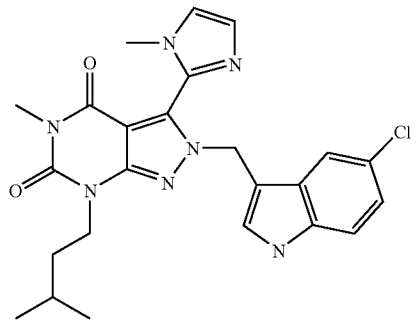

(a) 2-[(5-chloro-1H-indol-3-yl)methyl]-5-methyl-3-(1-methyl-1H-imidazol-2-yl)-2H-pyrazolo[3,4-d]pyrimidine-4,6(5H,7H)-dione This compound was made following the procedure described above, starting with 6-hydrazino-3-methylpyrimidine-2,4(1H,3H)-dione, and condensing first with 5-chloro-1H-indole-3-carbaldehyde, followed by 1-methyl-1H-imidazole-2-carbaldehyde (b) 2-[(5-chloro-1H-indol-3-yl)methyl]-5-methyl-7-(3-methylbutyl)-3-(1-methyl-1H-imidazol-2-yl)-2H-pyrazolo[3,4-d]pyrimidine-4,6(5H,7H)-dione This compound was synthesized by the reaction of 2-[(5-chloro-1H-indol-3-yl)methyl]-5-methyl-3-(1-methyl-1H-imidazol-2-yl)-2H-pyrazolo[3,4-d]pyrimidine-4,6(5H,7H)-dione and 1-bromo-3-methylbutane using potassium carbonate as a base in DMF at 80° C. Mass: 480.16 (M+H).

Example 99

2-[(5-chloro-1H-indol-3-yl)methyl]-7-(cyclobutylmethyl)-5-methyl-3-(1-methyl-1H-imidazol-2-yl)-2H-pyrazolo[3,4-d]pyrimidine-4,6(5H,7H)-dione

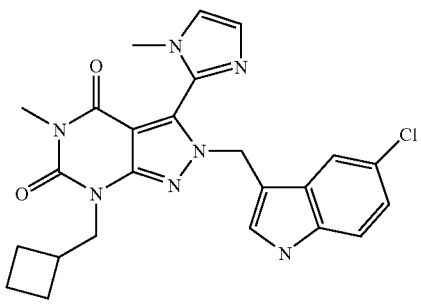

This compound was synthesized by the reaction of 2-[(5-chloro-1H-indol-3-yl)methyl]-5-methyl-3-(1-methyl-1H-imidazol-2-yl)-2H-pyrazolo[3,4-d]pyrimidine-4,6(5H,7H)-dione and (bromomethyl)cyclobutane using potassium carbonate as a base in DMF at 80° C. Mass: 478.16 (M+H).

Example 100

2-[(5-chloro-1H-indol-3-yl)methyl]-7-[(3,5-dimethylisoxazol-4-yl)methyl]-5-methyl-3-(1-methyl-1H-imidazol-2-yl)-2H-pyrazolo[3,4-d]pyrimidine-4,6(5H,7H)-dione

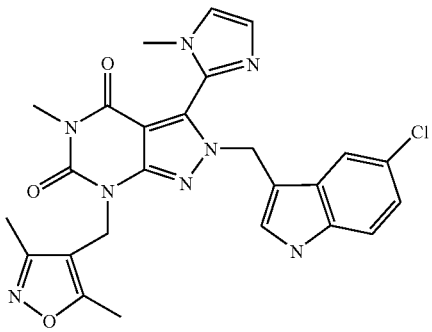

This compound was synthesized by the reaction of 2-[(5-chloro-1H-indol-3-yl)methyl]-5-methyl-3-(1-methyl-1H-imidazol-2-yl)-2H-pyrazolo[3,4-d]pyrimidine-4,6(5H,7H)-dione and 4-(bromomethyl)-3,5-dimethylisoxazole using potassium carbonate as a base in DMF at 80° C. Mass: 519.01 (M+H).

Example 101

2-[(5-chloro-1H-indol-3-yl)methyl]-5-methyl-3-(1-methyl-1H-imidazol-2-yl)-7-propyl-2H-pyrazolo[3,4-d]pyrimidine-4,6(5H,7H)-dione

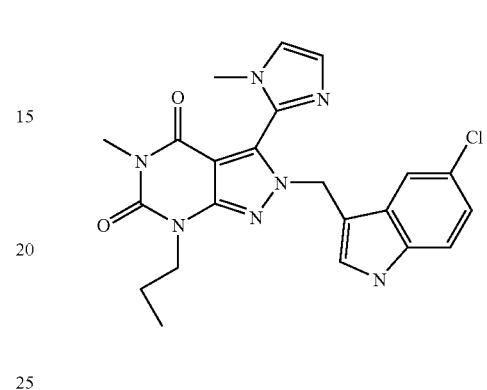

This compound was synthesized by the reaction of 2-[(5-chloro-1H-indol-3-yl)methyl]-5-methyl-3-(1-methyl-1H-imdazol-2-yl)-2H-pyrazolo[3,4-d]pyrimidine-4,6(5H,7H)-dione and 1-bromopropane using potassium carbonate as a base in DMF at 80° C. Mass: 452.08 (M+H).

Example 102

2-[(5-chloro-1H-indol-3-yl)methyl]-5-methyl-7-(2-methylbenzyl)-3-(1-methyl-1H-imidazol-2-yl)-2H-pyrazolo[3,4-d]pyrimidine-4,6(5H,7H)-dione

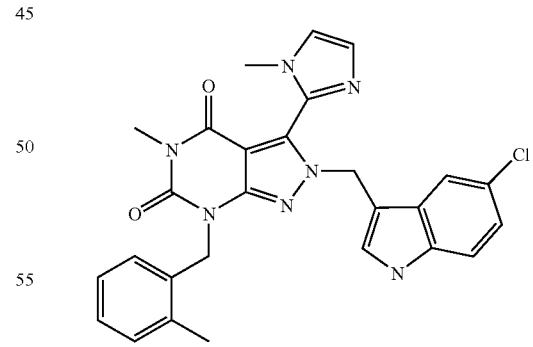

This compound was synthesized by the reaction of 2-[(5-chloro-1H-indol-3-yl)methyl]-5-methyl-3-(1-methyl-1H-imidazol-2-yl)-2H-pyrazolo[3,4-d]pyrimidine-4,6(5H,7H)-dione and 1-(bromomethyl)-2-methylbenzene using DBU as a base in DMF at 80° C., Mass: 514.11 (M+H).

Example 103

2-[(5-chloro-1H-indol-3-yl)methyl]-5-methyl-3-(1-methyl-1H-imidazol-2-yl)-7-propyl-2H-pyrazolo[3,4-d]pyrimidine,4,6(5H,7H)-dione

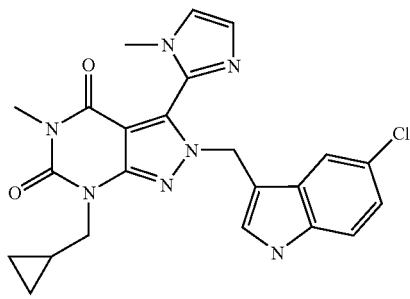

This compound was synthesized by the reaction of 2-[(5-chloro-1H-indol-3-yl)methyl]-5-methyl-3-methyl-1H-imidazol-2-yl)-2H-pyrazolo[3,4-d]pyrimidine-4,6(5H,7H)-dione and (bromomethyl)cyclopropane using potassium carbonate as a base in DMF at 80° C. Mass: 464.14 (M+H).

Example 104

7-[(3,5-dimethylisoxazol-4-yl)methyl]-5-methyl-2-(1-naphthylmethyl)-3-pyridin-4-yl-2H-pyrazolo[3,4-d]pyrimidine-4,6(5H,7H)-dione

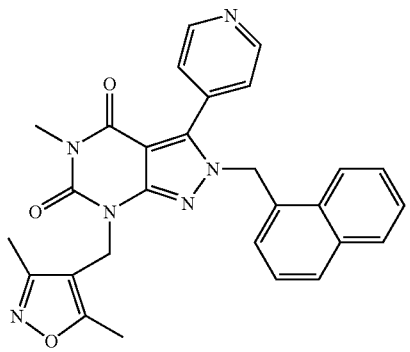

This compound was synthesized by the reaction of 5-methyl-2-(1-naphthylmethyl)-3-pyridin-4-yl-2H-pyrazolo[3,4-d]pyrimidine-4,6(5H,7H)-dione and 4-(bromomethyl)-3,5-dimethylisoxazole using potassium carbonate as abase in DMF at 80° C. Mass: 492.94 (M+H).

Example 105

7-(4-hydroxybenzyl)-5-methyl-2-(1-naphthylmethyl)-3-pyridin-4-yl-2H-pyrazolo[3,4-d]pyrimidine-4,6(5H,7H)-dione

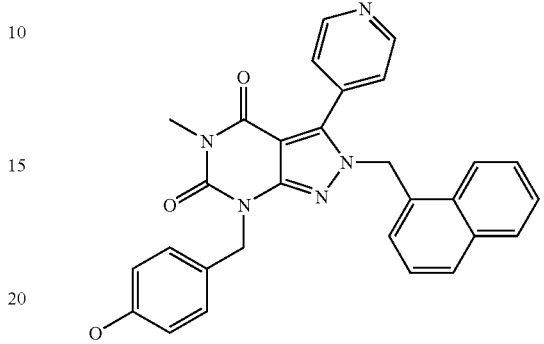

(a) 4-{[5-methyl-2-(1-naphthylmethyl)-4,6-dioxo-3-pyridin-4-yl-2,4,5,6-tetrahydro-7H-pyrazolo[3,4-d]pyrimidin-7-yl]methyl}phenyl acetate This compound was synthesized by the reaction of 5-methyl-2-(1-naphthylmethyl)-3-pyridin-4-yl-2H-pyrazolo[3,4-d]pyrimidine-4,6(5H,7H)-dione and 4-(chloromethyl)phenyl acetate using potassium carbonate as a base in DMF at 80° C.

(b) 7-(4-hydroxybenzyl)-5-methyl-2-(1-naphthylmethyl)-3-pyridin)-4-yl-2H-pyrazolo[3,4-d]pyrimidine-4,6(5H,7H)-dione This compound was synthesized by the hydrolysis of 4-{[5-methyl-2-(1-naphthylmethyl)-4,6-dioxo-3-pyridin-4-yl-2,4,5,6-tetrahydro-7H-pyrazolo[3,4-d]pyrimidin-7-yl]methyl}phenyl acetate with 0.5N LiOH at room temperature for six hours. Mass: 489.80 (M+H).

Example 106

3-{[5-methyl-2-(1-naphthylmethyl)-4,6-dioxo-3-pyridin-4-yl-2,4,5,6-tetrahydro-7H-pyrazolo[3,4-d]pyrimidin-7-yl]methyl}benzoic acid

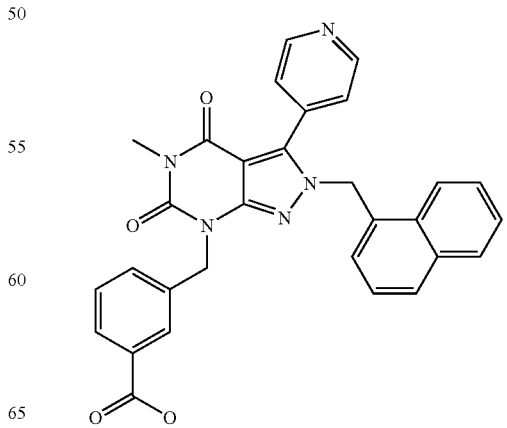

(a) methyl 3-{[5-methyl-2-(1-naphthylmethyl)-4,6-dioxo-3-pyridin-4-yl-2,4,5,6-tetrahydro-7H-pyrazolo[3,4-d]pyrimidin-7-yl]methyl}benzoate This compound was synthesized by the reaction of 5-methyl-2-(1-naphthylmethyl)-3-pyridin-4-yl-2H-pyrazolo[3,4-d]pyrimidine-4,6(5H,7H)-dione and methyl 3-(bromomethyl)benzoate using potassium carbonate as a base in DMF at 80° C.

(b) 3-{[5-methyl-2-(1-naphthylmethyl)-4,6-dioxo-3-pyridin-4-yl-2,4,5,6-tetrahydro-7H-pyrazolo[3,4-d]pyrimidin-7-yl]methyl}benzoic acid This compound was synthesized by the hydrolysis of methyl 3-{[5-methyl-2-(1-naphthylmethyl)-4,6-dioxo-3-pyridin-4-yl-2,4,5,6-tetrahydro-7H-pyrazolo[3,4-d]pyrimidin-7-yl]methyl}benzoate with 0.5N LiOH at room temperature for eight hours. Mass: 517.79 (M+H).

Example 107

3-[7-isobutyl-5-methyl-2-(1-naphthylmethyl)-4,6-dioxo-4,5,6,7-tetrahydro-2H-pyrazolo[3,4-d]pyrimidin-3-yl]benzoic acid

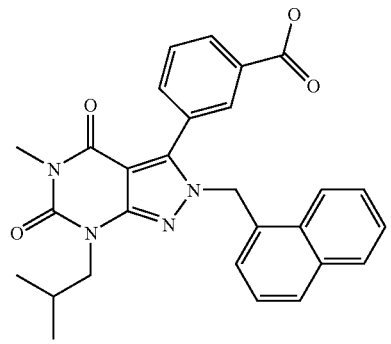

This compound was made following the procedure described above, starting with 6-hydrazino-1-isobutyl-3-methylpyrimidine-2,4(1H,3H)-dione, and condensing first with 1-naphthaldehyde, followed by 3-formylbenzoic acid. Mass: 482.72 (M+H).

Example 108

3-[7-isobutyl-5-methyl-2-(1-naphthylmethyl)-4,6-dioxo-4,5,6,7-tetrahydro-2H-pyrazolo[3,4-d]pyrimidin-3-yl]benzamide

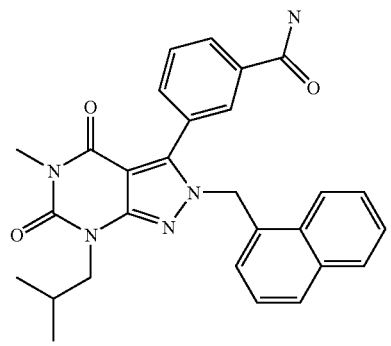

This compound was synthesized by the reaction of 3-[7-isobutyl-5-methyl-2-(1-naphthylmethyl)-4,6-dioxo-4,5,6,7-tetrahydro-2H-pyrazolo[3,4-d]pyrimidin-3-yl]benzoic acid and ammonia in water using diethyl isobutyl chloroformate as a coupling reagent Mass: 481.89 (M+H).

Example 109

3-[5-methyl-7-(3-methylbutyl)-2-(1-naphthylmethyl)-4,6-dioxo-4,5,6,7-tetrahydro-2H-pyrazolo[3,4-d]pyrimidin-3-yl]benzoic acid

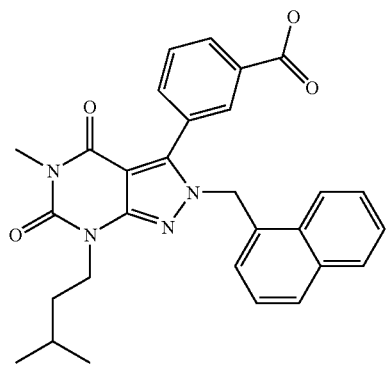

(a) Resin bound 3-[5-methyl-7-(3-methylbutyl)-2-(1-naphthylmethyl)-4,6-dioxo-4,5,6,7-tetrahydro-2H-pyrazolo[3,4-d]pyrimidin-3-yl]benzoic acid This compound was synthesized by the reaction of resin bound 3-[5-methyl-2-(1-naphthylmethyl)-4,6-dioxo-4,5,6,7-tetrahydro-2H-pyrazolo[3,4-d]pyrimidin-3-yl]benzoic acid and 1-bromo-3-methylbutane using potassium carbonate as a base in DMF at 85° C.

(b) 3-[5-methyl-7-(3-methylbutyl)-2-(1-naphthylmethyl)-4,6-dioxo-4,5,6,7-tetrahydro-2H-pyrazolo[3,4-d]pyrimidin-3-yl]benzoic acid This compound was synthesized by treating resin bound 3-[5-methyl-7-(3-methylbutyl)-2-(1-naphthylmethyl)-4,6-dioxo-4,5,6,7-tetrahydro-2H-pyrazolo[3,4-d]pyrimidin-3-yl]benzoic acid with 15% TFA in dichloromethane at room temperature for 2 hours. Mass: 496.92 (M+H).

Example 110

3-[7-(cyclopropylmethyl)-5-methyl-2-(1-naphthylmethyl)-4,6-dioxo-4,5,6,7-tetrahydro-2H-pyrazolo[3,4-d]pyrimidin-3-yl]benzoic acid

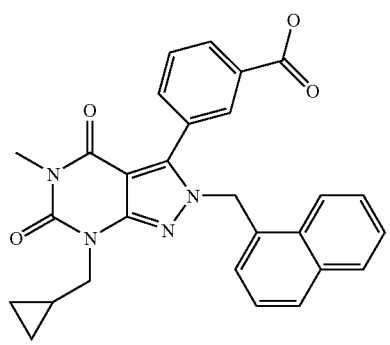

(a) Resin bound 3-[7-(cyclopropylmethyl)-5-methyl-2-(1-naphthylmethyl)-4,6-dioxo-4,5,6,7-tetrahydro-2H-pyrazolo[3,4-d]pyrimidin-3-yl]benzoic acid This compound was synthesized by the reaction of resin bound 3-[5-methyl-2-(1-naphthylmethyl)-4,6-dioxo-4,5,6,7-tetrahydro-2H-pyrazolo[3,4-d]pyrimidin-3-yl]benzoic acid and (bromomethyl)cyclopropane using potassium carbonate as a base in DMF at 85° C.

(b) 3-[7-(cyclopropylmethyl)-5-methyl-2-(1-naphthylmethyl)-4,6-dioxo-4,5,6,7-tetrahydro-2H-pyrazolo[3,4-d]pyrimidin-3-yl]benzoic acid This compound was synthesized by treating resin bound 3-[7-(cyclopropylmethyl)-5-methyl-2-(1-naphthylmethyl)-4,6-dioxo-4,5,6,7-tetrahydro-2H-pyrazolo[3,4-d]pyrimidin-3-yl]benzoic acid with 15% TFA in dichloromethane at room temperature for 2 hours. Mass: 480.93 (M+H).

Example 111

3-(4-amino-1-methyl-1H-imidazol-2-yl)-2-(1-benzothien-3-ylmethyl)-7-isobutyl-5-methyl-2H-pyrazolo[3,4-d]pyrimidine-4,6(5H,7H)-dione

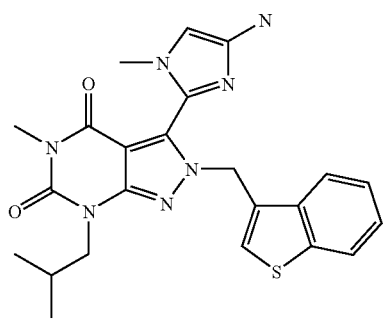

(a) tert-butyl 2-[2-(1-benzothien-3-ylmethyl)-7-isobutyl-5-methyl-4,6-dioxo-4,5,6,7-tetrahydro-2H-pyrazolo[3,4-d]pyrimidin-3-yl]-1-methyl-1H-imidazol-4-ylcarbamate This compound was made following the procedure described above, starting with 6-hydrazino-1-isobutyl-3-methylpyrimidine-2,4(1H,3H)-dione, and condensing first with 1-benzothiophene-3-carbaldehyde, followed by tert-butyl 2-formyl-1-methyl-1H-imidazol-4-ylcarbamate.

(b) 3-(4-amino-1-methyl-1H-imidazol-2-yl)-2-(1-benzothien-3-ylmethyl)-7-isobutyl-5-methyl-2H-pyrazolo[3,4-d]pyrimidine-4,6(5H,7H)-dione This compound was synthesized by treating tert-butyl 2-[2-(1-benzothien-3-ylmethyl)-7-isobutyl-5-methyl-4,6-dioxo-4,5,6,7-tetrahydro-2H-pyrazolo[3,4-d]pyrimidin-3-yl]-1-methyl-1H-imidazol-4-ylcarbamate with 4M HCl in dioxane at room temperature for 3 hours. Mass: 464.10 (M+H).

Example 112

N-{2-[2-(1-benzothien-3-ylmethyl)-7-isobutyl-5-methyl-4,6-dioxo-4,5,6,7-tetrahydro-2H-pyrazolo[3,4-d]pyrimidin-3-yl]-1-methyl-1H-imidazol-4-yl}acetamide

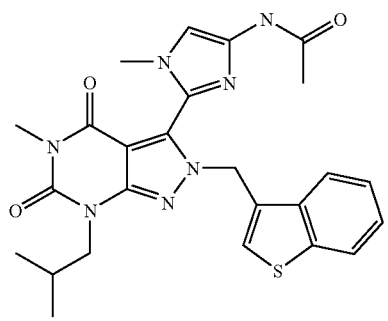

This compound was synthesized by the reaction of 3-(4-amino-1-methyl-1H-imidazol-2-yl)-2-(1-benzothien-3-ylmethyl)-7-isobutyl-5-methyl-2H-pyrazolo[3,4-d]pyrimidine-4,6(5H,7H)-dione hydrochloride and acetyl chloride using triethylamine as a base. Mass: 506.09 (M+H).

Example 113 tert-butyl 2-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-imidazol-4-ylcarbamate

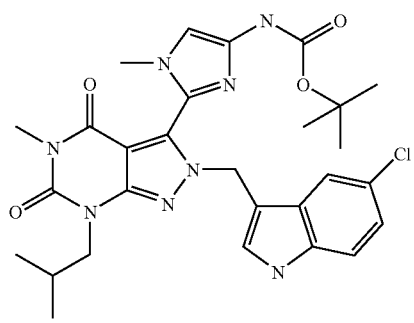

This compound was made following the procedure described above, starting with 6-hydrazino-1-isobutylpyrimidine-2,4(1H,3H)-dione, and condensing first with 5-chloro-1H-indole-3-carbaldehyde, followed by tert-butyl 2-formyl-1-methyl-1H-imidazol-4-ylcarbamate. Mass: 581.03 (M+H).

Example 114

3-(4-amino-1-methyl-1H-imidazol-2-yl)-2-[(6-chloroquinolin-4-yl)methyl]-7-(cyclopropylmethyl)-5-methyl-2H-pyrazolo[3,4-d]pyrimidine-4,6(5H,7H)-dione

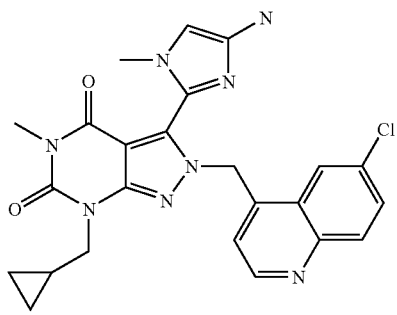

(a) tert-butyl 2-[2-[(6-chloroquinolin-4-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-imidazol-4-ylcarbamate This compound was made following the procedure described above, starting with 1-(cyclopropylmethyl)-6-hydrazino-3-methylpyrimidine-2,4(1H,3H)-dione, and condensing first with 6-chloroquinoline-4-carbaldehyde, followed by tert-butyl 2-formyl-1-methyl-1H-imidazol-4-ylcarbamate.

(b) 3-(4-amino-1-methyl-1H-imidazol-2-yl)-2-[(6-chloroquinolin-4-yl)methyl]-7-(cyclopropylmethyl)-5-methyl-2H-pyrazolo[3,4-d]pyrimidine-4,6(5H,7H)-dione This compound was synthesized by treating tert-butyl 2-[2-[(6-chloroquinolin-4-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-imidazol-4-ylcarbamate with 10% TFA in dichloromethane at room temperature for 5 hours. Mass: 491.26 (M+H).

Example 115

3-(2-amino-5-methyl-1,3-thiazol-4-yl)-2-[(6-chloroquinolin-4-yl)methyl]-7-(cyclopropylmethyl)-5-methyl-2H-pyrazolo[3,4-d]pyrimidine-4,6(5H,7H)-dione

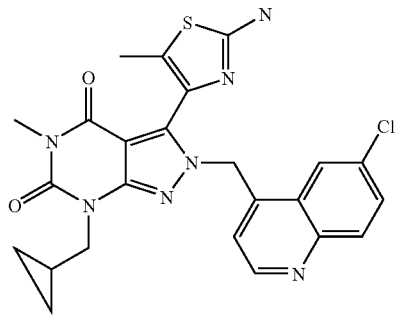

(a) tert-butyl 4-[2-[(6-chloroquinolin-4-yl)methyl]-7-(cyclopropylmethyl)-5-methyl-4,6-dioxo-4,5,6,7-tetrahydro-2H-pyrazolo[3,4-d]pyrimidin-3-yl]-5-methyl-1,3-thiazol-2-ylcarbamate This compound was made following the procedure described above, starting with 1-(cyclopropylmethyl)-6-hydrazino-3-methylpyrimidine-2,4(1H,3H)-dione, and condensing first with 6-chloroquinoline-4-carbaldehyde, followed by tert-butyl 4-formyl-5-methyl-1,3-thiazol-2-ylcarbamate.

(b) 3-(2-amino-5-methyl-1,3-thiazol-4-yl)-2-[(6-chloroquinolin-4-yl)methyl]-7-(cyclopropylmethyl)-5-methyl-2H-pyrazolo[3,4-d]pyrimidine-4,6(5H,7H)-dione This compound was synthesized by treating tert-butyl 4-[2-[(6-chloroquinolin-4-yl)methyl]-7-(cyclopropylmethyl)-5-methyl-4,6-dioxo-4,5,6,7-tetrahydro-2H-pyrazolo[3,4-d]pyrimidin-3-yl]-5-methyl-1,3-thiazol-2-ylcarbamate with 10% TFA in dichloromethane at room temperature for 5 hours. Mass: 508.13 (M+H).

Example 116

3-(2-amino-4-methyl-1,3-thiazol-5-yl)-2-[(6-chloroquinolin-4-yl)methyl]-7-(cyclopropylmethyl)-5-methyl-2H-pyrazolo[3,4-d]pyrimidine-4,6(5H1,7H)-dione

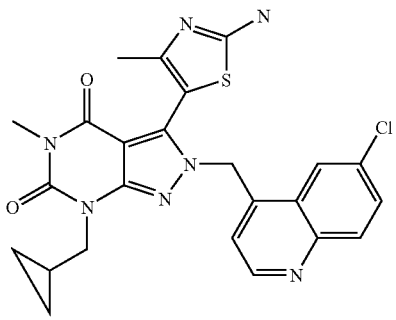

(a) tert-butyl 5-[2-[(6-chloro-4-quinolinyl)methyl]-7-(cyclopropylmethyl)-5-methyl-4,6-dioxo-4,5,6,7-tetrahydro-2H-pyrazolo[3,4-d]pyrimidin-3-yl]4-methyl-1,3-thiazol-2-ylcarbamate This compound was made following the procedure described above, starting with 1-(cyclopropylmethyl)-6-hydrazino-3-methylpyrimidine-2,4(1H,3H)-dione, and condensing first with 6-chloroquinoline-4-carbaldehyde, followed by tert-butyl 5-formyl-4-methyl-1,3-thiazol-2-ylcarbamate.

(b) 3-(2-amino-4-methyl-1,3-thiazol-5-yl)-2-[(6-chloroquinolin-4-yl)methyl]-7-(cyclopropylmethyl)-5-methyl-2H-pyrazolo[3,4-d]pyrimidine-4,6(5H,7H)-dione This compound was synthesized by treating tert-butyl 5-[2-[(6-chloroquinolin-4-yl)methyl]-7-(cyclopropylmethyl)-5-methyl-4,6-dioxo-4,5,6,7-tetrahydro-2H-pyrazolo[3,4-d]pyrimidin-3-yl]4-methyl-1,3-thiazol-2-ylcarbamate with 10% TFA in dichloromethane at room temperature for 5 hours. Mass: 508.13 (M+H).

Example 117

3-(2-amino-4-methyl-1,3-thiazol-5-yl)-2-[(5-chloro-1H-indol-3-yl)methyl]-7-isobutyl-5-methyl-2H-pyrazolo[3,4-d]pyrimidine-4,6(5H,7H)-dione

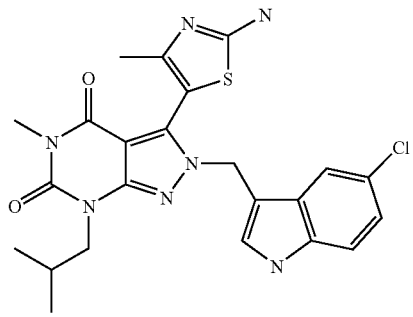

This compound was made following the procedure described above, starting with 6-hydrazino-1-isobutylpyrimidine-2,4(1H,3H)-dione, and condensing first with 5-chloro-1H-indole-3-carbaldehyde, followed by 2-amino-4-methyl-1,3-thiazole-5-carbaldehyde hydrochloride. Mass: 498.17 (M+H).

Example 118

3-(2-amino-5-methyl-1,3-thiazol-4-yl)-2-[(5-chloro-1H-indol-3-yl)methyl]-7-isobutyl-5-methyl-2H-pyrazolo[3,4-d]pyrimidine-4,6(5H,7H)-dione

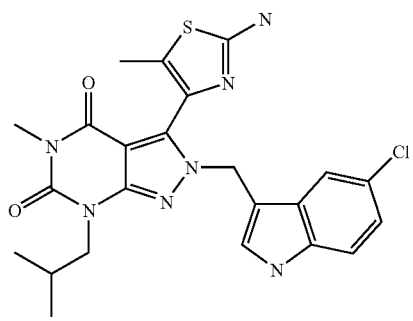

This compound was made following the procedure described above, starting with 6-hydrazino-1-isobutylpyrimidine-2,4(1H,3H)-dione, and condensing first with 5-chloro-1H-indole-3-carbaldehyde, followed by 2-amino-5-methyl-1,3-thiazole-4-carbaldehyde. Mass: 498.19 (M+H).

Example 119 tert-butyl 4-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-5-methyl-1,3-thiazol-2-ylcarbamate

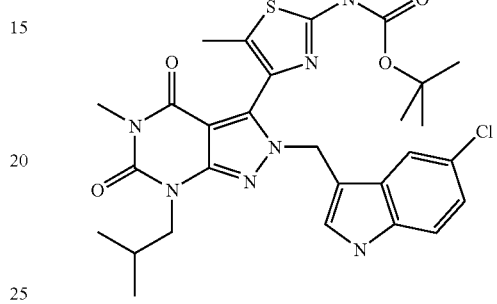

This compound was made following the procedure described above, starting with 6-hydrazino-1-isobutylpyrimidine-2,4(1H,3H)-dione, and condensing first with 5-chloro-1H-indole-3-carbaldehyde, followed by tert-butyl 4-formyl-5-methyl-1,3-thiazol-2-ylcarbamate. Mass: 598.22 (M+H).

Example 120

3-(2-amino-5-methyl-1,3-thiazol-4-yl)-2-(1-benzothien-3-ylmethyl)-7-isobutyl-5-methyl-2H-pyrazolo[3,4-d]pyrimidine-4,6(5H,7H)-dione

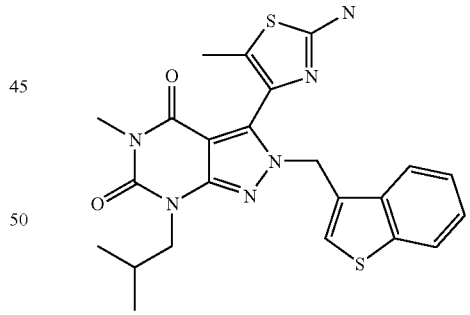

(a) tert-butyl 4-[2-(1-benzothien-3-ylmethyl)-7-isobutyl-5-methyl-4,6-dioxo-4,5,6,7-tetrahydro-2H-pyrazolo[3,4-d]pyrimidin-3-yl]-5-methyl-1,3-thiazol-2-ylcarbamate This compound was made following the procedure described above, starting with 6-hydrazino-1-isobutyl-3-methylpyrimidine-2,4(1H,3H)-dione, and condensing first with 1-benzothiophene-3-carbaldehyde, followed by tert-butyl 4-formyl-5-methyl-1,3-thiazol-2-ylcarbamate.

(b) 3-(2-amino-5-methyl-1,3-thiazol-4-yl)-2-(1-benzothien-3-ylmethyl)-7-isobutyl-5-methyl-2H-pyrazolo[3,4-d]pyrimidine-4,6(5H,7H)-dione This compound was synthesized by treating tert-butyl 4-[2-(1-benzothien-3-ylmethyl)-7-isobutyl-5-methyl-4,6-dioxo-4,5,6,7-tetrahydro-2H-pyrazolo[3,4-d]pyrimidin-3-yl]-5-methyl-1,3-thiazol-2-ylcarbamate with 4M HCl in dioxane at room temperature for 2.5 hours. Mass: 481.15 (M+H).

Example 121

N-{4-[2-(1-benzothien-3-ylmethyl)-7-isobutyl-5-methyl-4,6-dioxo-4,5,6,7-tetrahydro-2H-pyrazolo[3,4-d]pyrimidin-3-yl]-5-methyl-1,3-thiazol-2-yl}acetamide

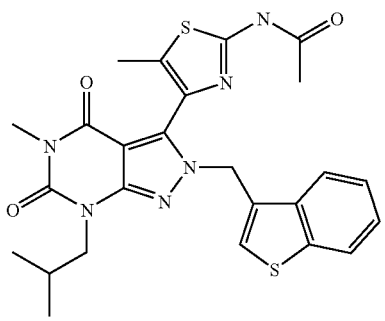

3-(2-amino-5-methyl-1,3-thiazol-4-yl)-2-(1-benzothien-3-ylmethyl)-7-isobutyl-5-methyl-2H-pyrazolo[3,4-d]pyrimidine-4,6(5H,7H)-dione hydrochloride was reacted with excess acetyl chloride using triethylamine as a base. The resulting bis acetylated product is treated with potassium carbonate to give the title compound. Mass: 523.22 (M+H).

Example 122

2-[(5-chloro-1H-indol-3-yl)methyl]-7-(cyclopropylmethyl)-5-methyl-3-{1-methyl-4-[(1Z)-2,2,2-trifluoro-N-hydroxyethanimidoyl]-1H-pyrrol-2-yl}-2H-pyrazolo[3,4-d]pyrimidine 4,6(5H,7H)-dione

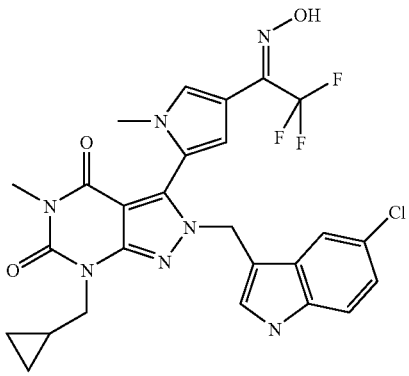

Hydroxylamine hydrochloride (0.062 g) was added to a solution of 2-[(5-chloro-1H-indol-3-yl)methyl]-7-(cyclopropylmethyl)-5-methyl-3-[1-methyl-4-(trifluoroacetyl)-1H-pyrrol-2-yl]-2H-pyrazolo[3,4-d]pyrimidine-4,6(5H,7H)-dione (0.05 g) and triethylamine (0.063 ml) in dimethylacetamide (5 ml) and the mixture heated at 80° C. for 2 hours. Additional hydroxylamine hydrochloride (0.062 g) was added and the reaction continued at 80° C. for another 3 hours. Cooled, concentrated, and the crude residue purified on preparative HPLC to give the title compound (0.015 g). Mass: 574.17 (M+H).

Synthesis of some common intermediates used in the above reaction sequence: methyl 5-formyl-1-methyl-1H-pyrrole-3-carboxylate Oxalylchloride (4.8 ml) in dichloroethane (10 ml) was added to a solution of dimethylformamide (4.25 ml) in dichloroethane (20 ml) over a period of 20 minutes at ice-cold temperature. The white suspension formed was stirred at room temperature for 20 minutes. Reaction cooled with ice-cold water and N-methyl pyrrole (4.44 ml) in dichloroethane (10 ml) was added dropwise over a period of 20 minutes. Resulting light yellow solution stirred at room temperature for 40 minutes. Aluminum chloride (13.33 g), followed by trichloroacetyl chloride (5.58 ml) was added rapidly and the resulting dark mixture stirred at room temperature for 2 hours.

Methanol (70 ml) was added and stirred for 5 minutes. Sodium (5.6 g) dissolved in 70 ml methanol was added (external cooling was applied during the addition) and stirred at room temperature for one hour. Reaction mixture poured in to ice cold water, acidified with concentrated hydrochloric acid, and extracted with ether. Ether layer dried over sodium sulfate and concentrated. The residue treated with 100 ml of 0.5M sodium methoxide in methanol for 30 minutes. Then acidified with concentrated hydrochloric acid and extracted with ethyl acetate. Organic layer was dried and concentrated. The crude product was triturated with ether. Off white solid precipitated was filtered, washed with ether, and dried to give desired product (4.0 g).

5-formyl-1-methyl-1H-pyrrole-3-carboxylic acid methyl 5-formyl-1-methyl-1H-pyrrole-3-carboxylate (0.5 g) dissolved in methanol (5 ml) was treated with 10% aqueous sodium hydroxide (5 ml) at 50° C. for 2 hours. Reaction cooled, acidified with 10% aqueous hydrochloric acid, and extracted with ethyl acetate. Ethyl acetate layer dried, and concentrated to give pure desired acid (0.4 g).

1-methyl-4-(trifluoroacetyl)-1H-pyrrole-2-carbaldehyde

Oxalylchloride (4.8 ml) in dichloroethane (10 ml) was added to a solution of dimethylformamide (4.25 ml) in dichloroethane (20 ml) over a period of 20 minutes at ice-cold temperature. The white suspension formed was stirred at room temperature for 20 minutes. Reaction cooled with ice-cold water and N-methyl pyrrole (4.44 ml) in dichloroethane (10 ml) was added dropwise over a period of 20 minutes. Resulting light yellow solution stirred at room temperature for 40 minutes. Aluminum chloride (13.33 g), followed by trifluoroacetic anhydride (7 ml) was added rapidly and the resulting dark mixture stirred at room temperature for 2 hours. Reaction quenched with the addition of 100 ml 10% aqueous hydrochloric acid and extracted with ethyl acetate. Ethyl acetate layer dried, and concentrated Crude product purified on column chromatography (silica-gel). Elution with 10-20% ethyl acetate in hexanes gave the desired product (0.1 g).

Substituted indole-3-carbaldehydes

Substituted indole-3-carbaldehydes used in the synthesis are either purchased from the commercial sources or synthesized from the corresponding indoles using Vilsmeier reaction by following the procedure described in "Organic Functional Group Preparations" Second Edition, Volume I, page 194, Academic Press, Inc. 1983, written by Stanley R. Sandler and Wolf Karo.

Example 123

Preparation of 1-benzothiophene-3-carbaldehyde N-(3-isobutyl-1-methyl-2,6-dioxo-1,2,3,6-tetrahydro-4-pyrimidinyl)hydrazone

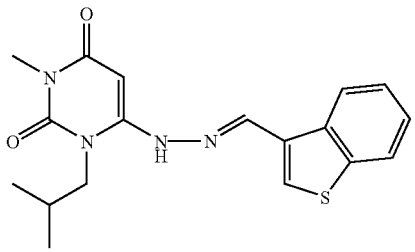

6-Hydrazino-1-isobutyl-3-methyl-2,4(1H,3H)-pyrimidinedione (1.2 g, 5.65 mmol) was dissolved in methanol (100 mL). To the yellow/brown solution was added thianaphthene-3-carboxaldehyde (917 mg, 5.65 mmol). A brown precipitate began to form after about 20 min. The mixture was stirred at room temperature for 3 h under nitrogen gas. HPLC showed complete formation of hydrazone (Rt=1.87 min, Kromasil, C8) The solvent was removed in vacuo and the brown slurry was pumped down to reveal a brown/yellow powder. Yield=1.85 g (92%), TLC, Rf=0.14 (CHCl$_3$/MeOH); Rt:1.87 min. MS:357 (M+H)

Example 124

Preparation of 2-(1-benzothiophen-3-ylmethyl)-7-isobutyl-5-methyl-3-(1-methyl-1H-pyrrol-2-yl)-2H-pyrazolo[3,4-d]pyrimidine-4,6(5H,7H)-dione

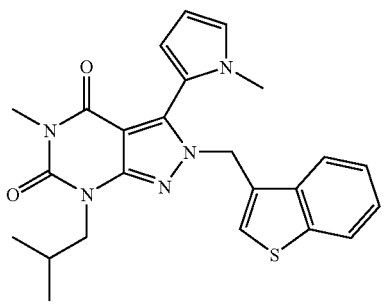

1-Benzothiophene-3-carbaldehyde N-(3-isobutyl-1-methyl-2,6-dioxo-1,2,3,6-tetrahydro-4-pyrimidinyl)hydrazone (100 mg, 0.284 mmol) was suspended in anh. DMA (3 mL) under an atmosphere of N$_2$ gas. To the suspension was added N-methylpyrrole-2-carboxaldehyde (37 mg, 0.34 mmol). To this suspension was added catalytic amounts of triethylamine (25 µL). The reaction mixture was placed in a preheated heating block maintained at 90° C. and heated under N$_2$ gas for 18 h. At the end of reaction the solvent was removed in vacuo and the resulting brown oil was resuspended in DMSO (1.5 mL) and was purified by semi preparative RPHPLC eluting with MeCN/water/TFA mixtures. Yield=37 mg, Rt=2.46 min, MS: 444,(M+H).

Examples 125 and 126

(±)5-methyl-2-(1-naphthylmethyl)-3-(4-pyridinyl)-7-{[(trifluoromethyl)sulfinyl]methyl}-2H-pyrazolo[3,4-d]pyrimidine-4,6(5H,7H)-dione,7H)-dione and 5-methyl-2-(1-naphthylmethyl)-3-(4-pyridinyl)-7-{[(trifluoromethyl)sulfonyl]methyl}-2H-pyrazolo[3,4-d]pyrimidine-4,6(5H,7H)-dione

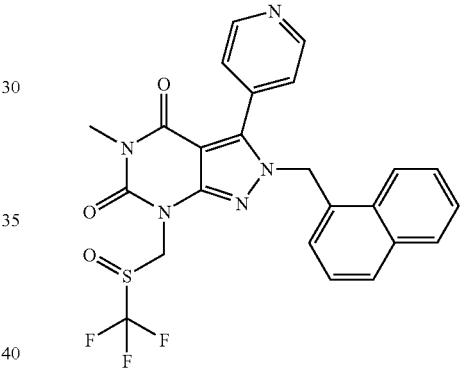

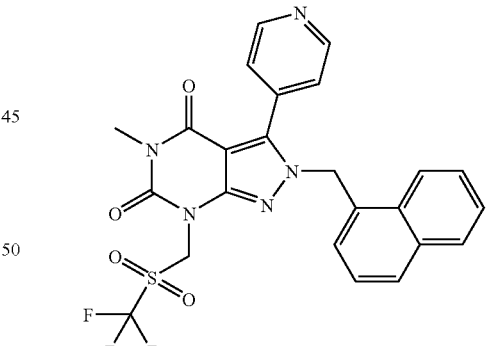

A solution of 38 mg (0.73 mmol) of 5-methyl-2-(1-naphthylmethyl)-3-(4-pyridinyl)-7-{[(tifluoromethyl)sulfanyl]methyl}-2H-pyrazolo[3,4-d]pyrimidine-4,6(5H,7H)-dione (Example 123) and 15 mg (0.73 mmol) of m-chloroperbenzoic acid in 1 mL CH$_2$Cl$_2$ was agitated at ambient temperature for 4 h. Solvent was removed and the residue was purified by HPLC (40%-80% gradient of CH$_3$CN-water with 0.1% TFA) to afford two materials as white solids as the trifluoroacetate salts. The longer retention time material was identified as the title sulfoxide and the shorter retention time material as the title sulfone.

MP 65-67° C. LC-MS: RT=2.31 min, ES⁺ (M+H) 529.7. LGDH I50: 18 uM MP 99-103° C. LC-MS: RT=2.52 min, ES⁺ (M+H) 513.75. LGDH I50:45.7 uM Example 127

(±)5-methyl-7-[(methylsulfinyl)methyl]-2-(1-naphthylmethyl)-3-pyridin-4-yl-2H-pyrazolo[3,4-d]pyrimidine-4,6(5H,7H)-dione

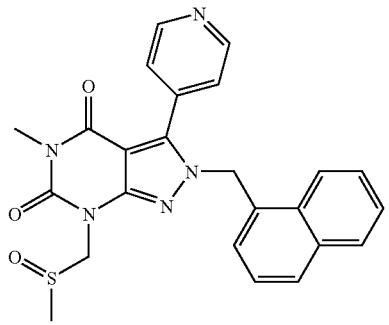

A solution of 40 mg (0.086 mmol) of 5-methyl-7-[(methylthio)methyl]-2-(1-naphthylmethyl)-3-pyridin-4-yl-2H-pyrazolo[3,4-d]pyrimidine-4,6(5H,7H)-dione 7-isobutyl-5-methyl-2-(1-naphthylmethyl)-3-[3-(1H-1,2,3,4-tetraazol-5-yl)phenyl]-2H-pyrazolo[3,4-d]pyrimidine-4,6(5H,7H)-dione (Example 124) in 2 mL MeOH and a solution of 19 mg (0.089 mmol) of NaIO₄ in 0.5 mL water were mixed together and agitated at ambient temperature for 3 d. The mixture was diluted with EtOAc which was washed with water and brine. Drying (MgSO₄) and removal of solvent gave 35 mg of the title material as a white solid.

MP 107-109° C. LC-MS: RT=1.98 min, ES⁺ (M+H) 459.84. LGDH I50: 26 uM

The following compound was made from 5-methyl-2-(1-naphthylmethyl)-7-[(phenylthio)methyl]-3-pyridin-4-yl-2H-pyrazolo[3,4-d]pyrimidine-4,6(5H,7H)-dione following the method described above.

Example 128

5-methyl-2-(1-naphthylmethyl)-7-[(phenylsulfinyl)methyl]-3-pyridin-4-yl-2H-pyrazolo[3,4-d]pyrimidine-4,6(5H,7H)-dione

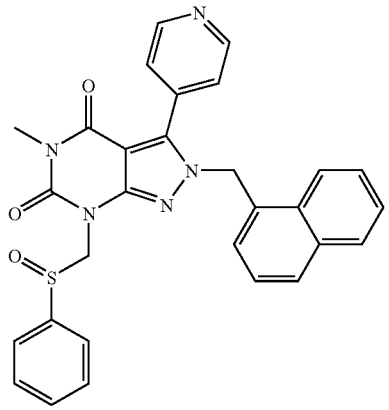

MP 130-135° C. LC-MS: RT=2.37 min, ES⁺ (M+H) 521.79.

Example 129

7-isobutyl-5-methyl-2-(1-naphthylmethyl)-3-[3-(1H-1,2,3,4-tetraazol-5-yl)phenyl]-2H-pyrazolo[3,4-d]pyrimidine-4,6(5H,7H)-dione

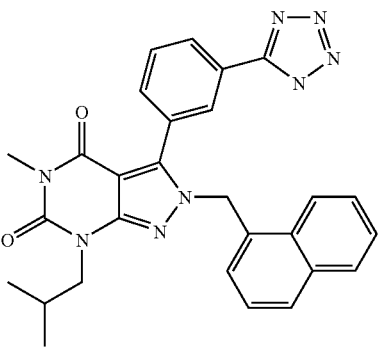

a) 3-[7-isobutyl-5-methyl-2-(1-naphthylmethyl)-4,6-dioxo-4,5,6,7-tetrahydro-2H-pyrazolo[3,4-d]pyrimidin-3-yl]benzonitrile A solution of 100 mg (0.26 mmol) of 1-naphthaldehyde (3-isobutyl-1-methyl-2,6-dioxo-1,2,3,6-tetrahydropyrimidin-4-yl)hydrazone, 36 mg (0.27 mmol) of 3-cyano benzaldehyde and 20 uL of triethylamine in 20 mL DMF was heated at 85° C. for 20 h. The mixture was diluted with ether and washed 4 times with water. The ether was dried (MgSO₄) and concentrated to give a yellow solid which was recrystallized from ethanol to give 84 mg of the subtitle product.

b) 7-isobutyl-5-methyl-2-(1-naphthylmethyl)-3-[3-(1H-1,2,3,4-tetraazol-5-yl)phenyl]-2H-pyrazolo[3,4-d]pyrimidine-4,6(5H,7H)-dione.

A solution of 84 mg (0.19 mmol) of the preceding product and 43 mg (0.21 mmol) of trimethyltin azide in 20 mL toluene was heated at reflux for 16 h. TLC (ether) showed the presence of starting material and a much more polar material. Additional trimethyltin azide (0.43 mg) was added, and the mixture was heated at reflux for 20 h. Starting material was still present by TLC, and 0.43 mg of trimethyltin azide was added. After heating at reflux 24 h, solvent was removed, and the residue was dissolved in 10 mL methanol. A solution of 3N HCl (5 mL) was added, and the mixture was stirred 60 min at ambient temperature. The mixture was partitioned between EtOAc and water. The organic layer was washed with brine, dried (MgSO₄) and concentrated to give an oil. The title product (13 mg) was isolated by HPLC (40%-80% gradient of CH₃CN-water with 0.1% TFA) as a white solid.

MP 251-254° C. LC-MS: RT=2.83 min, APCI⁺ (M+H) 506.85. LGDH I50: 1.6 uM

Example 130

±2-[5-methyl-2-(1-naphthylmethyl)-4,6-dioxo-3-(4-pyridinyl-2,4,5,6-tetrahydro-7H-pyrazolo[3,4-d]pyrimidin-7-yl]butanenitrile

Example 131

2-(1-benzothiophen-3-ylmethyl)-3-(2-fluorophenyl)-7-isobutyl-5-methyl-2H-pyrazolo[3,4-d]pyrimidine-4,6(5H,7H)-dione

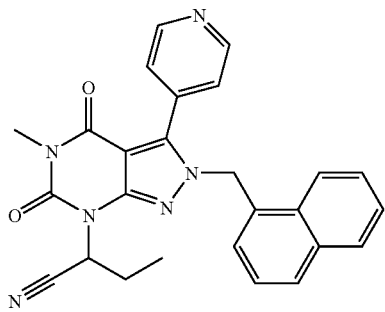

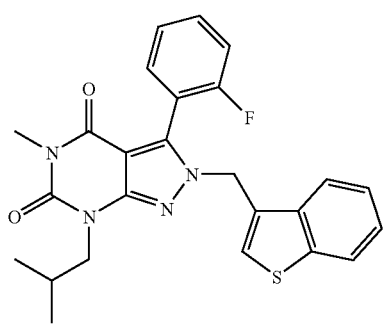

A solution of 100 mg (0.26 mmol) of 5-methyl-2-(1-naphthylmethyl)-3-pyridinyl-2H-pyrazolo[3,4-d]pyrimidine-4,6(5H,7H)-dione in 5 mL DMF was cooled in ice water before 280 μL (0.28 mmol) of 1 N potassium t-butoxide in THF was added. A solution of 51 mg (0.31 mmol) of 1-cyanopropyl methanesulfonate (Marco, J. L.; Ingate, S. T.; Jaime, C.; Bea, I. *Tetrahedron* 2000 56(16), 2523) in 1 mL DMF was added via syringe, and the mixture was heated at 80° C. overnight. Solvent was removed, and the residue was partitioned between EtOAc and water. The organic layer was washed twice more with water and once with brine before being concentrated to give an oil. Purification by HPLC (40%-80% gradient of $CH_3CN$-water with 0.1% TFA) afforded the title product as a white solid as the trifluoroacetate salt.

MP 75-77° C. LC-MS: RT=2.52 min, $ES^+$ (M+H) 450.91. LGDH I50:9.1 uM

A solution of 100 mg (0.47 mmol) of 6-hydrazino-1-isobutyl-3-methyl-2,4(1H,3H)-pyrimidinedione (Example 1d) and 76.4 mg (0.47 mmol) of 1-benzothiophene-3-carbaldehyde in 5 mL DMF was stirred at ambient temperature for 3 h. Added via syringe was 100 μL (0.95 mmol) of 2-fluorobenzaldehyde and 48 μL (0.48 mmol) of piperidine. The mixture was heated at 85° C. for 20 h. Solvent was removed, and the residue was purified by HPLC (60% $CH_3CN$-water with 0.1% TFA) to afford the title product as a white solid.

MP 55-57° C. LC-MS: RT=3.63 min, $APCI^+$ (M+H) 463.2.

The following compounds were made from 6-hydrazino-1-isobutyl-3-methyl-2,4(1H,3H)-pyrimidine-dione (123d) and the appropriate carboxaldehyde following the method of procedure described above.

| Example | | Name | Mp (° C.) | $ES^+$ (M + H) |
|---|---|---|---|---|
| 132 | (structure) | 3-(3-furyl)-7-isobutyl-5-methyl-2-(1-naphthylmethyl)-2H-pyrazolo[3,4-d]pyrimidine-4,6(5H,7R)-dione | 151–154 | 428.88 |

-continued

| Example | Name | Mp (° C.) | ES+ (M + H) |
|---|---|---|---|
| 133 | 2-(2,3-dichlorobenzyl)-3-(3-furyl)-7-isobutyl-5-methyl-2H-pyrazolo[3,4-d]pyrimidine-4,6(5H,7H)-dione | 160–161 | 446.77, 448.78 |
| 134 | 2-(1-benzothien-3-ylmethyl)-3-(3-furyl)-7-isobutyl-5-methyl-2H-pyrazolo[3,4-d]pyrimidine-4,6(5H,7H)-dione | 126–128 | 434.84 |
| 135 | 2-(3-bromobenzyl)-7-isobutyl-5-methyl-3-pyridin-4-yl-2H-pyrazolo[3,4-d]pyrimidine-4,6(5H,7H)-dione | 165–166 | 467.78 |
| 136 | 3-[(7-isobutyl-5-methyl-4,6-dioxo-3-pyridin-4-yl-4,5,6,7-tetrahydro-2H-pyrazolo[3,4-d]pyrimidin-2-yl)methyl]benzonitrile | 188–192 | 414.89 |

-continued

| Example | Name | Mp (° C.) | ES+ (M + H) |
|---|---|---|---|
| 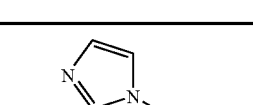 137 | 2-(3-iodobenzyl)-7-isobutyl-5-methyl-3-(1-methyl-1H-imidazol-2-yl)-2H-pyrazolo[3,4-d]pyrimidine-4,6(5H,7H)-dione | 146–148 | 518.76 |

Example 138

Preparation of 7-allyl-5-methyl-2-(1-naphthylmethyl)-3-(4-pyridinyl)-2H-pyrazolo[3,4-d]pyrimidine-4,6(5H,7H)-dione

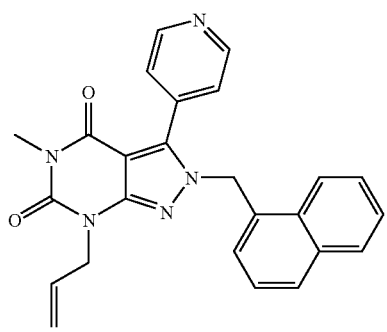

Allyl alcohol (17.7 µL, 0.261 mmol) was dissolved in anh. CH$_2$Cl$_2$ (1 mL) and cooled to −5° C. To this was added methanesulfonyl chloride (20.2 ul, 0.261 mmol) followed by N,N'diisopropylethylamine (45.4 µl, 0.261 mmol). The mixture was stirred at low temperature for 2 h. Meanwhile, 5-methyl-2-(1-naphthylmethyl)-3-(4-pyridinyl)-2H-pyrazolo[3,4-d]pyrimidine-4,6(5H,7H)-dione (100 mg, 0.261 mmol) was suspended in anh. N,N'dimethylacetamide (2 mL) followed by addition of cesium carbonate (85 mg, 0.261 mmol). at room temperature for 1 h. To the mixture was added the preformed mesylate and the mixture was heated at 100 ° C. for 4 h. Reaction was partitioned between ethylacetate and water. The organic phase was washed with water, brine and dried over sodium sulfate and concentrated in vacuo. The crude product was purified by semi prep HPLC eluting with acetonitrile/water/TFA mixtures.

Yield: 57 mg; Rt=2.03 min; MS: 424(M+H).

Example 139

7-[2-(Dimethylamino)ethyl]-5-methyl-2-(1-naphthylmethyl)-3-(4-pyridinyl)-2H-pyrazolo[3,4-d]pyrimidine-4,6(5H,7H)-dione

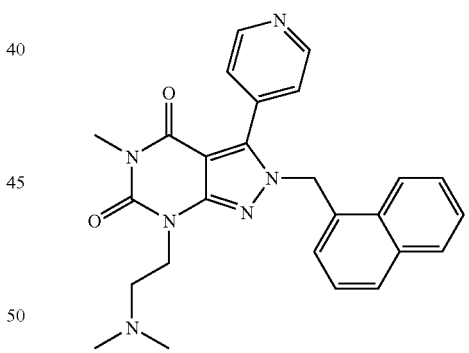

N-(2-Chloroethyl)-N,N-dimethylamine hydrichloride (0.058 g), followed by triethylamine (0.092 mL) and DBU (0.103 mL), were added to a solution of 5-methyl-2-(1-naphthylmethyl)-3-(4-pyridinyl)-2H-pyrazolo[3,4-d]pyrimidine-4,6(5H,7H)-dione (0.064 g) in 3:1 dimethylformamide and DMSO (1 mL). The mixture was heated at 90° C. for 18 h then cooled to room temperature. Crude reaction was purified on preparative HPLC to give the title compound (0.120 g). Mass 455.03 (M+H).

Example 140

3-[7-(2-chlorobenzyl)-5-methyl-2-(1-naphthylmethyl)-4,6-dioxo-4,5,6,7-tetrahydro-2H-pyrazolo[3,4-d]pyrimidin-3-yl]benzoic acid

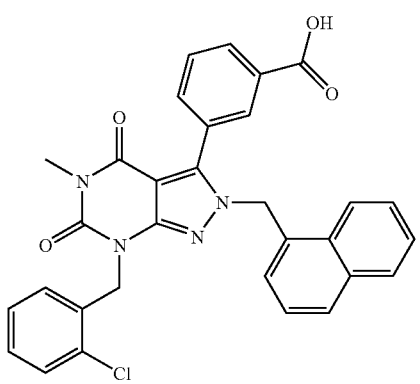

Diisipropylazodicarboxylate (0.157 g) was added to a mixture of resin bound 3-[5-methyl-2-(1-naphthylmethyl)-4,6-dioxo-4,5,6,7-tetrahydro-2H-pyrazolo[3,4-d]pyrimidin-3-yl]benzoic acid (0.120 g), triphenylphosphine (0.204 g), and 2-chlorophenylmethanol in dry THF (2 mL) at −15° C. Reaction temperature was allowed to come to room temperature and shaken for 20 h. The resin was filtered, washed (3 times) DMF, CH2Cl2, MeOH, CH2Cl2, and dried in vacuum. The dry resin was treated with 15% TFA in dichloromethane (1 mL) for 2 h, and filtered and washed (2 times) with dichloromethane. Combined filtrates were concentrated, and dried in vacuum to give the title compound (0.062 g). Mass 548.80 (M+H).

Example 141

3-[7-isobutyl-5-methyl-2-(1-naphthylmethyl)-4,6-dioxo-4,5,6,7-tetrahydro-2H-pyrazolo[3,4-d]pyrimidin-3-yl]-N-methylbenzamide

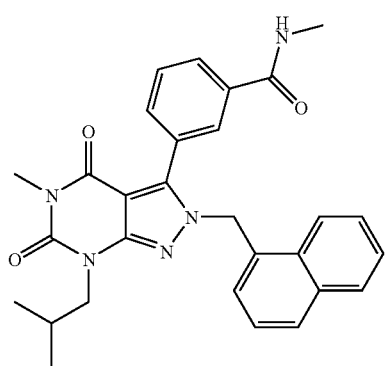

Triethylamine (0.04 mL) followed by isobutylchloroformate (0.033 g) were added to a solution of 3-[7-isobutyl-5-methyl-2-(1-naphthylmethyl)-4,6-dioxo-4,5,6,7-tetrahydro-2H-pyrazolo[3,4-d]pyrimidin-3-yl]benzoic acid (0.08 g) in THF (1 mL) at 0° C. The mixture was stirred at 0° C. for 1 hour. Methylamine (2M, 2 mL) was added and the mixture was stirred at 0° C. for 1 h, then at room temperature for 2 h. Reaction was diluted with water (10 mL) and extracted with dichloromethane (2×10 mL). Combined organic layers were dried over anhydrous sodium sulfate, filtered and evaporated under reduced pressure. The residue was purified on preparative HPLC to give the title compound (0.027 g).

Example 142

Preparation of N-(tert-butyl)-2-formyl-1-methyl-1H-imidazole-4-sulfonamide

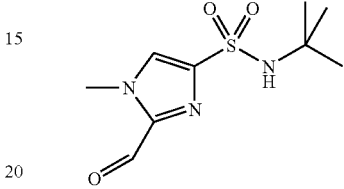

Step A) Preparation of N-(tert-butyl)-1-methyl-1H-imidazole-4-sulfonamide: A solution of 5.2 gm (29 mmol) 1-methyl-1H-imidazole-4-sulfonyl chloride in 30 mL THF was cooled in ice water while 7 mL tert-butylamine was added dropwise. The solution was warmed to room temperature and stirred overnight. Solids were filtered and rinsed with additional THF. The filtrate was concentrated to give a white solid that was recrystallized from water and dried in vacuo to give 4.8 gm of the subtitle compound, $^1$H NMR (d6-DMSO) δ 7.75 (s, 1H), 7.65 (s, 1H), 7.2 (s, 1H), 3.7 (s, 3H), 1.1 (s, 9H).

Step B) A solution of 13 mL (21 mmol) of 1.6 M n-butyllithium in hexanes was added dropwise to a solution of 2.0 gm (9.2 mmol) the preceding product in 30 mL THF was cooled to −70° C. The mixture was warmed to room temperature and stirred 4 h before being cooled to −70° C. Dimethylformamide (0.8 mL, 10 mmol) was added all at once, and the solution was warmed to room temperature. The mixture was diluted with EtOAc and washed with water and brine. Drying (MgSO$_4$) and removal of solvent gave a solid that was purified by normal phase chromatography: 100% CH$_2$Cl$_2$ followed by gradient elution to 50% EtOAc in CH$_2$Cl$_2$. Two components were separated. The first eluting component was identified as the title compound, $^1$H NMR (d6-DMSO) δ 9.8 (s, 1H), 8.0 (s, 1H), 7.6 (s, 1H), 4.0 (s, 3H), 1.2 (s, 9H).

Example 143

Preparation of N-[tert-butyl(dimethyl)silyl]-2-formyl-1-methyl-1H-imidazole-4-sulfonamide

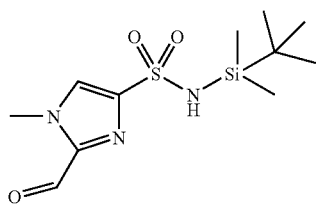

Step A) Preparation of N-[tert-butyl(dimethyl)silyl]-1-methyl-1H-imidazole-4-sulfonamide: A mixture of 2.2 g (14 mmol) 1-methyl-1H-imidazole-4-sulfonamide, 2.1 g (14 mmol) t-butyldimethylsilyl chloride and 3.9 mL (28 mmol) triethylamine in 15 mL DMF was stirred at room temperature overnight Solvent was removed, and the residue was dissolved in EtOAc before being washed with water and brine. Drying (MgSO$_4$) and removal of solvent gave 3 g of the subtitle product as a white solid, $^1$H NMR (DMSO) δ 7.7 (s, 1H), 7.6 (s, 1H), 7.35 (s, 1H), 3.7 (s, 3H), 0.9 (s, 9H)., 0.2 (s, 6H).

Step B) A solution of 1.6 N n-butyllithium in hexanes (7.4 mL, 12.mmol) was added dropwise to a solution of 1.62 g (5.9 mmol) of the preceding product in 30 mL THF cooled to −70° C. The mixture was warmed to room temperature and stirred 2 h before being cooled to −70° C. Dimethylformamide (0.8 mL, 10 mmol) was added all at once, and the solution was warmed to room temperature. The mixture was diluted with EtOAc and washed with water and brine. Drying (MgSO$_4$) and removal of solvent gave a solid that was purified by normal phase chromatography: 100% CH$_2$Cl$_2$ followed by gradient elution to 30% EtOAc in CH$_2$Cl$_2$. The first eluting component was identified as the title compound, $^1$H NMR (d6-DMSO) δ 9.7 (s, 1H), 8.0 (s, 1H), 7.7 (s, 1H), 4.0 (s, 3H), 0.9 (s, 9H), 0.2 (s, 6H).

Example 144

Preparation of 1-methyl-1H-imidazole-5-carbaldehyde

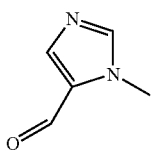

Step A) Preparation of 4-(diethoxymethyl)-1H-imidazole: A mixture of 6.0 g (62.5 mmol) 1H-imidazole-4-carbaldehyde, 13 g (60 mmol)p-toluenesulfonic acid, 30 mL (180 mmol) triethylorthoformate and 6 g 4 Å molecular sieves in 100 mL EtOH was stirred at room temperature overnight. The mixture was filtered and rinsed through with EtOAc. Solvent was removed from the filtrate, and the residue was dissolved in EtOAc, washed with NaHCO$_3$ (aq), water and brine. Drying (MgSO$_4$) and removal of solvent gave 8 g of the subtitle product as a white solid, $^1$H NMR (CDCl$_3$) δ 7.6 (s, 1H), 7.1 (s, 1H), 5.6 (s, 1H), 3.5-3.7 (m, 4H), 1.2 (m, 6H).

Step B) Preparation of 4-diethoxymethyl-1-trityl-1H-imidazole: A solution of 5.0 g (24 mmol) of the preceding product, 8.2 g (29.4 mmol) triphenylmethyl chloride and 4.1 mL (29 mmol) triethylamine in 200 mL THF was stirred at room temperature for 3 d. Solids were filtered, and the filtrate was diluted with Et$_2$O before being washed with water and brine.

Drying (MgSO$_4$) and removal of solvent gave 6.2 g of the subtitle product as an oil, $^1$H NMR (DMSO) δ 7.0-7.8 (m, 20H), 6.2 (s, 1H), 3.2-3.6 (m, 4H), 1.2 (m, 6H).

Step C) A solution of 6.2 g (15 mmol) of the preceding product and 10 g CH$_3$I in 200 mL Et$_2$O was stirred at room temperature for 3 d. Solids were filtered and rinsed with additional Et$_2$O. The solids were taken up in 50% aqueous HOAc and stirred for 1 h. Solvent was removed, and the residue was dissolved in water before extraction with Et$_2$O. The aqueous phase was neutralized with NaHCO$_3$ and continuously extracted with EtOAc overnight. The EtOAc was dried (MgSO$_4$) and concentrated to give 1.0 g of the title product as a white solid, $^1$H NMR (DMSO) δ 9.8 (s, 1H), 8.2 (s, 1H), 7.9 (s, 1H), 3.9 (s, 3H).

Example 145

Preparation of 1,3-dimethyl-2-thioxo-2,3-dihydro-1H-imidazole-4-carbaldehyde

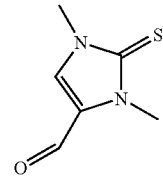

NaH (0.31 g, 13 mmol) was added to a solution of 2.0 g (12 mmol) 4-(diethoxymethyl)-1H-imidazole and 0.8 ml CH$_3$I in 30 mL DMF. Solvent was removed and the residue was dissolved in EtOAc and washed with water and brine. Drying (MgSO$_4$) and removal of solvent gave an oil that was dissolved in 50 mL THF along with 1 mL CH$_3$I. The solution was heated at reflux for h. Solvent was removed and the residue was dissolved in 10 mL EtOH. Sulfur (0.11 g, 3.4 mmol) and K$_2$CO$_3$ (0.38 gm, 3.4 mmol) were added, and the mixture was heated at reflux for 2 h. Solvent was removed and the residue was dissolved in 1:1 THF-1% aq HCl and stirred overnight. The mixture was partitioned between EtOAc and water. The organic layer was separated and washed with brine. Drying (MgSO$_4$) and removal of solvent gave 250 mg of the title product as a yellow solid, $^1$H NMR (CDCl$_3$) δ 9.4 (s, 1H), 7.7 (s, 1H), 7.5 (s, 1H), 3.9 (s, 3H), 3.7 (s, 3H).

Example 146

Preparation of 1-methyl-4-methylsulfonyl)-1H-imidazole-2-carbaldehyde

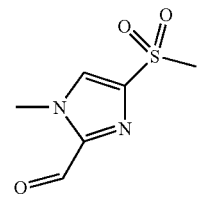

Step A) Preparation of 2-(5,5-dimethyl-1,3-dioxan-2-yl)-1-methyl-1H-imidazole: A solution of 11.3 g (0.1 mol) 1-methyl-1H-imidazole-2-carbaldehyde, 11 g (0.11 mol) 2,2-dimethyl-1,3-propanediol and 21 g (0.11 mol) p-toluenesulfonic acid in 200 mL benzene was heated to reflux with azeotropic removal of water for 3 h. After cooling to room temperature, the mixture was diluted with ether and washed with Na$_2$CO$_3$ (aq), water and brine. Drying (MgSO$_4$) and removal of solvent gave 18.7 g of an oil that slowly solidified, $^1$H NMR (DMSO) δ 7.1 (s, 1H), 7.8 (s, 1H), 5.55 (s, 1H), 4.0 (s, 3H), 3.6 (ABq, 4H), 1.2 (s, 3H), 0.8 (s, 3H).

Step B) Preparation of 4,5-dibromo-2-(5,5-dimethyl-1,3-dioxan-2-yl)-1-methyl-1H-imidazole: A solution of 15.2 g (77.5 mmol) of the preceding product and 27.6 g (155 mmol) N-bromosuccinimide in 200 mL CHCl$_3$ was heated at reflux for 2 h. Insoluble solids were filtered and rinsed with CHCl$_3$ and solvent was removed from the filtrate. The residue was dissolved in EtOAc, which was washed with 1N NaOH (aq), water and brine. Drying (MgSO$_4$) and removal of solvent gave 22 g of the subtitle compound as a solid, ¹H NMR (DMSO) δ 5.6 (s, 1H), 3.9 (s, 3H), 3.7 (ABq, 4H), 1.2 (s, 3H), 0.8 (s, 3H).

Step C) Preparation of 4-bromo-2-(5,5-dimethyl-1,3-dioxan-2-yl)-1-methyl-1H-imidazole: A solution of 45 mL of 1.6 N n-butyllithium in hexanes (72 mmol) was added dropwise to a solution of 22 g (62 mmol) of the preceding compound in 200 mL THF cooled in a dry ice-acetone bath to maintain a temperature below −60° C. After stirring 5 m, the mixture was quenched with NaHCO₃ (aq) and warmed to room temperature. Dilution of the mixture with EtOAc was followed by washing with water and brine. Drying (MgSO₄) and removal of solvent gave 16 g of a solid. Recrystallization from cyclohexane gave 11 g of the subtitle compound, ¹H NMR (DMSO) δ 7.3 (s, 1H), 5.5 (s, 1H), 3.8 (s, 3H), 3.7 (ABq, 4H), 1.4 (s, 3H), 0.8 (s, 3H).

Step D) Preparation of 2-(5,5-dimethyl-1,3-dioxan-2-yl)-1-methyl-4(methylthio)-1H-imidazole: A solution of 5.2 mL of 1.6 N n-butyllithium in hexanes (8.3 mmol) was added dropwise to a solution of 1.6 g (6.2 mmol) of the preceding compound in 200 mL THF cooled in a dry ice-acetone bath to maintain a temperature below −60° C. After stirring 5 m, (methyldithio)methane (750 µL, 8.3 mmol) was added in one portion, and the mixture was warmed to room temperature. Dilution with EtOAc was followed by washing with water and brine. Drying (MgSO₄) and removal of solvent gave a solid that was recrystallized from cyclohexane to give 390 mg of the subtitle compound, ¹H NMR (DMSO) δ 7.2 (s, 1H), 5.6 (s, 1H), 3.8 (s, 3H), 3.6 (ABq, 4H), 2.3 (s, 3H), 1.4 (s, 3H), 0.8 (s, 3H).

Step E) Preparation of 2-(5,5-dimethyl-1,3-dioxan-2-yl)-1-methyl-4-(methylsulfonyl)-1H-imidazole: A solution of 0.39 g (1.6 mmol) of the preceding compound and 0.8 g (3.3 mmol) of 70% m-chloroperoxybenzoic acid in 10 mL CH₂Cl₂ was stirred at room temperature for 2 h. The mixture was diluted with EtOAc and washed with NaHSO₃ (aq), Na₂CO₃ (aq) and brine. Drying (MgSO₄) and removal of solvent gave 0.44 g of the subtitle compound as a white solid, ¹H NMR (DMSO) δ 8.0 (s, 1H), 5.65 (s, 1H), 4.2 (s, 3H), 3.7 (ABq, 4H), 3.1 (s, 3H), 1.2 (s, 3H), 0.8 (s, 3H).

Step F) A solution of 0.44 g of the preceding compound in 30 mL of 2:1 THF-3N HCl was heated at reflux overnight. The mixture was basified with Na₂CO₃ (aq) and continuously extracted with EtOAc overnight. The EtOAc was dried (MgSO₄) and concentrated to give an oily solid. Trituration with Et₂O gave 170 mg of the title compound as a white solid, ¹H NMR (DMSO) δ 9.8 (s, 1H), 8.3 (s, 1H), 4.0 (s, 3H), 3.2 (s, 3H).

Example 147

Preparation of 5-formyl-N,1-dimethyl-1H-pyrrole-3-sulfonamide

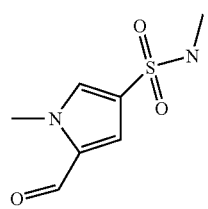

A solution of 0.8 g (3.3 mmol) N-(tert-butyl)-5-formyl-1-methyl-1H-pyrrole-3-sulfonamide, 1.2 g (9.8 mmol) K₂CO₃ and 1 mL (16 mmol) CH₃I in CH₃CN was heated at 60° C. overnight. Solvent was removed, and the residue was partitioned between EtOAc and water. The organic layer was separated and washed with brine. Drying (MgSO₄) and removal of solvent to give material that slowly solidified. The material was dissolved in 2 mL 1:1 CH₂Cl₂-TFA with stirring for 3 h. Solvent was removed to give the title compound as a solid, ¹H NMR (DMSO) δ 9.8 (s, 1H), 7.9 (s, 1H), 7.45 (s, 1H), 7.4 (s, 1H), 4.1 (s, 3H), 2.6 (s, 3H).

Example 148

Preparation of N-[(5-formyl-1-methyl-1H-pyrrol-3-yl)sulfonyl]glycine

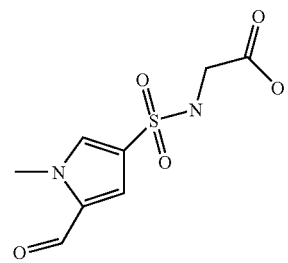

A solution of 0.8 g (3.3 mmol) N-(tert-butyl)-5-formyl-1-methyl-1H-pyrrole-3-sulfonamide, 1.2 g (9.8 mmol) K₂CO₃ and 1.4 g (7.2 mmol) tert-butyl bromoacetate in CH₃CN was heated at reflux overnight Solvent was removed, and the residue was partitioned between EtOAc and water. The organic layer was separated and washed with brine. Drying (MgSO₄) and removal of solvent gave an oil that was chromatographed by normal phase (100% CH₂Cl₂ followed by gradient elution to 20 EtOAc in CH₂Cl₂) to give material that was dissolved in 2 mL 1:1 CH₂Cl₂-TFA with stirring overnight. Solvent was removed to give the title compound as a solid, ¹H NMR (DMSO) δ 9.6 (s, 1H), 7.4 (s, 1H), 7.2 (s, 1H), 4.1 (s, 3H), 3.9 (s, 2H).

Example 149

Preparation of 1-methyl-4-(methylthio)-1H-pyrrole-2-carbaldehyde

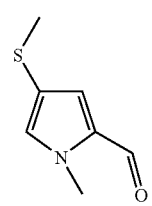

A solution of 22 mL of 1.6 N n-butyllithium (57 mmol) was added dropwise to a solution of 9.9 g (25 mmol) 2,7-dibromo-N,N,N',N'-tetramethyl-5H,10H-dipyrrolo[1,2-a:1',2'-d]pyrazine-5,10-diamine (Muchowski, J. M.; Hess, P. *Tetrahedron Lett.* 1988,29(26), 3215-3218) cooled in a dry ice acetone bath. The solution was stirred 10 m before 5 mL (57 mmol) of (methyldithio)methane was added in one portion. After warming to room temperature and stirring 2 h, 120 mL of NaHCO₃ (aq) were added, and the mixture was heated at reflux for 15 h. The mixture was diluted with EtOAc and washed with water and brine. Drying (MgSO$_4$) and removal of solvent gave a 7.5 g of a solid. The solid was dissolved in 50 mL DMF along with 6.9 g (50 mmol) K$_2$CO$_3$ and 3.1 mL (50 mmol) CH$_3$I. The mixture was heated at 50° C. overnight. Solvent was removed, and the residue was partitioned between EtOAc and water. The EtOAc was separated and washed with brine. Drying (MgSO$_4$) and removal of solvent gave an oil that was used further without purification, $^1$H NMR (DMSO) δ 9.5 (s, 1H), 7.3 (s, 1H), 7.0 (s, 1H), 3.9 (s, 3H), 2.4 (s, 3H).

Example 150

Preparation of 1-methyl-4-(methylsulfinyl)-1H-pyrrole-2-carbaldehyde

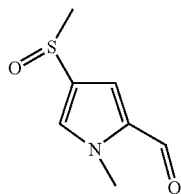

A solution of the preceding compound (0.54 g, 3.5 mmol) was dissolved in 20 mL MeOH, and a solution of 0.8 g (3.7 mmol) of NaIO$_4$ in 4 mL water was added. The mixture was stirred at room temperature overnight. MeOH was removed, and the residue was diluted with water before being extracted continuously with EtOAc overnight. The EtOAc was dried (MgSO$_4$) and concentrated to give the title compound, $^1$H NMR (DMSO) δ 9.6 (s, 1H), 7.8 (s, 1H), 7.4 (s, 1H), 3.9 (s, 3H), 2.8 (s, 3H).

Example 151

Preparation of 1-methyl-4-(methylsulfonyl)-1H-pyrrole-2-carbaldehyde

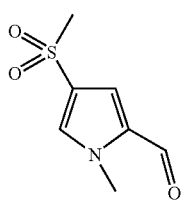

A solution of 1.0 g (6.4 mmol) 1-methyl-4-(methylthio)-1H-pyrrole-2-carbaldehyde and 3.1 g (13.3 mmol) m-chloroperoxybenzoic acid in 10 mL 1:1CH$_2$Cl$_2$—H$_2$O (saturated with NaHCO$_3$) was stirred at room temperature for 2 h. The mixture was diluted with EtOAc and washed with NaHSO$_3$ (aq), NaHCO$_3$ (aq), and brine before being dried (MgSO$_4$) and concentrated. The resultant solid residue was recrystallized from n-butylchloride to give the title compound as a white solid, $^1$H NMR (DMSO) δ 9.6 (s, 1H), 7.9 (s, 1H), 7.4 (s, 1H), 4.0 (s, 3H), 3.2 (s, 3H).

Example 152

Preparation of 5-chloro-1-(methylsulfonyl)-1H-indole-3-carbaldehyde

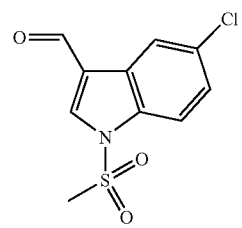

NaH (0.36 gm, 12.6 mmol) was added to a solution of 2.26 gm (12.6 mmol) 5-chloro-1H-indole-3-carbaldehyde in THF cooled in an ice water bath After 20 m stirring, 1.4 g (12.6 mmol) methanesulfonyl chloride was added, and the solution was warmed to room temperature with stirring overnight. The mixture was diluted with EtOAc and washed with water and brine, dried (MgSO$_4$) and concentrated. Normal phase chromatography (CH$_2$Cl$_2$ followed by gradient elution to 10% EtOAc in CH$_2$Cl$_2$) afforded 1.9 gm of the title compound as a white solid, $^1$H NMR (DMSO) δ 9.75 (s, 1H), 8.0 (s, 1H), 7.9 (s, 1H), 7.5 (d, 1H), 7.1 (d, 1H), 2.3 (s, 3H).

The preparations of 5-chloro-1-benzothiophene-3-carbaldehyde and 5-fluoro-1-benzothiophene-3-carbaldehyde are described in the literature (Branbander, H. J. *J. Heterocycl. Chem.* 1973, 10, 127).

Example 153 (old 160)

5-methyl-2-(1-naphthylmethyl)-3-(4-pyridinyl)-7-{[(trfluoromethyl)sulfanyl]methyl}-2-pyrazolo[3,4-d]pyrimidine-4,6(5H,7H)-dione

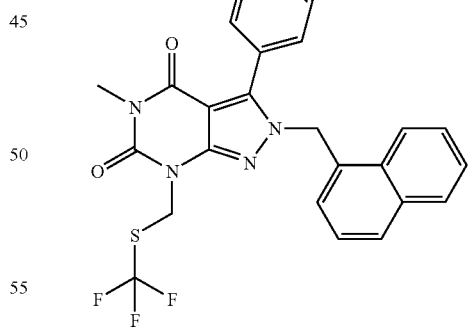

A solution of 150 mg (0.36 mmol) 5-methyl-2-(1-naphthylmethyl)-3-pyridin-4-yl-2H-pyrazolo[3,4-d]pyrimidine-4,6(5H,7H)-dione, 61 mg (0.47 mmol) K$_2$CO$_3$ and 50 μL (0.47 mmol) chloromethyl trifluoromethylsulfide in 10 mL DMF was heated at 80° C. for 20 h. The mixture was diluted with ether and washed 3 times with water. Drying (MgSO$_4$) and removal of solvent gave a yellow solid that was recrystallized from ethanol to give 95 mg of a white solid.

ES$^+$ (M+H) 497.78.

Following the method of Example 153, Compounds 154 and 155 were made by reaction of 5-methyl-2-(1-naphthylmethyl)-3-pyridin-4-yl-2H-pyrazolo[3,4-d]pyrimidine-4,6(5H,7H)-dione with chloromethyl methylsulfide and chloromethyl phenyl sulfide, respectively, of 1-naphthaldehyde (1-methyl-2,6-dioxo-1,2,3,6-tetrahydropyrimidin-4-yl)hydrazone. Isonicotinaldehyde (110 mg, 1.0 mmol) and piperidine (50 μL, 0.6 mmol) were added, and the mixture was heated at 70° C. for 20 h. 1,1,1-trifluoro-2-iodoethane (130 μL, 1.3 mmol) and DBU (200

| Example | Structure | Name | ES+ (M + H) |
|---|---|---|---|
| 154 | 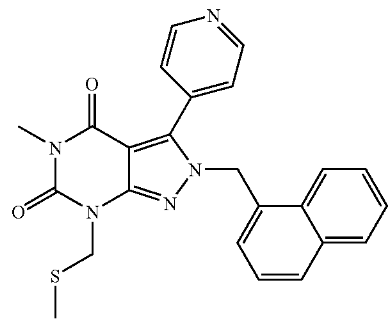 | 5-methyl-7-[(methylthio)methyl]-2-(1-naphthylmethyl)-3-pyridin-4-yl-2H-pyrazolo[3,4-d]pyrimidine-4,6(5H,7H)-dione | 443.94 |
| 155 | 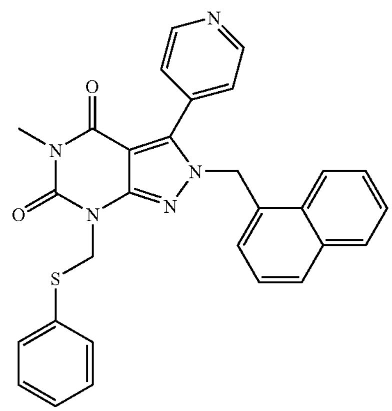 | 5-methyl-2-(1-naphthylmethyl)-7-[(phenylthio)methyl]-3-pyridin-4-yl-2H-pyrazolo[3,4-d]pyrimidine-4,6(5H,7H)-dione | 505.82 |

Example 156

5-methyl-2-(1-naphthylmethyl)-3-pyridin-4-yl-7-(2,2,2-trifluoroethyl)-2H-pyrazolo[3,4-d]pyrimidine-4,6(5H,7H)-dione

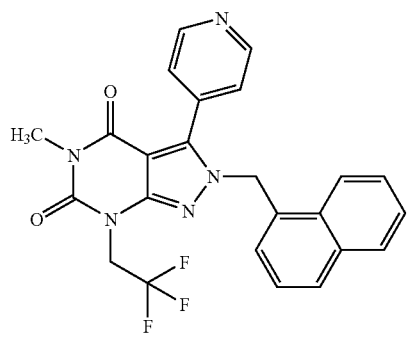

A solution of 84 mg (0.54 mmol) 6-hydrazino-3-methylpyrimidine-2,4(1H,3H)-dione and 84 mg (0.54 mmol) 1-naphthaldehyde in 3 mL DMF was heated to 70° C. for 30 min before cooling to room temperature affording a solution μL, 1.3 mmol) were added, and the mixture was heated at 90° C. for 20 h. Solvent was removed and the residue was purified by preparative reverse phase HPLC (30%-60% gradient of CH$_3$CN-water with 0.1% TFA) to afford the title compound as the trifluoroacetate salt.
ES+ (M+H) 466.38.

Following the method of Example 156, Compound 157 was made by preparation of 1-naphthaldehyde (1-methyl-2,6-dioxo-1,2,3,6-tetrahydropyrimidin-4-yl)hydrazone and condensation with 1-methyl-1H-imidazole-2-carbaldehyde followed by alkylation with 1,1,1-trifluoro-2-iodoethane.

Following the method of Example 156, the compound of Example 158 was made by preparation of 1-naphthaldehyde (1-methyl-2,6-dioxo-1,2,3,6-tetrahydropyrimidin-4-yl)hydrazone and condensation with isonicotinaldehyde followed by alkylation with 1-bromo-3-fluoropropane.

Following the method of Example 156, the compound of Example 159 was made by preparation of 1-benzothiophene-3-carbaldehyde (1-methyl-2,6-dioxo-1,2,3,6-tetrahydropyrimidin-4-yl)hydrazone and condensation with 1-methyl-1H-imidazole-2-carbaldehyde followed by alkylation with 1-bromo-3-fluoropropane.

Following the method of Example 156, the compound of Example 160 was made by condensation of 1-benzothiophene-3-carbaldehyde (1-methyl-2,6-dioxo-1,2,3,6- tetrahydropyrimidin-4-yl)hydrazone and condensation with 1-methyl-1H-imidazole-2-carbaldehyde followed by alkylation with n-propyl iodide.

Following the method of Example 156, the compound of Example 161 was made by preparation of 1-benzothiophene-3-carbaldehyde (1-methyl-2,6-dioxo-1,2,3,6-tetrahydropyrimidin-4-yl)hydrazone and condensation with 1-methyl-1H-imidazole-2-carbaldehyde followed by alkylation with 1,1,1-trifluoro-2-iodoethane.

Following the method of Example 156, the compound of Example 162 was made by condensation of 1-benzothiophene-3-carbaldehyde (1-methyl-2,6-dioxo-1,2,3,6-tetrahydropyrimidin-4-yl)hydrazone and condensation with isonicotinaldehyde followed by alkylation with 1,1,1-trifluoro-2-iodoethane.

Following the method of Example 156, the compound of Example 163 was made by preparation of 1-naphthaldehyde (1-methyl-2,6-dioxo-1,2,3,6-tetrahydropyrimidin-4-yl)hydrazone and condensation with 1-methyl-1H-imidazole-2-carbaldehyde followed by alkylation with n-propyl iodide.

| Example | Structure | Name | ES+ (M + H) |
|---|---|---|---|
| 157 | 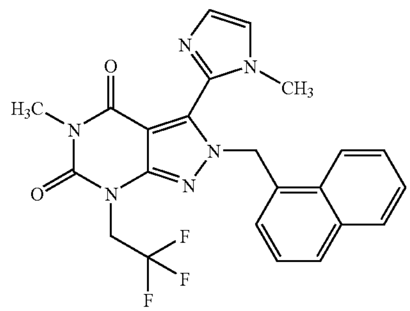 | 5-methyl-3-(1-methyl-1H-imidazol-2-yl)-2-(1-naphthylmethyl)-7-(2,2,2-trifluoroethyl)-2H-pyrazolo[3,4-d]pyrimidine-4,6(5H,7H)-dione | 469.38 |
| 158 | 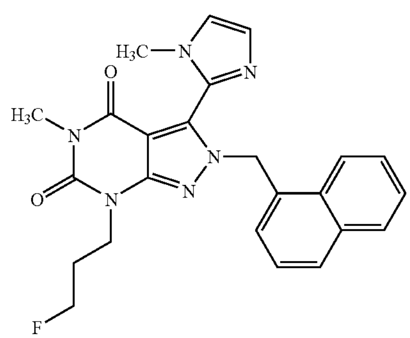 | 7-(3-fluoropropyl)-5-methyl-3-(1-methyl-1H-imidazol-2-yl)-2-(1-naphthylmethyl)-2H-pyrazolo[3,4-d]pyrimidine-4,6(5H,7H)-dione | 447.18 |
| 159 | 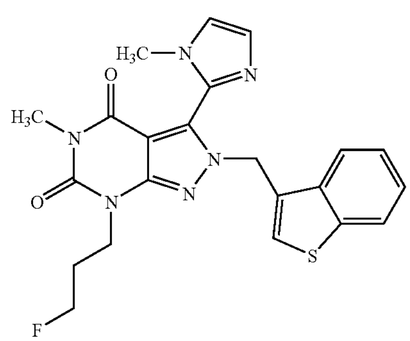 | 2-(1-benzothien-3-ylmethyl)-7-(3-fluoropropyl)-5-methyl-3-(1-methyl-1H-imidazol-2-yl)-2H-pyrazolo[3,4-d]pyrimidine-4,6(5H,7H)-dione | 453.20 |

| Example | Structure | Name | ES+ (M + H) |
|---|---|---|---|
| 160 | 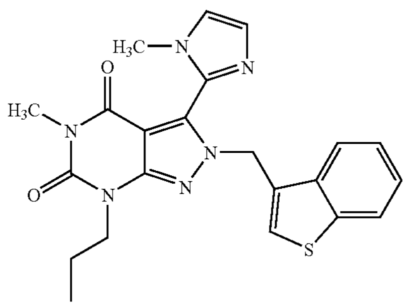 | 2-(1-benzothien-3-ylmethyl)-5-methyl-3-(1-methyl-1H-imidazol-2-yl)-7-propyl-2H-pyrazolo[3,4-d]pyrimidine-4,6(5H,7H)-dione | 429.4 |
| 161 | 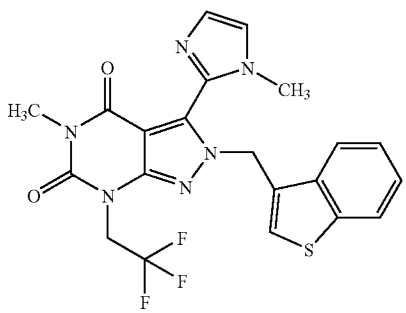 | 2-(1-benzothien-3-ylmethyl)-5-methyl-3-(1-methyl-1H-imidazol-2-yl)-7-(2,2,2-trifluoroethyl)-2H-pyrazolo[3,4-d]pyrimidine-4,6(5H,7H)-dione | 475.40 |
| 162 | 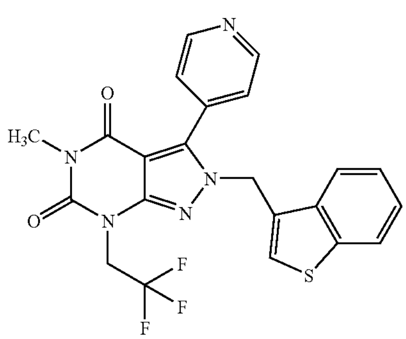 | 2-(1-benzothien-3-ylmethyl)-5-methyl-3-pyridin-4-yl-7-(2,2,2-trifluoroethyl)-2H-pyrazolo[3,4-d]pyrimidine-4,6(5H,7H)-dione | 472.40 |
| 163 | 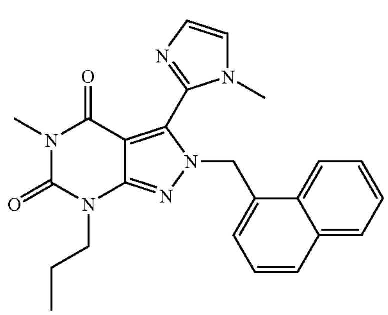 | 5-methyl-3-(1-methyl-1H-imidazol-2-yl)-2-(1-naphthalenylmethyl)-7-propyl-2H-pyrazolo[3,4-d]pyrimidine-4,6(5H,7H)-dione | 429.40 |

Example 164

N-(tert-butyl)-2-[7-isobutyl-5-methyl-2-(1-naphthylmethyl)-4,6-dioxo-4,5,6,7-tetrahydro-2H-pyrazolo[3,4 d]pyrimidin-3-yl]-1-methyl-1H-imidazole-4-sulfonamide

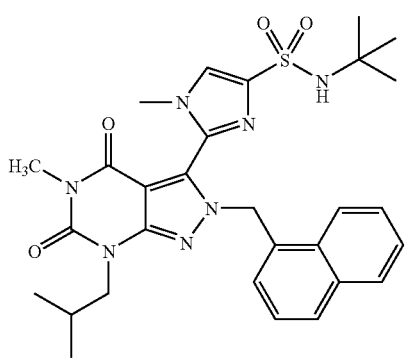

A solution of 190 mg (1.1 mmol) of 1-naphthaldehyde (3-isobutyl-1-methyl-2,6-dioxo-1,2,3,6-tetrahydropyrimidin-4-yl)hydrazone, 36 mg (0.27 mmol) of N-(tert-butyl)-2-formyl-1-methyl-1H-imidazole-4-sulfonamide and 40 µL of piperidine in 3 mL DMF was heated at 70° C. for 20 h. Solvent was removed, and the mixture was isolated by preparative reverse phase HPLC (60%-90% gradient of CH$_3$CN-water with 0.1% TFA) as a white solid.

ES$^+$ (M+H) 578.17.

Following the method of Example 164, the compound of Example 165 was made by condensation of 1-naphthaldehyde (3-isobutyl-1-methyl-2,6-dioxo-1,2,3,6-tetrahydropyrimidin-4-yl)hydrazone with N-(tert-butyl)-3-formylbenzenesulfonamide (Martin, L.; Cornille, F.; Turcaud, S.; Meudal, H.; Roques, B. P.; Fournie-Zaluski, M-C. *J. Med. Chem.* 42(3), 1999, 515-525).

Following the method of Example 164, the compound of Example 166 was made by condensation of 5-chloro-1H-indole-3-carbaldehyde (3-isobutyl-1-methyl-2,6-dioxo-1,2,3,6-tetrahydropyrimidin-4-yl)hydrazone with N-(tert-butyl) 1-methyl-1H-imidazole-4-sulfonamide.

Following the method of Example 164, the compound of Example 167 was made by condensation of 5-chloro-1H-indole-3-carbaldehyde (3-isobutyl-1-methyl-2,6-dioxo-1,2,3,6-tetrahydropyrimidin-4-yl)hydrazone with 1-methyl-1H-imidazole-5-carbaldehyde.

Following the method of Example 164, the compound of Example 168 was made by condensation of 1-naphthaldehyde (3-isobutyl-1-methyl-2,6-dioxo-1,2,3,6-tetrahydropyrimidin-4-yl)hydrazone with 1-methyl-1H-imidazole-5-carbaldehyde.

Following the method of Example 164, the compound of Example 169 was made by condensation of 1-naphthaldehyde (3-isobutyl-1-methyl-2,6-dioxo-1,2,3,6-tetrahydropyrimidin-4-yl)hydrazone with 1,3-dimethyl-2-thioxo-2,3-dihydro-1H-imidazole-4-carbaldehyde.

Following the method of Example 164, the compound of Example 170 was made by condensation of 5-fluoro-3a,7a-dihydro-1-benzothiophene-3-carbaldehyde (3-isobutyl-1-methyl-2,6-dioxo-1,2,3,6-tetrahydropyrimidin-4-yl)hydrazone with 3-formylbenzenesulfonamide (Roussel-UCLAF, NL 6405788; 1964; Chem. Abstr.: 63, 9917b, 1965).

Following the method of Example 164, the compound of Example 171 was made by condensation of 5-methyl-3a,7a-dihydro-1H-indole-3-carbaldehyde (3-isobutyl-1-methyl-2,6-dioxo-1,2,3,6-tetrahydropyrimidin-4-yl)hydrazone with 3-formylbenzenesulfonamide (Roussel-UCLAF, NL 6405788; 1964; Chem. Abstr.: 63, 9917b, 1965).

Following the method of Example 164, the compound of Example 172 was made by condensation of 5-methyl-3a,7a-dihydro-1H-indole-3-carbaldehyde (3-isobutyl-1-methyl-2,6-dioxo-1,2,3,6-tetrahydropyrimidin-4-yl)hydrazone with 3-formylbenzenesulfonamide (Roussel-UCLAF, NL 6405788; 1964; Chem. Abstr.: 63, 9917b, 1965).

Following the method of Example 164, the compound of Example 173 was made by condensation of 5-fluoro-3a,7a-dihydro-1-benzothiophene-3-carbaldehyde (3-isobutyl-1-methyl-2,6-dioxo-1,2,3,6-tetrahydropyrimidin-4-yl)hydrazone with 1-methyl-1H-imidazole-5-carbaldehyde.

Following the method of Example 164, the compound of Example 174 was made by condensation of 5-methyl-3a,7a-dihydro-1H-indole-3-carbaldehyde (3-isobutyl-1-methyl-2,6-dioxo-1,2,3,6-tetrahydropyrimidin-4-yl)hydrazone with 1-methyl-1H-imidazole-5-carbaldehyde.

Following the method of Example 164, the compound of Example 175 was made by condensation of 1-benzothiophene-3-carbaldehyde (1-methyl-2,6-dioxo-1,2,3,6-tetrahydropyrimidin-4-yl)hydrazone with 1-methyl-1H-imidazole-5-carbaldehyde.

Following the method of Example 164, the compound of Example 176 was made by condensation of 1-naphthaldehyde (3-isobutyl-1-methyl-2,6-dioxo-1,2,3,6-tetrahydropyrimidin-4-yl)hydrazone with 1,3-dimethyl-2-thioxo-2,3-dihydro-1H-imidazole-4-carbaldehyde.

Following the method of Example 164, the compound of Example 177 was made by condensation of 5-chloro-1H-indole-3-carbaldehyde (3-isobutyl-1-methyl-2,6-dioxo-1,2,3,6-tetrahydropyrimidin-4-yl)hydrazone with N-[tert-butyl(dimethyl)silyl]-2-formyl-1-methyl-1H-imidazole-4-sulfonamide.

Following the method of Example 164, the compound of Example 178 was made by condensation of 5-chloro-1H-indole-3-carbaldehyde[3-(cyclopropylmethyl)-1-methyl-2,6-dioxo-1,2,3,6-tetrahydropyrimidin-4-yl]hydrazone with N-[tert-butyl(dimethyl)silyl]-2-formyl-1-methyl-1H-imidazolesulfonamide.

Following the method of Example 164, the compound of Example 179 was made by condensation of 5-methyl-1H-indole-3-carbaldehyde[3-(cyclopropylmethyl)-1-methyl-2,6-dioxo-1,2,3,6-tetrahydropyrimidin-4-yl]hydrazone with N-[tert-butyl(dimethyl)silyl]-2-formyl-1-methyl-1H-imidazole-4-sulfonamide.

| Example | Structure | Name | ES+ (M + H) |
|---|---|---|---|
| 165 | 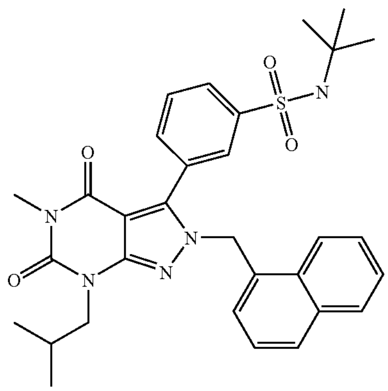 | N-(tert-butyl)-3-[7-isobutyl-5-methyl-2-(1-naphthylmethyl)-4,6-dioxo-4,5,6,7-tetrahydro-2H-pyrazolo[3,4-d]pyrimidin-3-yl]benzenesulfonamide | 574.18. |
| 166 | 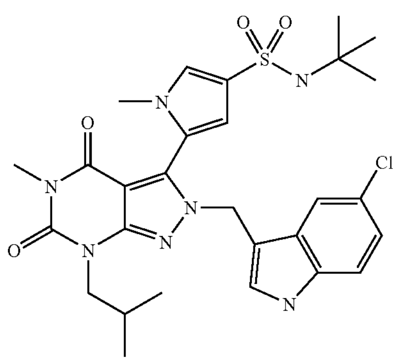 | N-(tert-butyl)-2-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-imidazole-4-sulfonamide | 601.09 |
| 167 | 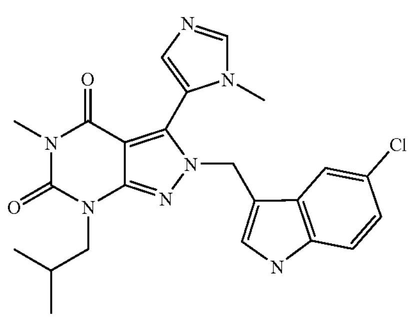 | 2-[(5-chloro-1H-indol-3-yl)methyl]-7-isobutyl-5-methyl-3-(1-methyl-1H-imidazol-5-yl)-2H-pyrazolo[3,4-d]pyrimidine-4,6(5H,7H)-dione | 466.14 |
| 168 | 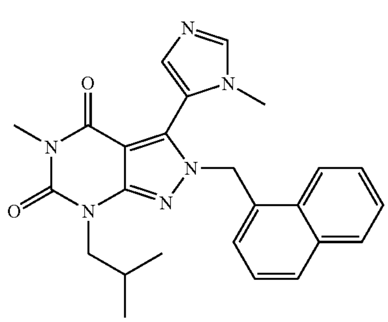 | 7-isobutyl-5-methyl-3-(1-methyl-1H-imidazol-5-yl)-2-(1-naphthylmethyl)-2H-pyrazolo[3,4-d]pyrimidine-4,6(5H,7H)-dione | 443.22 |

| Example | Structure | Name | ES+ (M + H) |
|---|---|---|---|
| 169 | 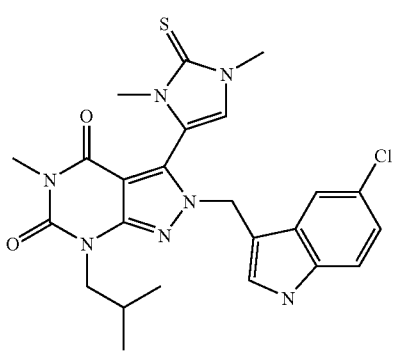 | 2-[(5-chloro-1H-indol-3-yl)methyl]-3-(1,3-dimethyl-2-thioxo-2,3-dihydro-1H-imidazol-4-yl)-7-isobutyl-5-methyl-2H-pyrazolo[3,4-d]pyrimidine-4,6(5H,7H)-dione | 512.17 |
| 170 | 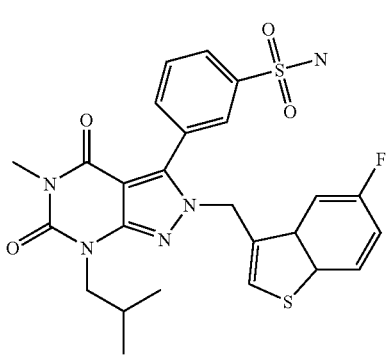 | 3-{2-[(5-fluoro-3a,7a-dihydro-1-benzothien-3-yl)methyl]-7-isobutyl-5-methyl-4,6-dioxo-4,5,6,7-tetrahydro-2H-pyrazolo[3,4-d]pyrimidin-3-yl}benzenesulfonamide | 542.03 |
| 171 | 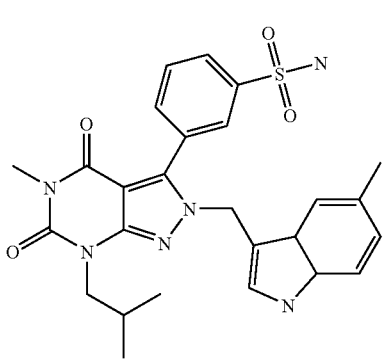 | 3-{7-isobutyl-5-methyl-2-[(5-methyl-3a,7a-dihydro-1H-indol-3-yl)methyl]-4,6-dioxo-4,5,6,7-tetrahydro-2H-pyrazolo[3,4-d]pyrimidin-3-yl}benzenesulfonamide | 521.08 |
| 172 | 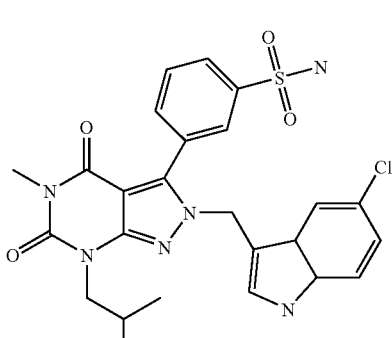 | 3-{2-[(5-chloro-3a,7a-dihydro-1H-indol-3-yl)methyl]-7-isobutyl-5-methyl-4,6-dioxo-4,5,6,7-tetrahydro-2H-pyrazolo[3,4-d]pyrimidin-3-yl}benzenesulfonamide | 541.07 |

-continued

| Example | Structure | Name | ES+ (M + H) |
|---------|-----------|------|-------------|
| 173 | 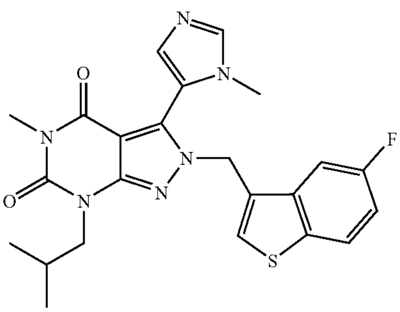 | 2-[(5-fluoro-1-benzothien-3-yl)methyl]-7-isobutyl-5-methyl-3-(1-methyl-1H-imidazol-5-yl)-2H-pyrazolo[3,4-d]pyrimidine-4,6(5H,7H)-dione | 467.04 |
| 174 | 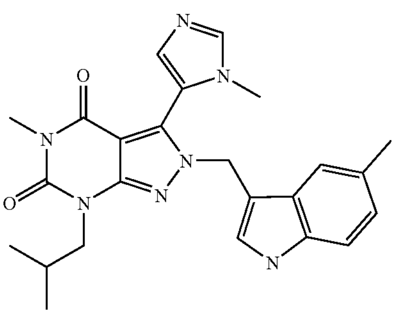 | 7-isobutyl-5-methyl-3-(1-methyl-1H-imidazol-5-yl)-2-[(5-methyl-1H-indol-3-yl)methyl]-2H-pyrazolo[3,4-d]pyrimidine-4,6(5H,7H)-dione | 446.31 |
| 175 | 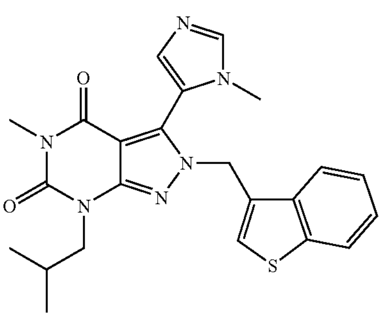 | 2-(1-benzothien-3-ylmethyl)-7-isobutyl-5-methyl-3-(1-methyl-1H-imidazol-5-yl)-2H-pyrazolo[3,4-d]pyrimidine-4,6(5H,7H)-dione | 449.19 |
| 176 | 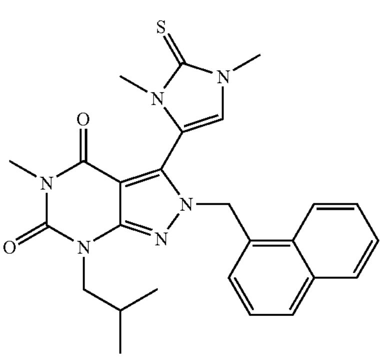 | 3-(1,3-dimethyl-2-thioxo-2,3-dihydro-1H-imidazol-4-yl)-7-isobutyl-5-methyl-2-(1-naphthylmethyl)-2H-pyrazolo[3,4-d]pyrimidine-4,6(5H,7H)-dione | 489.23 |

-continued

| Example | Structure | Name | ES+ (M + H) |
|---|---|---|---|
| 177 | 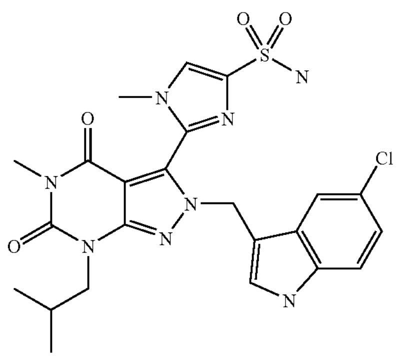 | 2-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-imidazole-4-sulfonamide | 545.12 |
| 178 | 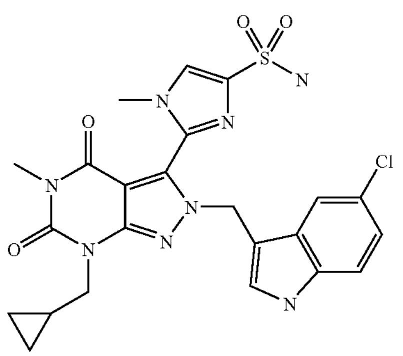 | 2-[2-[(5-chloro-1H-indol-3-nl yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-imidazole-4-sulfonamide | 543.12 |
| 179 | 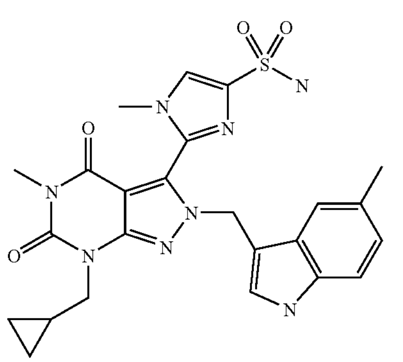 | 2-{7-(cyclopropylmethyl)-5-methyl-2-[(5-methyl-1H-indol-3-yl)methyl}-4,6-dioxo-4,5,6,7-tetrahydro-2H-pyrazolo[3,4-d]pyrimidin-3-yl}-1-methyl-1H-imidazole-4-sulfonamide | 523.15 |

Example 180

2-(2-{[-chloro-1-(methylsulfonyl)-1H-indol-3-yl]methyl}-7-isobutyl-5-methyl-4,6-dioxo-4,5,6,7-tetrahydro-2H-pyrazolo[3,4-d]pyrimidin-3-yl)-1-methyl-1H-imidazole-4-sulfonamide

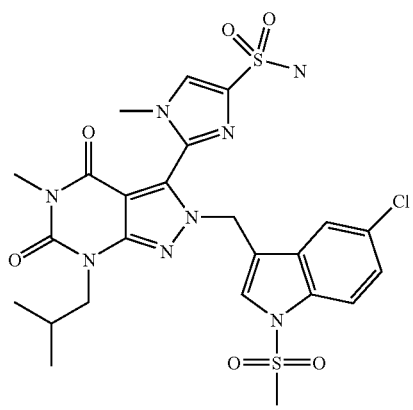

A solution of 38 mg (0.18 mmol) of 6-hydrazino-1-isobutyl-3-methylpyrimidine-2,4(1H,3H)-dione and 5-chloro-1-(methylsulfonyl)-1H-indole-3-carbaldehyde in 2 mL DMF was stirred at room temperature for 2 h. Added was 88 mg (0.36 mmol) N-(tert-butyl)-2-formyl-1-methyl-1H-imidazolesulfonamide and 15 μL piperidine. The solution was heated at 70° C. for 20 h. Solvent was removed, and the residue was dissolved in 2 mL 1:1 CH$_2$Cl$_2$-TFA with stirring overnight. Solvent was removed, and the mixture was isolated by preparative reverse phase HPLC (30%-50% gradient of CH$_3$CN-water with 0.1% TFA) as a white solid. ES$^+$ (M+H) 622.48.

Example 181

5-{2-[(6-chloroquinolin-4-yl)methyl]-5-methyl-4,6-dioxo-7-propyl-4,5,6,7-tetrahydro-2H-pyrazolo[3,4-d]pyrimidin-3-yl}-1-methyl-1H-pyrrole-3-sulfonamide

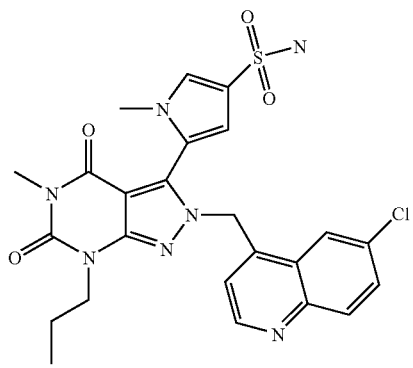

Following the method of Example 180, this compound was made by preparation of 6-chloroquinoline-4-carbaldehyde (1-methyl-2,6-dioxo-3-propyl-1,2,3,6-tetrahydropyrimidin-4-yl)hydrazone, condensation with N-(tert-butyl)-5-formyl-1-methyl-1H-pyrrole-3-sulfonamide and treatment with TFA.
ES$^+$ (M+H) 542.12.

Example 182

N-(tert-butyl)-2-[7-isobutyl-5-methyl-2-(1-naphthylmethyl)-4,6-dioxo-4,5,6,7-tetrahydro-2H-pyrazolo[3,4-d]pyrimidin-3-yl]-N,1-dimethyl-1H-imidazole-4-sulfonamide

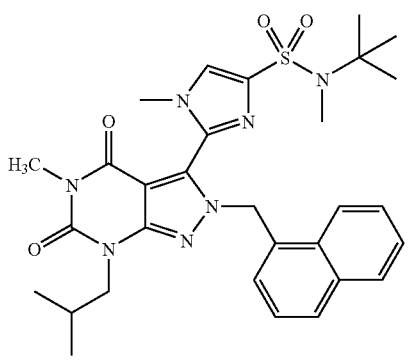

NaH (10 mg, 0.25 mmol) was added to a solution of the compound of Example 164 (84 mg, 0.14 mmol) and CH$_3$I (100 μL) in 2 mL DMF. After warming to room temperature and stirring for 16 h, solvent was removed and the residue was partitioned between water and EtOAc. The EtOAc was separated and washed with brine. Drying and removal of solvent gave an oil that was purified by preparative reverse phase HPLC (45%-75% gradient of CH$_3$CN-water with 0.1% TFA).
ES$^+$ (M+H) 592.19.

Example 183

N-(tert-butyl)-3-[7-isobutyl-5-methyl-2-(1-naphthylmethyl)-4,6-dioxo-4,5,6,7-tetrahydro-2H-pyrazolo[3,4-d]pyrimidin-3-yl]-N-methylbenzenesulfonamide

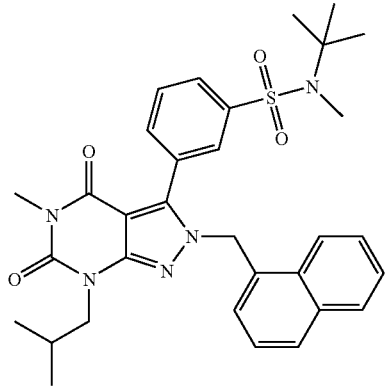

Following the method of Example 182, the title compound was made from the compound of Example 165.
ES$^+$ (M+H) 588.20.

Example 184

2-[7-isobutyl-5-methyl-2-(1-naphthylmethyl)-4,6-dioxo-4,5,6,7-tetrahydro-2H-pyrazolo[3,4-d]pyrimidin-3-yl]-1-methyl-1H-imidazolesulfonamide

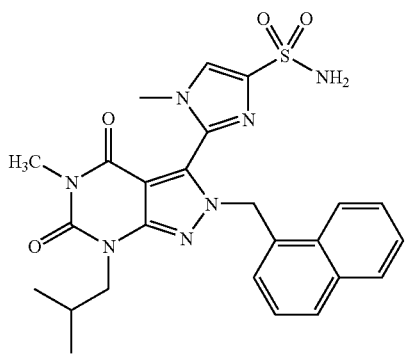

A solution of 200 mg (0.37 mmol) of the compound made in Example 164 in 4 mL of 1:1 CH$_2$Cl$_2$:TFA was stirred at room temperature overnight. Solvent was removed, and the residue was purified by preparative HPLC (30%-55% gradient of CH$_3$CN-water with 0.1% TFA) to give the title compound as a TFA salt

ES$^+$ (M+H) 522.08.

Following the method of Example 184, the compound of Example 185 was made from the compound of Example 165.

Following the method of Example 184, the compound of Example 186 was made from the compound from Example 182.

Following the method of Example 184, the compound of Example 187 was made from the from Example 183.

| Example | Structure | Name | ES$^+$ (M + H) |
|---|---|---|---|
| 185 | 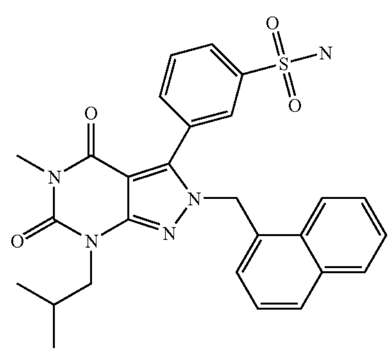 | 3-[7-isobutyl-5-methyl-2-(1-naphthylmethyl)-4,6-dioxo-4,5,6,7-tetrahydro-2H-pyrazolo[3,4-d]pyrimidin-3-yl]benzenesulfonamide | 518.11 |
| 186 | 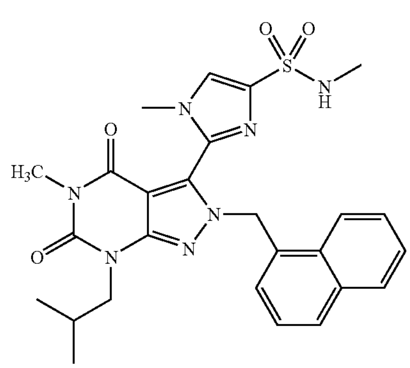 | 2-[7-isobutyl-5-methyl-2-(1-naphthylmethyl)-4,6-dioxo-4,5,6,7-tetrahydro-2H-pyrazolo[3,4-d]pyrimidin-3-yl]-N,1-dimethyl-1H-imidazole-4-sulfonamide | 536.13 |

-continued

| Example | Structure | Name | ES+ (M + H) |
|---|---|---|---|
| 187 | 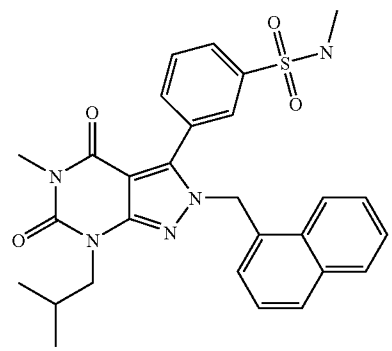 | 3-[7-isobutyl-5-methyl-2-(1-naphthylmethyl)-4,6-dioxo-4,5,6,7-tetrahydro-2H-pyrazolo[3,4-d]pyrimidin-3-yl]-N-methylbenzenesulfonamide | 532.13 |

Example 188

N-(aminocarbonyl)-2-[7-isobutyl-5-methyl-2-(1-naphthylmethyl)-4,6-dioxo-4,5,6,7-tetrahydro-2H-pyrazolo[3,4-d]pyrimidin-3-yl]-1-methyl-1H-imdazole-4-sulfonamide

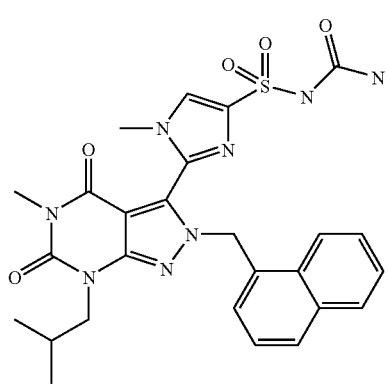

A solution of 44 mg (84 mmol) of the compound of Example 184, 65 mg (0.48 mmol) phenyl carbamate and 66 μL (0.48 mmol) DBU in 3 mL CH₃CN were stirred together at room temperature overnight Solvent was removed and the residue was purified by preparative HPLC (30%-50% gradient of CH₃CN-water with 0.1% TFA) to give the title compound as the TFA salt.

ES⁺ (M+H) 565.13.

Example 189

N-(aminocarbonyl)-3-[7-isobutyl-5-methyl-2-(1-naphthylmethyl)-4,6-dioxo-4,5,6,7-tetrahydro-2H-pyrazolo[3,4-d]pyrimidin-3-yl]benzenesulfonamide

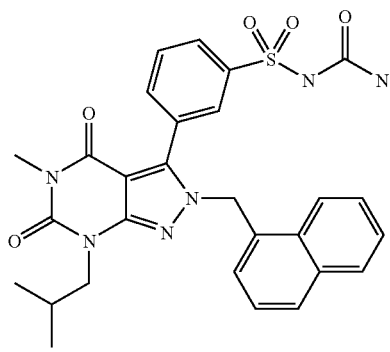

Following the method of Example 88, the title compound was made from the compound of

Example 185

ES+ (M+H) 561.26.

Example 190

7-(cyclopropylmethyl)-5-methyl-3-(1-methyl-1H-imidazol-5-yl)-2-[(5-methyl-1H-indol-3-yl)methyl]-2H-pyrazolo[3,4-d]pyrimidine-4,6(5H,7H)-dione

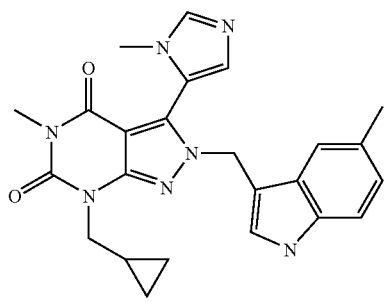

A solution of 90 mg (0.26 mmol) 5-methyl-1H-indole-3-carbaldehyde[3-(cyclopropylmethyl)-1-methyl-2,6-dioxo-1,2,3,6-tetrahydropyrimidin-4-yl]hydrazone, 39 mg (0.35 mmol) 1-methyl-1H-imidazole-5-carbaldehyde and 22 μL piperidine in 1 mL DMF was heated at 110° C. for 12 m via microwave irradiation. Purification was achieved by preparative HPLC (30%-50% gradient of $CH_3CN$-water with 0.1% TFA) to give the title compound as the TFA salt.

ES+ (M+H) 444.29.

Example 191

2-[(6chloroquinolin-4-yl)methyl]-7-(cyclopropylmethyl)-5-methyl-3-(1-methyl-1H-imidazol-5-yl)-2H-pyrazolo[3,4-d]pyrimidine-4,6(5H,7H)-dione

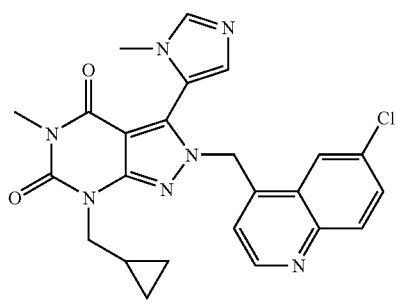

A solution of 49 mg (0.23 mmol) 1-(cyclopropylmethyl)-6-hydrazino-3-methylpyrimidine-2,4(1H,3H)-dione and 44 mg (0.23 mmol) 6-chloroquinoline-4-carbaldehyde in 1 mL DMF was stirred at room temperature for 5 h to form 6-chloroquinoline-4-carbaldehyde[3-(cyclopropylmethyl)-1-methyl-2,6-dioxo-1,2,3,6-tetrahydropyrimidin-4-yl]hydrazone. Added was 38 mg (0.34 mmol) 1-methyl-1H-imidazole-5-carbaldehyde and 20 μL piperidine. The mixture was heated at 110° C. for 12 via microwave irradiation. Purification was achieved by preparative HPLC (20%-40% gradient of $CH_3CN$-water with 0.1% TFA) to give the title compound as the bis-TFA salt.

ES+ (M+H) 476.21.

Following the method of Example 191, the compound of Example 192 was made by preparation of 6-chloroquinoline-4-carbaldehyde (3-isobutyl-1-methyl-2,6-dioxo-1,2,3,6-tetrahydropyrimidin-4-yl)hydrazone and condensation with 1-methyl-1H-imidazole-5-carbaldehyde.

Following the method of Example 191, the compound of Example 193 was made by preparation of 5-chloro-1H-indole-3-carbaldehyde (3-isobutyl-1-methyl-2,6-dioxo-1,2,3,6-tetrahydropyrimidin-4-yl)hydrazone and condensation with 1-methyl-1H-imidazole-5-carbaldehyde.

Following the method of Example 191, the compound of Example 194 was made by preparation of 5-chloro-1H-indole-3-carbaldehyde [3-(cyclopropylmethyl) 1-methyl-2,6-dioxo-1,2,3,6-tetrahydropyrimidin-4-yl]hydrazone and condensation with 1-methyl-1H-imidazole-5-carbaldehyde.

Following the method of Example 191, the compound of Example 195 was made by preparation of 6-chloroquinoline-4-carbaldehyde (3-isobutyl-1-methyl-2,6-dioxo-1,2,3,6-tetrahydropyrimidin-4-yl)hydrazone and condensation with N-[tert-butyl(dimethyl)silyl]-2-formyl-1-methyl-1H-imidazole-4-sulfonamide.

Following the method of Example 191, the compound of Example 196 was made by preparation of 6-chloroquinoline-4-carbaldehyde [3-(cyclopropylmethyl)-1-methyl-2,6-dioxo-1,2,3,6-tetrahydropyrimidin-4-yl]hydrazone and condensation with N-[tert-butyl(dimethyl)silyl]-2-formyl-1-methyl-1H-imidazole-4-sulfonamide.

Following the method of Example 191, the compound of Example 197 was made by preparation of 5-chloro-1H-indole-3-carbaldehyde (3-isobutyl-1-methyl-2,6-dioxo-1,2,3,6-tetrahydropyrimidin-4-yl)hydrazone and condensation with 1-methyl-4-(methylsulfonyl)-1H-imidazole-2-carbaldehyde.

Following the method of Example 191, the compound of Example 198 was made by preparation of 5-chloro-1H-indole-3-carbaldehyde[3-(cyclopropylmethyl)-1-methyl-2,6-dioxo-1,2,3,6-tetrahydropyrimidin-4-yl]hydrazone and condensation with 1-methyl-4-(methylsulfonyl)-1H-imidazole-2-carbaldehyde.

Following the method of Example 191, the compound of Example 199 was made by preparation of 6-chloroquinoline-4-carbaldehyde (1-methyl-2,6-dioxo-3-propyl-1,2,3,6-tetrahydropyrimidin-4-yl)hydrazone and condensation with 5-formyl-N,1-dimethyl-1H-pyrrole-3-sulfonamide.

Following the method of Example 191, the compound of Example 200 was made by preparation of 5-chloro-1H-indole-3-carbaldehyde[3-(cyclopropylmethyl)-1-methyl-2,6-dioxo-1,2,3,6-tetrahydropyrimidin-4-yl]hydrazone and condensation with 5-formyl-N,1-dimethyl-1H-pyrrole-3-sulfonamide.

Following the method of Example 191, the compound of Example 201 was made by preparation of 5-chloro-1H-indole-3-carbaldehyde (3-isobutyl-1-methyl-2,6-dioxo-1,2,3,6-tetrahydropyrimidin-4-yl)hydrazone and condensation with 5-formyl-N,1-dimethyl-1H-pyrrole-3-sulfonamide.

Following the method of Example 191, the compound of Example 202 was made by preparation of 5-methyl-1H-indole-3-carbaldehyde[3-(cyclopropylmethyl)-1-methyl-2, 6-dioxo-1,2,3,6-tetrahydropyrimidin-4-yl]hydrazone and condensation with 5-formyl-N,1-dimethyl-1H-pyrrole-3-sulfonamide.

Following the method of Example 191, the compound of Example 203 was made by preparation of 5-methyl-3a,7a-dihydro-1H-indole-3-carbaldehyde (3-isobutyl-1-methyl-2,6-dioxo-1,2,3,6-tetrahydropyrimidin-4-yl)hydrazone and condensation with 5-formyl-N,1-dimethyl-1H-pyrrole-3-sulfonamide.

Following the method of Example 191, the compound of Example 204 was made by preparation of 6-chloroquinoline-4-carbaldehyde[3-(cyclopropylmethyl)-1-methyl-2,6-dioxo-1,2,3,6-tetrahydropyrimidin-4-yl]hydrazone and condensation with 5-formyl-N,1-dimethyl-1H-pyrrole-3-sulfonamide.

Following the method of Example 191, the compound of Example 205 was made by preparation of 6-chloroquinoline-4-carbaldehyde (3-isobutyl-1-methyl-2,6-dioxo-1,2,3,6-tetrahydropyrimidin-4-yl)hydrazone and condensation with 5-formyl-N,1-dimethyl-1H-pyrrole-3-sulfonamide.

Following the method of Example 191, the compound of Example 206 was made by preparation of 5-fluoro-1-benzothiophene-3-carbaldehyde[3-(cyclopropylmethyl)-1-methyl-2,6-dioxo-1,2,3,6-tetrahydropyrimidin-4-yl]hydrazone and condensation with 5-formyl-N,1-dimethyl-1H-pyrrole-3-sulfonamide.

Following the method of Example 191, the compound of Example 207 was made by preparation of 5-fluoro-1-benzothiophene-3-carbaldehyde (3-isobutyl-1-methyl-2,6-dioxo-1,2,3,6-tetrahydropyrimidin-4-yl)hydrazone and condensation with 5-formyl-N,1-dimethyl-1H-pyrrole-3-sulfonamide.

Following the method of Example 191, the compound of Example 208 was made by preparation of 5-chloro-1H-indole-3-carbaldehyde (1-methyl-2,6-dioxo-3-propyl-1,2,3,6-tetrahydropyrimidin-4-yl)hydrazone and condensation with 5-formyl-N,1-dimethyl-1H-pyrrole-3-sulfonamide.

Following the method of Example 191, the compound of Example 209 was made by preparation of 5-chloro-1H-indole-3-carbaldehyde[3-(cyclopropylmethyl)-1-methyl-2,6-dioxo-1,2,3,6-tetrahydropyrimidin-4-yl]hydrazone and condensation with N-[(5-formyl-1-methyl-1H-pyrrol-3-yl)sulfonyl]glycine.

Following the method of Example 191, the compound of Example 210 was made by preparation of 5-methyl-3a,7a-dihydro-1H-indole-3-carbaldehyde (3-isobutyl-1-methyl-2,6-dioxo-1,2,3,6-tetrahydropyrimidin-4-yl)hydrazone and condensation with N-[(5-formyl-1-methyl-1H-pyrrol-3-yl)sulfonyl]glycine.

Following the method of Example 191, the compound of Example 211 was made by preparation of 5-chloro-1H-indole-3-carbaldehyde[3-isobutyl-1-(2-morpholin-4-yl-ethyl)-2,6-dioxo-1,2,3,6-tetrahydropyrimidin-4-yl]hydrazone and condensation with 1-methyl-1H-imidazole-5-carbaldehyde.

Following the method of Example 191, the compound of Example 212 was made by preparation of 5-fluoro-1-benzothiophene-3-carbaldehyde (3-isobutyl-2,6-dioxo-1,2,3,6-tetrahydropyrimidin-4-yl)hydrazone and condensation with isonicotinaldehyde.

Following the method of Example 191, the compound of Example 213 was made by preparation of 5-chloro-1-benzothiophene-3-carbaldehyde (3-isobutyl-2,6-dioxo-1,2,3,6-tetrahydropyrimidin-4-yl)hydrazone and condensation with isonicotinaldehyde.

Following the method of Example 191, the compound of Example 214 was made by preparation of 5-chloro-1-benzothiophene-3-carbaldehyde (3-isobutyl-2,6-dioxo-1,2,3,6-tetrahydropyrimidin-4-yl)hydrazone and condensation with 1-methyl-1H-imidazole-2-carbaldehyde.

Following the method of Example 191, the compound of Example 215 was made by preparation of 5-fluoro-1-benzothiophene-3-carbaldehyde (3-isobutyl-2,6-dioxo-1,2,3,6-tetrahydropyrimidin-4-yl)hydrazone and condensation with 1-methyl-1H-imidazole-2-carbaldehyde.

Following the method of Example 191, the compound of Example 216 was made by preparation of 5-fluoro-1-benzothiophene-3-carbaldehyde (3-isobutyl-1-methyl-2,6-dioxo-1,2,3,6-tetrahydropyrimidin-4-yl)hydrazone and condensation with 1-methyl-1H-pyrrole-2-carbaldehyde.

Following the method of Example 191, the compound of Example 217 was made by preparation of 5-fluoro-1-benzothiophene-3-carbaldehyde (3-isobutyl-1-methyl-2,6-dioxo-1,2,3,6-tetrahydropyrimidin-4-yl)hydrazone and condensation with isonicotinaldehyde.

Following the method of Example 191, the compound of Example 218 was made by preparation of 5-chloro-1H-indole-3-carbaldehyde (3-isobutyl-1-methyl-2,6-dioxo-1,2,3,6-tetrahydropyrimidin-4-yl)hydrazone and condensation with N-(5-formylpyridin-2-yl)acetamide.

Following the method of Example 191, the compound of Example 219 was made by preparation of 5-fluoro-1-benzothiophene-3-carbaldehyde (3-isobutyl-1-methyl-2,6-dioxo-1,2,3,6-tetrahydropyrimidin-4-yl)hydrazone and condensation with N-(5-formylpyridin-2-yl)acetamide.

Following the method of Example 191, the compound of Example 220 was made by preparation of 5-fluoro-1-benzothiophene-3-carbaldehyde (3-isobutyl-1-methyl-2,6-dioxo-1,2,3,6-tetrahydropyrimidin-4-yl)hydrazone and condensation with 1-methyl-1H-pyrrole-2-carbaldehyde.

Following the method of Example 191, the compound of Example 221 was made by preparation of 5-chloro-1H-indole-3-carbaldehyde (3-isobutyl-1-methyl-2,6-dioxo-1,2,3,6-tetrahydropyrimidin-4-yl)hydrazone and condensation with 4-methyl-4H-1,2,4-triazole-3-carbaldehyde.

Following the method of Example 191, the compound of Example 222 was made by preparation of 5-methyl-3a,7a-dihydro-1H-indole-3-carbaldehyde (3-isobutyl-1-methyl-2,6-dioxo-1,2,3,6-tetrahydropyrimidin-4-yl)hydrazone and condensation with 4-methyl-4H-1,2,4-triazole-3-carbaldehyde.

Following the method of Example 191, the compound of Example 223 was made by preparation of 5-methyl-3a,7a-dihydro-1H-indole-3-carbaldehyde[3-(cyclopropylmethyl)-1-methyl-2,6-dioxo-1,2,3,6-tetrahydropyrimidin-4-yl]hydrazone and condensation with 4-methyl-4H-1,2,4-triazole-3-carbaldehyde.

Following the method of Example 191, the compound of Example 224 was made by preparation of 5-chloro-1H-indole-3-carbaldehyde [3-(cyclopropylmethyl)-1-methyl-2, 6-dioxo-1,2,3,6-tetrahydropyrimidin-4-yl]hydrazone and condensation with 4-methyl-4H-1,2,4-triazole-3-carbaldehyde.

Following the method of Example 191, the compound of Example 225 was made by preparation of 5-chloro-1H-indazole-3-carbaldehyde (3-isobutyl-1-methyl-2,6-dioxo-1,2,3,6-tetrahydropyrimidin-4-yl)hydrazone and condensation with 1-methyl-1H-imidazole-2-carbaldehyde.

Following the method of Example 191, the compound of Example 226 was made by preparation of 5-chloro-1H-indazole-3-carbaldehyde[3-(cyclopropylmethyl)-1-methyl-2,6-dioxo-1,2,3,6-tetrahydropyrimidin-4-yl]hydrazone and condensation with 1-methyl-1H-imidazole-2-carbaldehyde.

Following the method of Example 191, the compound of Example 227 was made by preparation of 5-fluoro-1-benzothiophene-3-carbaldehyde (3-isobutyl-1-methyl-2,6-dioxo-1,2,3,6-tetrahydropyrimidin-4-yl)hydrazone and condensation with 4-methyl-4H-1,2,4-triazole-3-carbaldehyde.

Following the method of Example 191, the compound of Example 228 was made by preparation of 5-chloro-1H-indazole-3-carbaldehyde (3-isobutyl-1-methyl-2,6-dioxo-1,2,3,6-tetrahydropyrimidin-4-yl)hydrazone and condensation with 4-methyl-4H-1,2,4-triazole-3-carbaldehyde.

Following the method of Example 191, the compound of Example 229 was made by preparation of 6-chloroquinoline-4-carbaldehyde (3-isobutyl-1-methyl-2,6-dioxo-1,2,3,6-tetrahydropyrimidin-4-yl)hydrazone and condensation with 4-methyl-4H-1,2,4-triazole-3-carbaldehyde.

Following the method of Example 191, the compound of Example 230 was made by preparation of 5-fluoro-1-benzothiophene-3-carbaldehyde[3-(cyclopropylmethyl)-1-methyl-2,6-dioxo-1,2,3,6-tetrahydropyrimidin-4-yl]hydrazone and condensation with 4-methyl-4H-1,2,4-triazole-3-carbaldehyde.

Following the method of Example 191, the compound of Example 231 was made by preparation of 5-chloro-1H-indazole-3-carbaldehyde[3-(cyclopropylmethyl)-1-methyl-2,6-dioxo-1,2,3,6-tetrahydropyrimidin-4-yl]hydrazone and condensation with 4-methyl-4H-1,2,4-triazole-3-carbaldehyde.

Following the method of Example 191, the compound of Example 232 was made by preparation of 6-chloroquinoline-4-carbaldehyde[3-(cyclopropylmethyl)-1-methyl-2,6-dioxo-1,2,3,6-tetrahydropyrimidin-4-yl]hydrazone and condensation with 4-methyl-4H-1,2,4-triazole-3-carbaldehyde.

Following the method of Example 191, the compound of Example 233 was made by preparation of 5-chloro-1H-indole-3-carbaldehyde (3-isobutyl-1-methyl-2,6-dioxo-1,2,3,6-tetrahydropyrimidin-4-yl)hydrazone and condensation with 4-bromo-1-methyl-1H-pyrrole-2-carbaldehyde (Kaye, P. T.; Macrae, R.; Meakins, G. D.; Patterson, C. H. *J. Chem. Soc. Perkin Trans.* 2 1980, 1631-1635).

Following the method of Example 191, the compound of Example 234 was made by preparation of 5-chloro-1H-indole-3-carbaldehyde[3-(cyclopropylmethyl)-1-methyl-2,6-dioxo-1,2,3,6-tetrahydropyrimidin-4-yl]hydrazone and condensation with 1-methyl-4-(methylsulfinyl)-1H-pyrrole-2-carbaldehyde.

Following the method of Example 191, the compound of Example 235 was made by preparation of 5-fluoro-1-benzothiophene-3-carbaldehyde[3-(cyclopropylmethyl)-1-methyl-2,6-dioxo-1,2,3,6-tetrahydropyrimidin-4-yl]hydrazone and condensation with 1-methyl-4-(methylsulfinyl)-1H-pyrrole-2-carbaldehyde.

Following the method of Example 191, the compound of Example 236 was made by preparation of 5-methyl-3a,7a-dihydro-1H-indole-3-carbaldehyde[3-(cyclopropylmethyl)-1-methyl-2,6-dioxo-1,2,3,6-tetrahydropyrimidin-4-yl]hydrazone and condensation with 1-methyl-4-(methylsulfinyl)-1H-pyrrole-2-carbaldehyde.

Following the method of Example 191, the compound of Example 237 was made by preparation of 5-chloro-1H-indole-3-carbaldehyde (3-isobutyl-1-methyl-2,6-dioxo-1,2,3,6-tetrahydropyrimidin-4-yl)hydrazone and condensation with 1-methyl-4-(methylsulfinyl)-1H-pyrrole-2-carbaldehyde.

Following the method of Example 191, the compound of Example 238 was made by preparation of 5-methyl-3a,7a-dihydro-1H-indole-3-carbaldehyde (3-isobutyl-1-methyl-2,6-dioxo-1,2,3,6-tetrahydropyrimidin-4-yl)hydrazone and condensation with 1-methyl-4-(methylsulfinyl)-1H-pyrrole-2-carbaldehyde.

Following the method of Example 191, the compound of Example 239 was made by preparation of 6-chloroquinoline-4-carbaldehyde (3-isobutyl-1-methyl-2,6-dioxo-1,2,3,6-tetrahydropyrimidin-4-yl)hydrazone and condensation with 1-methyl-4-(methylsulfinyl)-1H-pyrrole-2-carbaldehyde.

Following the method of Example 191, the compound of Example 240 was made by preparation of 6-chloroquinoline-4-carbaldehyde[3-(cyclopropylmethyl)-1-methyl-2,6-dioxo-1,2,3,6-tetrahydropyrimidin-4-yl]hydrazone and condensation with 1-methyl-4-(methylsulfinyl)-1H-pyrrole-2-carbaldehyde.

Following the method of Example 191, the compound of Example 241 was made by preparation of 5-methyl-3a,7a-dihydro-1H-indole-3-carbaldehyde[3-(cyclopropylmethyl)-1-methyl-2,6-dioxo-1,2,3,6-tetrahydropyrimidin-4-yl]hydrazone and condensation with 1-methyl-4-(methylthio)-1H-pyrrole-2-carbaldehyde.

Following the method of Example 191, the compound of Example 242 was made by preparation of 5-chloro-1H-indole-3-carbaldehyde[3-(cyclopropylmethyl)-1-methyl-2,6-dioxo-1,2,3,6-tetrahydropyrimidin-4-yl]hydrazone and condensation with 1-methyl-4-(methylsulfonyl)-1H-pyrrole-2-carbaldehyde.

Following the method of Example 191, the compound of Example 243 was made by preparation of 5-methyl-3a,7a-dihydro-1H-indole-3-carbaldehyde[3-(cyclopropylmethyl)-1-methyl-2,6-dioxo-1,2,3,6-tetrahydropyrimidin-4-yl]hydrazone and condensation with 1-methyl-4-(methylsulfonyl)-1H-pyrrole-2-carbaldehyde.

Following the method of Example 191, the compound of Example 244 was made by preparation of 5-fluoro-1-benzothiophene-3-carbaldehyde[3-(cyclopropylmethyl)-1-methyl-2,6-dioxo-1,2,3,6-tetrahydropyrimidin-4-yl]hydrazone and condensation with 1-methyl-4-(methylsulfonyl)-1H-pyrrole-2-carbaldehyde.

Following the method of Example 191, the compound of Example 245 was made by preparation of 6-chloroquinoline-4-carbaldehyde 3-(cyclopropylmethyl)-1-methyl-2,6-dioxo-1,2,3,6-tetrahydropyrimidin-4-yl]hydrazone and condensation with 1-methyl-4-(methylsulfonyl)-1H-pyrrole-2-carbaldehyde.

| Example | Structure | Name | ES+ (M + H) |
|---|---|---|---|
| 192 | 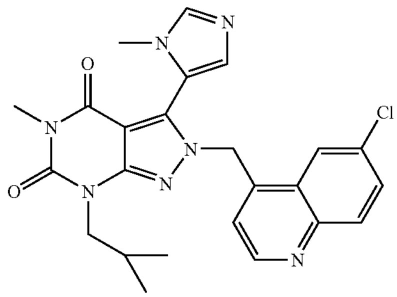 | 2-[(6-chloroquinolin-4-yl)methyl]-7-isobutyl-5-methyl-3-(1-methyl-1H-imidazol-5-yl)-2H-pyrazolo[3,4-d]pyrimidine-4,6(5H,7H)-dione | 478.21 |
| 193 | 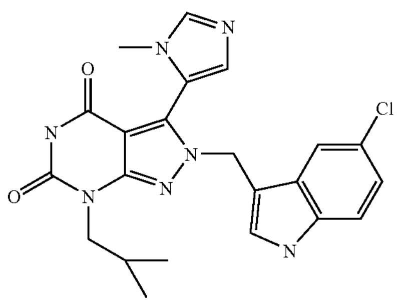 | 2-[(5-chloro-1H-indol-3-yl)methyl]-7-isobutyl-3-(1-methyl-1H-imidazol-5-yl)-2H-pyrazolo[3,4-d]pyrimidine-4,6(5H,7H)-dione | 452.17 |
| 194 | 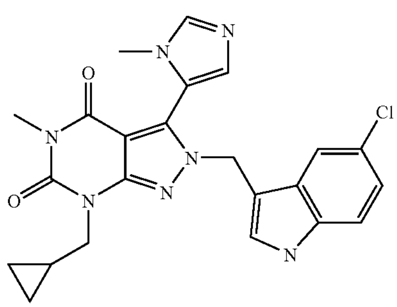 | 2-[(5-chloro-1H-indol-3-yl)methyl]-7-(cyclopropylmethyl)-5-methyl-3-(1-methyl-1H-imidazol-5-yl)-2H-pyrazolo[3,4-d]pyrimidine-4,6(5H,7H)-dione | 464.19 |
| 195 | 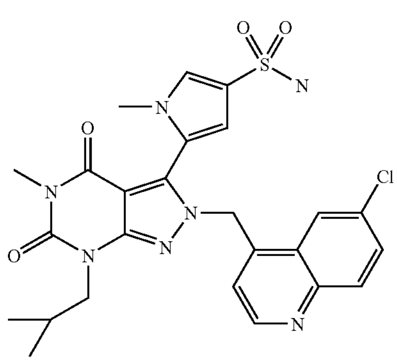 | 5-{2-[(6-chloroquinolin-4-yl)methyl]-7-isobutyl-5-methyl-4,6-dioxo-4,5,6,7-tetrahydro-2H-pyrazolo[3,4-d]pyrimidin-3-yl}-1-methyl-1H-pyrrole-3-sulfonamide | 556.07 |

| Example | Structure | Name | ES+ (M + H) |
|---|---|---|---|
| 196 | 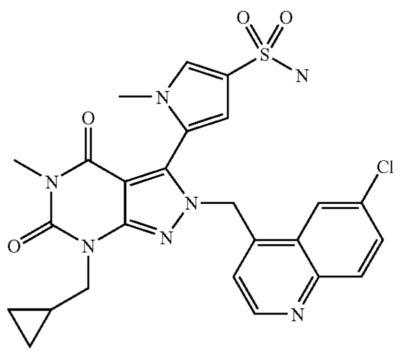 | 5-[2-[(6-chloroquinolin-4-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-pyrrole-3-sulfonamide | 554.07 |
| 197 | 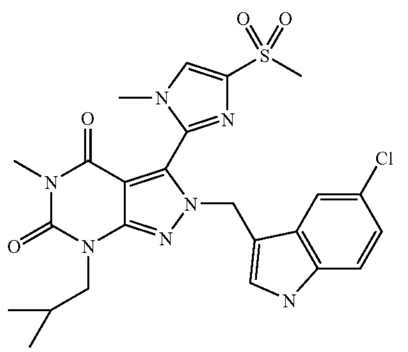 | 2-{(5-chloro-1H-indol-3-yl)methyl]-7-isobutyl-5-methyl-3-[1-methyl-4-(methylsulfonyl)-1H-imidazol-2-yl]-2H-pyrazolo[3,4-d]pyrimidine-4,6(5H,7H)-dione | 544.05 |
| 198 | 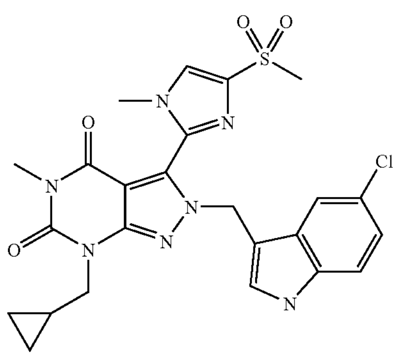 | 2-[(5-chloro-1H-indol-3-yl)methyl]-7-(cyclopropylmethyl)-5-methyl-3-[1-methyl-4-(methylsulfonyl)-1H-imidazol-2-yl]-2H-pyrazolo[3,4-d]pyrimidine-4,6(5H,7H)-dione | 542.05 |
| 199 | 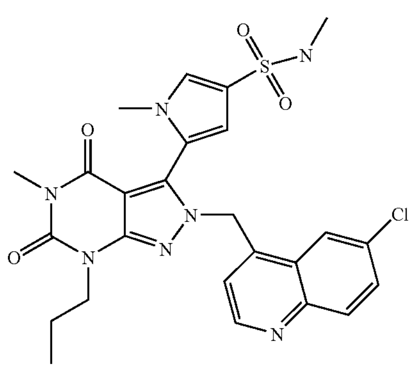 | 5-{2-[(6-chloroquinolin-4-yl)methyl]-5-methyl-4,6-dioxo-7-propyl-4,5,6,7-tetrahydro-2H-pyrazolo[3,4-d]pyrimidin-3-yl}-N,1-dimethyl-1H-pyrrole-3-sulfonamide | 556.18 |

-continued

| Example | Structure | Name | ES+ (M + H) |
|---|---|---|---|
| 200 | 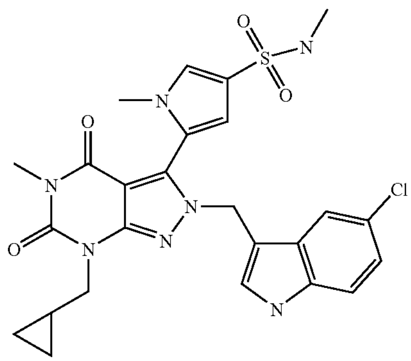 | 5-[2-[(5-chloro-1H-indol-3-yl)methyl]-7-(cyclopropylmethyl)-5-methyl-4,6-dioxo-4,5,6,7-tetrahydro-2H-pyrazolo[3,4-d]pyrimidin-3-yl]-N,1-dimethyl-1H-pyrrole-3-sulfonamide | 556.09 |
| 201 | 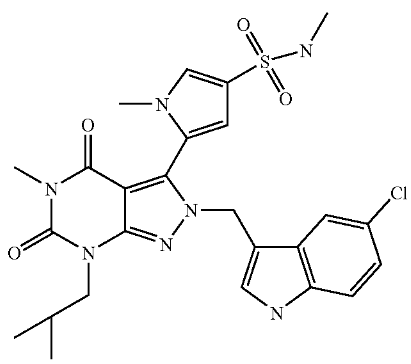 | 5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-N,1-dimethyl-1H-pyrrole-3-sulfonamide | 558.03 |
| 202 | 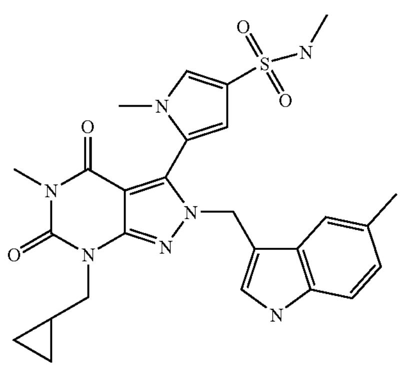 | 5-{7-(cyclopropylmethyl)-5-methyl-2-[(5-methyl-1H-indol-3-yl)methyl]-4,6-dioxo-4,5,6,7-tetrahydro-2H-pyrazolo[3,4-d]pyrimidin-3-yl}-N,1-dimethyl-1H-pyrrole-3-sulfonamide | 536.18 |
| 203 | 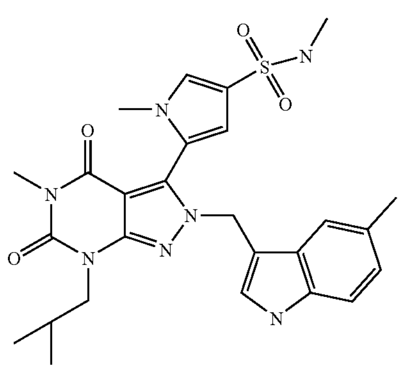 | 5-{7-isobutyl-5-methyl-2-[(5-methyl-1H-indol-3-yl)methyl]-4,6-dioxo-4,5,6,7-tetrahydro-2H-pyrazolo[3,4-d]pyrimidin-3-yl}-N,1-dimethyl-1H-pyrrole-3-sulfonamide | 538.16 |

| Example | Structure | Name | ES+ (M + H) |
|---|---|---|---|
| 204 | 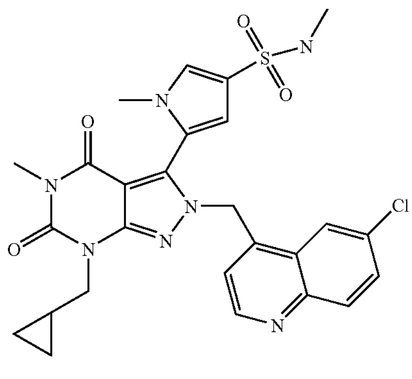 | 5-[2-[(6-chloroquinolin-4-yl)methyl]-7-(cyolopropylmethyl)-5-methyl-4,6-dioxo-4,5,6,7-tetrahydro-2H-pyrazolo[3,4-d]pyrimidin-3-yl]-N,1-dimethyl-1H-pyrrole-3-sulfonamide | 568.16 |
| 205 | 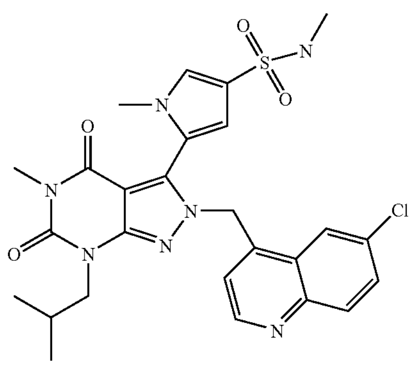 | 5-{2-[(6-chloroquinolin-4-yl)methyl]-7-isobutyl-5-methyl-4,6-dioxo-4,5,6,7-tetrahydro-2H-pyrazolo[3,4-d]pyrimidin-3-yl}-N,1-dimethyl-1H-pyrrole-3-sulfonamide | 570.17 |
| 206 | 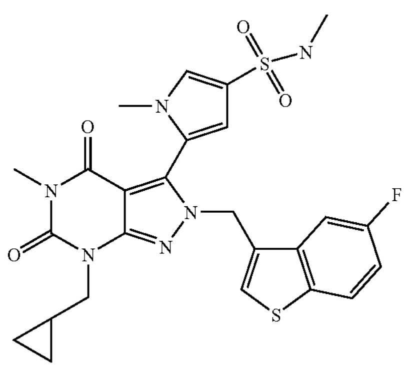 | 5-{7-(cyclopropylmethyl)-2-[(5-fluoro-1-benzothien-3-yl)methyl]-5-methyl-4,6-dioxo-4,5,6,7-tetrahydro-2H-pyrazolo[3,4-d]pyrimidin-3-yl}-N,1-dimethyl-1H-pyrrole-3-sulfonamide | 557.17 |
| 207 | 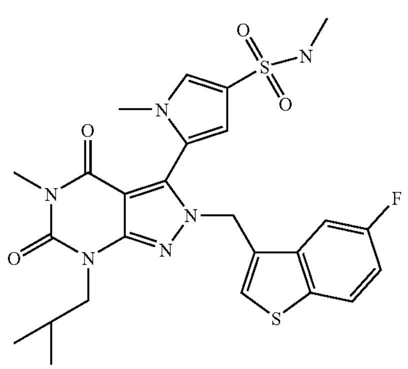 | 5-{2-[(5-fluoro-1-benzothien-3-yl)methyl]-7-isobutyl-5-methyl-4,6-dioxo-4,5,6,7-tetrahydro-2H-pyrazolo[3,4-d]pyrimidin-3-yl}-N,1-dimethyl-1H-pyrrole-3-sulfonamide | 559.15 |

-continued

| Example | Structure | Name | ES+ (M + H) |
|---|---|---|---|
| 208 | 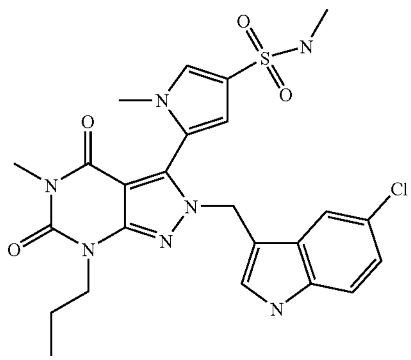 | 5-{2-[(5-chloro-1H-indol-3-yl)methyl]-5-methyl-4,6-dioxo-7-propyl-4,5,6,7-tetrahydro-2H-pyrazolo[3,4-d]pyrimidin-3-yl}-N-1-dimethyl-1H-pyrrole-3-sulfonamide | 544.04 |
| 209 | 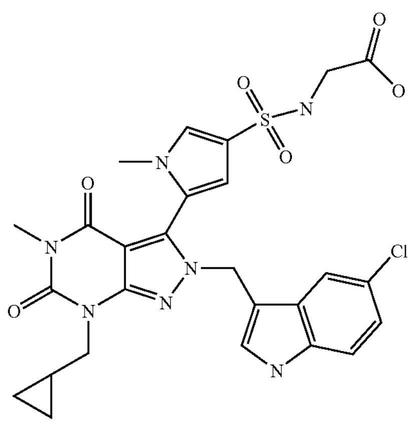 | N-({5-[2-[(5-chloro-1H-indol-3-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-pyrrol-3-yl}sulfonyl)glycine | 600.08 |
| 210 | 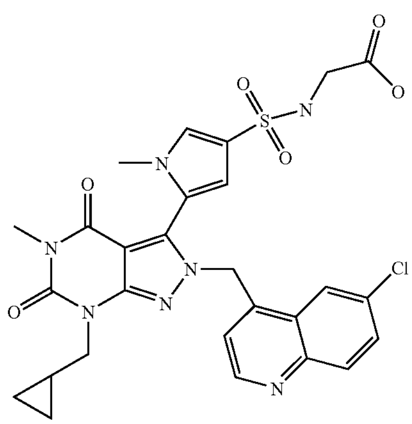 | N-({5-[2-[(6-chloroquinolin-4-yl)methyl]-7-(cyclopropylmethyl)-5-methyl-4,6-dioxo-4,5,6,7-tetrahydro-2H-pyrazolo[3,4-d]pyrimidin-3-yl]-1-methyl-1H-pyrrol-3-yl}sulfonyl)glycine | 612.11 |
| 211 | 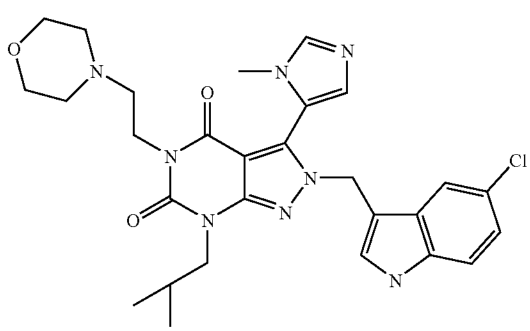 | 2-[(5-chloro-1H-indol-3-yl)methyl]-7-isobutyl-3-(1-methyl-1H-imidazol-5-yl)-5-(2-morpholin-4-ylethyl)-2H-pyrazolo[3,4-d]pyrimidine-4,6(5H,7H)-dione | 565.22 |

-continued

| Example | Structure | Name | ES+ (M + H) |
|---|---|---|---|
| 212 | 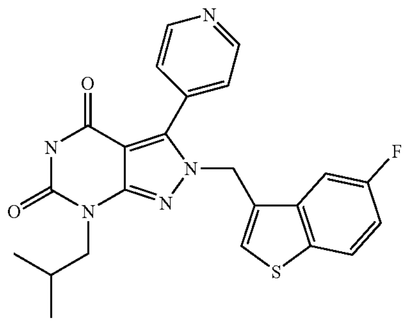 | 2-[(5-fluoro-1-benzothien-3-yl)methyl]-7-isobutyl-3-pyridin-4-yl-2H-pyrazolo[3,4-d]pyrimidine-4,6(5H,7H)-dione | 450.18 |
| 213 | 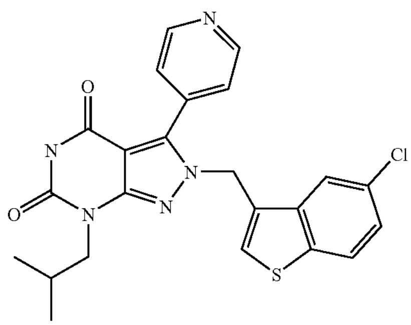 | 2-[(5-chloro-1-benzothien-3-yl)methyl]-7-isobutyl-3-pyridin-4-yl-2H-pyrazolo[3,4-d]pyrimidine-4,6(5H,7H)-dione | 466.23 |
| 214 | 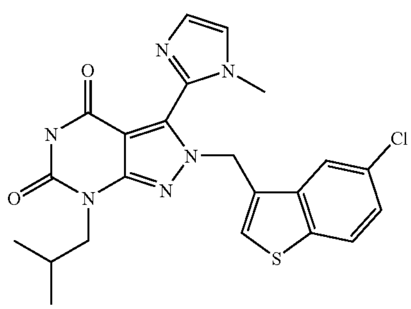 | 2-[(5-chloro-1-benzothien-3-yl)methyl]-7-isobutyl-3-(1-methyl-1H-imidazol-2-yl)-2H-pyrazolo[3,4-d]pyrimidine-4,6(5H,7H)-dione | 469.27 |
| 215 | 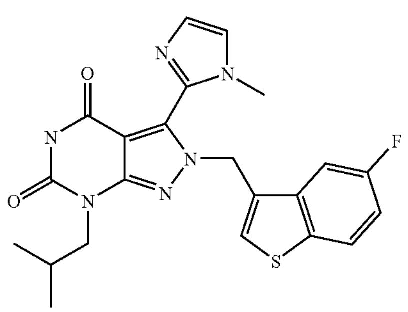 | 2-[(5-fluoro-1-benzothien-3-yl)methyl]-7-isobutyl-3-(1-methyl-1H-imidazol-2-yl)-2H-pyrazolo[3,4-d]pyrimidine-4,6(5H,7H)-dione | 453.14 |

-continued

| Example | Structure | Name | ES+ (M + H) |
|---|---|---|---|
| 216 | 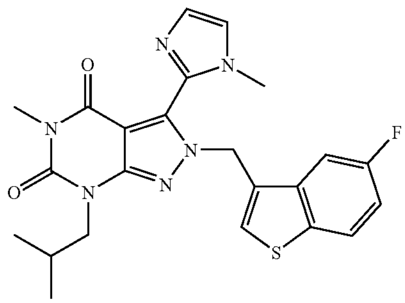 | 2-[(5-fluoro-1-benzothien-3-yl)methyl]-7-isobutyl-5-methyl-3-(1-methyl-1H-pyrrol-2-yl)-2H-pyrazolo[3,4-d]pyrimidine-4,6(5H,7H)-dione | 466.18 |
| 217 | 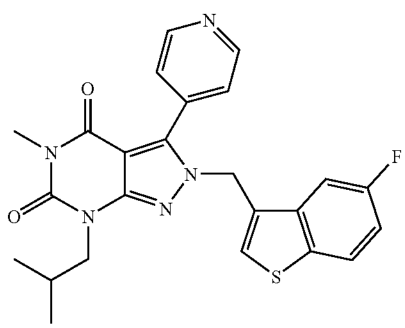 | 2-[(5-fluoro-1-benzothien-3-yl)methyl]-7-isobutyl-5-methyl-3-pyridin-4-yl-2H-pyrazolo[3,4-d]pyrimidine-4,6(5H,7H)-dione | 464.18 |
| 218 | 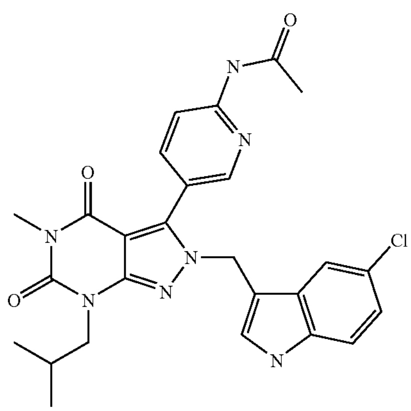 | N-(5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}pyridin-2-yl)acetamide | 520.07 |
| 219 | 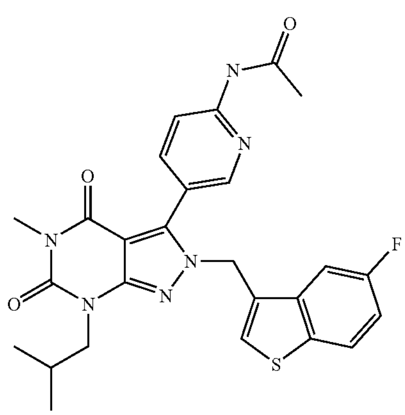 | N-(5-{2-[(5-fluoro-1-benzothien-3-yl)methyl]-7-isobutyl-5-methyl-4,6-dioxo-4,5,6,7-tetrahydro-2H-pyrazolo[3,4-d]pyrimidin-3-yl}pyridin-2-yl)acetamide | 521.08 |

-continued

| Example | Name | ES+ (M + H) |
|---|---|---|
| 220 | 2-[(5-fluoro-1-benzothien-3-yl)methyl]-7-isobutyl-5-methyl-3-(1-methyl-1H-imidazol-2-yl)-2H-pyrazolo[3,4-d]pyrimidine-4,6(5H,7H)-dione | 467.21 |
| 221 | 2-[(5-chloro-1H-indol-3-yl)methyl]-7-isobutyl-5-methyl-3-(4-methyl-4H-1,2,4-triazol-3-yl)-2H-pyrazolo[3,4-d]pyrimidine-4,6(5H,7H)-dione | 467.09 |
| 222 | 7-isobutyl-5-methyl-2-[(5-methyl-1H-indol-3-yl)methyl]-3-(4-methyl-4H-1,2,4-triazol-3-yl)-2H-pyrazolo[3,4-d]pyrimidine-4,6(5H,7H)-dione | 447.20 |
| 223 | 7-(cyclopropylmethyl)-5-methyl-2-[(5-methyl-1H-indol-3-yl)methyl]-3-(4-methyl-4H-1,2,4-triazol-3-yl)-2H-pyrazolo[3,4-d]pyrimidine-4,6(5H,7H)-dione | 445.23 |
| 224 | 2-[(5-chloro-1H-indol-3-yl)methyl]-7-(cyclopropylmethyl)-5-methyl-3-(4-methyl-4H-1,2,4-triazol-3-yl)-2H-pyrazolo[3,4-d]pyrimidine-4,6(5H,7H)-dione | 465.12 |

-continued

| Example | Structure | Name | ES+ (M + H) |
|---|---|---|---|
| 225 | 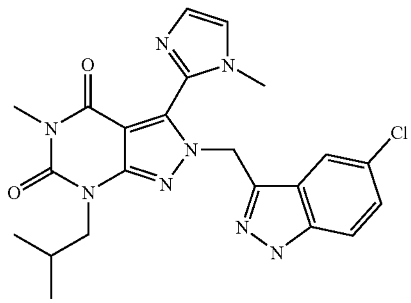 | 2-[(5-chloro-1H-indazol-3-yl)methyl]-7-isobutyl-5-methyl-3-(1-methyl-1H-imidazol-2-yl)-2H-pyrazolo[3,4-d]pyrimidine-4,6(5H,7H)-dione | 467.12 |
| 226 | 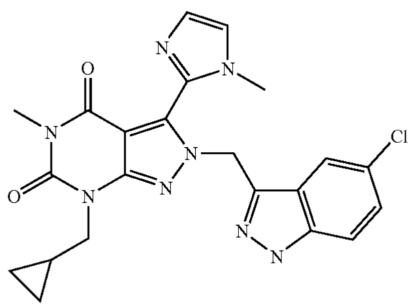 | 2-{(5-chloro-1H-indazol-3-yl)methyl]-7-(cyclopropylmethyl)-5-methyl-3-(1-methyl-1H-imidazol-2-yl)-2H-pyrazolo[3,4-d]pyrimidine-4,6(5H,7H)-dione | 465.11 |
| 227 | 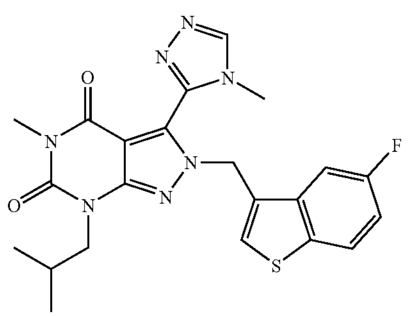 | 2-[(5-fluoro-1-benzothien-3-yl)methyl]-7-isobutyl-5-methyl-3-(4-methyl-4H-1,2,4-triazol-3-yl)-2H-pyrazolo[3,4-d]pyrimidine-4,6(5H,7H)-dione | 468.21 |
| 228 | 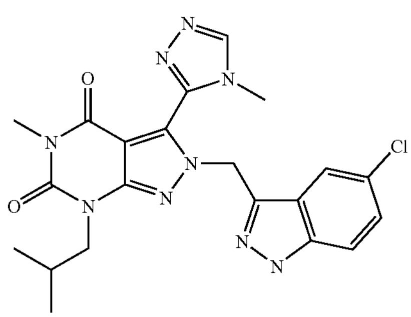 | 2-[(5-chloro-1H-indazol-3-yl)methyl]-7-isobutyl-5-methyl-3-(4-methyl-4H-1,2,4-triazol-3-yl)-2H-pyrazolo[3,4-d]pyrimidine-4,6(5H,7H)-dione | 468.22 |
| 229 | 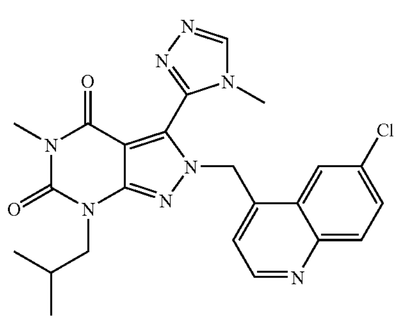 | 2-[(6-chloroquinolin-4-yl)methyl]-7-isobutyl-5-methyl-3-(4-methyl-4H-1,2,4-triazol-3-yl)-2H-pyrazolo[3,4-d]pyrimidine-4,6(5H,7H)-dione | 479.22 |

-continued

| Example | Structure | Name | ES+ (M + H) |
|---|---|---|---|
| 230 | 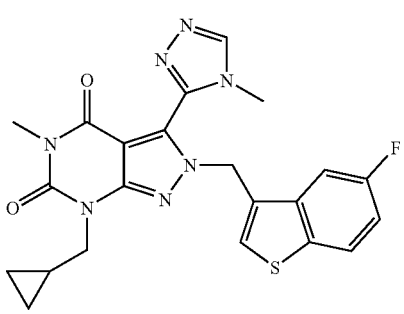 | 7-(cyclopropylmethyl)-2-[(5-fluoro-1-benzothien-3-yl)methyl]-5-methyl-3-(4-methyl-4H-1,2,4-triazol-3-yl)-2H-pyrazolo[3,4-d]pyrimidine-4,6(5H,7H)-dione | 466.20 |
| 231 | 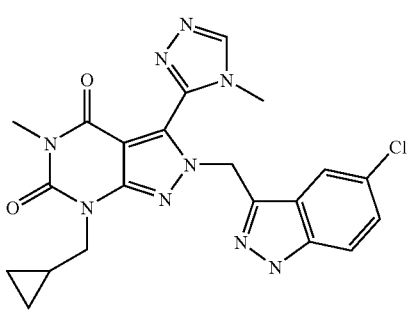 | 2-[(5-chloro-1H-indazol-3-yl)methyl]-7-(cyclopropylmethyl)-5-methyl-3-(4-methyl-4H-1,2,4-triazol-3-yl)-2H-pyrazolo[3,4-d]pyrimidine-4,6(5H,7H)-dione | 466.20 |
| 232 | 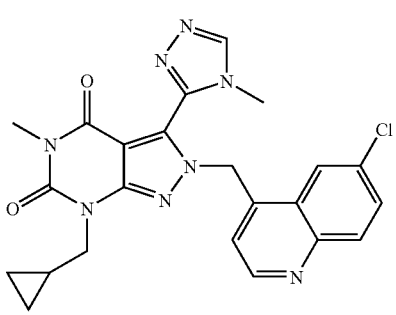 | 2-[(6-chloroquinolin-4-yl)methyl]-7-(cyclopropylmethyl)-5-methyl-3-(4-methyl-4H-1,2,4-triazol-3-yl)-2H-pyrazolo[3,4-d]pyrimidine-4,6(5H,7H)-dione | 477.22 |
| 233 | 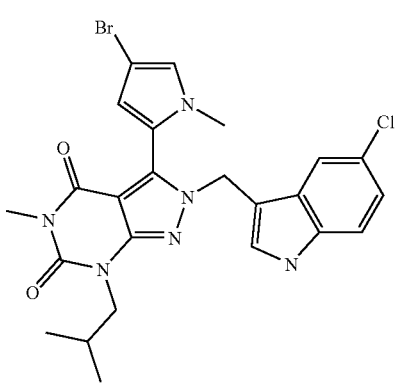 | 3-(4-bromo-1-methyl-1H-pyrrol-2-yl)-2-[(5-chloro-1H-indol-3-yl)methyl]-7-isobutyl-5-methyl-2H-pyrazolo[3,4-d]pyrimidine-4,6(5H,7H)-dione | 543.19 |

-continued

| Example | Structure | Name | ES+ (M + H) |
|---|---|---|---|
| 234 | 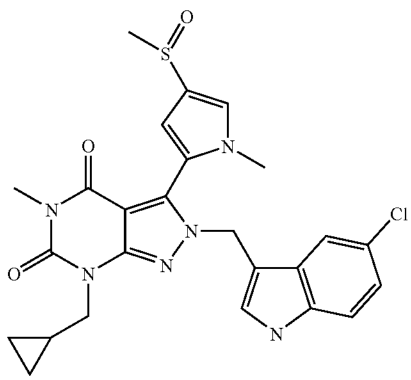 | 2-[(5-chloro-1H-indol-3-yl)methyl]-7-(cyclopropylmethyl)-5-methyl-3-[1-methyl-4-(methylsulfinyl)-1H-pyrrol-2-yl]-2H-pyrazolo[3,4-d]pyrimidine-4,6(5H,7H)-dione | 525.09 |
| 235 | 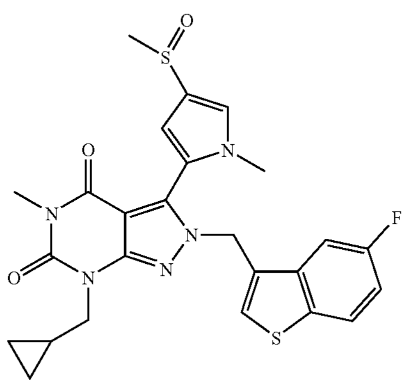 | 7-(cyclopropylmethyl)-2-[(5-fluoro-1-benzothien-3-yl)methyl]-5-methyl-3-[1-methyl-4-(methylsulfinyl)-1H-pyrrol-2-yl]-2H-pyrazolo[3,4-d]pyrimidine-4,6(5H,7H)-dione | 526.09 |
| 236 | 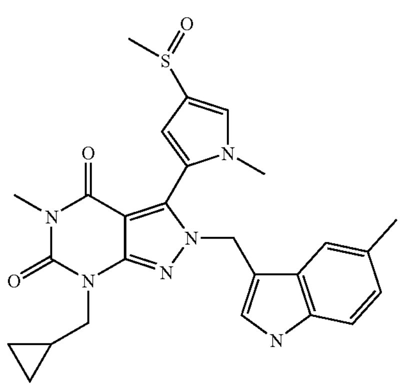 | 7-(cyclopropylmethyl)-5-methyl-2-[(5-methyl-1H-indol-3-yl)methyl]-3-[1-methyl-4-(methylsulfinyl)-1H-pyrrol-2-yl]-2H-pyrazolo[3,4-d]pyrimidine-4,6(5H,7H)-dione | 505.12 |
| 237 | 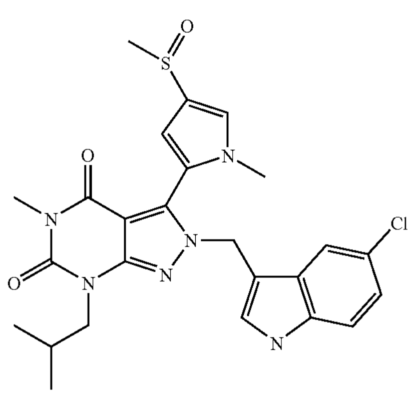 | 2-[(5-chloro-1H-indol-3-yl)methyl]-7-isobutyl-5-methyl-3-[1-methyl-4-(methylsulfinyl)-1H-pyrrol-2-yl]-2H-pyrazolo[3,4-d]pyrimidine-4,6(5H,7H)-dione | 527.09 |

| Example | Structure | Name | ES+ (M + H) |
|---|---|---|---|
| 238 | 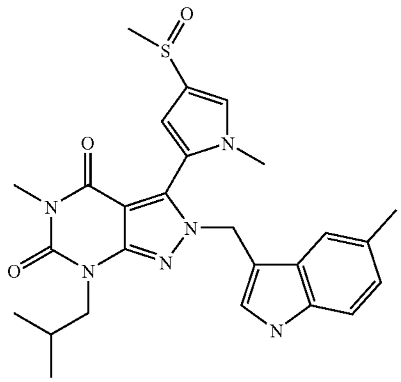 | 7-isobutyl-5-methyl-2-[(5-methyl-1H-indol-3-yl)methyl]-3-[1-methyl-4-(methylsulfinyl)-1H-pyrrol-2-yl]-2H-pyrazolo[3,4-d]pyrimidine-4,6(5H,7H)-dione | 507.13 |
| 239 | 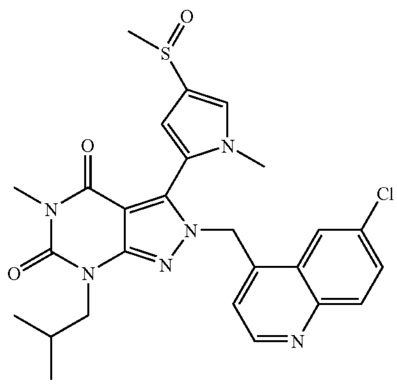 | 2-[(6-chloroquinolin-4-yl)methyl]-7-isobutyl-5-methyl-3-[1-methyl-4-(methylsulfinyl)-1H-pyrrol-2-yl]-2H-pyrazolo[3,4-d]pyrimidine-4,6(5H,7H)-dione | 539.11 |
| 240 | 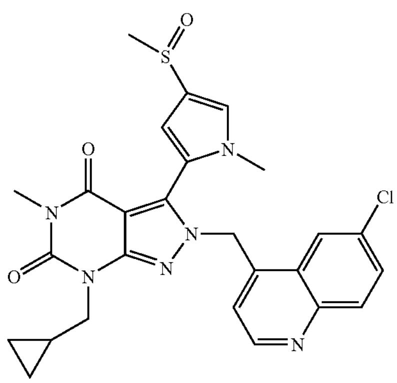 | 2-[(6-chloroquinolin-4-yl)methyl]-7-(cyclopropylmethyl)-5-methyl-3-[1-methyl-4-(methylsulfinyl)-1H-pyrrol-2-yl]-2H-pyrazolo[3,4-d]pyrimidine-4,6(5H,7H)-dione | 537.11 |
| 241 | 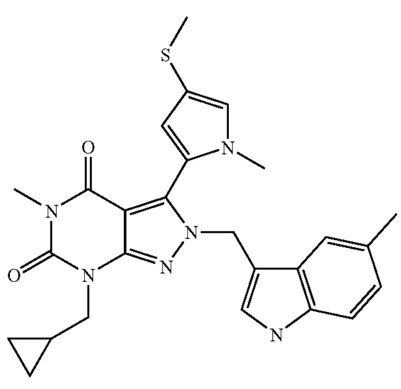 | 7-(cyclopropylmethyl)-5-methyl-2-[(5-methyl-1H-indol-3-yl)methyl]-3-[1-methyl-4-(methylthio)-1H-pyrrol-2-yl]-2H-pyrazolo[3,4-d]pyrimidine-4,6(5H,7H)-dione | 489.20 |

-continued

| Example | Structure | Name | ES+ (M + H) |
|---|---|---|---|
| 242 | 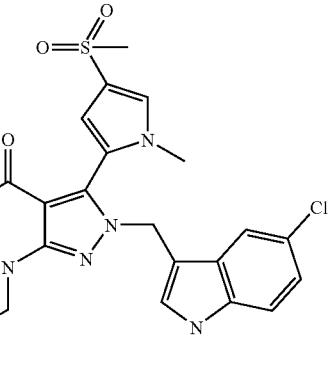 | 2-[(5-chloro-1H-indol-3-yl)methyl]-7-(cyclopropylmethyl)-5-methyl-3-[1-methyl-4-(methylsulfonyl)-1H-pyrrol-2-yl]-2H-pyrazolo[3,4-d]pyrimidine-4,6(5H,7H)-dione | 541.12 |
| 243 | 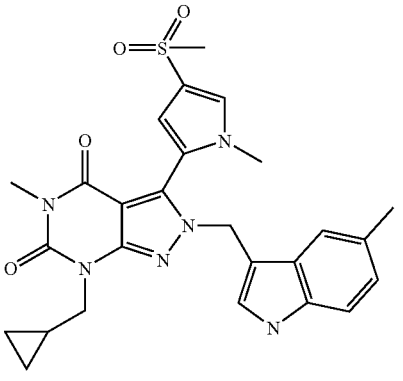 | 7-(cyclopropylmethyl)-5-methyl-2-[(5-methyl-1H-indol-3-yl)methyl]-3-[1-methyl-4-(methylsulfonyl)-1H-pyrrol-2-yl]-2H-pyrazolo[3,4-d]pyrimidine-4,6(5H,7H)-dione | 521.15 |
| 244 | 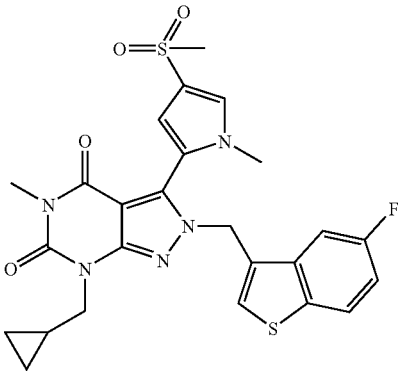 | 7-(cyclopropylmethyl)-2-[(5-fluoro-1-benzothien-3-yl)methyl]-5-methyl-3-[1-methyl-4-(methylsulfonyl)-1H-pyrrol-2-yl]-2H-pyrazolo[3,4-d]pyrimidine-4,6(5H,7H)-dione | 542.05 |
| 245 | 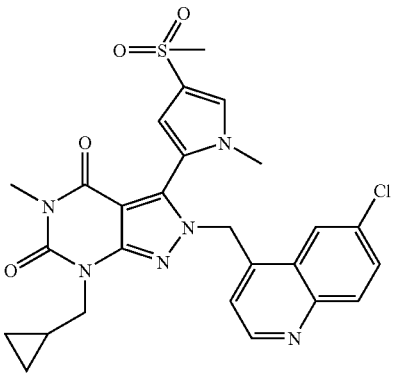 | 2-[(6-chloroquinolin-4-yl)methyl]-7-(cyclopropylmethyl)-5-methyl-3-[1-methyl-4-(methylsulfonyl)-1H-pyrrol-2-yl]-2H-pyrazolo[3,4-d]pyrimidine-4,6(5H,7H)-dione | 551.13 |

Example 246

Preparation of
4-acetyl-1-methyl-1-H-pyrrole-2-carbaldehyde

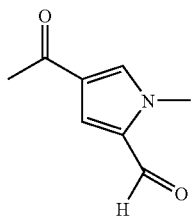

To a suspension of aluminium chloride (22.9 g, 172 mmol) in anhydrous dichloromethane (100 ml) and acetylchloride (4.5 g, 57.3 mmol)was added a solution of 1-methyl pyrrole-2-carboxaldehyde (5 g, 46 mmol) in anhydrous. dichloromethane (20 ml). The mixture was refluxed for 90 min, poured into ice and stirred until melted. The layers were separated and aqueous layer was extracted with dichloromethane (2×100 ml). The organic phase and extracts were combined, dried over sodium sulfate. The solvent was removed in vacuo to give the title compound (6.8 g, 94%), $^1$H NMR (d6-DMSO) d 9.6 (s, 1H), 7.9 (s, 1H), 7.4 (s, 1H), 3.9 (s, 3H),2.4 (s,3H)

Example 247

Preparation of
1-methyl-4-propionyl-1H-pyrrole-2-carbaldehyde

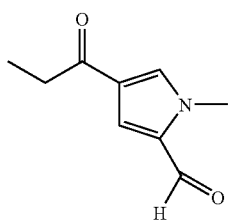

To a suspension of aluminium chloride (22.9 g, 172 mmol) in anhydrous dichloromethane (100 ml) and propionylchloride (5.3 g, 57.3 mmol)was added a solution of 1-methyl pyrrole-2-carboxaldehyde (5 g, 46 mmol) in anhydrous dichloromethane (20 ml). The mixture was refluxed for 90 min, poured into ice and stirred until melted. The layers were separated and aqueous layer was extracted with dichloromethane (2×100 ml). The organic phase and extracts were combined, dried over sodium sulfate. The solvent was removed in vacuo to give the title compound (7.2 g, 95%), $^1$H NMR (d6-DMSO) d 9.6 (s, 1H), 7.9 (s, 1H), 7.4 (s, 1H), 3.9 (s, 3H), 2.8 (q, 2H), 1.06 (t, 3H).

Example 248

Preparation of 1 ethyl-1H-2-carbaldehyde

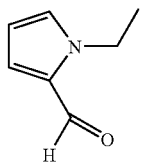

Lithium diisopropylamine (27 ml, 53.3 mmol) was cooled to −60° C. under nitrogen gas. To the cooled solution was added dropwise N-ethylimidazole in anhydrous THF (5 ml) at −50° C. The mixture was stirred at low temperature for 2 h, cooled to −70° C. and N,N-dimethylformamide (5 ml) added rapidly over a few minutes and warmed to room temperature. A solution of sodium dihydrogen phosphate was added to a cooled solution and aqueous layer was separated, filtered and the filtrate was extracted with dichloromethane (3×100 ml). The combined organic phase was dried over sodium sulfate, filtered and concentrated in vacuo to give a brown oil which was distilled giving the title compound (4.2 g). $^1$H NMR (CDCl$_3$) δ 9.8 (s, 1H), 7.3 (s, 1H), 7.18(s, 1H), 4.44 (q, 2H), 1.14 (t, 3H).

Example 249

Preparation of
6-trifluoromethylquinoline-4-carboxaldehyde

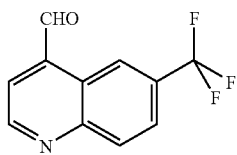

Example 250

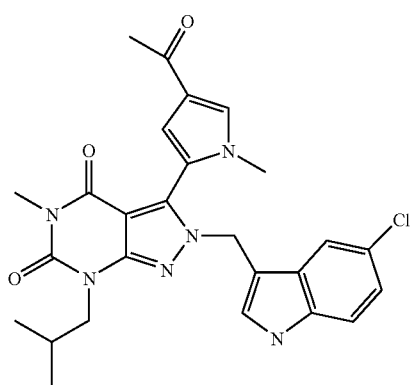

3-(4-acetyl-1-methyl-1H-pyrrol-2-yl)-2-[(5-chloro-1H-indol-3-yl)methyl]-7-isobutyl-5-methyl-2H-pyrazolo[3,4-d]pyrimidine-4,6(5H,7H)-dione This compound was made following the procedure described above, starting with 6-hydrazino-1-isobutyl-3-methylpyrimidine-2,4(1H,3H)-dione and condensing first with 5-chloro-1H-indole-3-carbaldehyde, followed by 4-acetyl-1-methyl-1H-pyrrole-2-carbaldehyde. 508.5 (M+H).

Example 251

1-(5-{2-[(5-chloro-1H-indol-3-yl)methyl]-7-isobutyl-5-methyl-4,6-dioxo-4,5,6,7-tetrahydro-2H-pyrazolo[3,4-d]pyrimidin-3-yl}-1-methyl-1H-pyrrol-3-yl)ethylidenecyanamide

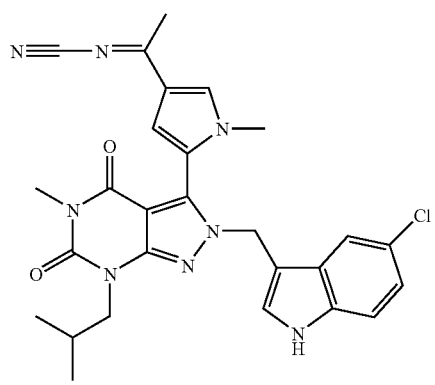

This compound was made in two steps following the procedure described above, starting with 6-hydrazino-1-isobutyl-3-methylpyrimidine-2,4(1H,3H)-dione, and condensing first 5-chloro-1H-indole-3-carbaldehyde, followed by 4-acetyl-1-methyl-1H-pyrrole-2-carbaldehyde. The isolated 3-(4-acetyl-1-methyl-1H-pyrrol-2-yl)-2-[(5-chloro-1H-indol-3-yl)methyl]-7-isobutyl-5-methyl-2H-pyrazolo[3,4-d]pyrimidine-4,6(5H,7H)-dione was treated with a cold solution of bis(trimethylsilyl)carbodiimide and TiCl$_4$ at 0° C. in anhydrous dichloromethane. The mixture was stirred at room temperature for 4 h. The crude reaction product was purified by semi-prep RPHPLC eluting with water/acetonitrile/trifluoroacetic acid mixtures. 531.2 (M+H).

Example 252

2-[(5-chloro-1H-indol-3-yl)methyl]-7-isobutyl-5-methyl-3-(1-methyl-4-propionyl-1H-pyrrol-2-yl)-2H-pyrazolo[3,4-d]pyrimidine-4,6(5H,7H) dione This compound was made following the procedure described above, starting with 6-hydrazino-1-isobutyl-3-methylpyrimidine-2,4(1H,3H)-dione and condensing first with 5-chloro-1H-indole-3-carbaldehyde, followed by 1-methyl-4-propionyl-1H-pyrrole-2-carbaldehyde. 521 (M+H).

Example 253

2-[(5-chloro-1H-indol-3-yl)methyl]-3-{4-[(1E)N-hydroxyethanimidoyl]-1-methyl-1H-pyrrol-2-yl}-7-isobutyl-5-methyl-2H-pyrazolo[3,4-d]pyrimidine-4,6(5H,7H)-dione This compound was made in one pot following the procedure described above, starting with 6-hydrazino-1-isobutyl-3-methylpyrimidine-2,4(1H,3H)-dione, and condensing first 5-chloro-1H-indole-3-carbaldehyde, followed by 4-acetyl-1-methyl-1H-pyrrole-2-carbaldehyde. To the crude 3-(4-acetyl-1-methyl-1H-pyrrol-2-yl)-2-[(5-chloro-1H-indol-3-yl)methyl]-7-isobutyl-5-methyl-2H-pyrazolo[3,4-d]pyrimidine-4,6(5H,7H)-dione was treated with hydroxylamine hydrochloride and heated at 80° C. in N,N'Dimethylacetamide for 18 h. The crude reaction product was purified by semi-prep RPHPLC eluting with water/acetonitrile/trifluoroacetic acid mixtures. 522 (M+H).

Example 254

2-[(5-chloro-1H-indol-3-yl)methyl]-3-[4-(1-hydroxyethyl)-1-methyl-1H-pyrrol-2-yl]-7-isobutyl-5-methyl-2H-pyrazolo[3,4-d]pyrimidine-4,6(5H,7H)-dione

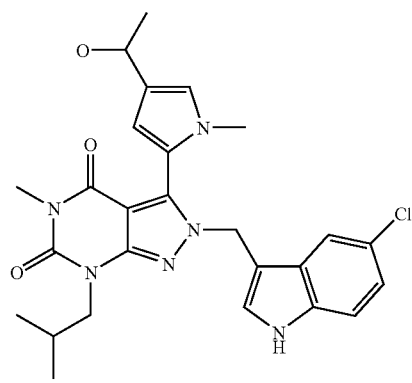

This compound was made in two steps following the procedure described above, starting with 6-hydrazino-1-isobutyl-3-methylpyrimidine-2,4(1H,3H)-dione, and condensing first 5-chloro-1H-indole-3-carbaldehyde, followed by 4-acetyl-1-methyl-1H-pyrrole-2-carbaldehyde. The isolated 3-(4-acetyl-1-methyl-1H-pyrrol-2-yl)-2-[(5-chloro-1H-indol-3-yl)methyl]-7-isobutyl-5-methyl-2H-pyrazolo[3,4-d]pyrimidine-4,6(5H,7H)-dione was treated sodium borohydride in anhydrous THF and heated at 80° C. for 1 h and the product was isolated by aqueous workup. The presence of alcohol peak (δ 64.8 ppm)was confirmed by $^{13}$C NMR (CDCl$_3$)— no ketone peak at (δ 193.5 ppm).

Example 255

2-[(5-chloro-1H-indol-3-yl)methyl]-7-isobutyl-3-{4-[(1E)-N-methoxyethanimidoyl]-1-methyl-1H-pyrrol-2-yl}-5-methyl-2H-pyrazolo[3,4-d]pyrimidine-4,6(5H,7H)-dione

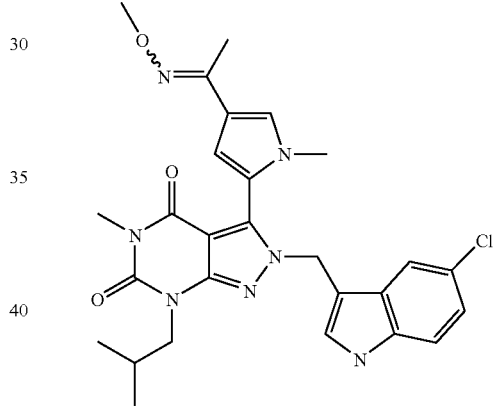

This compound was made following the procedure described above, starting with 6-hydrazino-1-isobutyl-3-methylpyrimidine-2,4(1H,3H)-dione, and condensing first 5-chloro-1H-indole-3-carbaldehyde, followed by 4-acetyl-1-methyl-1H-pyrrole-2-carbaldehyde. To the isolated 3-(4-acetyl-1-methyl-1H-pyrrol-2-yl)-2-[(5-chloro-1H-indol-3-yl)methyl]-7-isobutyl-5-methyl-2H-pyrazolo[3,4-d]pyrimidine-4,6(5H,7H)-dione was added 4 equivalents of methoxyamine hydrochloride, triethylamie and heated at 80° C. in N,N'dimethylacetamide for 4 h. The mixture was stirred at room temperature for 4 h. The crude reaction product was purified by semi-prep RPHPLC eluting with water/acetonitrile/trfluoroacetic acid mixtures. 536.2 (M+H).

Example 256

2-[(5-chloro-1H-indol-3-yl)methyl]-7-isobutyl-3-(4-isobutyryl-1-methyl-1H-imidazol-2-yl)-5-methyl-2H-pyrazolo[3,4-d]pyrimidine 4,6(5H,7H)-dione

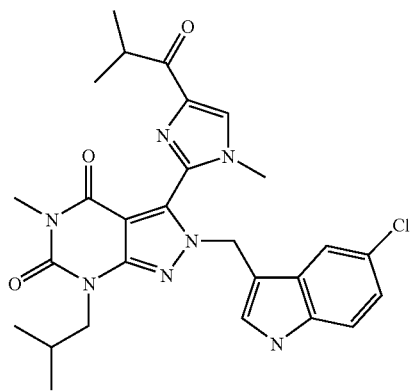

This compound was made following the procedure described above, starting with 6-hydrazino-1-isobutyl-3-methylpyrimidine-2,4(1H,3H)-dione, and condensing first 5-chloro-1H-indole-3-carbaldehyde, followed by 4-isobutyryl-1-methyl-1H-imidazole-2-carbaldehyde. 536 (M+H).

Example 257

2-[(5-chloro-1H-indol-3-yl)methyl]-7-isobutyl-3-{4[(1E)N-methoxyethanimidoyl]-1-methyl-1H-pyrrol-2-yl}-5-methyl-2H-pyrazolo[3,4-d]pyrimidine-4,6(5H,7H)-dione

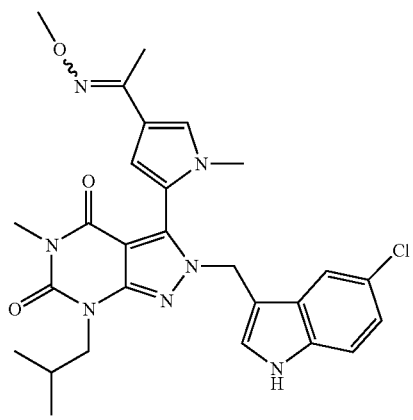

This compound was made in two steps following the procedure described above, stating with 6-hydrazino-1-isobutyl-3-methylpyrimidine-2,4(1H,3H)-dione, and condensing first 5-chloro-1H-indole-3-carbaldehyde, followed by 4-acetyl-1-methyl-1H-pyrrol-2-carbaldehyde. To the isolated 3-(4-acetyl-1-methyl-1H-pyrrol-2-yl)-2-[(5-chloro-1H-indol-3-yl)methyl]-7-isobutyl-5-methyl-2H-pyrazolo[3,4-d]pyrimidine-4,6(5H,7H)-dione was added 4 equivalents of methoxyamine hydrochloride, triethylamine and heated at 80° C. in N,N'dimethylacetamide for 4 h. A second peak, an isomer was isolated purification by semi-prep RPHPLC eluting with water/acetonitrile/trifluoroacetic acid mixtures. 536.2 (M+H).

Example 258

3-(4-acetyl-1-methyl-1H-imidazol-2-yl)-2-[(5-chloro-1H-indol-3-yl)methyl]-7-isobutyl-5-methyl-2H-pyrazolo[3,4-d]pyrimidine-4,6(5H,7H)-dione

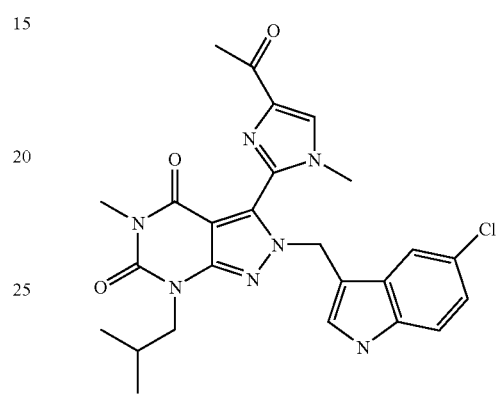

This compound was made following the procedure described above, starting 6-hydrazino-1-isobutyl-3-methylpyrimidine-2,4(1H,3H)-dione, and condensing first 5-chloro-1H-indole-3-carbaldehyde, followed by 4-acetyl-1-methyl-1H-imidazole-2-carbaldehyde. 508 (M+H).

Example 259

3-(4-acetyl-1-methyl-1H-pyrrol-2-yl)-2-[(6-chloro-quinolin-5-yl)methyl]-7-isobutyl-5-methyl-2H-pyrazolo[3,4-d]pyrimidine-4,6(5H,7H) dione

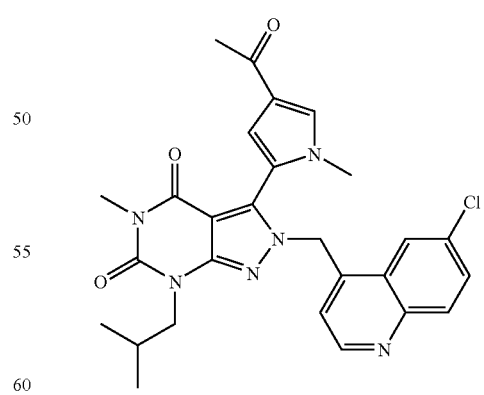

This compound was made following the procedure described above, starting with 6-hydrazino-1-isobutyl-3-methylpyrimidine-2,4(1H,3H)-dione, and condensing first with 6-chloroquinoline-4-carbaldehyde, followed by 4-acetyl-1-methyl-1H-pyrrole-2-carbaldehyde. 519 (M+H).

Example 260

2-(1-benzothien-3-ylmethyl)-5-(2-hydroxyethyl)-7-isobutyl-3-(1-methyl-1H-pyrrol-2-yl)-2H-pyrazolo[3,4-d]pyrimidine-4,6(5H,7H)-dione

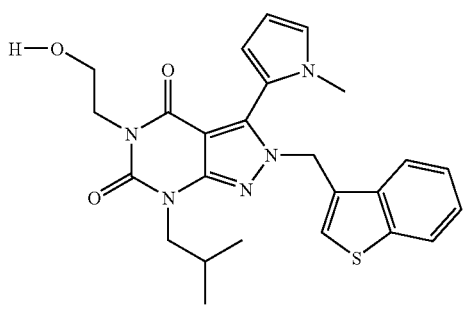

This compound was isolated as a byproduct from a two step preparation as described: A): 2-(1-benzothien-3-ylmethyl)-7-isobutyl-3-(1-methyl-1H-pyrrol-2-yl)-2H-pyrazolo[3,4-d]pyrimidine-4,6(5H,7H)-dione was prepared starting from 6-hydrazino-1-isobutylpyrimidine-2,4(1H,3H)-dione and condensing first with 1-benzothiophene-3-carbaldehyde, followed by 1-methyl-1H-pyrrole-2-carbaldehyde.

B): 2-(1-benzothien-3-ylmethyl)-7-isobutyl-3-(1-methyl-1H-pyrrol-2-yl)-2H-pyrazolo[3,4-d]pyrimidine-4,6(5H,7H)-dione was dissolved in anhydrous dimethylsulfoxide and 1,8-diazabicyclo[5.4.0]undec-7-ene was added. 1,2-dibromoethane was added and the mixture was heated at 80° C. for 18 h. The crude reaction product was purified by semi-prep RPHPLC eluting with water/acetonitrile/trifluoroacetic acid mixtures. 477 (M+H).

Example 261

2-[(6-chloroquinolin-4-yl)methyl]-7-isobutyl-5-methyl-3-(1-methyl-1H-pyrrol-2-yl)-2H-pyrazolo[3,4-d]pyrimidine-4,6(5H,7H)-dione

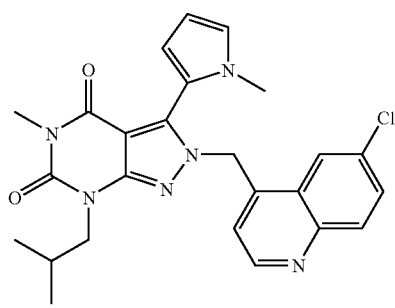

This compound was made following the procedure described above, starting with 6-hydrazino-1-isobutyl-3-methylpyrimidine-2,4(1H,3H)-dione, and condensing first with 6-chloroquinoline-4-carbaldehyde, followed by 1-methyl-1H-pyrrole-2-carbaldehyde. 477.9 (M+H).

Example 262

2-(1-benzothien-3-ylmethyl)-7-isobutyl-3-(1-methyl-1H-pyrrol-2-yl)-5-(pyridin-2-ylmethyl)-2H-pyrazolo[3,4-d]pyrimidine-4,6(5H,7H)-dione

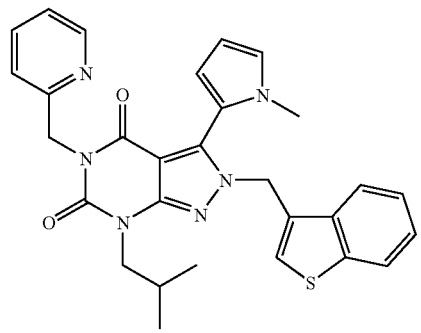

This compound was obtained from a two step preparation as described: A): 2-(1-benzothien-3-ylmethyl)-7-isobutyl-3-(1-methyl-1H-pyrrol-2-yl)-2H-pyrazolo[3,4-d]pyrimidine-4,6(5H,7H)-dione was prepared starting from 6 hydrazino-1-isobutylpyrimidine-2,4(1H,3H)-dione and condensing first with 1-benzothiophene-3-carbaldehyde, followed by 1-methyl-1H-pyrrole-2-carbaldehyde.

B): 2-(1-benzothien-3-ylmethyl)-7-isobutyl-3-(1-methyl-1H-pyrrol-2-yl)-2H-pyrazolo[3,4-d]pyrimidine-4,6(5H,7H)-dione was dissolved in anhydrous dimethylsulfoxide and 1,8-diazabicyclo[5.4.0]undec-7-ene was added. 2-picolyl chloride hydrochloride was added and the mixture was heated at 80° C. for 18 h. The crude reaction product was purified by semi-prep RPHPLC eluting with water/acetonitrile/trifluoroacetic acid mixtures. 525 (M+H).

Example 263

2-(1-benzothien-3-ylmethyl)-7-isobutyl-3-(1-methyl-1H-pyrrol-2-yl)-5-(pyridin-2-ylmethyl)-2H-pyrazolo[3,4-d]pyrimidine-4,6(5H,7H)-dione

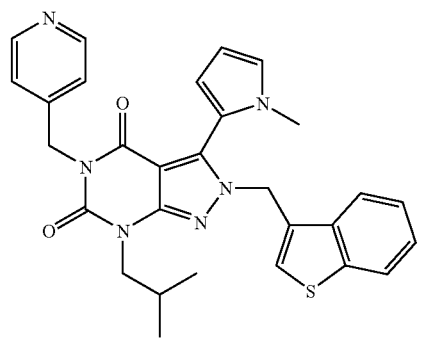

This compound was obtained from a two step preparation as described: A): 2-(1-benzothien-3-ylmethyl)-7-isobutyl-3-(1-methyl-1H-pyrrol-2-yl)-2H-pyrazolo[3,4-d]pyrimidine-4,6(5H,7H)-dione was prepared starting from 6 hydrazino-1-isobutylpyrimidine-2,4(1H,3H)-dione and condensing first with 1-benzothiophene-3-carbaldehyde, followed by 1-methyl-1H-pyrrole-2-carbaldehyde.

B): 2-(1-benzothien-3-ylmethyl)-7-isobutyl-3-(1-methyl-1H-pyrrol-2-yl)-2H-pyrazolo[3,4-d]pyrimidine-4,6(5H,7H)-dione was dissolved in anhydrous dimethylsulfoxide and 1,8-diazabicyclo[5.4.0]undec-7-ene was added. 4-chloromethylpyridine hydrochloride was added and the mixture was heated at 80° C. for 18 h. The crude reaction product was purified by semi-prep RPHPLC eluting with water/acetonitrlle/trifluoroacetic acid mixtures. 525 (M+H).

Example 264

2-[(6-fluoroquinolin-4-yl)methyl]-7-isobutyl-5-methyl-3-(1-methyl-4-propionyl-1H-pyrrol-2-yl)-2H-pyrazolo[3,4-d]pyrimidine-4,6(5H,7H)-dione

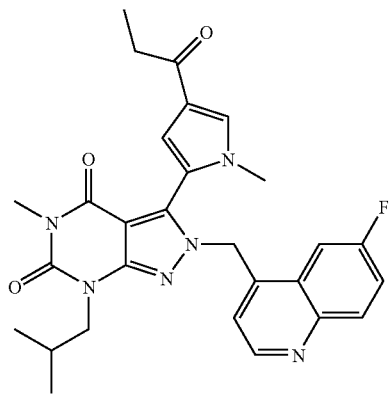

This compound was made following the procedure described above, starting with 6-hydrazino-1-isobutyl-3-methylpyrimidine-2,4(1H,3H)-dione, and condensing first with 6-fluoroquinoline-4-carbaldehyde, followed by 1-methyl-4-propionyl-1H-pyrrole-2-carbaldehyde. 517 (M+H).

Example 265

2-(1-benzothien-3-ylmethyl)-7-isobutyl-3-(1-methyl-1H-pyrrol-2-yl)-5-(2-morpholin-4-ylethyl)-2H-pyrazolo[3,4-d]pyrimidine-4,6(5H,7H)-dione

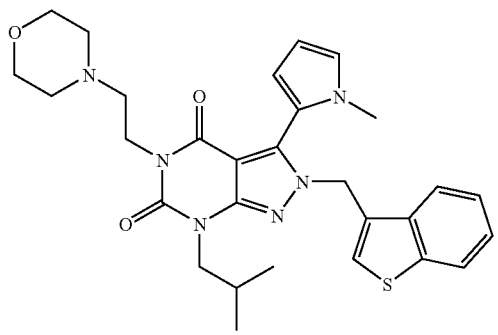

This compound was obtained from a two step preparation as described: A): 2-(1-benzothien-3-ylmethyl)-7-isobutyl-3-(1-methyl-1H-pyrrol-2-yl)-2H-pyrazolo[3,4-d]pyrimidine-4,6(5H,7H)-dione was prepared starting from 6-hydrazino-1-isobutylpyrimidine-2,4(1H,3H)-dione and condensing first with 1-benzothiophene-3-carbaldehyde, followed by 1-methyl-1H-pyrrole-2-carbaldehyde. B): 2-(1-benzothien-3-ylmethyl)-7-isobutyl-3-(1-methyl-1H-pyrrol-2-yl)-2H-pyrazolo[3,4-d]pyrimidine-4,6(5H,7H)-dione was dissolved in anhydrous dimethylsulfoxide and 1,8-diazabicyclo[5.4.0] undec-7-ene was added. 4(2-chloroethyl)morpholine hydrochloride was added and the mixture was heated at 80° C. for 18 h. The crude reaction product was purified by semi-prep RPHPLC eluting with water/acetonitrile/trifluoroacetic acid mixtures. 547 (M+H).

Example 266

3-(4-acetyl-1-methyl-1H-pyrrol-2-yl)-2-[(6-fluoroquinolin-4-yl)methyl]-7-isobutyl-5-methyl-2H-pyrazolo[3,4-d]pyrimidine-4,6(5H,7H)-dione

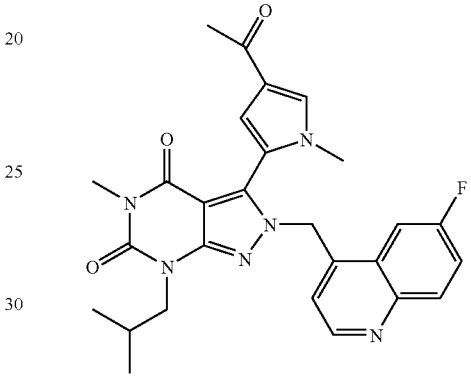

This compound was made following the procedure described above, starting with 6-hydrazino-1-isobutyl-3-methylpyrimidine-2,4(1,H,3H)-dione, and condensing first with 6-fluoroquinoline-4-carbaldehyde, followed by 1-methyl-4-acetyl-1H-pyrrole-2-carbaldehyde. 503(M+H).

Example 267

2-(1-benzothien-3-ylmethyl)-7-isobutyl-3-(1-methyl-1H-pyrrol-2-yl)-5-pyridin-3-ylmethyl)-2H-pyrazolo[3,4-d]pyrimidine-4,6(5H,7H)dione

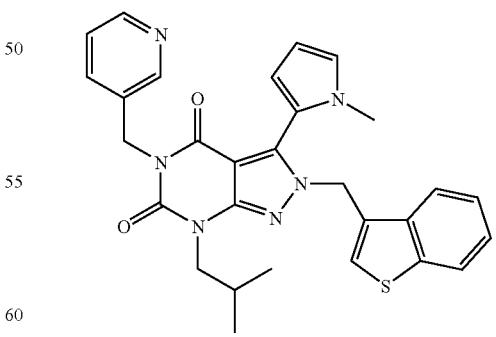

This compound was obtained from a two step preparation as described: A): 2-(1-benzothien-3-ylmethyl)-7-isobutyl-3-(1-methyl-1H-pyrrol-2-yl)-2H-pyrazolo[3,4-d]pyrimidine-4,6(5H,7H)-dione was prepared starting from 6-hydrazino-1-isobutylpyrimidine-2,4(1H,3H)-dione and condensing first with 1-benzothiophene-3-carbaldehyde, followed by 1-methyl-1H-pyrrole-2-carbaldehyde.

B): 2-(1-benzothien-3-ylmethyl)-7-isobutyl-3-(1-methyl-1H-pyrrol-2-yl)-2H-pyrazolo[3,4-d]pyrimidine-4,6(5H,7H)-dione was dissolved in anhydrous dimethylsulfoxide and 1,8-diazabicyclo[5.4.0]undec-7-ene was added. 3-chloromethylpyridine hydrochloride was added and the mixture was heated at 80° C. for 18 h The crude reaction product was purified by semi-prep RPHPLC eluting with water/acetonitrile/trifluoroacetic acid mixtures. 525 (M+H).

Example 268

2-(1-benzothien-3-ylmethyl)-5-(2-{(2S)-2-[(dimethylamino)methyl]morpholin-4-ylethyl}-7-isobutyl-3-(1-methyl-1H-pyrrol-2-yl)-2H-pyrazolo[3,4-d]pyrimidine-4,6(5H,7H)-dione

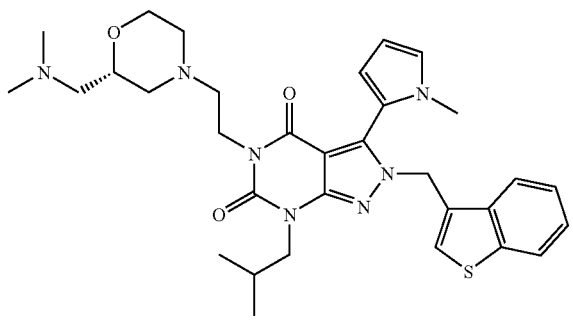

This compound was isolated from a three step preparation as described: A): 2-(1-benzothien-3-ylmethyl)-7-isobutyl-3-(1-methyl-1H-pyrrol-2-yl)-2H-pyrazolo[3,4-d]pyrimidine-4,6(5H,7H)-dione was prepared starting from 6-hydrazino-1-isobutylpyrimidine-2,4(1H,3H)-dione and condensing first with 1-benzothiophene-3-carbaldehyde, followed by 1-methyl-1H-pyrrole-2-carbaldehyde.

B): 2-(1-benzothien-3-ylmethyl)-7-isobutyl-3-(1-methyl-1H-pyrrol-2-yl)-2H-pyrazolo[3,4-d]pyrimidine-4,6(5H, 7H)-dione was dissolved in anhydrous dimethylsulfoxide and cooled to 0° C. To the solution was added sodium hydride until efferversence stopped. To the mixture was added 1-bromo2-chloroethane, warmed to 40° C. for 18 h.
C): The chloroethyl derivative was dissolved in anhydrous dimethylsulfoxide, treated with 1,8-diazabicyclo[5.4.0]undec-7-ene and N,N-dimethyl-N-[(2H)-morpholin-2-ylmethyl]amine derivative. The crude reaction product was purified by semi-prep RPHPLC eluting with water/acetonitrile/trifiuoroacetic acid mixtures. 604 (M+H).

Example 269

2-(1-benzothien-3-ylmethyl)-7-isobutyl-3-(1-methyl-1H-pyrrol-2-yl)-5-(2-piperidin-1-ylethyl)-2H-pyrazolo[3,4-d]pyrimidine-4,6(5H,7H)-dione

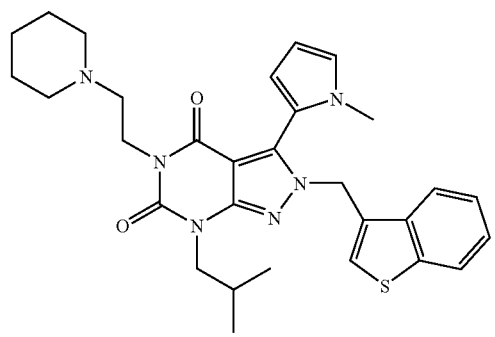

This compound was made following the procedure described above, alkylating with 1-(2-chloroethyl)piperidine hydrochloride. The crude reaction product was purified by semi-prep RPHPLC eluting with water/acetonitrile/trifluoroacetic acid mixtures. 544 (M+H).

Example 270

2-(1-benzothien-3-ylmethyl)-7-isobutyl-5-methyl-3-(1-methyl-1H-pyrrol-2-yl)-2H-pyrazolo[3,4-d]pyridine-4,6(5H,7H)-dione

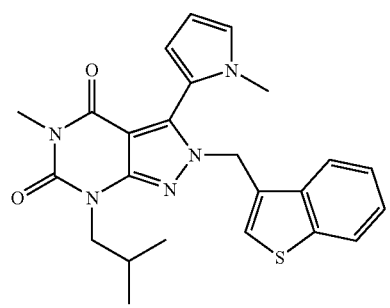

This compound was made following the procedure described above, starting with 6-hydrazino-1-isobutyl-3-methylpyrimidine-2,4(1H,3H)-dione, and condensing first with 1-benzothiophene-3-carbaldehyde, followed by 1-methyl-1H-pyrrole-2-carbaldehyde. 447 (M+H).

Example 271

2-(1-benzothien-3-ylmethyl)-5-[2-(dimethylamino)ethyl]-7-isobutyl-3-(1-methyl-1H-pyrrol-2-yl)-2H-pyrazolo[3,4-d]pyrimidine-4,6(5H,7H)-dione

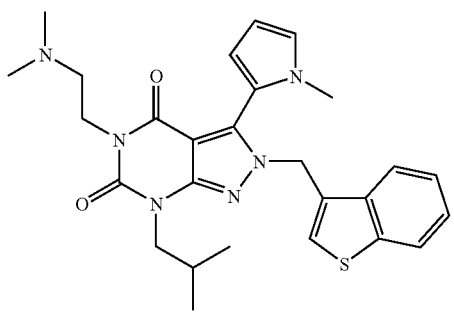

This compound was made following the procedure described above, alkylating with 2-dimethylaminoethyl chloride hydrochloride. The crude reaction product was purified by semi-prep RPHPLC eluting with water/acetonitrile/trifluoroacetic acid mixtures. 505 (M+H).

Example 272

2-(1-benzothien-3-ylmethyl)-7-isobutyl-5-[(1-methylpiperidin-3-yl)methyl]-3-(1-methyl-1H-pyrrol-2-yl)-2H-pyrazolo[3,4-d]pyrimidine-4,6(5H,7H)-dione

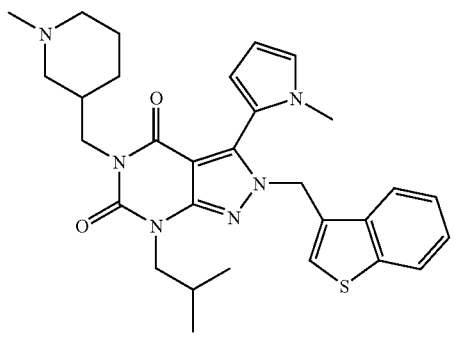

This compound was made following the procedure described above, alkylating with 3-chloromethyl-1-methylpiperidine hydrochloride. The crude reaction product was purified by semi-prep RPHPLC eluting with water/acetonitrile/trifluoroacetic acid mixtures. 545 (M+H).

Example 273

2-[(5-chloro-1H-indol-3-yl)methyl]-3-{4[(dimethylamino)acetyl]-1-methyl-1H-pyrrol-2-yl}-7-isobutyl-5-methyl-2H-pyrazolo[3,4-d]pyrimidine-4,6(5H,7H)-dione

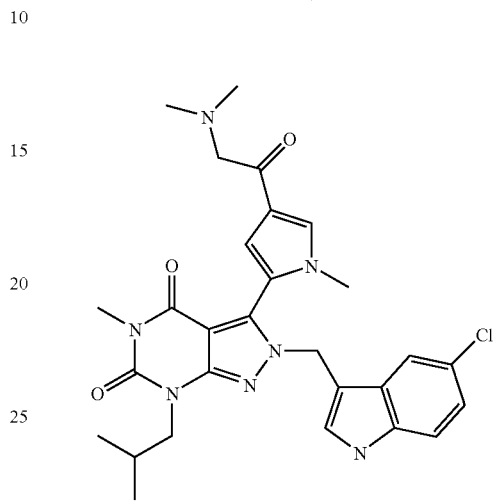

This compound was made in three steps following the procedure described above, starting with 6-hydrazino-1-isobutyl-3-methylpyrimidine-2,4(1H,3H)-dione, and condensing first 5-chloro-1H-indole-3-carbaldehyde, followed by 4-acetyl-1-methyl-1H-pyrrole-2-carbaldehyde. To the isolated 3-(4-acetyl-1-methyl-1H-pyrrol-2-yl)-2-[(5-chloro-1H-indol-3-yl)methyl]-7-isobutyl-5-methyl-2H-pyrazolo[3,4-d]pyrimidine-4,6(5H,7H)-dione in anhydrous THF was added benzyltrimethylammonium dichloroiodate and heated at 65° C. for 1 h. The isolated chloromethyl derivative was treated with dimethylamine in N,N-dimethylformamide for 0.5 h. The crude reaction product was purified by semi-prep RPHPLC eluting with water/acetonitrile/trifluoroacetic acid mixtures. 550.3 (M+H).

Example 274

2-(1-benzothien-3-ylmethyl)-7-isobutyl-5-methyl-3-(1-methyl-1H-imidazol-2-yl)-2H-pyrazolo[3,4-d]pyrimidine-4,6(5H,7H)-dione

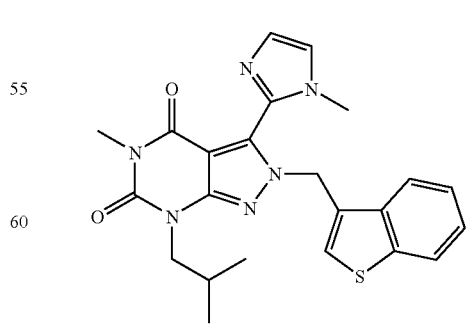

This compound was made following the procedure described above, starting with 6-hydrazino-1-isobutyl-3- methylpyrimidine-2,4(1H,3H)-dione, and condensing first with 1-benzothiophene-3-carbaldehyde, followed by 1-methyl-1H-imidazole-2-carbaldehyde. 448.5 (M+H).

Example 275

2-[(6-chloroquinolin-4-yl)methyl]-7-isobutyl-5-methyl-3-(1-methyl-1H-imidazol-2-yl)-2H-pyrazolo[3,4-d]pyrimidine-4,6(5H,7H)-dione

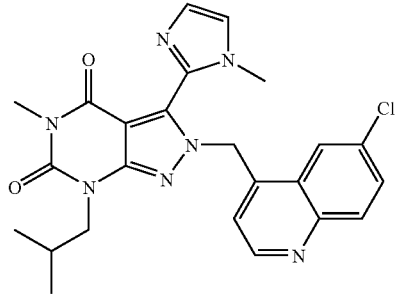

This compound was made following the procedure described above, starting with 6-hydrazino-1-isobutyl-3-methylpyrimidine-2,4(1H,3H)-dione, and condensing first 6-chloroquinoline-4-carbaldehyde, followed by, followed by 1-methyl-1H-imidazole-2-carbaldehyde. 478 (M+H).

Example 276

2-[(6-fluoroquinolin-4-yl)methyl]-7-isobutyl-5-methyl-3-(1-methyl-1H-imidazol-2-yl)-2H-pyrazolo[3,4-d]pyrimidine-4,6(5H,7H)-dione

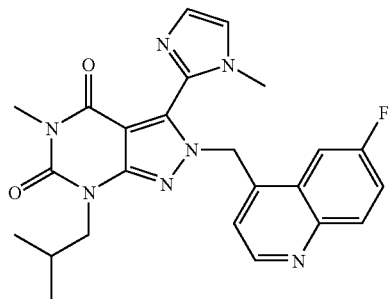

This compound was made following the procedure described above, starting with 6-hydrazino-1-isobutyl-3-methylpyrimidine-2,4(1H,3H)-dione, and condensing first 6-fluoroquinoline-4-carbaldehyde, followed by, followed by 1-methyl-1H-imidazole-2-carbaldehyde. 462 (M+H).

Example 277

2-(1-benzothien-3-ylmethyl-5-[2-(1H-imidazol-1-yl)ethyl]-7-isobutyl-3-(1-methyl-1H-pyrrol-2-yl)-2H-pyrazolo[3,4-d]pyrimidine-4,6(5H,7H)-dione

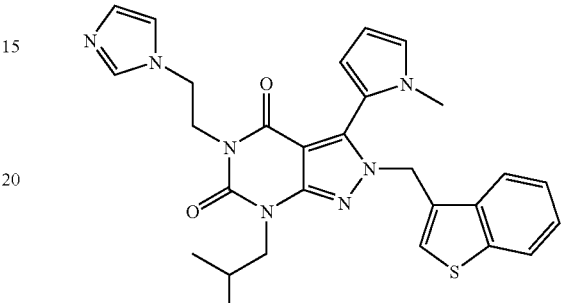

This compound was made following the procedure described above. The chloroethyl derivative was dissolved in anhydrous acetonitrile, treated with potassium carbonate and imidazole at 60° C. The crude reaction product was purified by semi-prep RPHPLC eluting with water/acetonitrile/trifluoroacetic acid mixtures. 528 (M+H).

Example 278

2-[(5-chloro-1H-indol-3-yl)methyl]-3-(1-ethyl-1H-pyrrol-2-yl)-7-isobutyl-5-methyl-2H-pyrazolo[3,4-d]pyrimidine-4,6(5H,7H)-dione

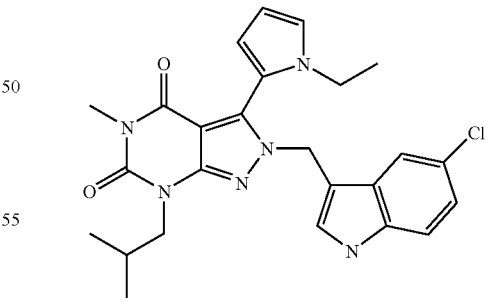

This compound was made following the procedure described above, starting with 6-hydrazino-1-isobutyl-3-methylpyrimidine-2,4(1H,3H)-dione and condensing first with 5-chloro-1H-indole-3-carbaldehyde, followed by 1-ethyl-1H-pyrrole-2-carbaldehyde. 479 (M+H).

Example 279

N-{2-[2-(1-benzothien-3-ylmethyl)-7-isobutyl-3-(1-methyl-1H-pyrrol-2-yl)-4,6-dioxo-2,4,6,7-tetrahydro-5H-pyrazolo[3,4-d]pyrimidin-5-yl]ethyl}guanidine

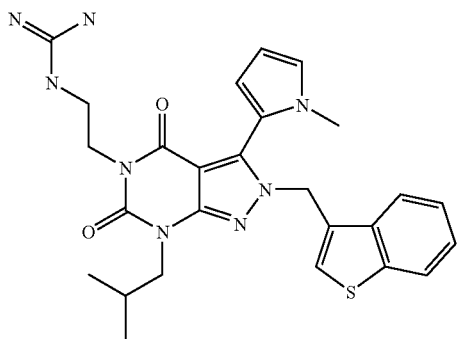

This compound was made following the procedure described above. The chloroethyl derivative was dissolved in anhydrous acetonitrile, treated with ammonia, followed by 1-H-Pyrazole-1-carboxamidine hydrochloride and heated for 80° C. for 18 h. The crude reaction product was purified by semi-prep RPHPLC eluting with water/acetonitrile/trifluoroacetic acid mixtures. 518 (M+H).

Example 280

3-(4-acetyl-1-methyl-1H-pyrrol-2-yl)-7-isobutyl-5-methyl-2-{[6-(trifluoromethyl)quinolin-4-yl]methyl}-2H-pyrazolo[3,4-d]pyrimidine-4,6(5H,7H)-dione

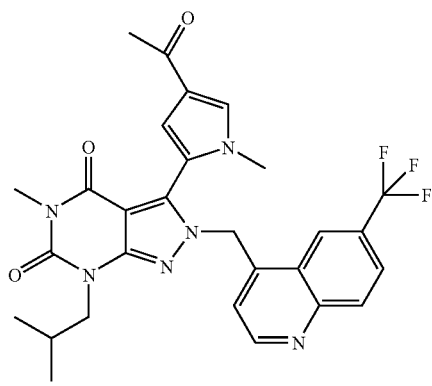

This compound was made following the procedure described above, starting with 6-hydrazino-1-isobutyl-3-methylpyrimidine-2,4(1H,3H)-dione, and condensing first with 6-trifluoromethylquinoline-4-carbaldehyde, followed by 1-methyl-4-acetyl-1H-pyrrole-2-carbaldehyde. 553(M+H).

Example 281

2-(1-benzothien-3-ylmethyl)-7-isobutyl-3-(1-methyl-1H-pyrrol-2-yl)-5-[2-(1H-pyrazol-1-yl)ethyl]-2H-pyrazolo[3,4-d]pyrimidine-4,6(5H,7H)-dione

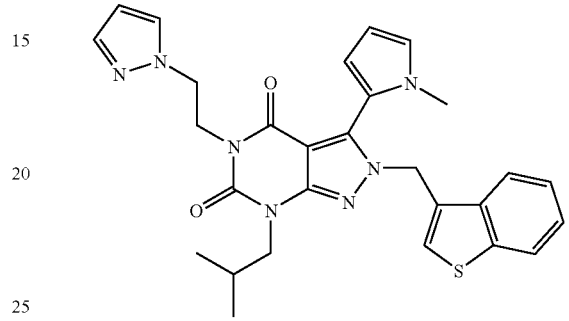

This compound was made following the procedure described above. The chloroethyl derivative was dissolved in anhydrous acetonitrile, treated with potassium carbonate and pyrazole. The crude reaction product was purified by semi-prep RPHPLC eluting with water/acetonitrile/trifluoroacetic acid mixtures. 528 (M+H).

Example 282

7-isobutyl-5-methyl-3-(1-methyl-4-propionyl-1H-pyrrol-2-yl)-2-{[6-(trifluoromethyl)quinolin-4-yl]methyl}-2H-pyrazolo[3,4-d]pyrimidine-4,6(5H,7H)-dione

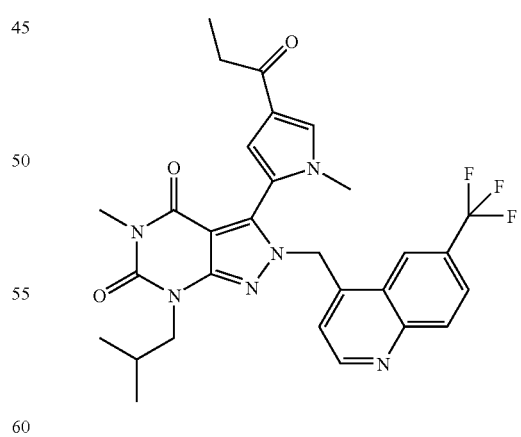

This compound was made following the procedure described above, starting with 6-hydrazino-1-isobutyl-3-methylpyrimidine-2,4(1H,3H)-dione, and condensing first with 6-trifluoromethylquinoline-4-carbaldehyde, followed by 1-methyl-4-propionyl-1H-pyrrole-2-carbaldehyde. 567 (M+H).

Example 283

7-(cyclopropylmethyl)-5-methyl-3-(1-methyl-1H-imidazol-2-yl)-2-{[5-(trifluoromethyl)-1H-indol-3-yl]methyl}-2H-pyrazolo[3,4-d]pyrimidine-4,6(5H,7H)-dione

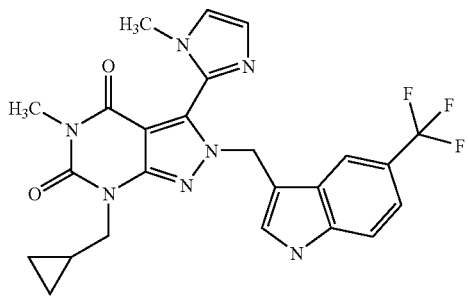

This compound was made following the procedure described above, starting with 1-(cyclopropylmethyl)-6-hydrazino-3-methylpyrimidine-2,4(1H,3H)-dione, and condensing first with 5-(trifluoromethyl)-1H-indole-3-carbaldehyde, followed by 1-methyl-1H-imidazole-2-carbaldehyde. 498.2 (M+H).

Example 284

7-(cyclopropylmethyl)-5-methyl-3-(1-methyl-1H-pyrrol-2-yl)-2-{[5-(trifluoromethyl)-1H-indol-3-yl]methyl}-2H-pyrazolo[3,4-d]pyrimidine-4,6(5H,7H)-dione

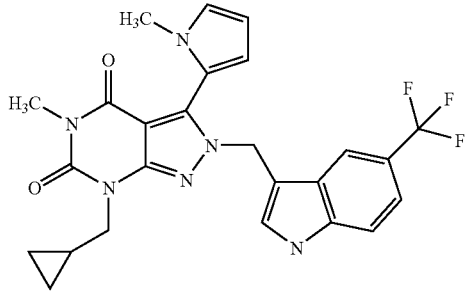

This compound was made following the procedure described above, starting with 1-(cyclopropylmethyl)-6-hydrazino-3-methylpyrimidine-2,4(1H,3H)-dione, and condensing first with 5-(trifluoromethyl)-1H-indole-3-carbaldehyde, followed by 1-methyl-1H-pyrrole-2-carbaldehyde. 497.2 (M+H).

Example 285

2-[(6-chloroquinolin-4-yl)methyl]-7-isobutyl-3-(4-methyl-4H-1,2,4-triazol-3-yl)-2H-pyrazolo[3,4-d]pyrimidine-4,6(5H,7H)-dione

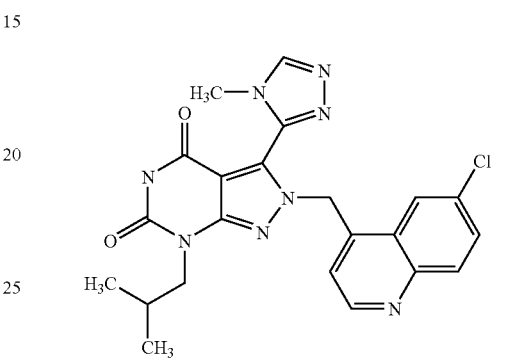

This compound was made following the procedure described above, starting with 6-hydrazino-1-isobutylpyrimidine-2,4(1H,3H)-dione, and condensing first with 6-chloroquinoline-4-carbaldehyde, followed by 4-methyl-4H-1,2,4-triazole-3-carbaldehyde. 460.2 (M+H).

Example 286

2-[(6-chloroquinolin-4-yl)methyl]-7-isobutyl-3-(4-methyl-4H-1,2,4-triazol-3-yl)-5-(2-morpholin-4-ylethyl)-2H-pyrazolo[3,4-d]pyrimidine-4,6(5H,7H)-dione

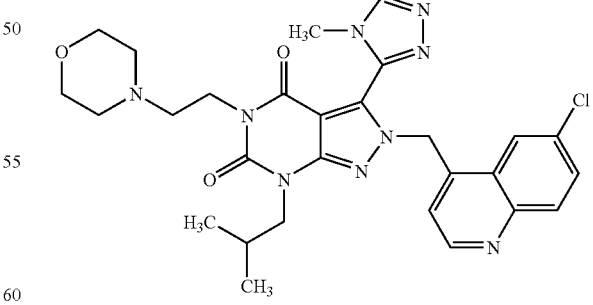

This compound was made by alkylation of 2-[(6-chloroquinolin-4-yl)methyl]-7-isobutyl-3-(4-methyl-4H-1,2,4-triazol-3-yl)-2H-pyrazolo[3,4-d]pyrimidine-4,6(5H,7H)-dione with 4-(2-chloroethyl)morpholine following conditions in Example 6.d. 578.2 (M+H).

Example 287

[2-[(6-chloroquinolin-4-yl)methyl]-7-isobutyl-3-(4-methyl-4H-1,2,4-triazol-3-yl)-4,6-dioxo-2,4,6,7-tetrahydro-5H-pyrazolo[3,4-d]pyrimidin-5-yl]acetonitrile

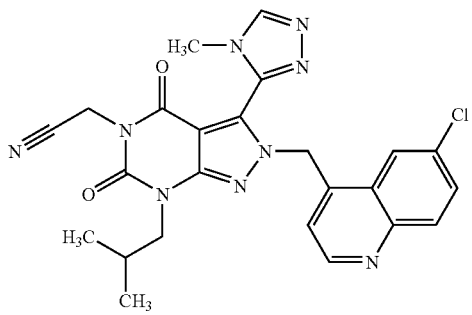

This compound was made by alkylation of 2-[(6-chloroquinolin-4-yl)methyl]-7-isobutyl-3-(4-methyl-4H-1,2,4-triazol-3-yl)-2H-pyrazolo[3,4-d]pyrimidine-4,6(5H,7H)-dione with bromoacetonitrile following conditions in Example 6.d. 504.2 (M+H).

Example 288

1-(Bromomethyl)naphthalene

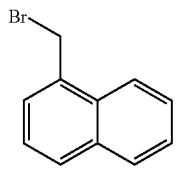

1-naphthylmethanol (3.2 g) was taken up in $CH_2Cl_2$ (10 mL) and cooled to 0° C. Phosphorus tribromide (25 mL, 1 M in $CH_2Cl_2$) was added drop wise and allowed to stir at RT for 2 h. Saturated sodium bicarbonate and sodium hydroxide was added slowly until alkaline. The organic layer was separated, dried over sodium sulfate, and evaporated under reduced pressure to give an off-white solid (4.4 g). Proton NMR was sufficient for the next step.

Example 289

4-(Bromomethyl)-6-chloroquinoline

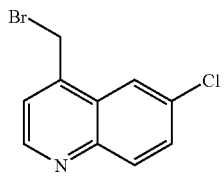

4-(Bromomethyl)-6-chloroquinoline was prepared from 6-chloroquinoline-4-carbaldehyde following the procedure described in the preparation of 1-(bromomethyl)naphthalene.

Example 290

3-(Bromomethyl)-5-chloro-1-benzothiophene

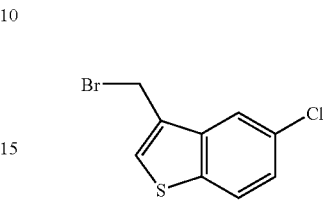

3-(Bromomethyl)-5-chloroquinoline was prepared from 5-chloro-1-benzothiophene-3-carbaldehyde following the procedure described in the preparation of 1-(bromomethyl)naphthalene.

Example 291

3-(Bromomethyl)-5-fluoro-1-benzothiophene

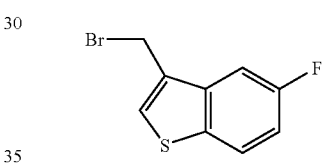

3-(Bromomethyl)-5-fluoroquinoline was prepared from 5-fluoro-1-benzothiophene-3-carbaldehyde following the procedure described in the preparation of 1-(bromomethyl)naphthalene.

Example 292

7-(Cyclopropylmethyl)-5-methyl-2H-pyrazolo[3,4-d]pyrimidine-4,6(5H,7H)-dione

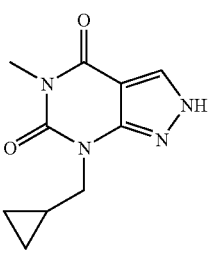

1-(Cyclopropylmethyl)-6-hydrazino-3-methylpyrimidine-2,4(1H,3H)-dione (5 g) was dissolved in DMF (5 mL) followed by addition of $POCl_3$ (4 mL) dropwise at 0° C. The reaction was warmed to 80 C. for 3 h, followed by stirring at RT overnight. The solution was added to 200 mL of water and filtered to give about 5 g of yellow solids. Proton NMR was sufficient to carry on to next step.

Example 293

3-Bromo-7-(cyclopropylmethyl)-5-methyl-2H-pyrazolo[3,4-d]pyrimidine-4,6(5H,7H)-dione

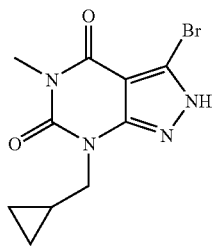

7-(Cyclopropylmethyl)-5-methyl-2H-pyrazolo[3,4-d]pyrimidine-4,6(5H,7H)-dione (6.0 g), N-bromosuccinimide (7.8 g), and 100 mg of AIBN was taken up in 50 mL of 1,2-dichloroethane. The heterogeneous mixture was brought to reflux overnight. Water (100 mL) was added to the solution and separated. The organic layer was dried over sodium sulfate, filtered and removed under reduced pressure to give a yellow solid. The compound was flashed through a plug of silica gel, gave 6.7 g of white powder.

Example 294

3-Bromo-7-(isobutyl)-5-methyl-2H-pyrazolo[3,4-d]pyrimidine-4,6(5H,7H)-dione

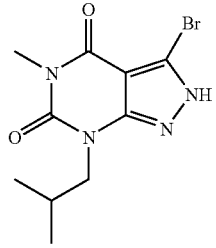

3-Bromo-7-isobutyl)-5-methyl-2H-pyrazolo[3,4-d]pyrimidine-4,6(5H,7H)-dione was prepared, starting from 1-hydrazino-1-isobutyl-3-methylpyrimidine-2,4(1H,3H)-dione following the procedure described in the preparation of 3-bromo-7-(cyclopropylmethyl)-5-methyl-2H-pyrazolo[3,4-d]pyrimidine-4,6(5H,7H)-dione.

Example 295

3-Bromo-7-(cyclopropylmethyl)-5-methyl-2-(1-naphthylmethyl)-2H-pyrazolo[3,4-d]pyrimidine-4,6(5H,7H)-dione

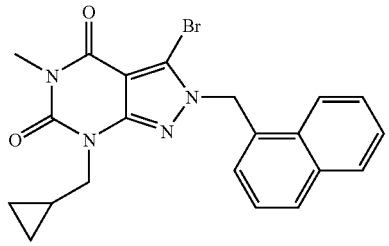

3-Bromo-7-(cyclopropylmethyl)-5-methyl-2-(1-naphthylmethyl)-2H-pyrazolo[3,4-d]pyrimidine-4,6(5H,7H)-dione (6.0 g), $K_2CO_3$ (3.0 g), and 1-(bromomethyl)naphthalene (4.4 g) were taken up in DMF (20 mL) and heated to 70 C overnight. The mixture was extracted with ethyl acetate and water. The organic layer was separated, dried over sodium sulfate, filtered and removed under reduced pressure. The oily product was column with ethyl acetate/hexane to give a white solid (4.1 g).

Example 296

7-(Cyclopropylmethyl)-3-[(3R)-3-hydroxypyrrolidin-1-yl]-5-methyl-2-(1-naphthylmethyl)-2H-pyrazolo[3,4-d]pyrimidine-4,6(5H,7H)-dione

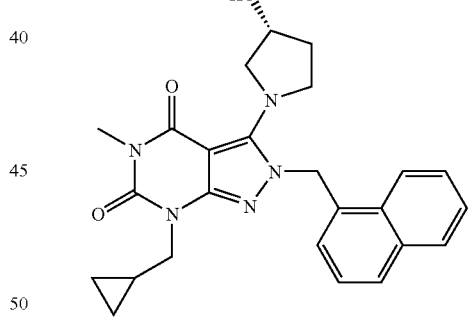

(3R)-3-Hydroxypyrrolidine (100 mg), (rac)-binap (17 mg), $Pd_2(dba)_3$ (13 mg) and toluene (5 mL) were combined and flushed with nitrogen for 2 min. 3-Bromo-7-(cyclopropylmethyl)-5-methyl-2-(1-naphthylmethyl)-2H-pyrazolo[3,4-d]pyrimidine-4,6(5H,7H)-dione (100 mg) was added and flushed with nitrogen again for 2 min, followed by addition of NaO$^t$Bu (55 mg). The mixture was flushed with nitrogen and brought to 60 C for 8 h. Water and ethyl acetate were added and the organic layer was separated, dried over sodium sulfate, filtered, removal of solvent under reduced pressure. The oil was subjected to reverse phase chromatography using a Gilson to give 60 mg of product, ES M+H$^+$=446.

The compounds in the following Table were made using the same method as was used in the example right above.

| Example | Structure | Name | ES+ (M + H) |
|---|---|---|---|
| 297 | 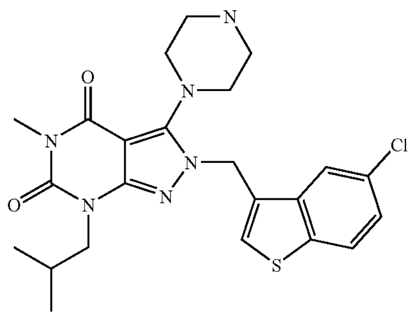 | 2-[(5-chloro-1-benzothien-3-yl)methyl]-7-isobutyl-5-methyl-3-piperazin-1-yl-2H-pyrazolo[3,4-d]pyrimidine-4,6(5H,7H)-dione | |
| 298 | 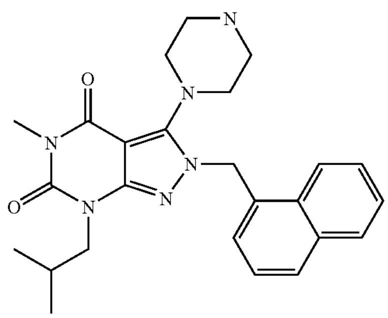 | 7-isobutyl-5-methyl-2-(1-naphthylmethyl)-3-piperazin-1-yl-2H-pyrazolo[3,4-d]pyrimidine-4,6(5H,7H)-dione | 447 |
| 299 | 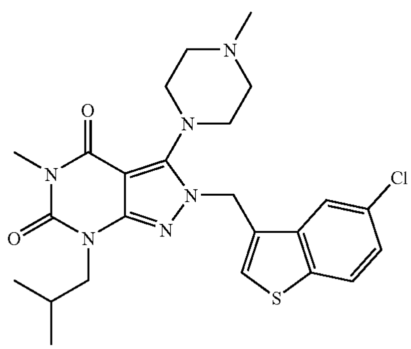 | 2-[(5-chloro-1-benzothien-3-yl)methyl]-7-isobutyl-5-methyl-3-(4-methylpiperazrn-1-yl-2H-pyrazolo[3,4-d]pyrimidine-4,6(5H,7H)-dione | 502 |
| 300 | 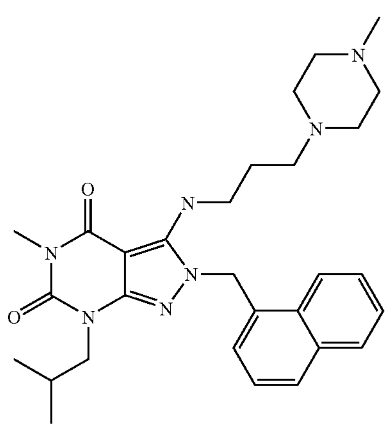 | 7-isobutyl-5-methyl-3-{[3-(4-methylpiperazin-1-y)propyl]amino}-2-(1-naphthylmethyl)-2H-pyrazolo[3,4-d]pyrimidine-4,6(5H,7H)-dione | 518 |

| Example | Structure | Name | ES+ (M + H) |
|---|---|---|---|
| 301 | 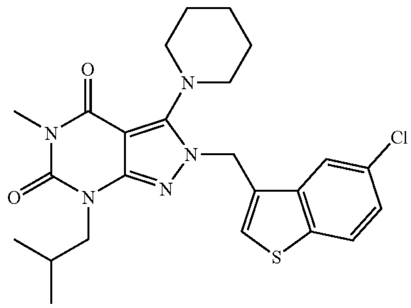 | 2-[(5-chloro-1-benzothien-3-yl)methyl]-7-isobutyl-5-methyl-3-piperidin-1-yl-2H-pyrazolo[3,4-d]pyrimidine-4,6(5H,7H)-dione | 487 |
| 302 | 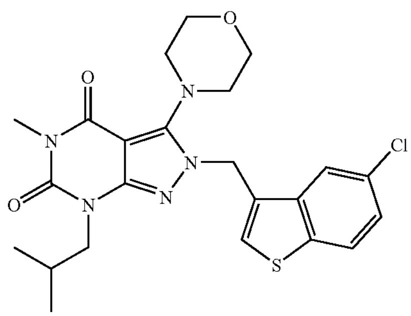 | 2-[(5-chloro-1-benzothien-3-yl)methyl]-7-isobutyl-5-methyl-3-morpholin-4-yl-2H-pyrazolo[3,4-d]pyrimidine-4,6(5H,7H)-dione | 489 |
| 303 | 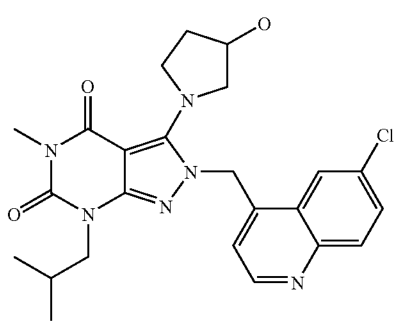 | 2-[(6-chloroquinolin-4-yl)methyl]-3-(3-hydroxypyrrolidin-1-yl)-7-isobutyl-5-methyl-2H-pyrazolo[3,4-d]pyrimidine-4,6(5H,7H)-dione | 484 |
| 304 | 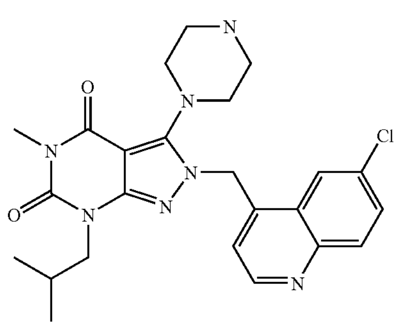 | 2-[(6-chloroquinolin-4-yl)methyl]-7-isobutyl-5-methyl-3-piperazin-1-yl)-2H-pyrazolo[3,4-d]pyrimidine-4,6(5H,7H)-dione | 483 |

-continued

| Example | Structure | Name | ES+ (M + H) |
|---|---|---|---|
| 305 | 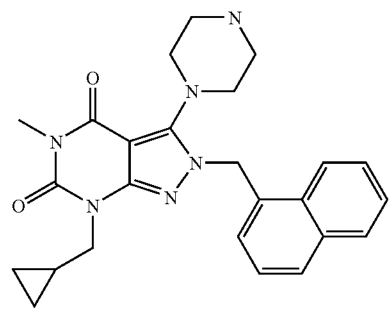 | 7-(cyclopropylmethyl)-5-methyl-2-(1-naphthylmethylpiperazin)-3-piperazin-1-yl-2H-pyrazolo[3,4-d]pyrimidine-4,6(5H,7H)-dione | 445 |
| 306 | 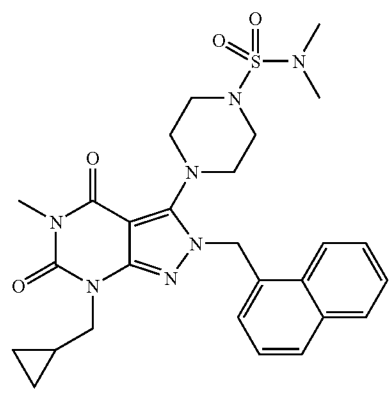 | 4-[7-(cyclopropylmethyl)-5-methyl-2-(1-naphthylmethyl)-4,6-dioxo-4,5,6,7-tetrahydro-2H-pyrazolo[3,4-d]pyrimidin-3-yl]-N,N-dimethylpiperazine-1-sulfonamide | 552 |
| 307 | 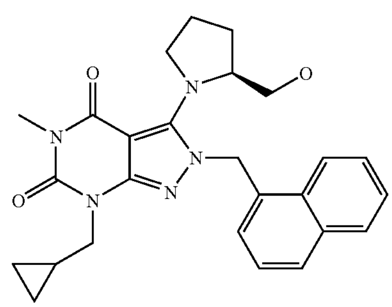 | 7-(cyclopropylmethyl)-3-[(2S)-2-(hydroxymethyl)pyrrolidin-1-yl]-5-methyl-2-(1-naphthylmethyl)-2H-pyrazolo[3,4-d]pyrimidine-4,6(5H,7B)-dione | 460 |
| 308 | 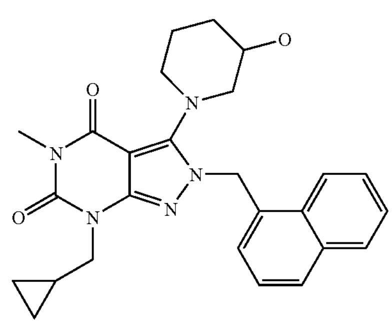 | 7-(cyclopropylmethyl)-3-(3-(hydroxypiperidin-1-yl]-5-methyl-2-(1-naphthylmethyl)-2H-pyrazolo[3,4-d]pyrimidine-4,6(5H,7H)-dione | 460 |

| Example | Structure | Name | ES+ (M + H) |
|---|---|---|---|
| 309 | 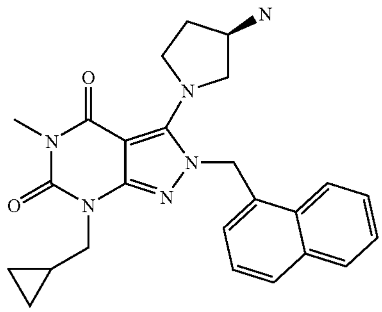 | 3-[(3S)-3-aminopyrrolidin-1-yl]-7-(cyclopropylmethyl)]-5-methyl-2-(1-naphthylmethyl)-2H-pyrazolo[3,4-d]pyrimidine-4,6(5H,7H)-dione | 445 |
| 310 | Chiral | 3-[(3R)-3-aminopyrrolidin-1-yl]-7-(cyclopropylmethyl)]-5-methyl-2-(1-naphthylmethyl)-2H-pyrazolo[3,4-d]pyrimidine-4,6(5H,7H)-dione | 445 |

Example 311

(3-Methylisoxazol-4-yl)methanol

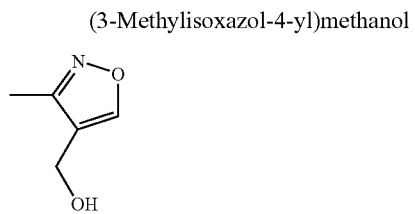

Ethyl-3-methylisoxazole-4-carboxylate (1.2 g) was taken up in toluene (10 mL) and cooled to −78 C. 20 mL of borane (1M in CH$_2$Cl$_2$) was added dropwise and allowed to stir for 1 hour at −78 C. The reaction was finished based on HPLC. The solution was quenched with methanol and filtered through a plug of celite. The organic solution was removed under reduced pressure gave a clear oil. The material was sufficiently clean to carry on to the next step.

Example 312

3-Methylisoxazole-4-carbaldehyde

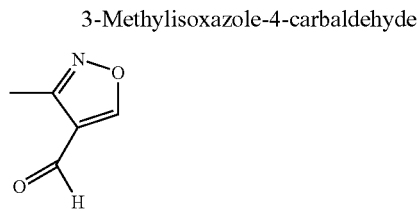

The crude material was dissolved in 25 mL of CH$_2$Cl$_2$ and pyridinium chlorochromate (PCC) (2.2 g), (20% on basic Al$_2$O$_3$) was added. The mixture was stirred overnight at RT. The heterogeneous mixture was filtered through a plug of celite. The brown solution was taken up in ethyl acetate and was column through a plug of silica gel to give clear oil.

Example 313

2-[(5-chloro-1H-indol-3-yl)methyl]-7-isobutyl-5-methyl-3-(3-methylisoxazol-4yl)-2H-pyrazolo[3,4-d]pyrimidine-4,6(5H,7H)-dione

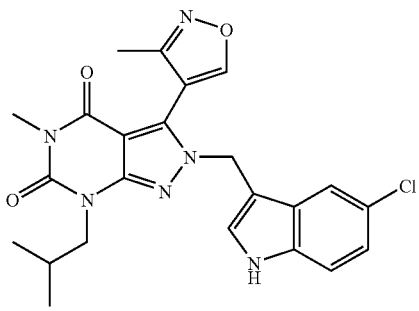

5-Chloro-1H-indole-3-carbaldehyde(3-isobutyl-1-methyl-2,6-dioxo-1,2,3,6-tetrahydropyrimidin-4-yl)hydrazone (100 mg) was added to a solution of isoxazolaldehyde (86 mg) in dimethylformamide at RT. Piperidine (100 uL) was then added and brought to 80 C for 8 h. After cooling to RT, ethyl acetate (25 mL) was added to brown solution and water (25 mL) was added and extracted. The aqueous layer was back extract with ethyl acetate and then combined. The organic layer was dried over sodium sulfate, filtered and removal of solvent to give an amorphous solid. The isoxazole was submitted the Gilson Preparatory chromatography to give a 100 mg of white solids. ES M+H$^+$467.

Example 314

5-{2-[(6-chloroquinolin-4-yl)methyl]-7-isobutyl-4,6-dioxo-4,5,6,7-tetrahydro-2H-pyrazolo[3,4-d]pyrimidin-3-yl}-1-methyl-1H-pyrrole-3-carbonitrile

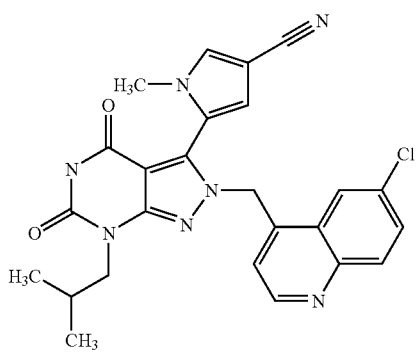

This compound was made following the procedure described above, starting with 6-hydrazino-1-isobutylpyrimidine-2,4(1H,3H)-dione, and condensing first with 6-chloroquinoline-4-carbaldehyde, followed by 5-formyl-1-methyl-1H-pyrrole-3-carbonitrile. ES M+H+=463.

Example 315

2-[(6-chloroquinolin-4-yl)methyl]-7-isobutyl-3-(1-methyl-1H-pyrrol-2-yl)-2H-pyrazolo[3,4-d]pyrimidine-4,6(5H,7H)-dione

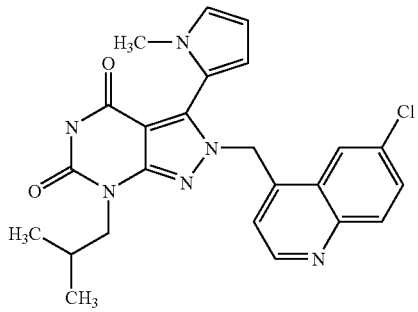

This compound was made following the procedure described above, starting with 6-hydrazino-1-isobutylpyrimidine-2,4(1H,3H)-dione, and condensing first with 6-chloroquinoline-4-carbaldehyde, followed by 1-methyl-2-pyrrolecarboxaldehyde. ES M+H+=488.

The remaining numbered examples contain intermediates that are used to make the compounds described the previous examples.

Examples 316

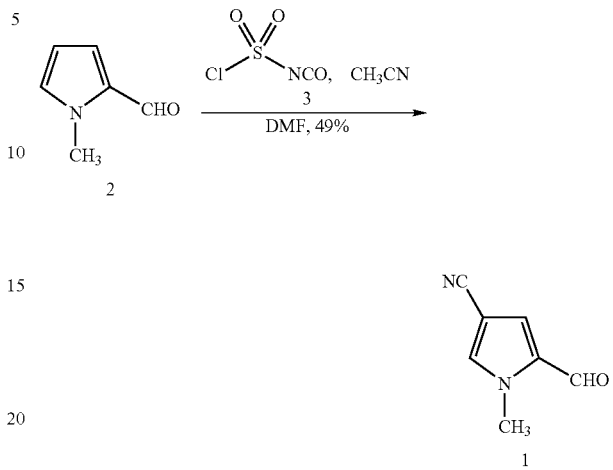

4-Cyano-1-methylpyrrole-2-carboxaldehyde (1): To a solution of 2 (19.70 g, 0.18 mol) in acetonitrile at −60° C., 3 (47.5 mL, 0.50 mol) was added dropwise and the reaction mixture was warmed to room temperature overnight, cooled to 0° C., added DMF (70 mL, 0.90 mol) and heated at 55° C. for 1 h. The reaction mixture was then poured on an ice-cold solution of 2N aq. NaOH (500 mL) and extracted with EtOAc. The organic extracts were dried over $Na_2SO_4$, filtered, and concentrated in vacuo. The crude product was purified by flash chromatography using 10-20% gradients of EtOAc/hexanes as eluent. Further purification was done by crystallization (EtOAc/hexanes) to obtain 1 (11.74 g, 49% yield) as a white solid. Mp 125-126° C. (lit.[1] 123-124° C.). $^1$H NMR (300 MHz, $CDCl_3$): δ 9.62 (s, 1H), 7.31 (s, 1H), 7.18 (d, 1.7 Hz, 1H), 4.01 (s, 3H). Analysis calcd. for $C_7H_6N_2O$; C, 62.68; H, 4.51; N, 20.88; found, C, 62.92; H, 4.45; N, 20.92.[1]

Ref: 1. Loader, C. E.; Anderson, H. J. *Can. J. Chem.* 1981, 59, 2673. 2. Sonnet, P. E. *J. Hetcycl. Chem.* 1973, 10, 113.

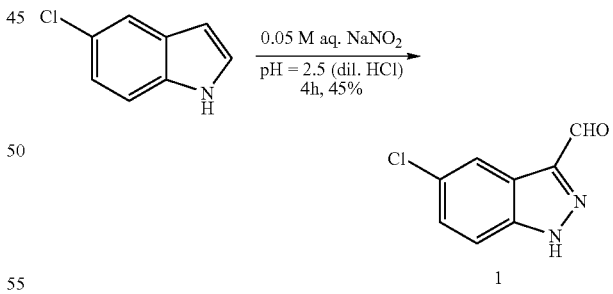

Examples 317

5-Chloro-1H-indazole-3-carboxaldehyde (1): A mixture of 5-chloroindole (6.04 g, 39.8 mmol) and 0.05 M aq. sodium nitrite (8 L, adjusted to pH 2.5 with dilute HCl) was stirred at room temperature for 4 h. The precipitated solid was removed by filtration and the filtrate was extracted with EtOAc (2 L). The organic extracts were washed with brine, dried over $Na_2SO_4$, filtered, and concentrated. The crude product was purified by flash chromatography on silica gel with 10-15% EtOAc/hexanes gradient to give 1 (3.23 g, 45% yield) as an off-white solid. Mp 213-214° C. (lit.[1] 209-210° C., dec). $^1$H NMR (300 MHz, CD$_3$CN): δ 10.17 (s, 1H), 8.18 (d, 1.9 Hz, 1H), 7.65 (dd, 8.8, 0.5 Hz, 1H), 7.47 (dd, 8.8, 2.2 Hz, 1H). Ms m/z: 181 (M+1). Analysis calcd. for C$_8$H$_5$ClN$_2$O; C, 53.21; H, 2.79; N, 15.51; Cl, 19.63; found, C, 53.31; H, 2.80; N, 15.55; Cl, 19.75.[1]

Ref: 1. Buchi, G.; Lee. G. C. M.; Yang, D.; Tannenbaum, S. R. *J. Am. Chem. Soc.* 1986, 108(14), 4115-4119.

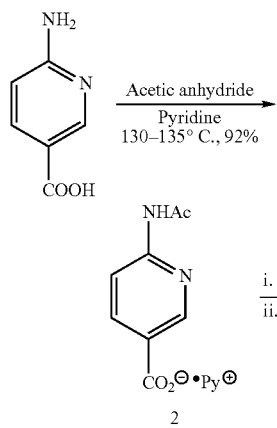

Examples 318

2-(N-acetylamido)pyridine-5-carboxylic acid pyridine salt (2): A mixture of 6-aminonicotinic acid (15.1 g, 109.1 mmol), acetic anhydride (12.4 mL, 131.4 mmol), and pyridine (450 mL) was heated at 130-135° C. for 24 h. The mixture was diluted with hexanes after cooling to room temperature, the precipitated solid 2 (26.0 g, 92%) was filtered, and dried in vacuo. $^1$H NMR (300 MHz, DMSO-d$_6$): δ 10.86 (bs, 1H), 8.81 (m, 1H), 8.58 (m, 2H), 8.24 (dd, 8.8, 2.2 Hz, 1H), 8.17 (d, 8.8 Hz, 2H), 7.79 (ttd, 7.7, 1.7, 0.5 Hz, 1H), 7.39 (m, 2H), 2.14 (s, 3H).

Examples 319

2-(N-acetylamido)pyridine-5-carboxaldehyde (1): To a solution of DMF (7.75 mL, 100 mmol) in dry CH$_2$Cl$_2$ (80 mL) cooled to 0° C., oxalyl chloride (26.0 mL, 298 mmol) was added dropwise. After 1 h excess solvent was stripped off and was replaced by acetonitrile (150 mL) and THF (200 mL). A suspension of 2 (26.0 g, 100 mmol) in THF was then added to the reaction flask at −30° C. and was allowed to stir for 1 h. The mixture was further cooled to −78° C. and CuI (1.94 g, 10.2 mmol) was added followed by a rapid addition of lithium tri-tert-butoxyaluminumhydride (200 mL, 1.0 M solution in THF). After 20 min. the reaction was quenched with 2N aq. HCl, warmed to room temperature and extracted with EtOAc (1 L). The organic extracts were dried over Na$_2$SO$_4$, filtered, and concentrated. The crude product was purified by flash chromatography using 15-40% gradients of EtOAc/hexanes as eluent. Pure 1 (4.08 g, 25% yield) was obtained as a white solid by crystallization from hot EtOAc. Mp 152-153° C. $^1$H NMR (300 MHz, CDCl$_3$): δ 10.99 (s, 1H), 9.96 (s, 1H), 8.85 (dd, 2.2, 0.8 Hz, 1H), 8.26 (bd, 8.8 Hz, 1H), 8.21 (dd, 8.8, 2.2 Hz, 1H), 2.12 (s, 3H). MS m/z: 165 (M+1). Analysis calcd. for C$_8$H$_8$N$_2$O$_2$; C, 58.53; H, 4.91, N, 17.06; found, C, 58.25; H, 4.81; N, 16.80.

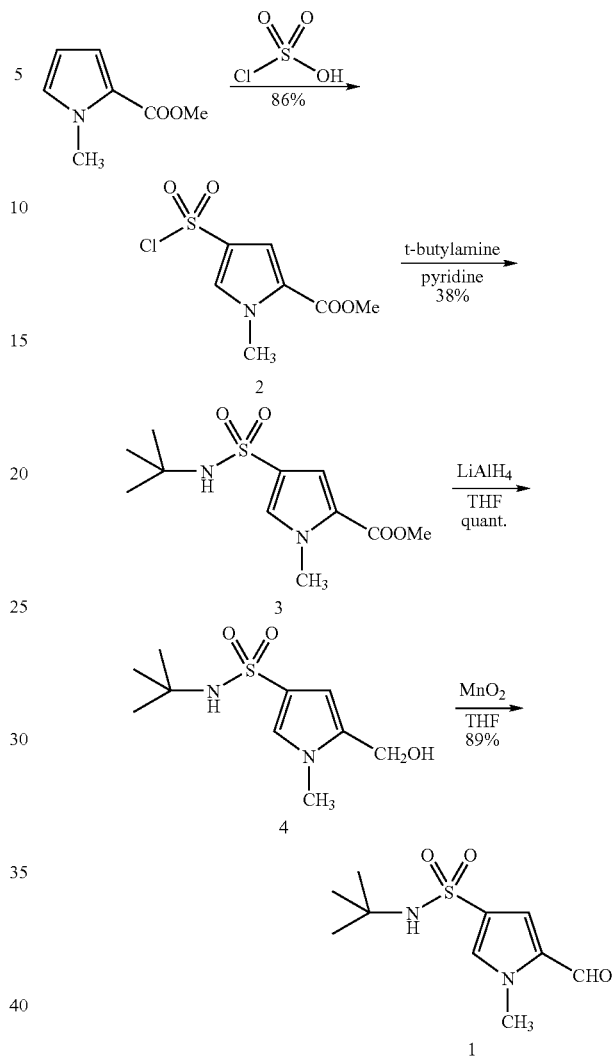

Examples 320

Methyl (4-chlorosulfamoyl-N-methylpyrrole)-2-carboxylate (2): Methyl N-methylpyrrole-2-carboxylate (9.83 g, 70.69 mmol) was added dropwise to chlorosulfonic acid (50 mL) at 0° C, under nitrogen atmosphere. The reaction mixture was then warmed to room temperature overnight. Work up was done by slow addition to ice cold water, followed by extraction with CH$_2$Cl$_2$. The combined organic extracts were dried over Na$_2$SO$_4$, filtered, and concentrated to give 2 (13.77, 86%) as a white solid. $^1$H NMR (300 MHz, CDCl$_3$): δ 7.48 (d, 1.9 Hz, 1H), 7.37 (d, 1.9 Hz, 1H), 4.01 (s, 3H), 3.87 (s, 3H).

Examples 321

Methyl (4-tert-butylsulfamoyl-N-methylpyrrole)-2-carboxylate (3): A premixed solution of butylamine (7.75 mL, 73.74 mmol) in pyridine was added slowly to a mixture of 2 (15.43 g, 68.38 mmol) in pyridine (80 mL) at 0° C. under nitrogen atmosphere. The reaction was allowed to warm to room temperature and stirred for 3 h. The mixture was then poured into H$_2$O (300 mL), extracted with EtOAc, the extracts were washed with brine, dried over Na$_2$SO$_4$, filtered, and concentrated The crude product was purified by flash chromatography over silica gel using 10-25% EtOAc/hexanes gradient as eluent to give 3 (18.76 g, 38% yield) as a white solid. $^1$H NMR (300 MHz, CDCl$_3$): δ 7.25 (d, 1.9 Hz, 1H), 7.17 (d, 1.9 Hz, 1H), 4.63 (bs, 1H), 3.97 (s, 3H), 3.84 (s, 3H), 1.27 (s, 9H). MS m/z: 274 (M−1).

Examples 322

4-tert-Butylsulfamoyl-N-methylpyrrole-2-methanol (4): A solution of 3 (7.12 g, 25.95 mmol) in dry THF (120 mL) at −78° C. under nitrogen was charged with LiAlH$_4$ (30 mL, 1.0 M solution in THF). The reaction mixture was warmed to 10° C. and stirred for 2 h. The mixture was poured onto EtOAc:H$_2$O (1:1, 300 mL), saturated with NaCl, extracted with EtOAc. The organic extracts were dried over Na$_2$SO$_4$, filtered, and concentrated to give 4 (6.40 g, quant.) as a white solid. $^1$H NMR (300 MHz, CDCl$_3$): δ 7.11 (d, 1.9 Hz, 1H), 6.35 (d, 1.9 Hz, 1H), 4.64 (s, 1H), 4.54 (d, 5.5 Hz, 2H), 3.68 (s, 3H), 2.18 (t, 5.5 Hz, 1H), 1.24 (s, 9H).

Examples 323

4-tert-Butylsulfamoyl-N-methylpyrrole-2-carboxaldehyde (1): A solution of 4 (6.40 g, 25.98 mmol) in dry THF (750 mL) under nitrogen was charged with MnO$_2$ (65.0 g, 0.64 mol) and was allowed to stir at room temperature for 1 h. The mixture was filtered through celite; the filtrate was concentrated. Purification by flash chromatography on silica gel using 10-25% EtOAc/hexanes gradient as eluent afforded 1 (5.67 g, 89%) as a white solid. Mp 97-98° C. $^1$H NMR (300 MHz, CDCl$_3$): δ 9.95(d, 0.8 Hz, 1H), 7.33 (bs, 1H), 7.18 (d, 1.9 Hz, 1H), 4.69 (bs, 1H), 3.97 (s, 3H), 1.27 (s, 9H). MS m/z: 243 (M−1). Analysis calcd. for C$_{10}$H$_{16}$N$_2$O$_3$S; C, 49.16; H, 6.60, N, 11.47; found, C, 48.99; H, 6.70; N, 11.45.

Ref: Mornata, C.; Molins-Pujol, A. M.; Pujol, M. D.; Bonal, J. *J. Chem. Soc. Perkin Trans.* 1 1998, 19,3285-3291.

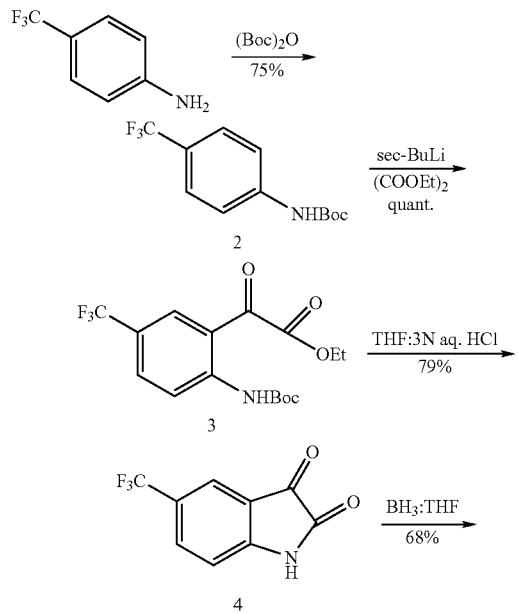

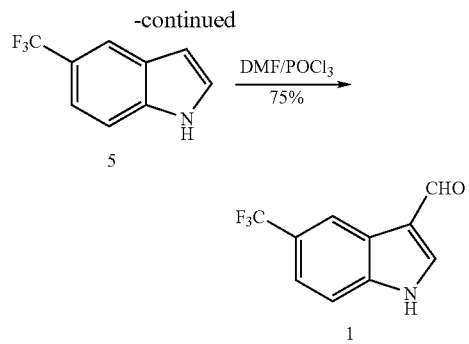

Examples 324

4-Trifluoromethyl-carbamic acid tert-butyl ester (2): A mixture of 4-trifluoromethyl aniline (7.8 mL, 62.1 mmol) and di-tert-butyl-dicarbonate (15.0 g, 68.9 mmol) was refluxed for 12 h under nitrogen atmosphere. The mixture was concentrated in vacuo. The crude product was purified by flash chromatography on silica gel using 10% EtOAc/hexanes as eluent to give 2 (12.2 g, 75% yield) as a white solid. $^1$H NMR (300 MHz, CDCl$_3$): δ 7.54 (d, 8.6 Hz, 2H), 7.47 (d, 8.6 Hz, 2H), 6.63 (bs, 1H), 1.52 (s, 9H). MS m/z: 260 (M−1).

Examples 325

Ethyl-2-(2-N-Boc-5-trifluoromethylphenyl)-2-oxo-carboxylate (3): A solution of 2 (5.24 g, 20.06 mmol) in dry THF (50 mL) was charged with sec-butyllithium (38 mL, 49.40 mmol, 1.3 M in cyclohexane) at −40° C. under nitrogen atmosphere. The mixture was further cooled to −78° C. and diethyloxalate (3.3 mL, 24.3 mmol) was added and allowed to stir for 1 h. The reaction was quenched with 1N HCl (60 mL), warmed to room temperature, extracted with ether, the extracts were dried over MgSO$_4$, filtered, and concentrated to give 3 (7.24 g, quant. yield) as a yellow oil. $^1$H NMR (300 MHz, CDCl$_3$): δ 10.56 (bs, 1H), 8.70 (d, 9.1 Hz, 1H), 7.96 (dd, 1.7, 0.8 Hz, 1H), 7.80 (m, 1H), 4.49 (q, 7.1 Hz, 2H) 1.45 (s, 9H), 1.29 (t, 7.1 Hz, 3H). MS m/z: 360 (M−1).

Examples 326

5-Trifluoromethyl-1H-indole-2,3-dione (4): A mixture of 3 (7.24 g, 20.06 mmol), THF (60 mL), and 3N HCl (60 mL) was refluxed for 3 h. The mixture was extracted with EtOAc (3×75 mL), the extracts were washed with brine, dried over MgSO$_4$, and concentrated. Purification of the crude product by flash chromatography on silica gel using 2% MeOH/CHCl$_3$ as eluent afforded 4 (3.41 g, 79% yield) as a yellow orange solid. $^1$H NMR (300 MHz, DMSO-d$_6$): δ 7.92 (dd, 8.2, 1.9 Hz, 1H), 7.80 (s, 1H), 7.07 (d, 8.2 Hz, 1H).

Examples 327

5-Trifluoromethyl-1H-indole (5): To a solution of 4 (6.75 g, 31.38 mmol) in dry THF (200 mL) at 0° C. under nitrogen atmosphere BH$_3$.THF solution (82 mL, 1 M in THF) was added dropwise. The mixture was allowed to warm to room temperature and stirred for 1 h. The reaction was quenched with 6N ice-cold aq. HCl (30 mL), made alkaline (pH 7-8) with 2 N NaOH, saturated with NaCl, extracted with EtOAc, the extracts were dried (MgSO$_4$), concentrated. Purification by chromatoghraphy on silica gel using CH$_2$Cl$_2$ as eluent afforded (3.95 g, 68% yield) as an off white solid. $^1$H NMR (300 MHz, MeOH-d$_4$): δ 7.87 (m, 1H), 7.51 (dd, 8.5, 0.8 Hz, 1H), 7.47 (d, 8.5 Hz, 1H), 7.37 (d, 3.2 Hz, 1H), 7.34 (dd, 8.5, 1.6 Hz, 1H), 6.57 (dd, 3.2, 0.8 Hz, 1H). MS m/z: 184 (M−1).

Examples 328

5-Trifluoromethyl-1H-indole-3-carbaldehyde (1): Phosphorous oxychloride (7.6 mL, 83.0 mmol) was added dropwise to DMF (150 mL) at 0° C. A solution of 5 (4.5 g, 24.4 mmol) in DMF (30 mL) was added after 15 min. and the reaction mixture was allowed to warm to room temperature for 2 h. The mixture was poured on ice-water (300 g), made alkaline (pH 7-8) with 2 N aq. NaOH, extracted with EtOAc, the extracts were washed with brine, dried (MgSO$_4$), and concentrated. The crude product was purified by flash chromatography on silica gel using 10% MeOH/CHCl$_3$ as eluent. Recrystallization by dissolving yellow solid in hot MeOH and pouring onto cold water afforded 1 (3.9 g, 75% yield) as a white solid. Mp 242-243° C. $^1$H NMR (300 MHz, MeOH-d$_4$): δ 9.95 (s, 1H), 8.48 (bs, 1H), 8.22 (s, 1H), 7.63 (d, 8.5 Hz, 1H), 7.53 (dd, 8.5, 1.7 Hz, 1H). MS m/z: 212 (M−1). Analysis calcd. for C$_{10}$H$_6$NOF$_3$; C, 56.35; H, 2.84, N, 6.57; found, C, 56.60; H, 2.92; N, 6.55.

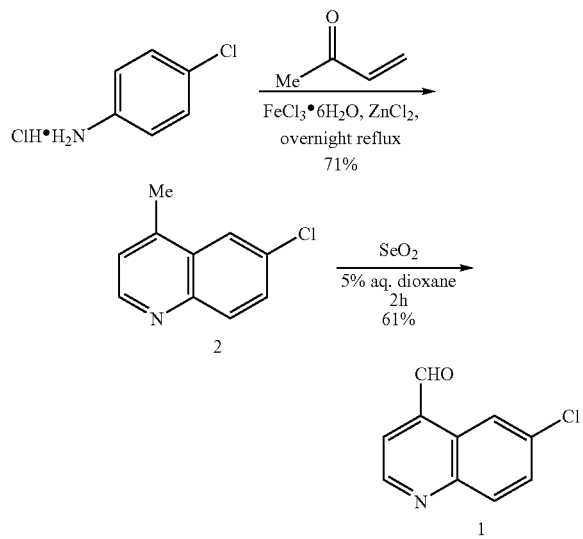

Examples 329

6-Chloro-4-methyl-quinoline (2): A 3 neck round bottom flask equipped with reflux condenser and stirrer was charged with 4-chloro-anilne.HCl salt (26.2 g, 160 mmol), FeCl$_3$.6H$_2$O (69.1 g, 256 mmol), and ZnCl$_2$ (2.54 g, 18.7 mmol) in 95% EtOH (200 mL) under N$_2$ atmosphere. The reaction mixture was heated to an internal temperature of 60° C. after which methylvinylketone (10.6 mL, 128 mmol) was added dropwise over 1 h. The mixture was refluxed overnight. The solvent was removed in vacuo and the black slurry was made alkaline with 25% aq. NaOH (400 mL). The product was extracted with ethyl acetate till no more florescence to the organic layer on TLC was observed. The combined organic extracts were dried over MgSO$_4$, filtered, and concentrated. Purification of the crude product by flash chromatography using 30% EtOAc/hexanes as eluent gave 2 (16.0 g, 71% yield) as a light brown solid. $^1$H NMR (300 MHz, CDCl$_3$): δ 8.77 (d, 3.6 Hz, 1H), 8.04 (d, 9.1 Hz, 1H), 7.97 (d, 2.2 Hz, 1H), 7.64 (dd, 9.1, 2.2 Hz, 1H), 7.26 (dd, 3.6, 0.8 Hz, 1H), 2.68 (s, 3H).[1]

Examples 330

6-Chloro-quinoline-4-carbaldehyde (1): A solution of 2 (16.04 g, 90.6 mmol) and SeO$_2$ (13.0 g, 117.3 mmol) in 5% aq. 1,4-dioxane (200 mL) was refluxed for 2 h. The precipitated selenium was filtered off and the filtrate was evaporated to dryness in vacuo. The residue was taken into CH$_2$Cl$_2$, and filtered through a short plug of silica gel. The filtrate was concentrated to give a light brown solid. Further purification by crystallization (EtOAc/Hexanes) gave 1 (11.6 g, 61%) as a pale yellow solid Mp 152-153° C. (lit.[2] 153-154° C). $^1$H NMR (300 MHz, CDCl$_3$): δ 10.43 (s, 1H), 9.20 (d, 4.4 Hz, 1H), 9.10 (d, 2.2 Hz, 1H), 8.16 (d, 9.1 Hz, 1H), 7.82 (d, 4.4 Hz, 1H), 7.77 (dd, 9.1, 2.2 Hz, 1H). MS m/z: 192 (M+1). Analysis calcd. for C$_{10}$H$_6$ClNO; C, 62.68; H, 3.16; N, 7.31; Cl, 18.50; found, C, 62.92; H, 3.33; N, 7.23; Cl, 18.60.[2]

Ref: 1. Campbell, K. N.; Sommers, A. H.; Kerwin, J. F.; Campbell, B. K. *J. Am. Chem. Soc.* 1945, 67, 86-89.

2. Jones, D. H.; Slack, R.; Squres, S.; Wooldridge, K. R. H. *J. Med. Chem.* 1965, 8, 676-680.

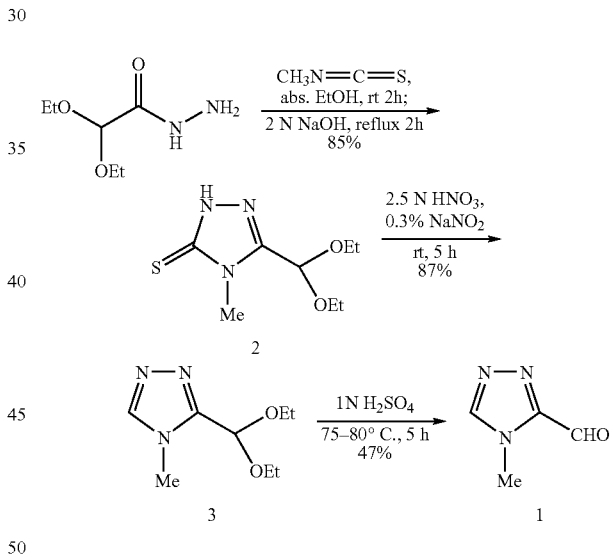

Examples 331

5-Diethoxymethyl-4-methyl-2,4-dihydro-[1,2,4]triazole-3-thione (2): A mixture of diethoxyacetic acid hydrazide[1] (13.36 g, 82.5 mmol) and methyl isocyanate (5.57 mL, 82.0 mmol) in absolute EtOH (100 mL) was allowed to stir at room temperature under N$_2$ atmosphere. After 2 h 2N aq. NaOH (150 mL) was added and the reaction mixture was refluxed for 2 h. The reaction mixture was then cooled to 0° C. and acidified with 6 N HCl (35 mL). The resulting solution was then extracted with CH$_2$Cl$_2$ (3×150 mL), dried over MgSO$_4$, filtered and concentrated to give 2 (15.15 g, 85% yield) as a yellow oil. $^1$H NMR (300 MHz, CDCl$_3$): δ 5.39 (s, 1H), 3.72 (m, 2H), 3.67 (s, 3H), 3.56 (m, 2H), 1.25 (t, 7.1 Hz, 6H).[2]

Examples 332

5-Diethoxymethyl-4-methyl-4H-[1,2,4]triazole (3): A solution of NaNO$_2$ (0.4 g, 5.7 mmol) in 2.5 N aq. HNO$_3$ (150 mL) was added to 2 (15.15, 70.5 mmol) at 0° C. in a dropwise manner over 1 h with constant stirring. The reaction mixture was warmed to room temperature and stirred for 4 h (monitored by TLC), then cooled to 0° C. and neutralized with 10 N NaOH. The resulting solution was extracted with CH$_2$Cl$_2$ (3×150 mL), dried over MgSO$_4$, filtered, and concentrated in vacuo to give 3 (11.3 g, 87%) as a yellow oil. $^1$H NMR (300 MHz, CDCl$_3$): δ 8.04 (s, 1H), 5.67 (s, 1H), 3.79 (m, 2H), 3.78 (s, 3H), 3.56 (m, 2H), 1.25 (t, 7.1 Hz, 6H).[2]

Examples 333

4-Methyl-4H-[1,2,4]triazole-3-carbaldehyde (1): A solution of 3 (11.4 g, 61.3 mmol) in 1N aq. H$_2$SO$_4$ (240 mL) was heated at 70-75° C. for 4 h (monitored by TLC). The mixture was cooled to 0° C. and neutralized with solid NaHCO$_3$. The resulting solution was saturated with NaCl and extracted with t-BuOH:CH$_2$Cl$_2$ (38:62, 3×150 mL). The combined organic extracts were dried over MgSO$_4$, filtered and concentrated. The residue obtained was purified by chromatography using 5% MeOH/CHCl$_3$ as an eluent to give 1 (3.21 g, 47% yield) as a white solid. Mp 101-102° C. (lit.[2] 103-104° C.); $^1$H NMR (300 MHz, CDCl$_3$): δ 10.15 (s, 1H), 8.27 (s, 1H), 4.01 (s, 3H). MS m/z: 112 (M+1). Analysis calcd. for C$_4$H$_5$N$_3$O; C, 43.24; H, 4.54; N, 37.82; found, C, 43.39; H, 4.61; N, 37.60.[2]

Ref: 1. Khorshidi, H. S.; Rodrigez, A. C.; *Nucleosides Nucleotides* 1994, 13, 1809-1818.

2. Moderhack, D.; Hoppe-Tichy, T. *J. Prakt. Chem.* 1996, 338, 169.171.

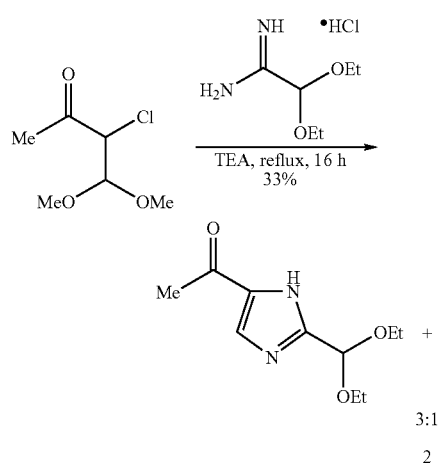

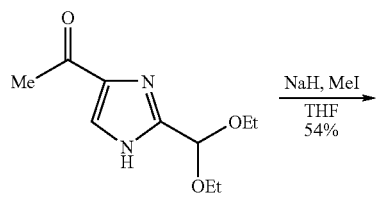

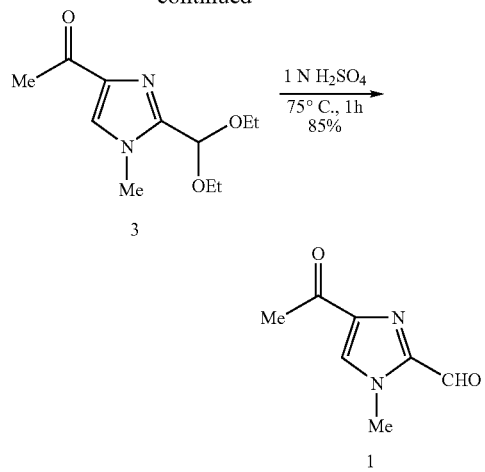

Examples 334

1-(2-Diethoxylethyl-3H-imidazole-4-yl)-ethanone (2): A mixture of 3-chloro-4,4-dimethoxy butan-2-one[1] (7.27 g, 43.5 mmol), diethoxyacetamidine.HCl salt[2] (18.2 g, 100 mmol) and triethylamine (30.0 mL, 216 mmol) in dry THF (200 mL) was refluxed for 60 h (monitored by $^1$H NMR) under N$_2$ atmosphere. The mixture was then filtered through celite, washed with ethyl acetate, and concentrated. The crude product was purified by flash chromatography on silica gel with 40-60% EtOAc/hexanes gradient to give 2 (3.01 g, 33% yield) as a yellow solid. $^1$H NMR (300 MHz, CDCl$_3$), 3:1 mixture of 1H:3H isomers: δ 10.05 (bs, 1H), 7.70, 7.67 (2s, 1H), 5.61, 5.59 (2s, 1H), 3.63 (m, 4H), 2.57 (2s, 3H), 1.25 (2t, 7.1 Hz, 6H). MS m/z: 213 (M+1, 20%), 167 (-EtOH, 100%).

Examples 335

1-(2-Diethoxymethyl-3-methyl-imidazole-4-yl)-ethanone (3): To a suspension of NaH (993 mg, 24.8 mmol, 60% suspension in mineral oil, washed with pentane) in THF (25 mL) at 0° C. under N$_2$ atmosphere was added a solution of 2 (3.51 g, 16.6 mmol) in THF (40 mL) in a dropwise manner over 30 min. Methyl iodide (1.13 mL, 18.2 mmol) was added after 20 min and the reaction mixture was allowed to warm to room temperature and stirred for 4 h (monitored by TLC). The mixture was then cooled back to 0° C., quenched by adding sat. NH$_4$Cl diluted with CHCl$_3$ (200 mL), filtered through celite, and the filtrate was concentrated. The crude product was purified by flash chromatography on silica gel with 40-60% EtOAc/hexanes gradient to give 3 (2.0 g, 54%) as a colorless oil. $^1$H NMR (300 MHz, CDCl$_3$): δ 7.51 (s, 1H), 5.49 (s, 1H), 3.82 (s, 3H), 3.77 (m, 2H), 3.56 (m, 2H), 2.51 (s, 3H), 1.24 (t, 7.1 Hz, 3H). MS m/z: 227 (M+1, 100%), 181 (-EtOH, 80%).

Examples 336

1-(2-carbaldehyde-imidazole-4-yl)-ethanone (1): The compound 3 (2.49 g, 11.0 mmol) was dissolved in 1N H$_2$SO$_4$ (20 mL) and was heated at 75-80° C. for 1 h (monitored by TLC). The reaction mixture was cooled to 0° C., quenched with solid NaHCO$_3$, extracted with CHCl$_3$ (3×75 mL), dried over MgSO$_4$, and concentrated. The crude product was purified by flash chromatography on silica gel with 40-50% EtOAc/hexanes gradient to give 1 (1.43 g, 85% yield) as a white solid. Mp 162-163° C. $^1$H NMR (300 MHz, CDCl$_3$): δ 9.85 (d, 0.8 Hz, 1H), 7.69 (s, 1H), 4.05 (s, 3H), 2.59 (s, 3H). $^{13}$C NMR (75 MHz, CDCl$_3$): δ 194.0, 182.4, 143.1, 142.9, 129.6, 35.7, 26.4. MS m/z: 153 (M+1).). Analysis calcd. for C$_7$H$_8$N$_2$O$_2$; C, 55.26; H, 5.30; N, 18.41; found, C, 55.50; H, 5.42; N, 18.49.

Ref: 1. Reiter, L. A. *J. Org. Chem.* 1984, 49(19), 3494-3498

2. Schaefer, F. C.; Peters, G. A. *J. Org. Chem.* 1961, 26, 412-418.

Other compounds that have been made by the above procedures are:

(5-{2-[(1-benzyl-1H-indol-3-yl)methyl]-7-isobutyl-5-methyl-4,6-dioxo-4,5,6,7-tetrahydro-2H-pyrazolo[3,4-d]pyrimidin-3-yl}-2-furyl)methyl acetate, (5-{2-[(4'-fluoro-1,1'-biphenyl-2-yl)methyl]-7-isobutyl-5-methyl-4,6-dioxo-4,5,6,7-tetrahydro-2H-pyrazolo[3,4-d]pyrimidin-3-yl}-2-furyl)methyl acetate, (5-{2-[2-(benzyloxy)benzyl]-7-isobutyl-5-methyl-4,6-dioxo-4,5,6,7-tetrahydro-2H-pyrazolo[3,4-d]pyrimidin-3-yl}-2-furyl)methyl acetate, (5-{7-isobutyl-2-[3-(4-methoxyphenoxy)benzyl]-5-methyl-4,6-dioxo-4,5,6,7-tetrahydro-2H-pyrazolo[3,4-d]pyrimidin-3-yl}-2-furyl)methyl acetate, (5-{7-isobutyl-5-methyl-2-[(1-methyl-1H-indol-3-yl)methyl]-4,6-dioxo-4,5,6,7-tetrahydro-2H-pyrazolo[3,4-d]pyrimidin-3-yl}-2-furyl)methyl acetate, (5-{7-isobutyl-5-methyl-2-[(2Z)-5-methyl-2-phenyl-2-hexenyl]4,6-dioxo-4,5,6,7-tetrahydro-2H-pyrazolo[3,4-d]pyrimidin-3-yl}-2-furyl)methyl acetate, (5-{7-isobutyl-5-methyl-4,6-dioxo-2-[(2Z)-2-phenyl-2-pentenyl]-4,5,6,7-tetrahydro-pyrazolo[3,4-d]pyrimidin-3-yl}-2-furyl)methyl acetate, (5-{7-isobutyl-5-methyl-4,6-dioxo-2-[(3-phenyl-1H-pyrazol-4-yl)methyl]-4,5,6,7-tetrahydro-2H-pyrazolo[3,4-d]pyrimidin-3-yl}-2-furyl)methyl acetate,

[5-methyl-2-(1-naphthylmethyl)-4,6-dioxo-3-(4-pyridinyl)-2,4,5,6-tetrahydro-7H-pyrazolo[3,4-d]pyrimidin-7-yl]acetonitrile,

[5-methyl-2-(1-naphthylmethyl)-4,6-dioxo-3-(4-pyridinyl)-2,4,5,6-tetrahydro-7H-pyrazolo[3,4-d]pyrimidin-7-yl] acetic acid, 2-(1-benzothien-3-ylmethyl)-3-[3-(2-hydroxyethoxy)phenyl]-7-isobutyl-5-methyl-2H-pyrazolo[3,4-d]pyrimidine-4,6(5H,7H)-dione, 2-(1-benzothien-3-ylmethyl)-3-cyclohexyl-7-isobutyl-5-methyl-2H-pyrazolo[3,4-d]pyrimidine-4,6(5H,7H)-dione, 2-(1-benzothien-3-ylmethyl)-7-isobutyl-5-methyl-3-(1-methyl-1H-imidazol-2-yl)-2H-pyrazolo[3,4-d]pyrimidine-4,6(5H,7H)-dione, 2-(1-benzothien-3-ylmethyl)-7-isobutyl-5-methyl-3-(1-methyl-1H-pyrrol-2-yl)-2H-pyrazolo[3,4-d]pyrimidine-4,6(5H,7H)-dione, 2-(1-benzothien-3-ylmethyl)-7-isobutyl-5-methyl-3-(4-methyl-1H-imidazol-5-yl)-2H-pyrazolo[3,4-d]pyridine-4,6(5H,7H)-dione, 2-(1H-indol-4-ylmethyl)-7-isobutyl-5-methyl-3-(4-pyridinyl)-2H-pyrazolo[3,4-d]pyrimidine-4,6(5H,7H)-dione, 2-(1H-indol-7-ylmethyl)-7-isobutyl-5-methyl-3-(4-pyridinyl)-2H-pyrazolo[3,4-d]pyrimidine-4,6(5H,7H)-dione, 2-(2,3-dichlorobenzyl)-3-[3-(2-hydroxyethoxy)phenyl]-7-isobutyl-5-methyl-2H-pyrazolo[3,4-d]pyrimidine-4,6(5H,7H)-dione, 2-(2,3-dichlorobenzyl)-7-isobutyl-3,5-dimethyl-2H-pyrazolo[3,4-d]pyrimidine-4,6(5H, 7H)-dione, 2-(2,3-dichlorobenzyl)-7-isobutyl-5-methyl-3-(1-methyl-1H-imidazol-2-yl)-2H-pyrazolo[3,4-d]pyrimidine-4,6(5H,7H)-dione, 2-(2,3-dichlorobenzyl)-7-isobutyl-5-methyl-3-(4-methyl-1H-imidazol-5-yl)-2H-pyrazolo[3,4-d]pyrimidine-4,6(5H,7H)-dione, 2-(2,3-difluorobenzyl)-7-isobutyl-5-methyl-3-(4-pyridinyl)-2H-pyrazolo[3,4-d]pyrimidine-4,6(5H,7H)-dione, 2-(2,4-dimethylbenzyl)-7-isobutyl-5-methyl-3-(4-pyridinyl)-2H-pyrazolo[3,4-d]pyrimidine-4,6(5H,7H)-dione, 2-(3,5-dichlorobenzyl)-3-[3-(2-hydroxyethoxy)phenyl]-7-isobutyl-5-methyl-2H-pyrazolo[3,4-d]pyrimidine-4,6(5H,7H)-dione, 2-(3,5-dichlorobenzyl)-7-isobutyl-3,5-dimethyl-2H-pyrazolo[3,4-d]pyrimidine-4,6(5H,7H)-dione, 2-(3,5-dichlorobenzyl)-7-isobutyl-5-methyl-3-(1,3-thiazol-5-yl)-2H-pyrazolo[3,4-d]pyrimidine-4,6(5H,7H)-dione, 2-(3,5-dichlorobenzyl)-7-isobutyl-5-methyl-3-(1-methyl-1H-imidazol-2-yl)-2H-pyrazolo[3,4-d]pyrimidine-4,6(5H,7H)-dione, 2-(3,5-dichlorobenzyl)-7-isobutyl-5-methyl-3-(2-methyl-2H-isoindol-1-yl)-2H-pyrazolo[3,4-d]pyrimidine-4,6(5H,7H)-dione, 2-(3,5-dichlorobenzyl)-7-isobutyl-5-methyl-3-(4-methyl-1H-imidazol-5-yl)-2H-pyrazolo[3,4-d]pyrimidine-4,6(5H,7H)-dione, 2-(3,5-difluorobenzyl)-7-isobutyl-5-methyl-3-(4-pyridinyl)-2H-pyrazolo[3,4-d]pyrimidine-4,6(5H,7H)-dione, 2-(3-{3-[benzyl(methyl)amino]-1-propynyl}benzyl)-7-isobutyl-5-methyl-3-(4-pyridinyl)-2H-pyrazolo[3,4-d]pyrimidine-4,6(5H,7H)-dione, 2-(3-aminobenzyl)-7-isobutyl-5-methyl-2H-pyrazolo[3,4-d]pyrimidine-4,6(5H,7H)-dione, 2-(3-benzoylbenzyl)-3-[(3-hydroxypropyl)thio]-7-isobutyl-5-methyl-2H-pyrazolo[3,4-d]pyrimidine-4,6(5H,7H)-dione, 2-(3-bromobenzyl)-7-isobutyl-5-methyl-3-(4-pyridinyl)-2H-pyrazolo[3,4-d]pyrimidine-4,6(5H,7H)-dione, 2-(3-fluoro-2-methylbenzyl)-7-isobutyl-5-methyl-3-(4-pyridinyl)-2H-pyrazolo[3,4-d]pyrimidine-4,6(5H,7H)-dione, 2-(3-iodobenzyl)-7-isobutyl-5-methyl-3-(1-methyl-1H-imidazol-2-yl)-2H-pyrazolo[3,4-d]pyrimidine-4,6(5H,7H)-dione, 2-(3-iodobenzyl)-7-isobutyl-5-methyl-3-(4-pyridinyl)-2H-pyrazolo[3,4-d]pyrimidine-4,6(5H,7H)-dione, 2-[(1-benzyl-1H-indol-3-yl)methyl]-3-(4-chloro-1-methyl-1H-pyrazol-3-yl)-7-isobutyl-5-methyl-2H-pyrazolo[3,4-d]pyrimidine-4,6(5H,7H)-dione, 2-[(1-benzyl-1H-indol-3-yl)methyl]-3-[3-(2-hydroxyethoxy)phenyl]-7-isobutyl-5-methyl-2H-pyrazolo[3,4-d]pyrimidine-4,6(5H,7H)-dione, 2-[(1-benzyl-1H-indol-3-yl)methyl]-7-isobutyl-5-methyl-3-(1-methyl-1H-pyrrol-2-yl)-2H-pyrazolo[3,4-d]pyrimidine-4,6(5H,7H)-dione, 2-[(4'-fluoro-1,1'-biphenyl-2-yl)methyl]-7-isobutyl-5-methyl-3-(1-methyl-1H-imidazol-2-yl)-2H-pyrazolo[3,4-d]pyrimidine-4,6(5H,7H)-dione, 2-[(4'-fluoro-1,1'-biphenyl-2-yl)methyl]-7-isobutyl-5-methyl-3-(1-methyl-1H-pyrrol-2-yl)-2H-pyrazolo[3,4-d]pyrimidine-4,6(5H,7H)-dione, 2-[(4'-fluoro-1,1'-biphenyl-2-yl)methyl]-7-isobutyl-5-methyl-3-(4-pyridinyl)-2H-pyrazolo[3,4-d]pyrimidine-4,6(5H,7H)-dione, 2-[2-(allyloxy)benzyl]-3-cyclohexyl-7-isobutyl-5-methyl-2H-pyrazolo[3,4-d]pyrimidine-4,6(5H,7H)-dione, 2-[2-(allyloxy)benzyl]-7-isobutyl-3,5-dimethyl-2H-pyrazolo[3,4-d]pyrimidine-4,6(5H,7H)-dione, 2-[2-(allyloxy)benzyl]-7-isobutyl-5-methyl-3-(1,3-thiazol-2-yl)-2H-pyrazolo[3,4-d]pyrimidine-4,6(5H,7H)-dione, 2-[2-(allyloxy)benzyl]-7-isobutyl-5-methyl-3-(1-methyl-1H-imidazol-2-yl)-2H-pyrazolo[3,4-d]pyrimidine-4,6(5H,7H)-dione, 2-[2-(allyloxy)benzyl]-7-isobutyl-5-methyl-3-(1-methyl-1H-pyrrol-2-yl)-2H-pyrazolo[3,4-d]pyrimidine-4,6(5H,7H)-dione, 2-[2-(allyloxy)benzyl]-7-isobutyl-5-methyl-3-(4-methyl-1H-imidazol-5-yl)-2H-pyrazolo[3,4-d]pyrimidine-4,6(5H,7H)-dione, 2-[2-(benzyloxy)benzyl]-3-(4-chloro-1-methyl-1H-pyrazol-3-yl)-7-isobutyl-5-methyl-2H-pyrazolo[3,4-d]pyrimidine-4,6(5H,7H)-dione, 2-[2-(benzyloxy)benzyl]-7-isobutyl-5-methyl-3-(1-methyl-1H-imidazol-2-yl)-2H-pyrazolo[3,4-d]pyrimidine-4,6(5H,7H)-dione, 2-[2-(benzyloxy)benzyl]-7-isobutyl-5-methyl-3-(4-pyridinyl)-2H-pyrazolo[3,4-d]pyrimidine-4,6(5H,7H)-dione, 2-[2-fluoro-3-(trifluoromethyl)benzyl]-7-isobutyl-5-methyl-3-(4-pyridinyl)-2H-pyrazolo[3,4-d]pyrimidine-4,6(5H,7H)-dione, 2-[3-(3-hydroxy-1-butynyl)benzyl]-7-isobutyl-5-methyl-3-(4-pyridinyl)-2H-pyrazolo[3,4-d]pyrimidine-4,6(5H,7H)-dione, 2-[3-(3-hydroxy-3-phenyl-1-propynyl)benzyl]-7-isobutyl-5-methyl-3-(4-pyridinyl)-2H-pyrazolo[3,4-d]pyrimidine-4,6(5H,7H)-dione, 2-[5-methyl-2-(1-naphthylmethyl)-4,6-dioxo-3-(4-pyridinyl)-2,4,5,6-tetrahydro-7H-pyrazolo[3,4-d]pyrimidin-7-yl]butanenitrile, 2-[5-methyl-2-(1-naphthylmethyl)-4,6-dioxo-3-(4-pyridinyl)-2,4,5,6-tetrahydro-7H-pyrazolo[3,4-d]pyrimidin-7-yl]acetamide, 2-[7-isobutyl-2-(1-naphthylmethyl)-4,6-dioxo-3-(4-pyridinyl)-2,4,6,7-tetrahydro-5H-pyrazolo[3,4-d]pyrimidin-5-yl]acetamide, 2-[7-isobutyl-5-methyl-2-(1-naphthylmethyl)-4,6-dioxo-4,5,6,7-tetrahydro-2H-pyrazolo[3,4-d]pyrimidin-3-yl]benzoic acid, 2-{3-[(3E)-5-hydroxy-3-penten-1-ynyl]benzyl}-7-isobutyl-5-methyl-3-(4-pyridinyl)-2H-pyrazolo[3,4-d]pyrimidine-4,6(5H,7H)-dione, 2-{3-[3-(1,3-dioxo-1,3-dihydro-2H-isoindol-2-yl)-1-propynyl]benzyl}-7-isobutyl-5-methyl-3-(1-methyl-1H-imidazol-2-yl)-2H-pyrazolo[3,4-d]pyrimidine-4,6(5H,7H)-dione, 2-{3-[3-(1,3-dioxo-1,3-dihydro-2H-isoindol-2-yl)-1-propynyl]benzyl}-7-isobutyl-5-methyl-3-(4-pyridinyl)-2H-pyrazolo[3,4-d]pyrimidine-4,6(5H,7H)-dione, 2-{3-[3-(1H-1,2,3-benzotrazol-1-yl)-1-propynyl]benzyl}-7-isobutyl-5-methyl-3-(4-pyridinyl)-2H-pyrazolo[3,4-d]pyrimidine-4,6(5H,7H)-dione, 2-{3-[3-(dimethylamino)-1-propynyl]benzyl}-7-isobutyl-5-methyl-3-(4-pyridinyl)-2H-pyrazolo[3,4-d]pyrimidine-4,6(5H,7H)-dione, 2-benzyl-7-isobutyl-5-methyl-3-(4-pyridinyl)-2H-pyrazolo[3,4-d]pyrimidine-4,6(5H,7H)-dione, 3-(1,3-benzodioxol-4-yl)-2-(2,3-dichlorobenzyl)-7-isobutyl-5-methyl-2H-pyrazolo[3,4-d]pyrimidine-4,6(5H,7H)-dione, 3-(1,3-benzodioxol-4-yl)-2-(3,5-dichlorobenzyl)-7-isobutyl-5-methyl-2H-pyrazolo[3,4-d]pyrimidine-4,6(5H,7H)-dione, 3-(1,3-benzodioxol-4-yl)-7-isobutyl-5-methyl-2-(4-quinolinylmethyl)-2H-pyrazolo[3,4-d]pyrimidine-4,6(5H,7H)-dione, 3-(1,5-dihydroxypentyl)-5-methyl-7-(2-methyl-2-propenyl)-2-(1-naphthylmethyl)-2H-pyrazolo[3,4-d]pyrimidine-4,6(5H,7H)-dione, 3-(1-benzyl-1H-imidazol-2-yl)-7-isobutyl-5-methyl-2-(1-naphthylmethyl)-2H-pyrazolo[3,4-d]pyrimidine-4,6(5H,7H)-dione, 3-(1H-imidazol-2-yl)-7-isobutyl-5-methyl-2-(1-naphthylmethyl)-2H-pyrazolo[3,4-d]pyrimidine-4,6(5H,7H)-dione, 3-(2,2-difluoro-1,3-benzodioxol-5-yl)-7-isobutyl-5-methyl-2-(1-naphthylmethyl)-2H-pyrazolo[3,4-d]pyrimidine-4,6(5H,7H)-dione, 3-(2-ethyl-4-methyl-1H-imidazol-5-yl)-7-isobutyl-5-methyl-2-(1-naphthylmethyl)-2H-pyrazolo[3,4-d]pyrimidine-4,6(5H,7H)-dione, 3-(3-aminophenyl)-2-[(1-benzyl-1H-indol-3-yl)methyl]-7-isobutyl-5-methyl-2H-pyrazolo[3,4-d]pyrimidine-4,6(5H,7H)-dione, 3-(3-aminophenyl)-7-isobutyl-2-[3-(4-methoxyphenoxy)benzyl]-5-methyl-2H-pyrazolo[3,4-d]pyrimidine-4,6(5H,7H)-dione, 3-(3-aminophenyl)-7-isobutyl-5-methyl-2-[(2Z)-2-phenyl-2-pentenyl]-2H-pyrazolo[3,4-d]pyrimidine-4,6(5H,7H)-dione, 3-(3-aminophenyl)-7-isobutyl-5-methyl-2-[(2Z)-5-methyl-2-phenyl-2-hexenyl]-2H-pyrazolo[3,4-d]pyrimidine-4,6(5H,7H)-dione, 3-(3-aminophenyl)-7-isobutyl-5-methyl-2-[(4-phenyl-1H-pyrazol-3-yl)methyl]-2H-pyrazolo[3,4-d]pyrimidine-4,6(5H,7H)-dione, 3-(3-chlorophenyl)-7-isobutyl-5-methyl-2-(1-naphthylmethyl)-2H-pyrazolo[3,4-d]pyrimidine-4,6(5H,7H)-dione, 3-(3-fluorophenyl)-7-isobutyl-5-methyl-2-(1-naphthylmethyl)-2H-pyrazolo[3,4-d]pyrimidine-4,6(5H,7H)-dione, 3-(3-hydroxyphenyl)-7-isobutyl-5-methyl-2-(1-naphthylmethyl)-2H-pyrazolo[3,4-d]pyrimidine-4,6(5H,7H)-dione, 3-(4-butoxyphenyl)-7-isobutyl-5-methyl-2-(1-naphthylmethyl)-2H-pyrazolo[3,4-d]pyrimidine-4,6(5H,7H)-dione, 3-(4-chloro-1-methyl-1H-pyrazol-3-yl)-2-[(4'-fluoro-1,1'-biphenyl-2-yl)methyl]-7-isobutyl-5-methyl-2H-pyrazolo[3,4-d]pyrimidine-4,6(5H,7H)-dione, 3-(4-chloro-1-methyl-1H-pyrazol-3-yl)-7-isobutyl-2-[3-(4-methoxyphenoxy)benzyl]-5-methyl-2H-pyrazolo[3,4-d]pyrimidine-4,6(5H,7H)-dione, 3-(4-chloro-1-methyl-1H-pyrazol-3-yl)-7-isobutyl-5-methyl-2-[(1-methyl-1H-indol-3-yl)methyl]-2H-pyrazolo[3,4-d]pyrimidine-4,6(5H,7H)-dione, 3-(4-chloro-1-methyl-1H-pyrazol-3-yl)-7-isobutyl-5-methyl-2-[(2Z)-2-phenyl-2-pentenyl]-2H-pyrazolo[3,4-d]pyrimidine-4,6(5H,7H)-dione, 3-(4-chloro-1-methyl-1H-pyrazol-3-yl)-7-isobutyl-5-methyl-2-[(2Z)-5-methyl-2-phenyl-2-hexenyl]-2H-pyrazolo[3,4-d]pyrimidine-4,6(5H,7H)-dione, 3-(4-chloro-1-methyl-4H-1lamda~5~-pyrazol-3-yl)-isobutyl-5-methyl-2-[(3-phenyl-1H-pyrazol-4-yl)methyl)-]2H-pyrazolo[3,4-d]pyrimidine-4,6(5H,7H)-dione, 3-(4-fluorophenyl)-7-isobutyl-5-methyl-2-(1-naphthylmethyl)-2H-pyrazolo[3,4-d]pyrimidine-4,6(5H,7H)-dione, 3-(4-hydroxybutyl)-7-isobutyl-5-methyl-2-(1-naphthylmethyl)-2H-pyrazolo[3,4-d]pyrimidine-4,6(5H,7H)-dione, 3-(4-hydroxyphenyl)-7-isobutyl-5-methyl-2-(1-naphthylmethyl)-2H-pyrazolo[3,4-d]pyrimidine-4,6(5H,7H)-dione, 3-(benzylthio)-7-isobutyl-5-methyl-2-(1-naphthylmethyl)-2H-pyrazolo[3,4-d]pyrimidine-4,6(5H,7H)-dione,
3-[(3-hydroxypropyl)thio]-7-isobutyl-5-methyl-2-(1-naphthylmethyl)-2H-pyrazolo[3,4-d]pyrimidine-4,6(5H,7H)-dione,
3-[(3-hydroxypropyl)thio]-7-isobutyl-5-methyl-2-(2-quinolinylmethyl)-2H-pyrazolo[3,4-d]pyrimidine-4,6(5H,7H)-dione,
3-[(3-hydroxypropyl)thio]-7-isobutyl-5-methyl-2-{2-[(phenylsulfonyl)methyl]benzyl}-2H-pyrazolo[3,4-d]pyrimidine-4,6(5H,7H)-dione,
3-[2-(1-benzothien-3-ylmethyl)-7-isobutyl-5-methyl-4,6-dioxo-4,5,6,7-tetrahydro-2H-pyrazolo[3,4-d]pyrimidin-3-yl]benzoic acid,
3-[2-(2,3-dichlorobenzyl)-7-isobutyl-5-methyl-4,6-dioxo-4,5,6,7-tetrahydro-2H-pyrazolo[3,4-d]pyrimidin-3-yl]benzoic acid,
3-[3-(2-hydroxyethoxy)phenyl]-7-isobutyl-2-[(2-methoxy-1-naphthyl)methyl]-5-methyl-2H-pyrazolo[3,4-d]pyrimidine-4,6(5H,7H)-dione,
3-[3-(2-hydroxyethoxy)phenyl]-7-isobutyl-2-[3-(4-methoxyphenoxy)benzyl]-5-methyl-2H-pyrazolo[3,4-d]pyrimidine-4,6(5H,7H)-dione,
3-[3-(2-hydroxyethoxy)phenyl]-7-isobutyl-5-methyl-2-(1-naphthylmethyl)-2H-pyrazolo[3,4-d]pyrimidine-4,6(5H,7H)-dione,
3-[3-(2-hydroxyethoxy)phenyl]-7-isobutyl-5-methyl-2-(4-quinolinylmethyl)-2H-pyrazolo[3,4-d]pyrimidine-4,6(5H,7H)-dione,
3-[3-(2-hydroxyethoxy)phenyl]-7-isobutyl-5-methyl-2-[(2Z)-5-methyl-2-phenyl-2-hexenyl]-2H-pyrazolo[3,4-d]pyrimidine-4,6(5H,7H)-dione,
3-[3-(2-hydroxyethoxy)phenyl]-7-isobutyl-5-methyl-2-[(3-phenyl-1H-pyrazol-4-yl)methyl]-2H-pyrazolo[3,4-d]pyrimidine-4,6(5H,7H)-dione,
3-[4-(dimethylamino)phenyl]-7-isobutyl-5-methyl-2-(1-naphthlyhmethyl)-2H-pyrazolo[3,4-d]pyrimidine-4,6(5H,7H)-dione,
3-[5,7-dimethyl-2-(1-naphthylmethyl)-4,6-dioxo-4,5,6,7-tetrahydro-2H-pyrazolo[3,4-d]pyrimidin-3-yl]benzoic acid,
3-[5-methyl-2-(1-naphthylmethyl)-4,6-dioxo-4,5,6,7-tetrahydro-2H-pyrazolo[3,4-d]pyrimidin-3-yl]benzoic acid,
3-[5-methyl-2-(1-naphthylmethyl)-4,6oxo-7-(2-phenoxyethyl)-4,5,6,7-tetrahydro-2H-pyrazolo[3,4-d]pyridin-3-yl]benzoic acid,
3-[5-methyl-2-(1-naphthylmethyl)-4,6-dioxo-7-(2-phenylpropyl)-4,5,6,7-tetrahydro-2H-pyrazolo[3,4-d]pyrimidin-3-yl]benzoic acid,
3-[5-methyl-2-(1-naphthylmethyl)-4,6-dioxo-7-(3-pyridinylmethyl)-4,5,6,7-tetrahydro-2H-pyrazolo[3,4-d]pyrimidin-3-yl]benzoic acid,
3-[5-methyl-2-(1-naphthylmethyl)-4,6-dioxo-7-(3-thienylmethyl)-4,5,6,7-tetrahydro-2H-pyrazolo[3,4-d]pyrimidin-3-yl]benzoic acid,
3-[5-methyl-2-(1-naphthylmethyl)-4,6-dioxo-7-(tetrahydro-2-furanylmethyl)-4,5,6,7-tetrahydro-2H-pyrazolo[3,4-d]pyrimidin-3-yl]benzoic acid,
3-[5-methyl-2-(1-naphthylmethyl)-4,6-dioxo-7-(tetrahydro-2H-pyran-2-ylmethyl)-4,5,6,7-tetrahydro-2H-pyrazolo[3,4-d]pyrimidin-3-yl]benzoic acid,
3-[5-methyl-2-(1-naphthylmethyl)-4,6-dioxo-7-pentyl-4,5,6,7-tetrahydro-2H-pyrazolo[3,4-d]pyrimidin-3-yl]benzoic acid,
3-[5-methyl-2-(1-naphthylmethyl)-4,6-dioxo-7-propyl-4,5,6,7-tetrahydro-2H-pyrazolo[3,4-d]pyrimidin-3-yl]benzoic acid,
3-[5-methyl-7-(2-methylbenzyl)-2-(1-naphthylmethyl)-4,6-dioxo-4,5,6,7-tetrahydro-2H-pyrazolo[3,4-d]pyrimidin-3-yl]benzoic acid,
3-[5-methyl-7-(3-methylbenzyl)-2-(1-naphthylmethyl)-4,6-dioxo-4,5,6,7-tetrahydro-2H-pyrazolo[3,4-d]pyrimidin-3-yl]benzoic acid,
3-[5-methyl-7-[(6-methyl-2-pyridinyl)methyl]-2-(1-naphthylmethyl)-4,6-dioxo-4,5,6,7-tetrahydro-2H-pyrazolo[3,4-d]pyrimidin-3-yl]benzoic acid,
3-[5-methyl-7-[2-(4-methyl-1,3-thiazol-5-yl)ethyl]-2-(1-naphthylmethyl)-4,6-dioxo-4,5,6,7-tetrahydro-2H-pyrazolo[3,4-d]pyrimidin-3-yl]benzoic acid,
3-[7-(2,4-difluorobenzyl)-5-methyl-2-(1-naphthylmethyl)-4,6-dioxo-4,5,6,7-tetrahydro-2H-pyrazolo[3,4-d]pyrimidin-3-yl]benzoic acid,
3-[7-(2-bromobenzyl)-5-methyl-2-(1-naphthylmethyl)-4,6-dioxo-4,5,6,7-tetrahydro-2H-pyrazolo[3,4-d]pyrimidin-3-yl]benzoic acid,
3-[7-(2-chlorobenzyl)-5-methyl-2-(1-naphthylmethyl)-4,6-dioxo-4,5,6,7-tetrahydro-2H-pyrazolo[3,4-d]pyrimidin-3-yl]benzoic acid,
3-[7-(2-cyanoethyl)-5-methyl-2-(1-naphthylmethyl)-4,6-dioxo-4,5,6,7-tetrahydro-2H-pyrazolo[3,4-d]pyrimidin-3-yl]benzoic acid,
3-[7-(2-isopropoxyethyl)-5-methyl-2-(1-naphthylnethyl)-4,6-dioxo-4,5,6,7-tetrahydro-2H-pyrazolo[3,4-d]pyrimidin-3-yl]benzoic acid,
3-[7-(3,4-dimethylbenzyl)-5-methyl-2-(1-naphthylmethyl)-4,6-dioxo-4,5,6,7-tetrahydro-2H-pyrazolo[3,4-d]pyrimidin-3-yl]benzoic acid,
3-[7-(3-cyanobenzyl)-5-methyl-2-(1-naphthylmethyl)-4,6-dioxo-4,5,6,7-tetrahydro-2H-pyrazolo[3,4-d]pyrimidin-3-yl]benzoic acid,
3-[7-(3-cyclopentylpropyl)-5-methyl-2-(1-naphthylmethyl)-4,6-dioxo-4,5,6,7-tetrahydro-2H-pyrazolo[3,4-d]pyrimidin-3-yl]benzoic acid,
3-[7-(3-fluorobenzyl)-5-methyl-2-(1-naphthylmethyl)-4,6-dioxo-4,5,6,7-tetrahydro-2H-pyrazolo[3,4-d]pyrimidin-3-yl]benzoic acid,
3-[7-(4-butylbenzyl)-5-methyl-2-(1-naphthylmethyl)-4,6-dioxo-4,5,6,7-tetrahydro-2H-pyrazolo[3,4-d]pyrimidin-3-yl]benzoic acid,
3-[7-(4-chlorobenzyl)-5-methyl-2-(1-naphthylmethyl)-4,6-dioxo-4,5,6,7-tetrahydro-2H-pyrazolo[3,4-d]pyrimidin-3-yl]benzoic acid,
3-[7-(4-ethylbenzyl)-5-methyl-2-(1-naphthylmethyl)-4,6-dioxo-4,5,6,7-tetrahydro-2H-pyrazolo[3,4-d]pyrimidin-3-yl]benzoic acid,
3-[7-(cyclobutylmethyl)-5-methyl-2-(1-naphthylmethyl)-4,6-dioxo-4,5,6,7-tetrahydro-2H-pyrazolo[3,4-d]pyrimidin-3-yl]benzoic acid,
3-[7-(cyclohexylmethyl)-5-methyl-2-(1-naphthylmethyl)-4,6-dioxo-4,5,6,7-tetrahydro-2H-pyrazolo[3,4-d]pyrimidin-3-yl]benzoic acid,
3-[7-(cyclopropylmethyl)-5-methyl-2-(1-naphthylmethyl)-4,6-dioxo-4,5,6,7-tetrahydro-2H-pyrazolo[3,4-d]pyrimidin-3-yl]benzoic acid,
3-[7-[(3,5-dimethyl-4-isoxazolyl)methyl]-5-methyl-2-(1-naphthylmethyl)-4,6-dioxo-4,5,6,7-tetrahydro-2H-pyrazolo[3,4-d]pyrimidin-3-yl]benzoic acid,
3-[7-[(5-chloro-2-thienyl)methyl]-5-methyl-2-(1-naphthylmethyl)-4,6-dioxo-4,5,6,7-tetrahydro-2H-pyrazolo[3,4-d]pyrimidin-3-yl]benzoic acid,
3-[7-[2-(3-chlorophenyl)ethyl]-5-methyl-2-(1-naphthylmethyl)-4,6-dioxo-4,5,6,7-tetrahydro-2H-pyrazolo[3,4-d]pyrimidin-3-yl]benzoic acid, 3-[7-[2-(diethylamino)-2-oxoethyl]-5-methyl-2-(1-naphthylmethyl)-4,6-dioxo-4,5,6,7-tetrahydro-2H-pyrazolo[3,4-d]pyrimidin-3-yl]benzoic acid,
3-[7-[2-(isobutylthio)ethyl]-5-methyl-2-(1-naphthylmethyl)-4,6-dioxo-4,5,6,7-tetrahydro-2H-pyrazolo[3,4-d]pyrimidin-3-yl]benzoic acid,
3-[7-[2-(isonicotinoylamino)ethyl]-5-methyl-2-(1-naphthylmethyl)-4,6-dioxo-4,5,6,7-tetrahydro-2H-pyrazolo[3,4-d]pyrimidin-3-yl]benzoic acid,
3-[7-{2-[benzyl(methyl)amino]ethyl}-5-methyl-2-(1-naphthylmethyl)-4,6-dioxo-4,5,6,7-tetrahydro-2H-pyrazolo[3,4-d]pyrimidin-3-yl]benzoic acid,
3-[7-benzyl-5-methyl-2-(1-naphthylmethyl)-4,6-dioxo-4,5,6,7-tetrahydro-2H-pyrazolo[3,4-d]pyrimidin-3-yl]benzoic acid,
3-[7-isobutyl-5-methyl-2-(1-naphthylmethyl)-4,6-dioxo-4,5,6,7-tetrahydro-2H-pyrazolo[3,4-d]pyrimidin-3-yl]benzonitrile,
3-[7-isobutyl-5-methyl-2-(1-naphthylmethyl)-4,6-dioxo-4,5,6,7-tetrahydro-2H-pyrazolo[3,4-d]pyrimidin-3-yl]benzamide,
3-[7-isobutyl-5-methyl-2-(1-naphthylmethyl)-4,6-dioxo-4,5,6,7-tetrahydro-2H-pyrazolo[3,4-d]pyrimidin-3-yl]-N-methylbenzamide,
3-[7-isobutyl-5-methyl-2-(1-naphthylmethyl)-4,6-dioxo-4,5,6,7-tetrahydro-2H-pyrazolo[3,4-d]pyrimidin-3-yl]benzoic acid,
3-[7-isobutyl-5-methyl-2-(1-naphthylmethyl)-4,6-dioxo-4,5,6,7-tetrahydro-2H-pyrazolo[3,4-d]pyrimidin-3-yl]phenylboronic acid,
3-[7-isobutyl-5-methyl-4,6-dioxo-2-(4-quinolinylmethyl)-4,5,6,7-tetrahydro-2H-pyrazolo[3,4-d]pyrimidin-3-yl]benzoic acid,
3-[7-isopentyl-5-methyl-2-(1-naphthylmethyl)-4,6-dioxo-4,5,6,7-tetrahydro-2H-pyrazolo[3,4-d]pyrimidin-3-yl]benzoic acid,
3-[7-isopropyl-5-methyl-2-(1-naphthylmethyl)-4,6-dioxo-4,5,6,7-tetraydro-2H-pyrazolo[3,4-d]pyrimidin-3-yl]benzoic acid,
3-[hydroxy(phenyl)methyl]-7-isobutyl-5-methyl-2-(1-naphthylmethyl)-2H-pyrazolo[3,4-d]pyrimidine-4,6(5H,7H)-dione,
3-{[-isobutyl-5-methyl-4,6-dioxo-3-(4-pyridinyl)-4,5,6,7-tetrahydro-2H-pyrazolo[3,4-d]pyrimidin-2-yl]methyl}benzonitrile,
3-{2-[(4'-fluoro-1,1'-biphenyl-2-yl)methyl]-7-isobutyl-5-methyl-4,6-dioxo-4,5,6,7-tetrahydro-2H-pyrazolo[3,4-d]pyrimidin-3-yl}benzoic acid,
3-{2-[(4-fluoro-1-naphthyl)methyl]-7-isobutyl-5-methyl-4,6-dioxo-4,5,6,7-tetrahydro-2H-pyrazolo[3,4-d]pyrimidin-3-yl}benzoic acid,
3-{2-[2-(benzyloxy)benzyl]-7-isobutyl-5-methyl-4,6-dioxo-4,5,6,7-tetrahydro-2H-pyrazolo[3,4-d]pyrimidin-3-yl}benzoic acid,
3-{5-methyl-2-(1-naphthylmethyl)-4,6-dioxo-7-[2-(2-thienyl)ethyl]-4,5,6,7-tetrahydro-2H-pyrazolo[3,4-d]pyrimidin-3-yl}benzoic acid,
3-{7-isobutyl-2-[(2-methoxy-1-naphthyl)methyl]-5-methyl-4,6-dioxo-4,5,6,7-tetrahydro-2H-pyrazolo[3,4-d]pyrimidin-3-yl}benzoic acid,
3-{7-isobutyl-2-[3-(4-methoxyphenoxy)benzyl]-5-methyl-4,6-dioxo-4,5,6,7-tetrahydro-2H-pyrazolo[3,4-d]pyrimidin-3-yl}benzoic acid,
3-{7-isobutyl-5-methyl-2-[(2Z)-5-methyl-2-phenyl-2-hexenyl]-4,6-dioxo-4,5,6,7-tetrahydro-2H-pyrazolo[3,4-d]pyrimidin-3-yl}benzoic acid,
3-{7-isobutyl-5-methyl-4,6-dioxo-2-[(3-phenyl-1H-pyrazol-4-yl)methyl]4,5,6,7-tetrahydro-2H-pyrazolo[3,4-d]pyrimidin-3-yl}benzoic acid,
3-cyclohexyl-2-(3,5-dichlorobenzyl)-7-isobutyl-5-methyl-2H-pyrazolo[3,4-d]pyrimidine-4,6(5H,7H)-dione,
3-cyclohexyl-7-isobutyl-2-[(2-methoxy-1-naphthyl)methyl]-5-methyl-2H-pyrazolo[3,4-d]pyrimidine-4,6(5H,7H)-dione,
3-cyclohexyl-7-isobutyl-5-methyl-2-(4-quinolinylmethyl)-2H-pyrazolo[3,4-d]pyrimidine-4,6(5H,7H)-dione,
4-[7-isobutyl-5-methyl-2-(1-naphthylmethyl)-4,6-dioxo-4,5,6,7-tetrahydro-2H-pyrazolo[3,4-d]pyrimidin-3-yl]benzoic acid,
4-{[5-methyl-2-(1-naphthylmethyl)-4,6-dioxo-3-(4-pyridinyl)-2,4,5,6-tetrahydro-7H-pyrazolo[3,4-d]pyrimidin-7-yl]methyl}phenyl acetate,
4-{[7-isobutyl-5-methyl-2-(1-naphthylmethyl)-4,6-dioxo-4,5,6,7-tetrahydro-2H-pyrazolo[3,4-d]pyrimidin-3-yl]thio}butanoic acid,
4-bromo-3-[(7-isobutyl-5-methyl-4,6-dioxo-4,5,6,7-tetrahydro-2H-pyrazolo[3,4-d]pyrimidin-2-yl)methyl]benzoic acid,
5-(2-hydroxyethyl)-7-isobutyl-2-(1-naphthylmethyl)-3-(4-pyridinyl)-2H-pyrazolo[3,4-d]pyrimidine-4,6(5H,7H)-dione,
5,7-dimethyl-2-(1-naphthylmethyl)-3-(4-pyridinyl)-2H-pyrazolo[3,4-d]pyrimidine-4,6(5H,7H)-dione,
5-[2-(diethylamino)ethyl]-7-isobutyl-2-(1-naphthylmethyl)-3-(4-pyridinyl)-2H-pyrazolo[3,4-d]pyrimidine-4,6(5H,7H)-dione,
5-[7-isobutyl-5-methyl-2-(1-naphthylmethyl)-4,6-dioxo-4,5,6,7-tetrahydro-2H-pyrazolo[3,4-d]pyrimidin-3-yl]-3-thiophenecarboxylic acid,
5-[7-isobutyl-5-methyl-2-(1-naphthylmethyl)-4,6-dioxo-4,5,6,7-tetrahydro-2H-pyrazolo[3,4-d]pyrimidin-3-yl]-2-thiophenecarboxylic acid,
5-{2-[2-(benzyloxy)benzyl]-7-isobutyl-5-methyl-4,6-dioxo-4,5,6,7-tetraydro-2H-pyrazolo[3,4-d]pyridin-3-yl}-2-furoic acid,
5-{7-isobutyl-2-[3-(4-methoxyphenoxy)benzyl]-5-methyl-4,6-dioxo-4,5,6,7-tetrahydro-2H-pyrazolo[3,4-d]pyrimidin-3-yl}-2-furoic acid,
5-{7-isobutyl-5-methyl-2-[(2)-5-methyl-2-phenyl-2-hexenyl]-4,6-dioxo-4,5,6,7-tetrahydro-2H-pyrazolo[3,4-d]pyrimidin-3-yl}-2-furoic acid,
5-{7-isobutyl-5-methyl-4,6-dioxo-2-[(2Z-2-phenyl-2-pentenyl]4,5,6,7-tetrahydro-2H-pyrazolo[3,4-d]pyrimidin-3-yl}-2-furoic acid,
5-methyl-2-(1-naphthylmethyl)-3-(4-pyridinyl)-2H-pyrazolo[3,4-d]pyrimidine-4,6(5H,7H)-dione,
5-methyl-2-(1-naphthylmethyl)-3-(4-pyridinyl)-7-(2-pyridinylmethyl)-2H-pyrazolo[3,4-d]pyrimidine-4,6(5H,7H)-dione,
5-methyl-2-(1-naphthylmethyl)-3-(4-pyridinyl)-7-(4-pyridinylmethyl)-2H-pyrazolo[3,4-d]pyrimidine-4,6(5H,7H)-dione,
5-methyl-2-(1-naphthylmethyl)-3-(4-pyridinyl)-7-(tetrahydro-2H-pyran-2-ylmethyl)-2H-pyrazolo[3,4-d]pyrimidine-4,6(5H,7H)-dione,
5-methyl-2-(1-naphthylmethyl)-3-(4-pyridinyl)-7-[2-(trifluoromethyl)benzyl]-2H-pyrazolo[3,4-d]pyrimidine-4,6(5H,7H)-dione,
5-methyl-2-(1-naphthylmethyl)-3-(4-pyridinyl)-7-[3-(1H-pyrrol-1-yl)propyl]-2H-pyrazolo[3,4-d]pyrimidine-4,6(5H,7H)-dione, 5-methyl-2-(1-naphthylmethyl)-3-(4-pyridinyl)-7-[4-(trifluoromethoxy)benzyl]-2H-pyrazolo[3,4-d]pyrimidine-4,6(5H,7H)-dione, 5-methyl-2-(1-naphthylmethyl)-3-(4-pyridinyl)-7-{[(trifluoromethyl)thio]methyl}-2H-pyrazolo[3,4-d]pyrimidine-4,6(5H,7H)-dione, 5-methyl-2-(1-naphthylmethyl)-3-(4-pyridinyl)-7-{[(trifluoromethyl)sulfonyl]methyl}-2H-pyrazolo[3,4-d]pyrimidine-4,6(5H,7H)-dione, 5-methyl-2-(1-naphthylmethyl)-3-(4-pyridinyl)-7-{[(trifluoromethyl)sulfinyl]methyl}-2H-pyrazolo[3,4-d]pyrimidine-4,6(5H,7H)-dione, 5-methyl-2-(1-naphthylmethyl)-7-(2-oxopropyl)-3-(4-pyridinyl)-2H-pyrazolo[3,4-d]pyrimidine-4,6(5H,7H)-dione, 5-methyl-2-(1-naphthylmethyl)-7-(2-phenylethyl)-3-(4-pyridinyl)-2H-pyrazolo[3,4-d]pyrimidine-4,6(5H,7H)-dione, 5-methyl-2-(1-naphthylmethyl)-7-[(phenylsulfinyl)methyl]-3-(4-pyridinyl)-2H-pyrazolo[3,4-d]pyrimidine-4,6(5H,7H)-dione, 5-methyl-2-(1-naphthylmethyl)-7-[(phenylthio)methyl]-3-pyridinyl)-2H-pyrazolo[3,4-d]pyrimidine-4,6(5H,7H)-dione, 5-methyl-2-(1-naphthylmethyl)-7-[2-(1-piperidinyl)ethyl]-3-(4-pyridinyl)-2H-pyrazolo[3,4-d]pyrimidine-4,6(5H,7H)-dione, 5-methyl-2-(1-naphthylmethyl)-7-pentyl-3-(4-pyridinyl)-2H-pyrazolo[3,4-d]pyrimidine-4,6(5H,7H)-dione, 5-methyl-7-(2-methyl-2-propenyl)-2-(1-naphthylmethyl)-3-(2-pyridinyl)-2H-pyrazolo[3,4-d]pyrimidine-4,6(5H,7H)-dione, 5-methyl-7-(2-methylbenzyl)-2-(1-naphthylmethyl)-3-(4-pyridinyl)-2H-pyrazolo[3,4-d]pyrimidine-4,6(5H,7H)-dione, 5-methyl-7-(3-methyl-2-butenyl)-2-(1-naphthylmethyl)-3-(4-pyridinyl)-2H-pyrazolo[3,4-d]pyrimidine-4,6(5H,7H)-dione, 5-methyl-7-(3-methylbenzyl)-2-(1-naphthylmethyl)-3-(4-pyridinyl)-2H-pyrazolo[3,4-d]pyrimidine-4,6(5H,7H)-dione, 5-methyl-7-(5-methyl-2-nitrobenzyl)-2-(1-naphthylmethyl)-3-(4-pyridinyl)-2H-pyrazolo[3,4-d]pyrimidine-4,6(5H,7H)-dione, 5-methyl-7-[(1-methyl-3-piperidinyl)methyl]-2-(1-naphthylmethyl)-3-(4-pyridinyl)-2H-pyrazolo[3,4-d]pyrimidine-4,6(5H,7H)-dione, 5-methyl-7-[(6-methyl-2-pyridinyl)methyl]-2-(1-naphthylmethyl)-3-(4-pyridinyl)-2H-pyrazolo[3,4-d]pyrimidine-4,6(5H,7H)-dione, 5-methyl-7-[(methylsulfinyl)methyl]-2-(1-naphthylmethyl)-3-(4-pyridinyl)-2H-pyrazolo[3,4-d]pyrimidine-4,6(5H,7H)-dione, 5-methyl-7-[(methylsulfonyl)methyl]-2-(1-naphthylmethyl)-3-(4-pyridinyl)-2H-pyrazolo[3,4-d]pyrimidine-4,6(5H,7H)-dione 1-oxide, 5-methyl-7-[(methylthio)methyl]-2-(1-naphthylmethyl)-3-(4-pyridinyl)-2H-pyrazolo[3,4-d]pyrimidine-4,6(5H,7H)-dione, 5-methyl-7-[2-(4-methyl-1,3-thiazol-5-yl)ethyl]-2-(1-naphthylmethyl)-3-(4-pyridinyl)-2H-pyrazolo[3,4-d]pyrimidine-4,6(5H,7H)-dione, 5-methyl-7-[2-(4-morpholinyl)ethyl]-2-(1-naphthylmethyl)-3-(4-pyridinyl)-2H-pyrazolo[3,4-d]pyrimidine-4,6(5H,7H)-dione, 5-methyl-7-{2-[1-(methylsulfonyl)-4-piperidinyl]ethyl}-2-(1-naphthylmethyl)-3-(4-pyridinyl)-2H-pyrazolo[3,4-d]pyrimidine-4,6(5H,7H)-dione, 5-methyl-7-{2-methyl-3-[2-(4-morpholinyl)-2-oxoethoxy]benzyl}-2-(1-naphthylmethyl)-3-(4-pyridinyl)-2H-pyrazolo[3,4-d]pyrimidine-4,6(5H,7H)-dione, 5-methyl-7-{2-methyl-3-[2-(4-morpholinyl)ethoxy]benzyl}-2-(1-naphthylmethyl)-3-(4-pyridinyl)-2H-pyrazolo[3,4-d]pyrimidine-4,6(5H,7H)-dione, 7-(2,3-dihydro-1,4-benzodioxin-5-ylmethyl)-5-methyl-2-(1-naphthylmethyl)-3-(4-pyridinyl)-2H-pyrazolo[3,4-d]pyrimidine-4,6(5H,7H)-dione, 7-(2,6-dichlorobenzyl)-5-methyl-2-(1-naphthylmethyl)-3-(4-pyridinyl)-2H-pyrazolo[3,4-d]pyrimidine-4,6(5H,7H)-dione, 7-(2,6-dimethylbenzyl)-5-methyl-2-(1-naphthylmethyl)-3-(4-pyridinyl)-2H-pyrazolo[3,4-d]pyrimidine-4,6(5H,7H)-dione, 7-(2-butynyl)-5-methyl-2-(1-naphthylmethyl)-3-(4-pyridinyl)-2H-pyrazolo[3,4-d]pyrimidine-4,6(5H,7H)-dione, 7-(2-chlorobenzyl)-5-methyl-2-(1-naphthylmethyl)-3-(4-pyridinyl)-2H-pyrazolo[3,4-d]pyrimidine-4,6(5H,7H)-dione, 7-(2-hydroxyethyl)-5-methyl-2-(1-naphthylmethyl)-3-(4-pyridinyl)-2H-pyrazolo[3,4-d]pyrimidine-4,6(5H,7H)-dione, 7-(3-isobutoxy-2-methylbenzyl)-5-methyl-2-(1-naphthylmethyl)-3-(4-pyridinyl)-2H-pyrazolo[3,4-d]pyrimidine-4,6(5H,7H)-dione, 7-(3-isobutoxybenzyl)-5-methyl-2-(1-naphthylmethyl)-3-(4-pyridinyl)-2H-pyrazolo[3,4-d]pyrimidine-4,6(5H,7H)-dione, 7-(4-isopropylbenzyl)-5-methyl-2-(1-naphthylmethyl)-3-(4-pyridinyl)-2H-pyrazolo[3,4-d]pyrimidine-4,6(5H,7H)-dione, 7-[(3,5-dimethyl-4-isoxazolyl)methyl]-5-methyl-2-(1-naphthylmethyl)-3-(4-pyridinyl)-2H-pyrazolo[3,4-d]pyrimidine-4,6(5H,7H)-dione, 7-[(4-chloro-3-methyl-2-pyridinyl)methyl]-5-methyl-2-(1-naphthylmethyl)-3-(4-pyridinyl)-2H-pyrazolo[3,4-d]pyrimidine-4,6(5H,7H)-dione, 7-[(6-fluoro-4H-1,3-benzodioxin-8-yl)methyl]-5-methyl-2-(1-naphthylmethyl)-3-(4-pyridinyl)-2H-pyrazolo[3,4-d]pyrimnidine-4,6(5H,7H)-dione, 7-[2-(dimethylamino)ethyl]-5-methyl-2-(1-naphthylmethyl)-3-(4-pyridinyl)-2H-pyrazolo[3,4-d]pyrimidine-4,6(5H,7H)-dione, 7-allyl-5-methyl-2-(1-naphthylmethyl)-3-(4-pyridinyl)-2H-pyrazolo[3,4-d]pyrimidine-4,6(5H,7H)-dione, 7-benzyl-5-methyl-2-(1-naphthylmethyl)-3-(4-pyridinyl)-2H-pyrazolo[3,4-d]pyrimidine-4,6(5H,7H)-dione, 7-isobutyl-2-(1-naphthylmethyl)-3-(4-pyridinyl)-2H-pyrazolo[3,4-d]pyrimidine-4,6(5H,7H)-dione, 7-isobutyl-2-(1-naphthylmethyl)-3-(4-pyridinyl)-5-(2-pyridinylmethyl)-2H-pyrazolo[3,4-d]pyrimidine-4,6(5H,7H)-dione, 7-isobutyl-2-(1-naphthylmethyl)-3-(4-pyridinyl)-5-(4-pyridinylmethyl)-2H-pyrazolo[3,4-d]pyrimidine-4,6(5H,7H)-dione, 7-isobutyl-2-(1-naphthylmethyl)-5-[2-(1-piperidinyl)ethyl]-3-(4-pyridinyl)-2H-pyrazolo[3,4-d]pyrimidine-4,6(5H,7H)-dione, 7-isobutyl-2-(3-{3-[(mesitylmethyl)amino]-1-propynyl}benzyl)-5-methyl-3-(1-methyl-1H-imidazol-2-yl)-2H-pyrazolo[3,4-d]pyrimidine-4,6(5H,7H)-dione, 7-isobutyl-2-(3-{3-[(mesitylmethyl)amino]-1-propynyl}benzyl)-5-methyl-3-(4-pyridinyl)-2H-pyrazolo[3,4-d]pyrimidine-4,6(5H,7H)-dione,
7-isobutyl-2-[(2-methoxy-1-naphthyl)methyl]-5-methyl-3-(1-methyl-1H-imidazol-2-yl)-2H-pyrazolo[3,4-d]pyrimidine-4,6(5H,7H)-dione,
7-isobutyl-2-[(2-methoxy-1-naphthyl)methyl]-5-methyl-3-(5-methyl-1H-imidazol-2-yl)-2H-pyrazolo[3,4-d]pyrimidine-4,6(5H,7H)-dione,
7-isobutyl-2-[3-(3-methoxy-1-propynyl)benzyl]-5-methyl-3-(1-methyl-1H-imidazol-2-yl)-2H-pyrazolo[3,4-d]pyrimidine-4,6(5H,7H)-dione,
7-isobutyl-2-[3-(3-methoxy-1-propynyl)benzyl]-5-methyl-3-(4-pyridinyl)-2H-pyrazolo[3,4-d]pyrimidine-4,6(5H,7H)-dione,
7-isobutyl-2-[3-(4-methoxyphenoxy)benzyl]-5-methyl-3-(1-methyl-1H-imidazol-2-yl)-2H-pyrazolo[3,4-d]pyrimidine-4,6(5H,7H)-dione,
7-isobutyl-3-(3-methoxyphenyl)-5-methyl-2-(1-naphthylmethyl)-2H-pyrazolo[3,4-d]pyrimidine-4,6(5H,7H)-dione,
7-isobutyl-3,5-dimethyl-2-(1-naphthylmethyl)-2H-pyrazolo[3,4-d]pyrimidine-4,6(5H, 7H)-dione,
7-isobutyl-3,5-dimethyl-2-(4-quinolinylmethyl)-2H-pyrazolo[3,4-d]pyrimidine-4,6(5H, 7H)-dione,
7-isobutyl-5-[2-(4-morpholinyl)ethyl]-2-(1-naphthylmethyl)-3-(4-pyridinyl)-2H-pyrazolo[3,4-d]pyrimidine-4,6(5H,7H)-dione,
7-isobutyl-5-methyl-2-(1-naphthylmethyl)-2H-pyrazolo[3,4-d]pyrimidine-4,6(5H,7H)-dione,
7-isobutyl-5-methyl-2-(1-naphthylmethyl)-3-(1,3-thiazol-2-yl)-2H-pyrazolo[3,4-d]pyrimidine-4,6(5H,7H)-dione,
7-isobutyl-5-methyl-2-(1-naphthylmethyl)-3-(2-phenyl-1H-imidazol-4-yl)-2H-pyrazolo[3,4-d]pyrimidine-4,6(5H,7H)-dione,
7-isobutyl-5-methyl-2-(1-naphthylmethyl)-3-(2-phenylethyl)-2H-pyrazolo[3,4-d]pyrimidine-4,6(5H,7H)-dione,
7-isobutyl-5-methyl-2-(1-naphthylmethyl)-3-(2-thienyl)-2H-pyrazolo[3,4-d]pyrimidine-4,6(5H,7H)-dione,
7-isobutyl-5-methyl-2-(1-naphthylmethyl)-3-(3-nitrophenyl)-2H-pyrazolo[3,4-d]pyrimidine-4,6(5H,7H)-dione,
7-isobutyl-5-methyl-2-(1-naphthylmethyl)-3-(3-phenoxyphenyl)-2H-pyrazolo[3,4-d]pyrimidine-4,6(5H,7H)-dione,
7-isobutyl-5-methyl-2-(1-naphthylmethyl)-3-(3-pyridinyl)-2H-pyrazolo[3,4-d]pyrimidine-4,6(5H,7H)-dione,
7-isobutyl-5-methyl-2-(1-naphthylmethyl)-3-(3-thienyl)-2H-pyrazolo[3,4-d]pyrimidine-4,6(5H,7H)-dione,
7-isobutyl-5-methyl-2-(1-naphthylmethyl)-3-(4-nitrophenyl)-2H-pyrazolo[3,4-d]pyrimidine-4,6(5H,7H)-dione,
7-isobutyl-5-methyl-2-(1-naphthylmethyl)-3-(4-pyridinyl)-2H-pyrazolo[3,4-d]pyrimidine-4,6(5H,7H)-dione,
7-isobutyl-5-methyl-2-(1-naphthylmethyl)-3-(propylthio)-2H-pyrazolo[3,4-d]pyrimidine-4,6(5H,7H)-dione,
7-isobutyl-5-methyl-2-(1-naphthylmethyl)-3-[3-(1H-tetraazol-5-yl)phenyl]-2H-pyrazolo[3,4-d]pyrimidine-4,6(5H,7H)-dione,
7-isobutyl-5-methyl-2-(1-naphthylmethyl)-3-[3-(trifluoromethyl)phenyl]-2H-pyrazolo[3,4-d]pyrimidine-4,6(5H,7H)-dione,
7-isobutyl-5-methyl-2-(1-naphthylmethyl)-3-[4-(trifluoromethyl)phenyl]-2H-pyrazolo[3,4-d]pyrimidine-4,6(5H,7H)-dione,
7-isobutyl-5-methyl-2-(1-naphthylmethyl)-3-phenyl-2H-pyrazolo[3,4-d]pyrimidine-4,6(5H,7H)-dione,
7-isobutyl-5-methyl-2-(1-naphthylsulfonyl)-2H-pyrazolo[3,4-d]pyrimidine-4,6(5H,7H)-dione,
7-isobutyl-5-methyl-2-(2-naphthylmethyl)-3-(4-pyridinyl)-2H-pyrazolo[3,4-d]pyrimidine-4,6(5H,7H)-dione,
7-isobutyl-5-methyl-2-(3-phenoxybenzyl)-3-(4-pyridinyl)-2H-pyrazolo[3,4-d]pyrimidine-4,6(5H,7H)-dione,
7-isobutyl-5-methyl-2-(4-quinolinylmethyl)-3-(1,3-thiazol-5-yl)-2H-pyrazolo[3,4-d]pyrimidine-4,6(5H,7H)-dione,
7-isobutyl-5-methyl-2-[(2Z)-5-methyl-2-phenyl-2-hexenyl]-3-(4-pyridinyl)-2H-pyrazolo[3,4-d]pyrimidine-4,6(5H,7H)-dione,
7-isobutyl-5-methyl-2-[1-(1-naphthyl)-2-phenylethyl]-2H-pyrazolo[3,4-d]pyrimidine-4,6(5H,7H)-dione,
7-isobutyl-5-methyl-2-[3-(3-phenyl-1-propynyl)benzyl]-3-(4-pyridinyl)-2H-pyrazolo[3,4-d]pyrimidine-4,6(5H,7H)-dione,
7-isobutyl-5-methyl-2-{3-[3-(methylamino)-1-propynyl]benzyl}-3-(4-pyridinyl)-2H-pyrazolo[3,4-d]pyrimidine-4,6(5H,7H)-dione,
7-isobutyl-5-methyl-2H-pyrazolo[3,4-d]pyrimidine-4,6(5H,7H)-dione,
7-isobutyl-5-methyl-3-(1-methyl-1H-benzimidazol-2-yl)-2-(1-naphthylmethyl)-2H-pyrazolo[3,4-d]pyrimidine-4,6(5H,7H)-dione,
7-isobutyl-5-methyl-3-(1-methyl-1H-imidazol-2-yl)-2-(1-naphthylmethyl)-2H-pyrazolo[3,4-d]pyrimidine-4,6(5H,7H)-dione,
7-isobutyl-5-methyl-3-(1-methyl-1H-imidazol-2-yl)-2-(4-quinolinylmethyl)-2H-pyrazolo[3,4-d]pyrimidine-4,6(5H,7H)-dione,
7-isobutyl-5-methyl-3-(1-methyl-1H-imidazol-2-yl)-2-[(2Z)-2-phenyl-2-pentenyl]-2H-pyrazolo[3,4-d]pyrimidine-4,6(5H,7H)-dione,
7-isobutyl-5-methyl-3-(1-methyl-1H-imidazol-2-yl)-2-[(2Z)-5-methyl-2-phenyl-2-hexenyl]-2H-pyrazolo[3,4-d]pyrimidine-4,6(5H,7H)-dione,
7-isobutyl-5-methyl-3-(1-methyl-1H-imidazol-2-yl)-2-[(3-phenyl-1H-pyrazol-4-yl)methyl]-2H-pyrazolo[3,4-d]pyrimidine-4,6(5H,7H)-dione,
7-isobutyl-5-methyl-3-(1-methyl-1H-indol-2-yl)-2-(1-naphthylmethyl)-2H-pyrazolo[3,4-d]pyrimidine-4,6(5H,7H)-dione,
7-isobutyl-5-methyl-3-(1-methyl-1H-indol-3-yl)-2-(1-naphthylmethyl)-2H-pyrazolo[3,4-d]pyrimidine-4,6(5H,7H)-dione,
7-isobutyl-5-methyl-3-(1-methyl-1H-pyrrol-2-yl)-2-(4-quinolinylmethyl)-2H-pyrazolo[3,4-d]pyrimidine-4,6(5H,7H)-dione,
7-isobutyl-5-methyl-3-(1-methyl-1H-pyrrol-2-yl)-2-[(3-phenyl-1H-pyrazol-4-yl)methyl]-2H-pyrazolo[3,4-d]pyrimidine-4,6(5H,7H)-dione,
7-isobutyl-5-methyl-3-(2-methyl-2H-isoindol-1-yl)-2-(4-quinolinylmethyl)-2H-pyrazolo[3,4-d]pyrimidine-4,6(5H,7H)-dione,
7-isobutyl-5-methyl-3-(3-methyl-2-thienyl)-2-(1-naphthylmethyl)-2H-pyrazolo[3,4-d]pyrimidine-4,6(5H,7H)-dione,
7-isobutyl-5-methyl-3-(4-methyl-1H-imidazol-5-yl)-2-(4-quinolinylmethyl)-2H-pyrazolo[3,4-d]pyrimidine-4,6(5H,7H)-dione,
7-isobutyl-5-methyl-3-(4-pyridinyl)-2-(4-quinolinylmethyl)-2H-pyrazolo[3,4-d]pyrimidine-4,6(5H,7H)-dione,
7-isobutyl-5-methyl-3-(4-pyridinyl)-2-[2-(trifluoromethoxy)benzyl]-2H-pyrazolo[3,4-d]pyrimidine-4,6(5H,7H)-dione,
7-isobutyl-5-methyl-3-(4-pyridinyl)-2-[3-(trifluoromethoxy)benzyl]-2H-pyrazolo[3,4-d]pyrimidine-4,6(5H,7H)-dione, 7-isobutyl-5-methyl-3-(4-pyridinyl)-2-[3-(trifluoromethyl) benzyl]-2H-pyrazolo[3,4-d]pyrimidine-4,6(5H,7H)-dione, 7-isobutyl-5-methyl-3-(6-methyl-2-pyridinyl)-2-(1-naphthylmethyl)-2H-pyrazolo[3,4-d]pyrimidine-4,6(5H,7H)-dione, 7-isobutyl-5-methyl-3-(methylthio)-2-(1-naphthylmethyl)-2H-pyrazolo[3,4-d]pyrimidine-4,6(5H,7H)-dione, 7-isobutyl-5-methyl-3-[4-(methylsulfonyl)phenyl]-2-(1-naphthylmethyl)-2H-pyrazolo[3,4-d]pyrimidine-4,6(5H,7H)-dione, methyl[(2-methyl-3-{[5-methyl-2-(1-naphthylmethyl)-4,6-dioxo-3-(4-pyridinyl)-2,4,5,6-tetrahydro-7H-pyrazolo[3,4-d]pyrimidin-7-yl]methyl}phenyl)thio]acetate, methyl 3-[2-(3-{3-[benzyl(methyl)amino]-1-propynyl}benzyl)-7-isobutyl-5-methyl-4,6-dioxo-4,5,6,7-tetrahydro-2H-pyrazolo[3,4-d]pyrimidin-3-yl]benzoate, methyl 3-[2-(3-bromobenzyl)-7-isobutyl-5-methyl-4,6-dioxo-4,5,6,7-tetrahydro-2H-pyrazolo[3,4-d]pyrimidin-3-yl]benzoate, methyl 3-[2-(3-iodobenzyl)-7-isobutyl-5-methyl-4,6-dioxo-4,5,6,7-tetrahydro-2H-pyrazolo[3,4-d]pyrimidin-3-yl]benzoate, methyl 3-[7-isobutyl-2-(1-naphthylmethyl)-4,6-dioxo-3-(4-pyridinyl)-2,4,6,7-tetrahydro-5H-pyrazolo[3,4-d]pyrimidin-5-yl]propanoate, methyl 3-[7-isobutyl-5-methyl-2-(1-naphthylmethyl)-4,6-dioxo-4,5,6,7-tetrahydro-2H-pyrazolo[3,4-d]pyrimidin-3-yl]benzoate, methyl 3-{[5-methyl-2-(1-naphthylmethyl)-4,6-dioxo-3-(4-pyridinyl)-2,4,5,6-tetrahydro-7H-pyrazolo[3,4-d]pyrimidin-7-yl]methyl}benzoate, methyl 3-{2-[3-(3-hydroxy-1-butynyl)benzyl]-7-isobutyl-5-methyl-4,6-dioxo-4,5,6,7-tetrahydro-2H-pyrazolo[3,4-d]pyrimidin-3-yl}benzoate, methyl 3-{7-isobutyl-2-[3-(3-methoxy-1-propynyl)benzyl]-5-methyl-4,6-dioxo-4,5,6,7-tetrahydro-2H-pyrazolo[3,4-d]pyrimidin-3-yl}benzoate, methyl 4-{[7-isobutyl-5-methyl-2-(1-naphthylmethyl)-4,6-dioxo-4,5,6,7-tetrahydro-2H-pyrazolo[3,4-d]pyrimidin-3-yl]thio}butanoate, N-(4-{2-[(1-benzyl-1H-indol-3-yl)methyl]-7-isobutyl-5-methyl-4,6-dioxo-4,5,6,7-tetrahydro-2H-pyrazolo[3,4-d]pyrimidin-3-yl}phenyl)acetamide, N-(4-{2-[(4'-fluoro-1,1'-biphenyl-2-yl)methyl]-7-isobutyl-5-methyl-4,6-dioxo-4,5,6-tetrahydro-2H-pyrazolo[3,4-d]pyrimidin-3-yl}phenyl)acetamide, N-(4-{2-[2-(allyloxy)benzyl]-7-isobutyl-5-methyl-4,6-dioxo-4,5,6,7-tetrahydro-2H-pyrazolo[3,4-d]pyrimidin-3-yl}phenyl)acetamide, N-(4-{ 7-isobutyl-2-[(2-methoxy-1-naphthyl)methyl]-5-methyl-4,6-dioxo-4,5,6,7-tetrahydro-2H-pyrazolo[3,4-d]pyrimidin-3-yl}phenyl)acetamide, N-(4-{7-isobutyl-2-[3-(4-methoxyphenoxy)benzyl]-5-methyl-4,6-dioxo-4,5,6,7-tetrahydro-2H-pyrazolo[3,4-d]pyrimidin-3-yl}phenyl)acetamide, N-(4-{7-isobutyl-5-methyl-2-[(1-methyl-1H-indol-3-yl)methyl]-4,6-dioxo-4,5,6,7-tetrahydro-2H-pyrazolo[3,4-d]pyrimidin-3-yl}phenyl)acetamide, N-(4-{7-isobutyl-5-methyl-2-[(2Z)-5-methyl-2-phenyl-2-hexenyl]-4,6-dioxo-4,5,6,7-tetrahydro-2H-pyrazolo[3,4-d]pyrimidin-3-yl}phenyl)acetamide, N-(4-{7-isobutyl-5-methyl-4,6-dioxo-2-[(2Z)-2-phenyl-2-pentenyl]-4,5,6,7-tetrahydro-2H-pyrazolo[3,4-d]pyrimidin-3-yl}phenyl)acetamide, N-(4-{7-isobutyl-5-methyl-4,6-dioxo-2-[(3-phenyl-1H-pyrazol-4-yl)methyl]4,5,6,7-tetrahydro-2H-pyrazolo[3,4-d]pyrimidin-3-yl}phenyl)acetamide, N,N-diethyl-2-[7-isobutyl-2-(1-naphthylmethyl)-4,6-dioxo-3-(4-pyridinyl)-2,4,6,7-tetrahydro-5H-pyrazolo[3,4-d]pyrimidin-5-yl]acetamide, N-[2-({[5-(dimethylamino)-1-naphthyl]sulfonyl}amino) ethyl]-3-[7-isobutyl-5-methyl-2-(1-naphthylmethyl)-4,6-dioxo-4,5,6,7-tetrahydro-2H-pyrazolo[3,4-d]pyrimidin-3-yl]benzamide, N-[3-(3-{[7-isobutyl-5-methyl-3-(1-methyl-1H-imidazol-2-yl)-4,6-oxo-4,5,6,7-tetrahydro-2H-pyrazolo[3,4-d]pyrimidin-2-yl]methyl}phenyl)-2-propynyl]-5-methyl-3-phenyl-4-isoxazolecarboxamide, N-{4-[2-(1-benzothien-3-ylmethyl)-7-isobutyl-5-methyl-4,6-dioxo-4,5,6,7-tetrahydro-2H-pyrazolo[3,4-d]pyrimidin-3-yl]phenyl}acetamide, N-{[2-(2,3-dichlorobenzyl)-7-isobutyl-5-methyl-4,6-dioxo-4,5,6,7-tetrahydro-2H-pyrazolo[3,4-d]pyrimidin-3-yl] phenyl}acetamide, N-{4-[2-(3,5-dichlorobenzyl)-7-isobutyl-5-methyl-4,6-dioxo-4,5,6,7-tetrahydro-2H-pyrazolo[3,4-d]pyrimidin-3-yl]phenyl}acetamide, N-{4-[7-isobutyl-5-methyl-2-(1-naphthylmethyl)-4,6-dioxo-4,5,6,7-tetrahydro-2H-pyrazolo[3,4-d]pyrimidin-3-yl]phenyl}acetamide, N-{[7-isobutyl-5-methyl-4,6-dioxo-2-(4-quinolinylmethyl)-4,5,6,7-tetrahydro-2H-pyrazolo[3,4-d]pyrimidin-3-yl] phenyl}acetamide, tert-butyl[5-methyl-2-(1-naphthylmethyl)-4,6-dioxo-3-(4-pyridinyl)-2,4,5,6-tetrahydro-7H-pyrazolo[3,4-d]pyrimidin-7-yl]acetate.

What is claimed is:
1. A compound of formula (I)

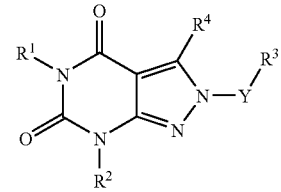

wherein, $R^1$ is H, optionally substituted alkyl, optionally substituted alkenyl, optionally substituted alkynyl, optionally substituted cycloalkyl, optionally substituted cycloalkenyl, optionally substituted cycloalkynyl, optionally substituted aryl, optionally substituted alkoxy, amino, or optionally substituted heterocycle;

$R^2$ is H, optionally substituted alkyl, optionally substituted alkenyl, optionally substituted alkynyl, optionally substituted cycloalkyl, optionally substituted cycloalkenyl, optionally substituted cycloalkynyl, optionally substituted aryl, optionally substituted alkoxy, amino, or optionally substituted heterocycle;

$R^3$ is a monocyclic or bicyclic, saturated or unsaturated, ring system comprising 0, 1, 2 or 3 of heteroatoms independently selected from N, O, or S, the ring being substituted by 0, 1, 2 or 3 substituents selected from =O, halogen, —$OR^a$, $C_{1-6}$alkyl, $C_{1-6}$haloalkyl, —CN, nitro, —S(=O)$_n R^c$, —O(CH$_2$)$_m$Het, —O(CH$_2$)$_m$C (=O)Het, —O(CH$_2$)$_m$C(=O)NR$^a$R$^a$, —O(CH$_2$)$_m$C (=O)OR$^a$, —O(CH$_2$)$_m$NR$^a$R$^a$, —O(CH$_2$)$_m$OR$^a$, —S(CH$_2$)$_m$Het, —S(CH$_2$)$_m$C(=O)Het, —S(CH$_2$)$_m$C (=O)NR$^a$R$^a$, —S(CH$_2$)$_m$C(=O)OR$^a$, —S(CH$_2$)$_m$NR$^a$R$^a$, —S(CH$_2$)$_m$OR$^a$, —NHR$^a$, —NR$^a{}_2$, —NHC(=O)R$^a$, N=NR$^a$, aminocarbonyl, phenyl or benzyl; or R$^3$ is represented by -Het, -Het-Het, R$^5$, R$^5$-Het, -Het-R$^5$, -Het-O—R$^5$, -phenyl-R$^5$ or -phenyl-OR$^5$;

R$^4$ is —(CH$_2$)$_n$phenyl-Het, -Het, -Het-Het, -Het-R$^5$, -Het-O—R$^5$, the ring system being substituted by 0, 1, 2 or 3 substituents selected from B(OH)$_2$, vicinal —OCH$_2$CH$_2$O—, vicinal —OC$_{1-2}$haloalkylO—, vicinal —OCH$_2$O—, vicinal —CH$_2$OCH$_2$O—, =O, halogen, —R$^b$OR$^a$, —SR$^a$, —OR$^a$, C$_{1-6}$alkyl, C$_{1-6}$haloalkyl, —CN, —S(=O)$_n$R$^c$, —O(CH$_2$)$_m$Het, —O(CH$_2$)$_m$C(=O)Het, —O(CH$_2$)$_m$C(=O)NR$^a$R$^a$, —O(CH$_2$)$_m$C(=O)OR$^a$, —O(CH$_2$)$_m$NR$^a$R$^a$, —O(CH$_2$)$_m$OR$^a$, —S(CH$_2$)$_m$Het, —S(CH$_2$)$_m$C(=O)Het, —S(CH$_2$)$_m$C(=O)NR$^a$R$^a$, —S(CH$_2$)$_m$C(=O)OR$^a$, —S(CH$_2$)$_m$NR$^a$R$^a$, —S(CH$_2$)$_m$OR$^a$, —NHR$^a$, —NR$^a{}_2$, —NHC(=O)R$^a$, N=NR$^a$, NO$_2$, —C(=O)NR$^a$R$^a$, —C(=O)NR$^a$OR$^a$, —C(=O)NR$^a$R$^b$NR$^a$R$^a$, —C(=O)NR$^a$R$^b$OR$^a$, —C(=O)NR$^a$R$^b$S(=O)$_n$R$^a$, —C(=O)NR$^a$R$^b$Het, —C(=O)OR$^a$, —OC(=O)R$^a$, —C(=O)OR$^b$NR$^a$R$^a$, —C(O)R$^a$, —C(=O)R$^b$NR$^a$R$^a$, —C(=NOR$^a$)R$^a$, —C(=NCN)R$^a$, —S(=O)$_2$NR$^a$R$^a$, —NR$^a$S(=O)$_2$R$^a$, —S(=O)$_2$NR$^a$R$^b$C(=O)NR$^a$R$^a$, —S(=O)$_2$NR$^a$R$^b$C(=O)OR$^a$, aminocarbonyl, phenyl or benzyl;

R$^5$ is independently at each instance, phenyl substituted by 0, 1, 2, or 3 groups selected from halogen, C$_{1-6}$haloalkyl, —OC$_{1-6}$haloalkyl, C$_{1-6}$alkyl, —CN, nitro, —OH, —OR$^c$, —S(=O)$_n$R$^c$, —O(CH$_2$)$_m$Het, —O(CH$_2$)$_m$C(=O)Het, —O(CH$_2$)$_m$C(=O)NR$^a$R$^a$, —O(CH$_2$)$_m$C(=O)OR$^a$, —O(CH$_2$)$_m$NR$^a$R$^a$, —O(CH$_2$)$_m$OR$^a$, —S(CH$_2$)$_m$Het, —S(CH$_2$)$_m$C(=O)Het, —S(CH$_2$)$_m$C(=O)NR$^a$R$^a$, —S(CH$_2$)$_m$C(=O)OR$^a$, —S(CH$_2$)$_m$NR$^a$R$^a$, —S(CH$_2$)$_m$OR$^a$, —R$^b$OR$^a$, —SR$^a$, —C(=O)NR$^a$R$^a$, —C(=O)NR$^a$OR$^a$, —C(=O)NR$^a$R$^b$NR$^a$R$^a$, —C(=O)NR$^a$R$^b$OR$^a$, —C(=O)NR$^a$R$^b$S(=O)$_n$R$^a$, —C(=O)NR$^a$R$^b$Het, —C(=O)OR$^a$, —OC(=O)R$^a$, —C(=O)OR$^b$NR$^a$R$^a$, —C(=O)R$^a$, —C(=O)R$^b$NR$^a$R$^a$, —C(=NOR$^a$)R$^a$, —C(=NCN)R$^a$, —S(=O)$_2$NR$^a$R$^a$, —NR$^a$S(=O)$_2$R$^a$, —S(=O)$_2$NR$^a$R$^b$C(=O)NR$^a$R$^a$, —S(=O)$_2$NR$^a$R$^b$C(=O)OR$^a$;

R$^a$ is, independently at each instance, H, C$_{1-6}$alkyl, —C(=O)C$_{1-4}$alkyl, C$_{1-4}$haloalkyl, —(CH$_2$)$_q$—, phenyl, benzyl, or 5 or 6-membered ring, saturated or unsaturated heterocycle containing 1 2, 3, or 4 heteroatoms independently selected from N, O or S and wherein q is 0, 1, 2, 3, 4, 5 or 6;

R$^b$ is, independently at each instance C$_{1-6}$alkyl, —C(=O)C$_{1-4}$alkyl, C$_{1-4}$haloalkyl, —(CH2)$_q$—, phenyl, benzyl, or 5 or 6-membered ring, saturated or unsaturated heterocycle containing 1, 2, 3, or 4 heteroatoms independently selected from N, O or S and wherein q is 0, 1, 2, 3, 4, 5 or 6;

R$^c$ is C$_{1-6}$alkyl, C$_{1-4}$haloalkyl, phenyl or benzyl;

R$^d$ is phenyl substituted by 0, 1, 2 or 3 groups selected from —CN, halogen, nitro, C$_{1-6}$alkyl, C$_{1-4}$haloalkyl, —OH, —OR$^c$, —NR$^a$R$^b$, —S(=O)$_n$R$^c$, —C(=O)Ra, —S(=O)NR$^a$R$^b$, —C(=O)NR$^a$R$^a$, —C(=O)OR$^a$, —NR$^a$C(=O)R$^a$, —OC(=O)R$^a$, B(OH)$_2$, vicinal —OCH$_2$CH$_2$O—, vicinal —OC$_{1-2}$haloalkylO—, vicinal —OCH$_2$O—, vicinal —CH$_2$OCH$_2$O—, phenyl, benzyl and a 5- or 6-membered ring, saturated or unsaturated heterocycle containing 1, 2, 3 or 4 heteroatoms independently selected from N, O, or S;

Y is CH$_2$, CHCH$_3$, S(=O) or S(=O)$_2$;

m is 1, 2 or 3;

n is 0, 1 or 2; and

Het, unless otherwise defined, is a 5- or 6-membered ring, saturated or unsaturated heterocycle containing 1, 2, 3 or 4 heteroatoms independently selected from N, O, or S, and substituted by 0, 1, 2 or 3 substituents selected from halogen, —(CH$_2$)$_n$R$^d$, C$_{1-4}$alkyl, —S(=O)$_n$R$^c$, —C(=O) R$^a$, or —S(=O)$_2$NR$^a$R$^a$ vicinal —OCH$_2$CH$_2$O—, vicinal —OC$_{1-2}$haloalkylO—, vicinal —OCH$_2$O—, or vicinal —CH$_2$OCH$_2$O—, =O, halogen, cyano, —R$^b$OR$^a$, —R$^b$SR$^a$, —SR$^a$, —OR$^a$, C$_{1-6}$alkyl, C$_{1-6}$haloalkyl, —CN, nitro, —OH, —NHR$^a$, —NR$^a{}_2$, —NHC(=O)R$^a$, N=NR$^a$, —C(=O)NR$^a$R$^a$, —C(=O)NR$^a$OR$^a$, —C(=O)NR$^a$R$^b$NR$^a$R$^a$, —C(=O)NR$^a$R$^b$OR$^a$, —C(=O)NR$^a$R$^b$S(=O)$_n$R$^a$, —C(=O)NR$^a$R$^b$Het, —C(=O)OR$^a$, —OC(=O)R$^a$, —C(=O)OR$^b$NR$^a$R$^a$, —C(=O)R$^b$NR$^a$R$^a$, —C(=NOR$^a$)R$^a$, —C(=NCN)R$^a$, —NR$^a$S(=O)$_2$R$^a$, —S(=O)$_2$NR$^a$R$^b$C(=O)NR$^a$R$^a$, or —S(=O)$_2$NR$^a$R$^b$C(=O)OR$^a$;

or a pharmaceutically acceptable salt thereof.

2. The compound as recited in claim 1 wherein R$^1$ is C$_{1-4}$alkyl, Het-C$_{1-10}$alkyl-, R$^d$—C$_{1-10}$alkyl- or C$_{1-10}$alkyl, or —OH wherein it is optionally substituted by 1 or 2 substituents selected from halogen, —OR$^a$, —NR$^a$R$^a$, —C(=O)OR$^a$, —C(=O)NR$^a$R$^a$, —OC(=O)C$_{1-4}$alkyl or —NR$^a$C(=O)C$_{1-4}$alkyl.

3. The compound as recited in claim 1 wherein R$^1$ is Het-C$_{1-3}$alkyl-, R$^d$—(CH$_2$)$_n$— or —C$_{1-6}$alkyl that is substituted by 1 or 2 substituents selected from halogen, —OR$^a$, —NR$^a$R$^a$, —C(=O)OR$^a$, —C(=O)NR$^a$R$^a$, —OC(=O)C$_{1-4}$ alkyl or —NR$^a$C(=O)C$_{1-4}$alkyl.

4. The compound as recited in claim 1 wherein R$^3$ is represented by -Het, -Het-Het, R$^5$,R$^5$-Het, -Het-R$^5$, -Het-O—R$^5$, -phenyl-R$^5$ or -phenyl-.

5. The compound as recited in claim 1 where R$^1$ is represented by C$_{1-6}$alkyl, wherein it is optionally substituted by 1 or 2 substituents selected from halogen, —OR$^a$, —NR$^a$R$^a$, —C(=O)OR$^a$, —C(=O)NR$^a$R$^a$, —OC(=O)C$_{1-4}$ alkyl or —NR$^a$C(=O)C$_{1-4}$alkyl.

6. The compound as recited in claim 1 wherein R$^1$ is methyl or ethyl optionally substituted with a substituted 5 or 6-membered heterocyclic ring.

7. The compound as recited in claim 6 wherein the heterocyclic is selected from imidazoyly, piperidinyl, methylpiperidinyl, or morpholinyl.

8. The compound as recited in claim 1 wherein R$^2$ is —C$_{1-3}$alkyl-C(=O)R$^a$; —C$_{1-3}$alkyl-C(=O)OR$^a$; —C$_{1-3}$alkyl-C(=O)NR$^a$R$^a$; —C$_{1-3}$alkyl-S(=O)$_n$R$^c$; Het-C$_{1-3}$alkyl-; R$^5$—C$_{1-3}$alkyl-; or C$_{1-12}$alkyl substituted with 0, 1, 2 or 3 substituents selected from —OH, halogen, —CN, —OR$^a$, —NR$^a$R$^a$ and —SR$^c$.

9. The compound as recited in claim 1 wherein R$^2$ is Het-C$_{1-3}$alkyl-; R$^5$—C$_{1-3}$alkyl-; C$_{1-6}$alkyl substituted with 0, 1 or 2 substituents selected from —OH, halogen, —CN, —OR$^a$, —NR$^a$R$^a$ and SR$^c$.

10. The compound as recited in claim 9 wherein R$^2$ is —CH$_2$CH$_2$CH$_3$, —CH$_2$-cyclopropyl, —CH$_2$ CH(CH$_3$)$_2$, —CH$_2$ CH$_2$ CH$_2$F, CH$_2$cyclobutyl, —CH$_2$C(CH$_3$)$_3$, —CH$_2$CH$_2$ CH(CH$_3$)$_2$, —CH$_2$ CF$_3$, —CH$_2$-phenyl, —CH$_2$-phenyl, CH$_2$-isoxazolyl, —CH$_2$—S-phenyl, —CH$_2$-phenylcarboxyl, or —CH$_2$SCF$_3$.

11. The compound as recited in claim 1 wherein R$^3$ is represented by Formula (i):

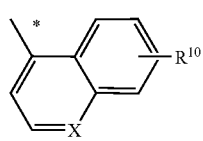

wherein * is the location where (i) is attached to Y, $R^{11}$ is optionally substituted alkyl, optionally substituted —S(=O)$NR^aR^a$ or S(=O)n, wherein n=1 or 2 and wherein X is represented by C or N and Y is represented by C, N, S or O and wherein $R^{10}$ is, at any position on the bicyclic ring, H, optionally substituted $C_{1-6}$alkyl, halogen, —CN, nitro,— $CF_3$, or —S(=O)$_2CH_3$.

12. The compound as recited in claim 1 wherein $R^3$ is represented by Formula (ii):

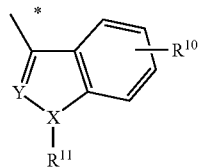

wherein * is the location where (ii) is attached to Y, wherein $R^{11}$ is optionally substituted alkyl, optionally substituted —S(=O)$NR^aR^a$ or S(=O)n, wherein n=1 or 2 and wherein X and Y are independently represented by C, N, S, or O wherein X and Y are not simultaneously C, S, or O C and wherein X and Y are not S and O respectively or vice versa and wherein $R^{10}$ is, at any position on the bicyclic ring, H, optionally substituted $C_{1-6}$alkyl, halogen, —CN, nitro, $CF_3$, or —S(=O)$_2CH_3$.

13. The compound as recited in claim 1 wherein $R^4$ is a saturated or unsaturated 5- or 6-membered heterocyclic ring, containing 1, 2, 3 or 4 heteroatoms independently selected from N, O, or S, wherein the not more than one of the heteroatoms is S or O, and the ring is substituted by 0, 1 or 2 groups selected from —CN, nitro, $C_{1-6}$alkyl, $C_{1-4}$haloalkyl, —OH, —$OR^c$, —$NR^aR^a$, —S(=O)$_nR^c$, —S(=O)$_2NR^a_2$, —C(=O)$NR^aR^a$, —C(=O)$OR^a$, —$NR^aC(=O)R^a$, —OC(=O)$R^a$, B(OH)$_2$, vicinal —OCH$_2$CH$_2$O—, vicinal —OC$_{1-2}$haloalkylO—, vicinal —OCH$_2$O—, vicinal —CH$_2$OCH$_2$O—, phenyl or benzyl.

14. A pharmaceutical composition for the treatment of *H. Pylori* infection, comprising:
   a therapeutically-effective amount of a compound according to claim 1 and
   a pharmaceutically-acceptable diluent or carrier.

15. A process for making a compound of claim 1, comprising:
   (a) reacting a compound of formula Ia with a dicarboxylic acid, acetic anhydride and acetic acid to form a compound of formula Ib;

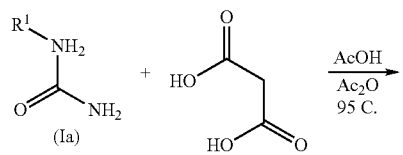

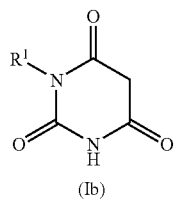

(b) reacting a compound of formula Ib with a chlorinating to form a compound of formula Ic;

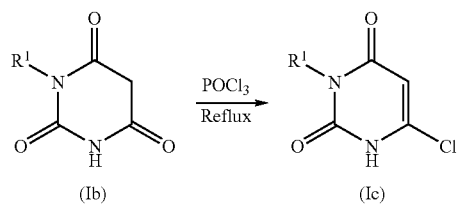

(c) reacting a compound of formula Ic with $R^2$—X wherein X is a leaving group such as a halogen, mesylate, or tosylate, to form a compound of formula Id;

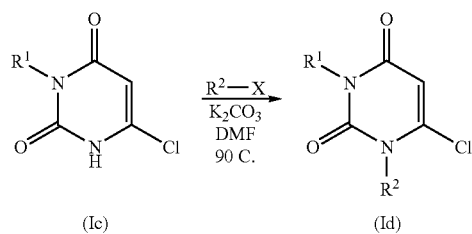

(d) reacting a compound of formula Id with $NH_2NH_2H_2O$ in a solvent such as ethanol and refluxed to form a compound of formula Ie;

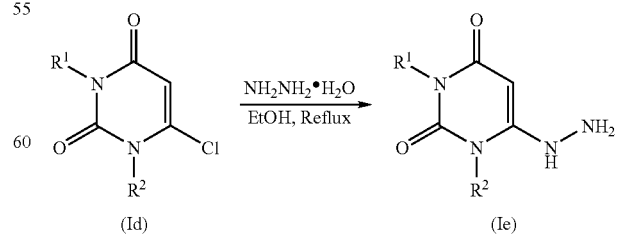

(e) reacting a compound of formula Ie with $R^3$—CHO in a solvent to form a compound of formula If;

-continued

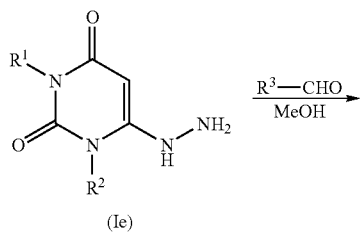
(Ie)

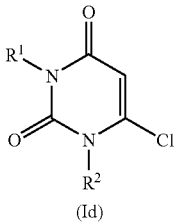
(Id)

(b) reacting a compound of formula Id with NH₂NH₂H₂O in a solvent such as ethanol and refluxed to form a compound of formula Ie;

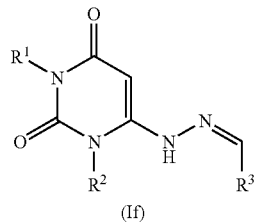
(If)

and (f) reacting a compound of formula If with R⁴—CHO in a polar protic or aprotic solvent in the presence or absence of an amine catalyst to form a compound of formula I;

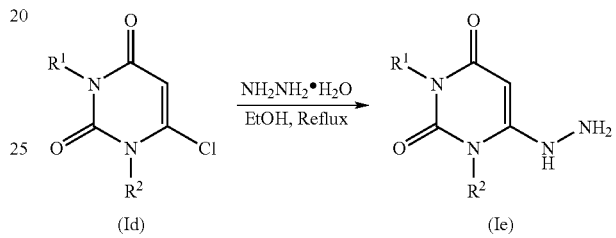
(Id) (Ie)

(c) reacting a compound of formula Ie with R³—CHO in a solvent to form a compound of formula If;

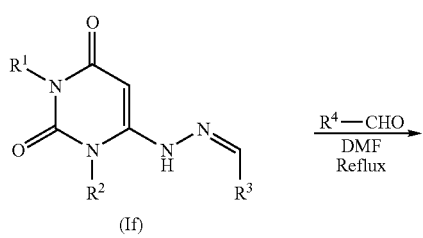
(If)

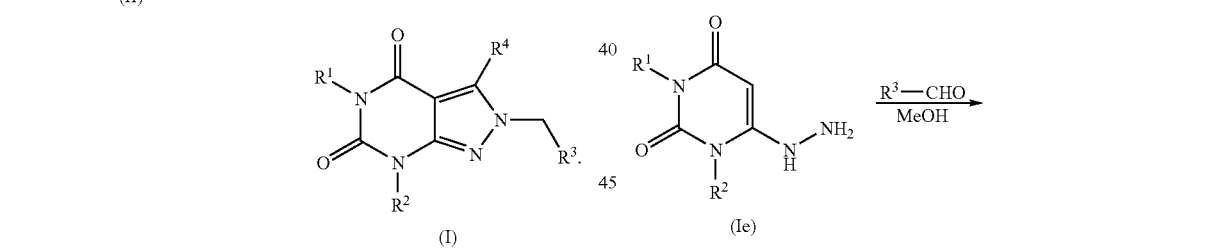
(I) (Ie)

16. A process for making a compound of claim 1, comprising:

(a) reacting a compound of formula Ig with R²—X to form Ih and subsequently R¹—X to form a compound of formula Id;

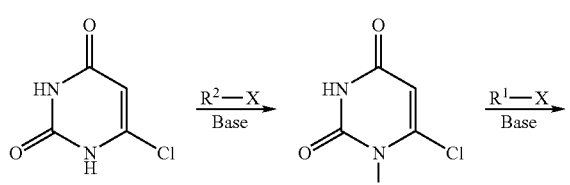

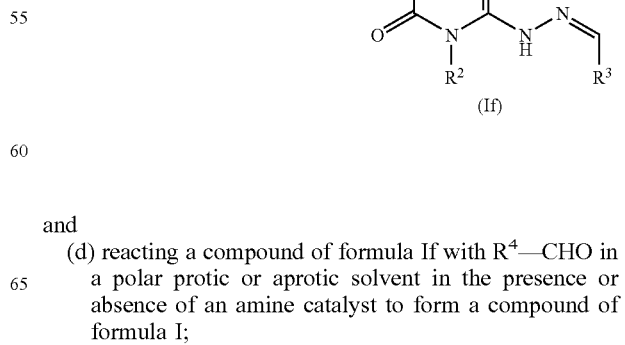
(If)

and (d) reacting a compound of formula If with R⁴—CHO in a polar protic or aprotic solvent in the presence or absence of an amine catalyst to form a compound of formula I;

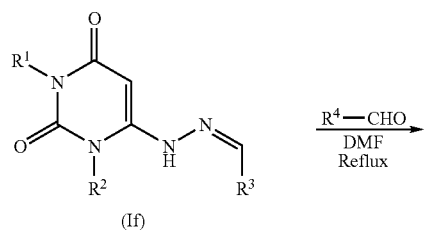  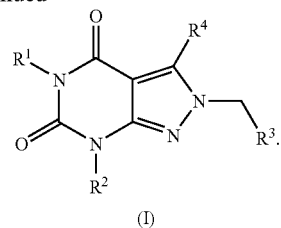
* * * * *